US006274576B1

(12) United States Patent
Grimley et al.

(10) Patent No.: US 6,274,576 B1
(45) Date of Patent: *Aug. 14, 2001

(54) METHOD OF DYNAMIC RETARDATION OF CELL CYCLE KINETICS TO POTENTIATE CELL DAMAGE

(75) Inventors: Philip M. Grimley, Potomac, MD (US); Sunil Mehta, Rumford, RI (US)

(73) Assignee: The Henry Jackson Foundation for the Advancement of Military Medicine, Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/168,106

(22) Filed: Oct. 8, 1998

Related U.S. Application Data

(63) Continuation of application No. 08/667,543, filed on Jun. 21, 1996, now abandoned.
(60) Provisional application No. 60/000,546, filed on Jun. 27, 1995.

(51) Int. Cl.$^7$ .................... A61K 31/553; A61K 31/55; A61K 31/7064; A61K 31/7026

(52) U.S. Cl. ................. 514/211; 514/45; 514/49

(58) Field of Search ................. 514/45, 49, 211, 514/482

(56) References Cited

U.S. PATENT DOCUMENTS 5,262,409   11/1993   Margolis et al. .............. 514/183

FOREIGN PATENT DOCUMENTS

| 0 359 981 | 10/1998 | (EP) . |
|---|---|---|
| WO 91/07180 | 5/1991 | (WO) . |
| WO 92/19765 | 11/1992 | (WO) . |
| WO 93/00909 | 1/1993 | (WO) . |
| WO 93/09782 | 5/1993 | (WO) . |
| WO 94/04541 | 3/1994 | (WO) . |
| WO 94/18990 | 9/1994 | (WO) . |
| WO 95/00520 | 1/1995 | (WO) . |

OTHER PUBLICATIONS

Soma et al. "In vivo enhanced antitumor . . . " Can. Res. 55, pp. 597–602, 1995.*
Liu et al. "Arrest in late G2 . . . " Int. J. Cancer. 51, pp. 792–797, 1992.*
Wexler "Encyclopedia of toxicology . . . " vol. 1, pp. 508–510, 1998.*
Akman et al., "Synergistic Inhibition of Human Leukemia Cell Growth by Deoxyguanosine and 1–β–D–Arabinofuranosylcytosine," Biochem. Pharmacol. 33(7):1059–1063 (1984).

Ashman et al., "Bromodeoxyuridine Mutagenesis . . . ", CA 96:80757 (1981).
Basu et al., "Sensitization of Human Cervical Carcinoma Cells to cis–Diamminedichloroplatinum (II) by Bryostatin 1," Cancer Res. 52:3119–3124 (1992).
Benz et al., "Tamoxifen and 5–Fluorouracil in Breast Cancer: Cytotoxic Synergism in Vitro," Cancer Res. 43:5298–5303 (1983).
Berenbaum, "What is Synergy?", Pharmacological Reviews 41:93–141 (1989).
Bergerat et al., "Synergistic Lethal Effect of cis–Dichlorodiammineplatinum and 1–β–D–Arabinofuranosylcytosine," Cancer Res. 41:25–30 (1981).
Bhalla et al., "Effects of thymidine and hydroxyurea on the metabolism and cytotoxicity of 1–B–D arabinofuranosylcytosine in highly resistant human leukemia cells," Blood 78(11):2937–2944 (1991).
Blumenreich et al., "Thymidine as a Kinetic and Biochemical Modulator of 1–β–D–Arabinofuranosylcytosine in Human Acute Nonlymphocytic Leukemia," Cancer Res. 44:825–830 (1984).
Damia et al., "Activity of aphidicolin glycinate alone or in combination with cisplatin in a murine ovarian tumor resistant to cisplatin," Cancer Chemother. Pharmacol. 30:459–464 (1992).
Ellims, "Thymidine as an Anticancer Agent, Alone or in Combination," Cancer Chemother. Pharmacol. 10:1–6 (1982).
Erba et al., "Potentiation of Etoposide Cytotoxicity against a Human Ovarian Cancer Cell Line by Pretreatment with Non–toxic Concentrations of Methotrexate or Aphidicolin," Eur. J. Cancer 28(1):66–71 (1992).
Frankfurt, "Combination Chemotherapy and DNA Repair Inhibition," Anticancer Research 12(6A):1795–1796 (1992).

(List continued on next page.)

Primary Examiner—Ceila Chang
(74) Attorney, Agent, or Firm—Finnegan, Henderson, Farabow, Garrett & Dunner, L.L.P.

(57) ABSTRACT

The invention relates to a method of potentiating cell damage in a target cell population by administering a "restraining agent" and concomitantly or subsequently applying a "targeted cytotoxic insult." The restraining agent is administered at a concentration and under conditions sufficient to retard, but not to arrest, the progress of the target cell population through the cell cycle, a concept termed "dynamic retardation." With such a mechanism, all the cells intended for damage by the targeted cytotoxic insult are likely to cycle into the relevant interval of vulnerability (target interval) within the cell cycle, resulting in a larger number of susceptible cells, and the time period during which those cells are vulnerable to the action of a given targeted cytotoxic insult is increased, resulting in a higher probability and percentage of cell killing.

15 Claims, 40 Drawing Sheets

OTHER PUBLICATIONS

Grant et al., "Modulation of 1-[β-D-Arabinofuranosyl] Cytosine–Induced Apoptosis in Human Myeloid Leukemia Cells by Staurosporine and Other Pharmacological Inhibitors of Protein Kinase $C^a$," Oncology Res. 6(2):87–99 (1994).

Grant et al., "Enhancement of 1–β–D–Arabinofuranosylcytosine Accumulation within L1210 Cells and Increased Cytotoxicity following Thymidine Exposure," Cancer Res. 40:1525–1531 (1980).

Grant et al., "Induction of Apoptosis and Potentiation of the Action of 1–β–D–Arabinofuranosyl–cytosine (ara–C) in Human Promyelocytic Leukemia Cells by Pharmacological Inhibitors of Protein Kinase C (PKC)," Blood 82(10)(Suppl. 1):251a (1993), Abstr. No. 989.

Grimley et al., "A novel approach of cell cycle kinetic restraint potentiates the cytotoxic action of indol carbozole protein kinase inhibitors (ICI) in human lymphoma cells," Blood 86:761a (1995).

Hartwell et al., "Cell Cycle Control and Cancer," Science 266:1821–1828 (1994).

Higashihara et al., "Combined Antiproliferative Activity of 5–Fluorouracil and Mitomycin–C against Primary Human Ovarian Tumors and Cell Lines in a Clonogenic Assay," Gynecologic Oncology 48:171–179 (1993).

Hofmann et al., "Enhancement of the Antiproliferative Effect of cis–Diamminedichloroplatinum(II) and Nitrogen Mustard by Inhibitors of Protein Kinase C," Int. J. Cancer 42:382–388 (1988).

Jekunen et al., "Synergism between Dipyridamole and Cisplatin in Human Ovarian Carcinoma Cells In Vitro," Cancer Res. 52:3566–3571 (1992).

Kinahan et al., "Biochemical and Antitumor Effects of the Combination of Thymidine and 1–β–D–Arabinofuranosylcytosine against Leukemia L1210," Cancer Res. 41:445–451 (1981).

Klein et al., "Chemotherapy After Synchronization of Tumor Cells," Seminars in Hematology 11(2):203–227 (1974).

Lorico et al., "Increase in Etoposide–induced Topoisomerase II–mediated DNA Breaks After Cell Synchronization Induced by Low Doses of Methotrexate," Biochem. Pharmacol. 37(9):1883–1884 (1988).

Lynch et al., "Continuous–Infusion Cisplatin, 5–Fluorouracil, and Bolus Methotrexate in the Treatment of Advanced Non–Small Cell Lung Cancer," Cancer 70(7):1880–1885 (1992).

Mehta et al., "S–phase enhancement of p53–independent apoptosis induced by staurosporine in human lymphoma cells," Mol. Biol. Cell 6:247a (1995).

Moran et al., "Synchronization of L1210 Leukemia with Hydroxyurea Infusion and the Effect of Subsequent Pulse Dose Chemotheraphy," Cancer Treatment Reports 64(1):81–86 (1980).

O'Dwyer et al., "Role of Thymidine in Biochemical Modulation: A Review," Cancer Res. 47:3911–3919 (1987).

Plucinski et al., "Allosteric Interaction of Components of the Replitase Complex is Responsible for Enzyme Cross–inhibition," Mol. Pharmacol. 38:114–120 (1990).

Poot et al., "Cytostatic Synergism Between Bromodeoxyundine, Bleomycin, Cisplatin and Chlorambucil Demonstrated by a Sensitive Cell Kinetic Assay," Biochem. Pharmacol. 41(12):1903–1909 (1991).

Ritch et al.,"Schedule–dependent Synergism of Combinations . . . " CA 95:180777 (1981).

Ross et al., "Bromodeoxyuridine Enhancement of 1–β–D–Arabinofuranosylcytosine Metabolic Activation and Toxicity in HL–60 Leukemic Cells," Cancer Res. 48:517–521 (1988).

Sobrero et al., "Synergism and Lack of Cross–resistance Between Short–term and Continuous Exposure to Fluorouracil in Human Colon Adenocarcinoma Cells," J. Nat'l Cancer Inst. 85(23):1937–1944 (1993).

Squires et al., "Deoxyguanosine enhances the cytotoxicity of the topoisomerase I inhibitor camptothecin by reducing the repair of double–strand breaks induced in replicating DNA," J. Cell Science 100:883–893 (1991).

Srivastava et al., "The status of the p53 gene in human papilloma virus positive or negative cervical carcinoma cell lines," Carcinogenesis 13(7):1273–1275 (1992).

Streifel et al., "Synergistic interaction between 1–β–D–Arabinofuranosylcytosine, thymidine, and hydroxyurea against human B cells and leukemic blasts in vitro," Proc. Natl. Acad. Sci. USA 78(8):5132–5136 (1981).

Tefferi et al., "Phase I Study of Combined 2–Chlorodeoxyadenosine and Chlorambucil in Chronic Lymphoid Leukemia and Low–Grade Lymphoma," J. Clin. Oncol. 12(3):569–574 (1994).

Ubezio et al., "Increasing 1–β–D–Arabinofuranosylcytosine Efficacy by Scheduled Dosing Intervals Based on Direct Measurements of Bone Marrow Cell Kinetics," Cancer Res. 54:6446–6451 (1994).

Van Echo et al., "A Phase II Trial of Arabinosylcytosine and Thymidine (Ara–C) + TdR in Acute Leukemia," Proceedings, Asco Abstracts, p. 437, (1980), Abstr. No. C–466.

Van Echo et al., "A Phase III Trial of Arabinocylcytosine and Thymidine (Ara–C + TdR) in Adult Relapsed Acute Leukemia," Proceedings, Asco Abstracts, p. 483, (1981), Abstr. No. C–586.

Wang et al., "Apoptosis in 7–Hydroxystaurosporine–treated T Lymphoblasts Correlates with Activation of Cyclin–dependent Kinases 1 and 2," Cell Growth & Differentiation 6:927–936 (1995).

Wilson et al., "A feasibility study of the MTT assay for chemosensitivity testing in ovarian malignancy," Br. J. Cancer 62:189–194 (1990).

Musk et al. "Override of the radiation–induced mitotic . . ." CA 113:55125, 1990.*

* cited by examiner

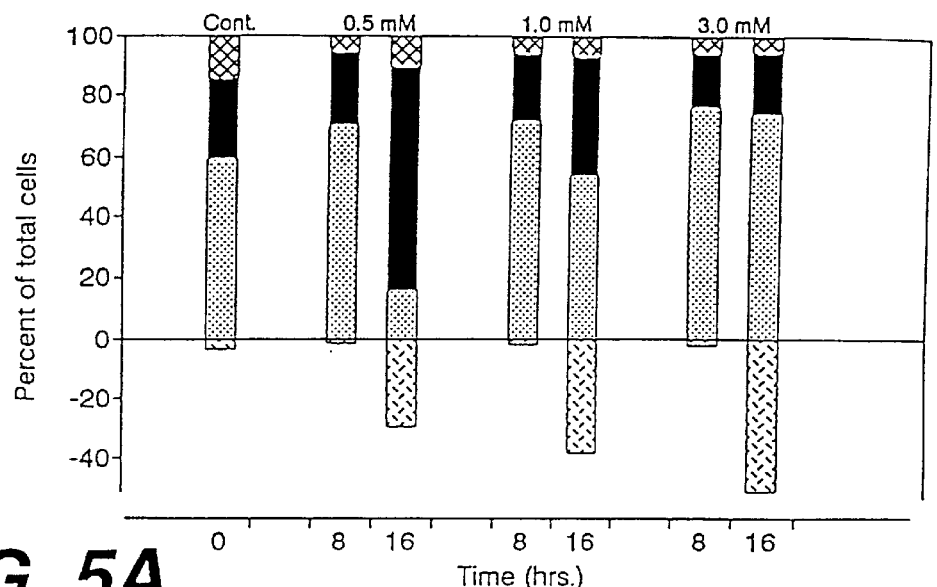
FIG. 5A
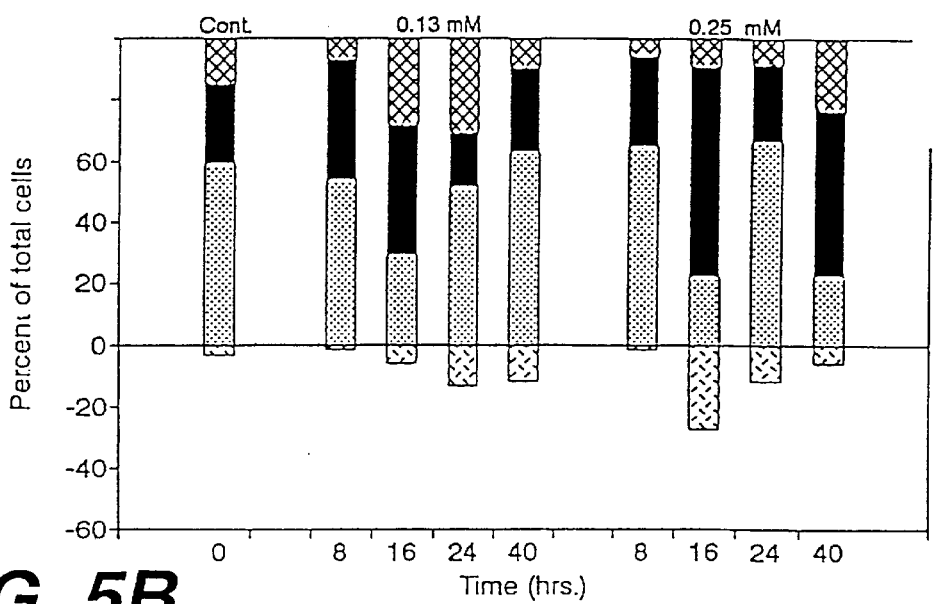
FIG. 5B
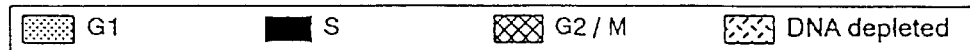

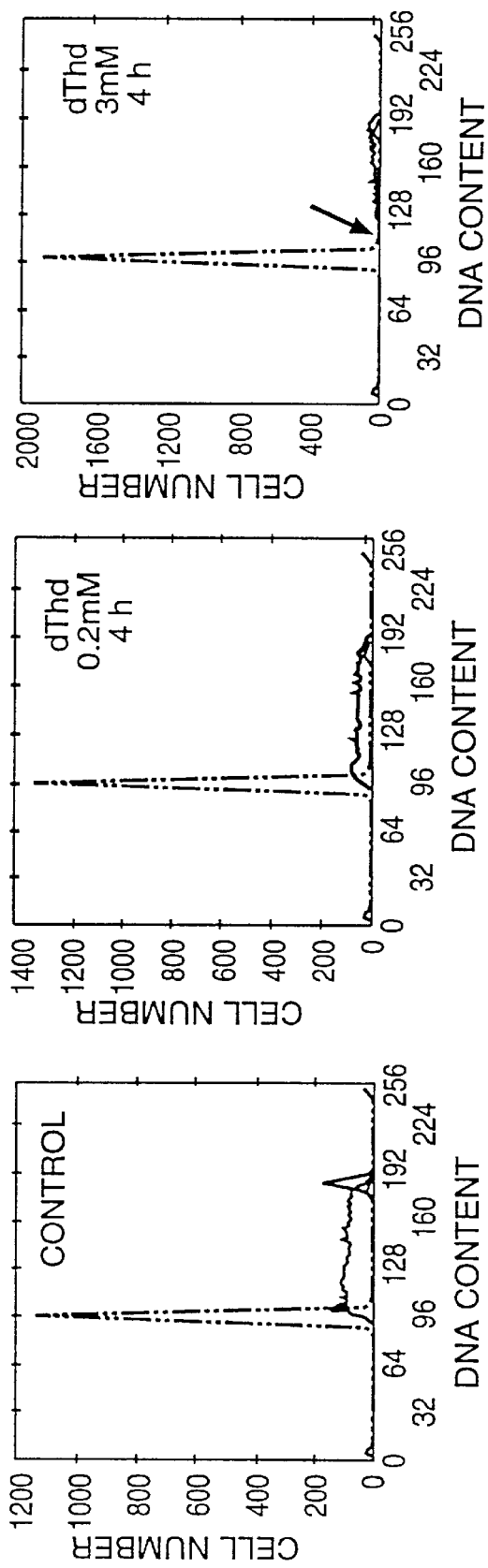

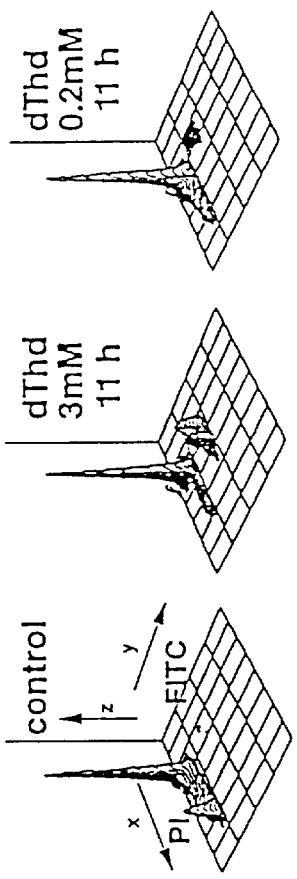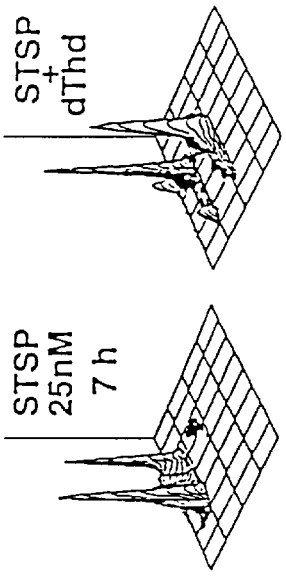
dThd potentiation of apoptosis
bivariate DNA histograms
terminal transferase b-dUTP end labelling
FIG. 25A   FIG. 25B   FIG. 25C
FIG. 25D   FIG. 25E

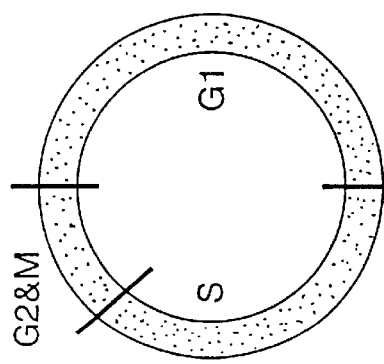
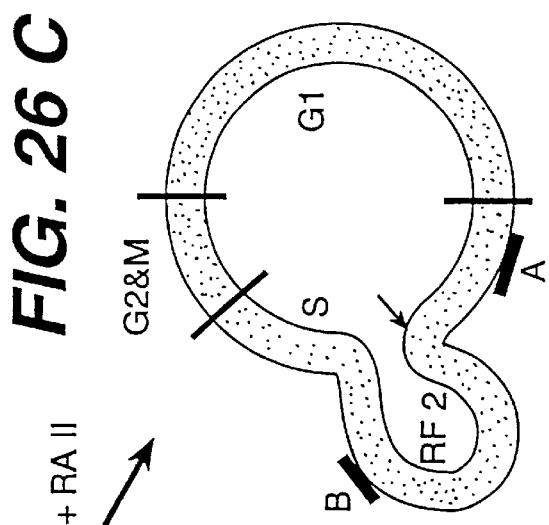
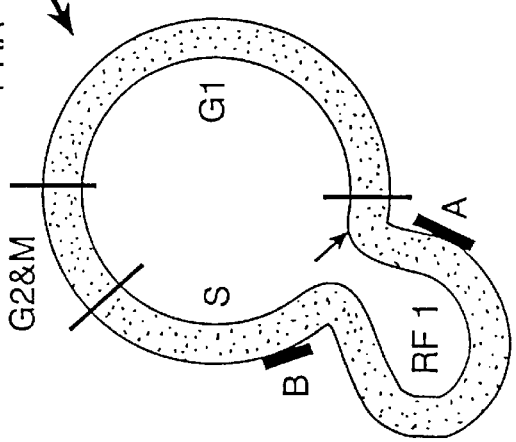
FIG. 26 A
FIG. 26 B
FIG. 26 C
HOMEOSTASIS
+ RA I
+ RA II
DYNAMIC RETARDATION
↙ - REFERENCE POINT
A, B - TARGET INTERVALS FOR DIFFERENT TCI dThd potentiates STSP-induced apoptosis by inhibiting ribonucleotide reductase

Effect of STSP and ATA on CDC2 Activity and c-Myc Expression

Changes in Activities of MAP Kinases During Treatments With dThd and STSP

JNK — GST-c-JUN

ERK — MBP control 4 h | STSP 25 nM | control 12 h | dThd 0.2 mM / STSP 25 nM | dThd 0.2 mM Cell line: U937

METHOD OF DYNAMIC RETARDATION OF CELL CYCLE KINETICS TO POTENTIATE CELL DAMAGE

CROSS-REFERENCE TO RELATED APPLICATION

This is a continuation of application Ser. No. 08/667,543, filed Jun. 21 1996 abandoned the benefit of U.S. provisional application No. 60/000,546, filed Jun. 27, 1995, both of which are incorporated herein by reference.

GOVERNMENT INTEREST

The invention described herein may be manufactured, licensed, and used for United States of America governmental purposes without the payment of any royalties to the inventors, or assignee.

FIELD OF THE INVENTION

This invention relates to a method of potentiating cell damage by administering an agent that retards the rate of movement of a target cell through some portion of the cell-division cycle and administering a cytotoxic agent that acts within a portion of the cell-division cycle through which movement has been slowed. The method of the invention can be used in chemotherapy as well as in other medical and non-medical applications. In a specific embodiment, deoxythymidine (dThd) is the agent retarding the rate of movement of a target cell through a portion of the cell-division cycle and staurosporine is the cytotoxic agent. The invention also relates to a method of using a microculture indicator system (MIS) and auxiliary data analysis procedures to determine the degree of interaction between agents. In a specific embodiment, data are collected reflecting the effect on cell growth of two or more agents arrayed in serial bivariate dilutions, and a database is caused to process the data in a spreadsheet according to predetermined relationships with reference measurements of cell growth and to present, in graphical or tabular form, the spectrum of interaction of the agents with respect to reference measurements.

BACKGROUND OF THE INVENTION

The use of drugs or other agents for destroying or inflicting permanent damage on living cells serves a number of valuable and legitimate objectives. A major clinical use is for the ablation of malignant tumors or other abnormal tissue growths. V T DeVita, Jr., IN: Cancer, Principles and Practice of Oncology, 4th ed., pp. 276–292, JB Lippincott Co. Philadelphia (1994).

Other valuable clinical uses have included (1) medical control of abnormal immunologic reactions, K Wilson et al., Rheumatol. 21:1674–7 (1994); C M Neuwelt et al., Am. J. Med. 98:32–41; (1995); (2) exfoliative dermatological disease, G D Weinstein et al., J. Am. Acad. Dermatol. 28:454–9 (1993), R J Van Dooren-Greebe et al., Br. J. Dermatol. 130:204–10 (1994); (3) killing of cells infected by viruses, viral replicative elements, or prions, P Calabresi et al., Section XII—Chemotherapy of neoplastic diseases IN: Goodman and Gilman's The; Pharmacologic Basis of Therapeutics, 8th ed., 1202–1263 (Pergammon Press, New York 1990):, S Chou et al., Antiviral chemotherapy, Chapter 17 IN: Virology, pp. 323–348, ed. B N Field; et al., Raven Press, New York (1985); (4) therapies for systemic or topical elimination of infective agents including bacteria, mycobacteria, mycoplasma, rickettsia, fungi, yeast, or parasitic organisms, H P Willett, The action of chemotherapeutic agents, Chapter 10, IN: Zinsser Microbiology, 17th ed., pp. 234–277, ed. Joklik et al., Appleton-Century-Crofts, NY (1980); Lorian, Antibiotics in Laboratory Medicine, 3d ed., Williams and Wilkins, Baltimore (1991); S Sternberg, Science 266:1632–1634 (1994), (5) and fertility control. Non-clinical uses cf agents capable of inflicting permanent damage on living cells occur in agriculture, horticulture, or public health, e.g., application of specific pesticides or herbicides.

A vast array of physical, chemical, or biological agents are hazardous to living cells and can inflict damage upon biological systems such as tissues or organs. In many cases, however, the damage is not specifically targeted to events related to the cell-division cycle.

In other cases, cell damage may be initiated in direct relation to the hierarchy of the cell-division cycle. A cytotoxic agent that acts during some portion of the cell-division cycle, causing biologically significant or irreversible damage to a proliferating cell, may serve as a "targeted cytotoxic insult" or "TCI", as defined herein. The portion of the cell-division cycle during which a given TCI initiates a relevant action is its "target interval."

Known agents that can act as TCIs are diverse and include natural substances, products of microbial or other cellular origins, synthetic or semi-synthetic organic or inorganic chemical compounds, or simple inorganic reagents. Other factors that can act as a TCI are also known and may include deprivation of nutrients essential to cell growth or sustenance as well as changes in the physicochemical environment. Examples of the latter include temperature changes and exposure of the cells to radiant or particulate energies, vibrational waves, or various other physical forces.

Cytotoxic effects of a TCI may not be immediate, so that cell damage initiated in one phase of the cell-division cycle may not become manifest until a later phase or a subsequent cell cycle. As just one example, in cisplatin treatment, permanently injured progeny cells may be sterile or exhibit a reduced capacity to proliferate or survive. M Sorenson, J Natl. Cancer Inst. 82:749–55 (1990). Thus, an understanding of the cell-division cycle hierarchy becomes useful to further understanding of agents that can act as TCIs.

I. The Cell-Division Cycle

All growing cells must duplicate their genomic DNA and pass identical copies of this genetic information to their progeny. In order to accomplish this task, proliferating somatic (non-reproductive) and germ (reproductive) cells of all living organisms undergo repetitive cell-division cycles (hereinafter "cell cycle" or "CC"). Each completed cell-division cycle results in the duplication of the cell's genetic information and the division of the parent cell into two daughter cells, with an equal division of the parental cell DNA.

The biochemical and biomolecular processes that comprise the cell cycle include, among other things, enzyme-dependent DNA replication, enzyme-dependent phosphorylation, signal cascades, association and dissociation of transcriptional activating molecular complexes, and formation and dissociation of macromolecular assemblies of cytostructural elements including cytomembranes and the cytoskeleton.

A. Cell Cycle Hierarchy

The processes characterizing the cell cycle form a regulated hierarchy and advance in a strict order dependence under the control of a cell cycle "engine" or "control system." The control system functions as a biomolecular "clock" or "oscillator" and includes critical controls at "checkpoints." L N Edmunds, Jr., Ann. N.Y. Acad. Sci. 719:77–96 (1994); I A Carre et al., J Cell Sci. 104:1163–73 (1993); B G Gabrielli et al., J. Biol Chem 267:1969–75 (1992); A Goldbeter, Proc. Natl. Acad. Sci. (USA) 88:9107–11 (1991); Murray A W and Kirschner M W, Science 246:614–621 (1989).

In the normal cell cycle hierarchy, DNA replication is followed by mitosis and cytokinesis. See generally A W Murray, Nature 359:599–604 (1992); B Alberts et al., The cell-division cycle, IN: *Molecular Biology of the Cell*, 3d edition, Garland Publishing Inc., New York (1994); B A Edgar et al., Genes Dev 8:440–52 (1994). A series of molecular processes, each process functioning in an appropriate order during the cell cycle, moves the cell in the direction of cell division with a downstream momentum. In this context, the term "downstream" refers to events that occupy a "subordinate position" in the cell cycle hierarchy as defined by Alberts, supra. Order dependence in the cell cycle hierarchy ensures that DNA replication proceeds with maximal fidelity. See L H Hartwell et al., Science 246:629–634 (1989); P M O'Connor et al., Semin. Cancer Biol. 3:409–416 (1992).

The hierarchy of the eukaryotic cell cycle relates to four conserved functional landmarks (FIG. 1): S phase, in which nucleotides are synthesized and DNA is semi-conservatively replicated in double-stranded helixes of polynucleotides; $G_2$ phase, which follows completion of DNA synthesis and during which DNA associates with nucleoproteins; M phase, in which nuclear filaments condense as chromosomes and chromosomes segregate for mitosis; and $G_1$. phase, during which cells prepare for renewed division by replacement of depleted products and repair of any lesions in DNA. See Alberts, supra. Cells entering S phase normally are committed to completion of $G_2$ phase, M phase, and cytokinesis.

B. Cell Cycle Checkpoints

Transitions between phases are the major checkpoints in the cell cycle. In normal cells, they are tightly regulated by a decision point in $G_1$ (START) and checkpoint controls associate d with the boundaries between $G_1$ and S ($G_1$/S) and $G_2$ and M ($G_2$/M). See K A Heichman et al., Cell 79:557–562 (1994); P Nurse, Cell 79:547–550 (1994); A W Murray, supra.; A W Murray et al., Sci. Am. 264:56–63 (1991); Hartwell, supra. Controlled interactions of specific proteins such as cyclins, cyclin-dependent kinases (cdk or cdc), and a series of accessory proteins (including p16, p21, p27, p45 or p53), which regulate cdk or cdc cyclin complexes, regulate successive phases of the cell cycle. T Hunter et al., Cell 79:573–582 (1994); Heichman, supra.; Nurse, supra.; R W King et al., Cell 79:563–571 (1994); L H Tsai et al., Oncogene 8: 1593–602 (1993); M Doree et al., FASEB J. 8:1114–1121 (1991). Moreover, function of p53 and phosphorylation of the Rb tumor suppressor gene product (pRb) are also associated with the $G_1$/S transition. V Karantza et al., Mol. Cell Biol. 13:6640–52 (1993); M E Ewen et al., Cell 73:487–97 (1993); S J Kuerbitz et al., Proc. Natl. Acad. Sci. USA 89:7491–95 (1992); M B Kastan Cell, 71:587–597 (1992).

C. Cell Cycle Kinetics

In a population of cells, the mean duration of each cell cycle phase is proportional to the probability of finding a cell within a given phase. If it is assumed that no loss, quiescence, or differentiation of progeny cells will occur during the continuous proliferation of a cell population, then for any given population, i.e., cohort, the mean duration of a single cell cycle will equal the time to double; i.e., the time required for the starting cell population to double, i.e., its generation time. See, L A Perez et al., Cancer Res. 55:392–398 (1995). This concept can be expressed mathematically. Thus, $T_{DBL}$ is defined as the time required for the present population ($N_P$) divided by the original population ($N_0$) to double ($N/N_0$=2).

The $T_{DBL}$ provides a yardstick for determining the "fractional duration" of major phases in the cell cycle phases, i.e., the time required for a fraction of the cell population to complete $G_1$ ($T_{G1}$), S ($T_S$), or $G_2$ & M ($T_{G2\ \&\ M}$). Assuming continuous proliferation of an ideal cohort without any loss, quiescence, or differentiation of progeny, the fractional duration of each phase of the cell cycle is directly proportional to the fraction of the cell population (F) that is cycling through that phase at any moment in time, i.e., the $F_{G1}$, $F_S$ or $F_{G2\ \&\ M}$; for example, $T_S$, can be calculated as $T_S=F_S\times T_{DBL}$. See Alberts, supra, and Perez, supra. Practically, this is an important equation since $T_{DBL}$ can be determined from serial cell counts, or flow cytometry, AC Begg et al., Cytometry 6:620–626 (1985), while $F_S$, $F_{G2+M}$ or $F_{G1/G0}$ can be measured in DNA histograms obtained from flow cytometry.

In standard flow cytometry, nuclei are stained with propidium iodide, a dye which intercalates into the minor groove of DNA. N M Shapiro, Practical Flow Cytometry, Alan R Liss, N.Y. (1988). Histograms of dye absorbance discriminate the fractions of cells with different amounts of DNA/nucleus. Thus cells in the process of synthesizing DNA (S phase), or with a complete duplication of DNA ($G_2$ phase and M phase), are distinguished from cells that have not begun to replicate their DNA ($G_1$ or $G_0$). Flow cytometric DNA histograms are reproducible and accurate under most testing conditions. See Perez, supra; J Pierrez et al., Acta Biotheor. 40: 131–7 (1992). DNA synthesis is also measured by BudR incorporation (Begg, supra).

When changes in physiological stimuli or ambient growth conditions slow down the growth of a cell population, the fraction of cells found in $G_1$ phase (the preparation phase) typically increases at the expense of cells in S phase or in the growth fraction, i.e., $G_2$ and M phases. Such changes or abnormal conditions may include hormonal, nutritional, or environmental changes. If abnormal conditions prevail, then cells in $G_1$ phase may retire temporarily from the cell cycle to become "quiescent" or non-active. Quiescent cells are commonly designated to be in $G_0$ phase. R Baserga, Cell Division, Molecular Biology, IN: Encyclopedia of Human Biology 2:253–266 (1991); A B Pardee, Science 246:609–613 (1989).

The process of differentiation, or specialization of cells, is also associated with a retirement of cells to $G_0$. In terminal differentiation, the transition out of the cell cycle, i.e., into $G_0$, becomes irreversible. Examples of terminally differentiated cells are adult neurons, keratinized epithelia, and voluntary muscle cells.

D. Apoptosis

Apoptosis is referred to as a process of "programmed cell death." During normal somatic development, cell populations in specific organs or tissues may be programmed for death as part of the developmental progression of tissue remodeling or obsolescence. See J J Cohen, Avd. Immunol 50:55–85 (1991); M Baringa, Science 259:762–3 (1993). Apoptosis is internally triggered by biochemical or biomolecular mechanisms intrinsic to the cell cycle, resulting in an activation of endogenous endonucleases (enzymes that degrade DNA), leading to DNA strand breaks between nucleosomes and degradation of the genomic DNA by fragmentation. A H Wyllie, Nature 284:555–6 (1980). Apoptosis in mature tissues occurs in normal processes such as inflammation or rejuvenation. M Schmied et al., Am J Pathol 143:446–52 (1993). Abnormal clonal proliferations in immunologic diseases or malignancies may be related to a failure of normal apoptosis. J Marx, Science 259:760–1 (1993).

The relationship of apoptosis and/or cell damage to the cell cycle, including checkpoint controls, during cancer chemotherapy is a subject of interest to oncologists and molecular biologists. See T Shimizu et al., Cancer Res. 55:228–231 (1995); O'Connor, supra. (1992). The expression of p53 in damaged cells is one factor in determining the course of divergent biochemical pathways, which can lead to either DNA repair or apoptosis. E Yonish-Rouach et al., Mol Cell Biol 13:1415–23 (1993); D E Fisher, Cell 78:539–542 (1994).

Conflicting signals in the cell-division cycle may underlie the diversion of cell activities from proliferation to apoptosis. Fisher, supra. Cells entering or traversing the cell cycle transition boundaries or in the process of DNA replication or repair are most susceptible to apoptosis. In cells treated with a TCI, or in neoplastic cells, checkpoint controls such as cyclin-dependent kinases may be deregulated. This deregulation can release DNA replication or cell division events from START and homeostatic order dependence, intensifying cell damage. Id.

II. The Role of Cytotoxic Agents in Chemotherapy

Current models of cancer chemotherapy are based largely upon two central dogmas. First, any mass of tumor cells which is clinically detectable must include a significant number of cells which will exhibit some biologically significant level of resistance to any single chemotherapeutic agent. J H Goldie et al., Cancer Treat Rep. 53:1727–1733 (1979). Second, according to the accepted Gompertzian model, tumor cell killing relates to the fraction of cells in active growth. L A Norton, Cancer Res. 48:7067–71 (1988).

In chemotherapy for malignancy, treatments with TCI have involved a number clinical considerations: they may be used in the primary effort to control cancer (induction chemotherapy), or as an adjunct to surgery or radiotherapy (adjuvant chemotherapy). DeVita, supra (1994). Local treatments have included infusion of TCI into body cavities to control the spread of malignancies such as breast or ovarian cancers. Id.

A. Single Agent Chemotherapy

In single agent induction, the usual objective is to administer the highest safe and tolerated dose to achieve maximal cancer cell killing or growth arrest. However, due to a cancer patient's decreased ability to mount a cell mediated immune response against malignant cells, single agent chemotherapies rarely prove sufficient to control cancer in the human body. Neoplastic (cancerous) populations are heterogeneous and a fraction of resistant cells typically escape death. The subpopulation of malignant cells with protective mechanisms eventually replaces the original populations of susceptible cells.

The first of the single agents, folic acid antagonists, targeted DNA biosynthesis. See V T DeVita, New Engl. J. Med. 298:907–910 (1978). Both replication of DNA and cell division, associated with the S phase, have been targets of chemotherapy. Examples of TCI targeting DNA synthesis have included antimetabolites, alkylating agents, natural toxins or antibiotics, platinum coordination complexes, and substituted urea. Known actions of these agents have been discussed by Calabresi, supra.

An agent that can act as a TCI can initiate cell damage during the cell cycle hierarchy in various ways. For example, a TCI can inhibit enzymes, compete for substrates, inhibit the transcriptional, translational or post-translational steps in molecular biosynthesis, introduce transcriptional or translational errors, disrupt molecular conformational changes, inhibit molecular transport, compete for energy transfer molecules, interfere with macromolecular polymerization, form molecular crosslinks, alkylate or cause strand breaks in DNA, or intercalate into the DNA helix. Thus, a TCI may impair cell cycle processes such as RNA transcription and translation, DNA strand elongation, replication, repair, supramolecllar organization or separation, molecular transport, or macromolecular segregation. Alternatively, it may selectively injure any of the multiple cellular organelles associated with successful completion of specific subsets of the cell cycle hierarchy.

Another possible mode of selective damage by a TCI in neoplastic cells is a loss or deficiency of a checkpoint control, such as a cyclin-dependent kinase (cdk or cdc), which normally controls the cell cycle hierarchy. The role of checkpoint controls has been defined by observed effects of agents or mutations which relieve order dependence. See H A Crissman et al., Proc. Natl. Acad. Sci. (USA) 88:7580–84 (1991); Kastan, supra.; Murray, supra. (1992); Hartwell, supra. The cell cycle of normally cycling cells must traverse the $G_1$ decision point (START) which commits a cell to continue through S phase resulting in DNA replication. Heichman, supra. Thus, cells exposed to a TCI prior to START may be partially protected from DNA damage by a delay within $G_1$. This $G_1$ delay can be mediated by the tumor suppressor p53 and enables cells to repair damaged strands of DNA prior to replication. Kastan, supra. Damage to DNA after START or DNA damage and bypass of START can be biologically deleterious, P M O'Connor et al., Cancer Res. 4776 (1994), possibly leading to DNA replication infidelity in S phase, with resulting genetic instability and ultimately premature cell death. Hartwell, supra; Kuerbitz, supra.; Shaw et al., Proc. Natl. Acad. Sci. USA 89:4496–9 (1992); T. Weinert, Semin. Cancer Biol. 4:129–140 (1993).

The actions of agents targeting S phase in eukaryotic cells are intrinsically complex due to the nature of DNA replication in S phase. For example, replication origins are discontinuous, chain elongation proceeds asynchronously, and progression at replication forks may be irregular. C S Newlon, Science 262:1830–31 (1993); V Levenson et al., Nucleic Acids Res. 21:3997–4004 (1993). Even as the DNA strands replicate in parallel process hierarchies within the overall cell cycle hierarchy, however, they share critical enzymes or metabolic intermediates. Murray, supra (1992); Laskey et al., Science 246:609–613 (1989); Nurse, supra; Heichman, supra.

Modern approaches to cancer chemotherapy developed during a time when knowledge of the cell cycle was advancing rapidly. Thus, it was recognized that neoplastic cells are vulnerable to agents that act during the S phase of the cell cycle. To better study the S phase, anti-metabolic agents were used to inhibit enzymes associated with purine or pyrimidine nucleotide biosynthesis affecting the ability of the DNA to replicate. These included ribonucleotide reductase (RNR) inhibitors, such as dThd or hydroxyurea (HU); dihydrofolate reductase inhibitors, such as methotrexate (MTX); or DNA polymerase inhibitors such as aphidicolin (Aph) to completely arrest progress of the target cells through the cell cycle at $G_1$/S. G Galavazi et al., Exp. Cell Res. 41:428–51 (1966); D Thomas et al., Cell 5:57–32 (1975); T Ashihara et al., Methods Enzymol. 58:248–262 (1979); Levenson, supra.

It also was established that an excess of the normal metabolite dThd could reversibly arrest DNA replication in many cell lines of malignant origin or other proliferating cells. D. Kufe et al., Cancer Treat. Rep. 64:1307–1317 (1980).

In other studies, the use of excess dThd was found to be less damaging than MTX or HU and removal of dThd could be followed by a synchronous progression of cells through the remainder of the cell cycle. H R Zielke et al., Methods in Cell Biology 8:107–121 (1974); R E Meyn et al., Methods in Cell Biology 9: 103–113 (1975). As a result, repetitive synchronization of the cell cycle with dThd produced relatively pure cell population in S phase. Zielke, supra.

Use of RNR inhibitors such as dThd or HU as a single agent in high dosages was also explored in cancer therapy. Many of the published reports concerning use of dThd have been critically reviewed. See Ellims, supra; O'Dwyer et al., Cancer Res 47:3911 (1987); S O Ooi et al., Experientia 49:576–81 (1993). Some successful results in patients with leukemia, lymphomas, or solid tumors were reported. D W Kufe et al., Cancer 48:1513–6 (1981); A Levya et al., J Cancer Res. Clin. Oncol. 107:211–216 (1984); R L Schilsky et al., Cancer Res. 46:4184–4188 (1986). Blood levels of up to 6 mM dThd could be achieved with oral doses. M S Blumenreich et al., Cancer Res. 44:2203 (1984); O'Dwyer, supra. In general, however, the use of dThd as a single agent chemotherapy was considered marginally potent for damage to malignant cells. Toxic side-effects often were intolerable at the dosages required to produce any therapeutic benefits.

B. Combination Chemotherapy

In cancer therapy, the survival of even a few malignant cells is more critical than in anti-infective therapies, since host immune mechanisms for killing of malignant cells typically are not effective. Therefore, exogenous cell killing plays a major role in prolonging clinical remissions or achieving cure. In the context of conventional chemotherapy, however, cell killing is described by first order kinetics: increasing doses of a single TCI will selectively damage an increasing percentage of the remaining malignant cells, but cannot destroy every potentially malignant cell without sacrificing the host. Calibresi, supra. Mathematically, this is analogous to Zeno's paradox of fast and slow runners (W L McLaughlin, Sci. Amer. 271:84–89, 1994).

Since the 1960s, heavy reliance has been placed upon combinations of agents to produce more durable clinical responses than are possible with single agents. R L Capizzi et al., Sem. Oncol. 4:227–253 (1977); DeVita et al., Cancer 35:98–110 (1975). DeVita, supra (1994), discusses the generally agreed objectives of agent combinations: to maximize cell killing with tolerable toxicity, to provide coverage of cancer cells with differing levels of vulnerability in a heterogeneous tumor population, and to prevent or slow the evolution of neoplastic clones that develop increasing resistance.

DeVita also sets forth several principles in the current selection of agent combinations:

(i) each agent should be effective as a single agent in cell killing;
(ii) agents should be combined from different classes of actions to allow maximum dose intensity;
(iii) additive patient morbidity or mortality should be avoided; and
(iv) schedules or intervals of agent administration should be optimized.

As mentioned above, development of cell resistance to cytotoxic agents may involve mutations in p53 or other cell cycle control genes and may be accompanied by abnormalities in the cell cycle order dependence or checkpoint controls. C S Morrow et al., Ann. N.Y. Acad. Sci. 698:289–312 (1993). Appropriate selection of multiple agents and achievement of high dose intensity are currently perceived as the critical issues in the design of chemotherapeutic protocols to avoid the development of that resistance.

Efforts have been aimed at modulating the cell cycle as a means for increasing cell damage by combinations of chemotherapy agents. The objective was to maintain malignant cells within the S phase of the cell cycle, where they may be most vulnerable to damage. See H O Klein et al., Semin. Hematol. 11:203–27 (1974). R L Stolfi et al., Pharmac. Ther. 49:43–54 (1991), have referred to these strategies as "cytokinetic modulation".

Some uses of MTX, dThd, or pyrimidine analogs to arrest cell populations at a specific point in the cell cycle to modulate synergistic killing by application of a successive cytotoxic agent have been tested. B Bhutan et al., Cancer Res. 33:888–894 (1973); Ellims, supra; S D Henderson et al., Invest. New Drugs 5:142–154 (1987); Stolfi, supra. This approach often has been referred to as "synchronization" of the cell cycle. Capizzi, supra. Cells exposed to high concentrations of anti-metabolites are detained within a limited subset of the cell-division cycle hierarchy, typically at a specific point within late $G_1$ or early S phase. Thus, few or no cells in the population can proceed beyond this point of detention. Therefore, this type cf effect is better described either as a cell cycle "arrest" or a "static synchronization". W Vogel et al., Hum. Genet. 45:193–8 (1978).

A number of other efforts to control cancer cell growth by manipulating the cell-division cycle have been directed to altering the cell cycle distribution within the cell population targeted for damage. Other protocols were designed to stimulate malignant cells from $G_0$ phase or $G_1$ phase into proliferative status and thus increase their vulnerability to anti-metabolic drugs acting during DNA replication. H H Euler et al., Ann. Med. Interne. (Paris) 145:296–302 (1994); B C Lampkin et al., J. Clin. Invest. 50:2204–14 (1971); Alama et al., Anticancer Res. 10:853–8 (1990). Conversely, other protocols were designed to prohibit normal cells from entering S phase and thus protect them from unintended damage by anti-metabolites. Capizzi, supra.

Agents in combination may have additive, synergistic or antagonistic effects. Intuitively, it might be supposed that a combination of agents causing a cell cycle arrest or static synchronization of the malignant cells would circumvent the problem of first order kinetics, combined dosages can be increased to a level sufficient to fill all malignant cells without sacrificing the host. Restriction of a malignant cell population to a limited set of the cell cycle hierarchy, where the cells were specifically vulnerable to damage by a successive TCI, might be expected to shift the dynamics of cell killing toward greater efficiency, and reduce side-effects by diminishing the cumulative time of host exposure to a TCI.

However, in actual trials, strategies of cell cycle arrest or static synchronization often have been disappointing. Capizzi, supra. This is due to an essential incongruity of the procedure. When the cell cycle is arrested, all cells are within a specific fraction of the cell cycle. If this subset of the cell cycle does not completely overlap the subset of the cell cycle where the TCI is most effective, the cell cycle arrest will not result in synergistic or even an additive action of the successive TCI. Cell cycle arrest or static synchronization can be advantageous only when the affected phase of the cell cycle actually encompasses a relevant target interval of the successive TCI. The target interval of a successive TCI may be located downstream and not within the kinetic boundaries of the arrested or statically synchronized population. Since a high concentration of an agent effecting cell cycle arrest or static synchronization can also act as a single agent TCI, some cell killing or damage will occur even prior to the addition of a successive TCI. Indeed, if a successive TCI were actually the more potent killing agent and acted downstream from the point of cell cycle arrest, then cell cycle arrest or static synchronization would actually protect cells from the successive agent. This problem was exemplified in previous trials with dThd used in high doses as a synchronizing agent. Doses of dThd required to achieve effective blood concentrations for cell cycle arrest (>3 mM) often caused toxic side effects which were not well tolerated by patients, and could not be justified in relation to the therapeutic effect. In one set of trials, the stated objective was to deliver maximally tolerable doses, and blood levels of up to 6 mM were achieved with oral doses. Blumenreich, supra. O'Dwyer, supra. This concentration range had been used successfully in vitro to prohibit cells in $G_1$-phase from entering S phase (i.e. a $G_1/S$ block). J H Kim Biochem Pharmacol 14:1821–9 (1965); Littlefield, supra.; Kufe, supra, but it did not prove sufficiently potent to induce clinical inhibition of malignant cell growth in the patients. Thus, secondary toxicities proved difficult for patients to tolerate and the further use of dThd was discouraged and its use is no longer advocated or reported. Blumenreich, supra; O'Dwyer, supra; Ooi, supra.

Most of the agents previously used in chemotherapy to effect cell cycle arrest or static synchronization in chemotherapy have probably acted late in Gphase or early in S phase. Capizzi, supra. Therefore, they would be unlikely to potentiate TCI with actions beginning later in the cell cycle hierarchy, e.g., later in S phase.

In modified approaches to static synchronization for cancer chemotherapy, a number of investigators noted that the scheduling of particular drug combinations was critical for production of synergistic lethal effects either in vitro or in vivo. Capizzi, supra; Stolfi, supra. However, many of these combinations have only been tested on a trial and error basis without a clear rationale for the agent sequence, concentration ratios, schedule or duration employed. See A L Adel et al., Cancer Invest 11: 15–24 (1993). In clinical parlance, therapeutic approaches of combining cell cycle arrest with sequential applications of a second agent have been referred to as "schedule dependent enhancement," e.g., Capizzi, supra., or "biochemical modulation." F M Muggia et al., Semin. Oncol. (3 Suppl) 9:90–3 (1992).

One special strategy of cell cycle manipulation was referred to as "pulse dose chemotherapy". R E Moran et al., Cancer Treat. Rep. 64:81–6 (1980). In this particular approach, leukemic tumor cells in mice were detained in S phase of the cell cycle during infusion treatment of the mice with hydroxyurea (HU). After the infusion of HU was ended, the cells were "released" to continue transit of the cell cycle. At finite times after termination of the HU infusion, experimental animals were treated with a "pulse" of a second agent (Ara-C). This method can be compared to the arrest method of H R Zielke, supra and J L Littlefield et al., 1974, in which an arrest of the cell-division cycle at a specific detention points is reversed so that the cells then move in concert through the cell cycle at a normal or possibly an accelerated rate.

The intention of "pulse dose chemotherapy" was to maximize impact of the second agent as cells were moving in concert through the cell cycle. Mean survival time of the mice was determined. Mice treated with Ara-C at zero time, just after the HU infusion ended, showed improved survival, but treatments with Ara-C at later times after stopping the HU infusion did not potentiate the effect of HU. This procedure of cell cycle synchronization followed by a second agent relies on the nonsimultaneous action of the two agents. Moreover, the indirect results with respect to mean survival time of the animals cannot be directly translated to effects on tumor cell damage.

A major challenge in combination chemotherapy is to determine an optimal synergy in view of the multiple variables of dose, pharmacokinetics, sequence, and scheduling. Even for two agents, the most effective utilization is not necessarily clear from a simple combinational analysis of the optimum for each agent. Empirical variables include the dose or effective concentration of each agent, sequence of agents, intervals between doses, i.e., schedule, duration of dosages and numbers of doses per course of therapy. See Capizzi, supra; Adel, supra. See also M C Berenbaum, Pharmacol. Rev. 41:93–141 (1989).

In vitro testing using tissue cultures or testing in animal models can provide guidance on proposed combinations prior to clinical application. J Plowman et al., Cancer Res. 55:862–7 (1995); M E Wall et al., Cancer Res. 55:753–60 (1995); J Higashihara et al., Gynecologic Oncology 48:171–179 (1993); Berenbaum, supra. Rev. 41:93–141 (1989); P C Schroy III et al., Cancer Res. 48:3236–3244 (1988); R H Shoemaker et al., Cancer Res. 45:2145–53 (1985); Capizzi, supra.

Technical methods of in vitro evaluation of chemotherapeutic agents have varied, but, measuring inhibition of cell growth by staining or dye uptake is accepted by the National Cancer Institute as a method for quantitative analysis. Plowman, supra. Uptake of $^3$H-thymidine to obtain the labelling index is another common method of analyzing tumor cell sensitivity to chemotherapeutic agents. G H Baltuch et al., Neurosurgery 33:495–501 (1993); I P Hayward et al., Int J. Cell Cloning 10:182–9 (1992); Schroy, supra. Differences in nucleic acid salvage pool sizes or thymidine kinase activities can make this approach unreliable. A similar approach is provided by the technique of flow cytometry in which antibodies against halogenated pyrimidine analog or a Hoechst dye track cells in S phase. Perez, supra; J P Perras et al., Cytometry 14:441–8 (1993); P Ubezio et al., Cytometry 12:119–126 (1991); M Poot et al., Biochem. Pharmacol. 41:1903–9 (1991).

Classically, the synergistic interaction of two agents is assessed using a series of dose-response curves from which fractional inhibitory concentrations can be calculated. G B Elion et al., J. Biol. Chem. 208:477–88 (1954); Berenbaum, supra; G M Eliopoulos et al., Chapter 13, pp. 432–492, IN: Antibiotics in Laboratory Medicine, 3d ed. V Lorian ed. The data can be obtained by a checkerboard technique, see Lorian, supra; Howard et al., Int. J. Cell Cloning 10:182–9 (1992). This method of analysis is known as an isobologram.

There are several practical problems with the isobologram method. First, the dose response curve of many agents used in chemotherapy becomes nonlinear at very high concentrations. Second, if agents to be compared prove asymmetrically potent or weak in single use, comparisons may be impossible. Third, results could be highly variable as coefficients of synergy calculated from an isobologram can be different for each fixed level of cytotoxicity.

Thus, collection of data for isobolograms can be laborious, and the isobologram method has limited scope for demonstrating an optimal range of agent combinations for practical effects. Berenbaum, supra. Efforts to resolve this shortcoming have proposed analyses of data as a three dimensional surface construct. W R Greco et al., Cancer Res. 50:5318–27 (1990) or other special methods (R C Li et al. Antimicrobial Agents & Chemotherapy 37:523–531, 1993. However, these solutions ultimately involve isobole data presentation. The problem becomes inordinately complex for therapeutic strategies involving multivariate interactions of more than two agents.

C. Other Cytotoxic Agents Affecting the Cell Cycle

Other recent efforts to relate the application of chemotherapeutic agents to cell cycle events have focused upon the role of checkpoint controls, O'Connor, supra (1992), or the regulation of apoptosis by manipulation of the induction of p53 gene product or related products of p21$^{Waf1/CIP1}$, W S El-Deiry et al., Cell 75:817–825 (1993).

For instance, protein kinases play an important role in neoplasia. Overexpression has been associated with hematologic malignancy. G Q Daley et al., Science 247:824–30 (1990). Neoplastic cells may be deficient in kinase-mediated control of progression through $G_1$ and commitment to DNA replication. High levels of several protein kinases in cancer cells have been associated with multidrug resistance to conventional chemotherapeutic agents which are targeted to S phase. Baltuch, supra; J A Posada et al., Cancer Commun. 1:285–92 (1989); K Kawamura, Hokkaido Igaku Zasshi 69:354–71 (1994).

Use of protein kinase inhibitors in cancer control appears promising, since some are very potent toxins, but are less likely to be mutagenic than conventional agents which alkylate or crosslink DNA. C A O'Brian et al., J. Natl. Cancer Inst. 82: 1734–5 (1990); S Akinaga et al., Cancer Chemother. Pharmacol. 33:273–80 (1994); G K Schwartz et al., J. Natl. Cancer Inst. 85:402–7 (1993). The potent protein kinase inhibitor staurosporine (STSP) and several functional analogues have been of interest since they can (1) reverse or modulate multidrug resistance, K E Sampson et al., J Cell Biochem 52:384–95 (1993); C H Versantvoort et al., Br. J. Cancer 68:939046 (1993); K Miyamoto et al., Cancer Res. 53:1555–9 (1993); I Utz et al., Int. J. Cancer 57:104–10 (1994); (2) arrest cell cycle progression, S Bruno et al., Cancer Res. 51:470–473 (1992); Crissman, supra.; or (3) induce apoptosis, Bertrand et al., Exp. Cell Res. 211:314–321 (1994); D W Jarvis et al., Cancer Res. 54:1707–14 (1994).

STSP is a product of *Streptomyces staurosporous*, Meksuriyen D and Cordell G A, J of Nat. Products 51:893–899 (1988), and is one of the most powerful broad spectrum inhibitors of protein kinases, Tamaoki, Methods Enzym. 201:340–347 (1991). In addition to actions on protein kinase C and tyrosine kinases, C D Smith et al., Biochem. Biophys. Res. Comm. 156:1250–1256 (1988), STSP inhibits cyclin-dependent kinases associated with the $S/G_2$ transition, D M Gadbois, Biochem. Biophys. Res. Comm. 189:80–85 (1993), and it can arrest neoplastic cells in $G_2$ phase of the cell cycle.

Work within human glioma cell lines, see Baltuch, supra, and an appended editorial comment by P L Kornblith, as well as previous reports by Schwartz, supra, and studies of its effects on multidrug resistance, discussed herein, indicated that STSP has potential in cancer chemotherapy. However, there have been no reports to date of clinical trials in humans. The work in rats and dogs by R A Buchholz et al., In Cellular and Molecular Mechanisms in Hypertension, p. 199–204, Plenum Press, N.Y. (1992) and Hypertension 17:91–100 (1991), suggest that human plasma levels of 500 nM might be testable (see Table 35). However, this is not yet certain.

The kinase inhibitor agents K252A, KT5720, and KT5926, have different ranges of potency with regard to inhibition of protein kinases. They are described in a series of references: W E Payne et al., J. Biol Chem. 263:7190 (1988); R L Raynor, J. Biol Chem. 266:2753 (1993); C. Schachtele et al., Biophys Biochem Res Comm 115:542 (1968); H Kase et al., Biochem Biophys Res Comm 142:436 (1987); S Nakanishi et al., Mol Pharmacol 37:482 (1990); W H Fletcher et al., J Biol Chem 261:5504 (1986); and H C Chang et al., J Biol Chem 261:989 (1986). They have not been tested clinically as yet.

D. Problems with Chemotherapy

Several problems are widely recognized in the current use of TCI for chemotherapy and the other purposes. The first problem is non-specificity. A TCI may not be sufficiently selective, resulting in the injury of cells not intended for damage. See I, E M Ross, Chapter 2, p. 33–48, Pharmacodynamics: Mechanisms of drug action and the relationship between drug concentration and effect, IN: Goodman and Gilman's The Pharmacologic Basis of Therapeutics, 8th ed., (A G Gilman et al., ed., Pergammon Press, New York, 1990). A second problem is heterogeneous vulnerability where the inherent genetic variability of cells in a population intended for killing can frustrate efforts to achieve absolute and specific lethality. See Calabresi, supra. A third problem is acquired resistance, where some fraction of the cells intended for damage by a TCI acquire resistance to the TCI by physiological or metabolic adaptation, or by genetic mutation. Id.

In single or multiple clinical chemotherapies, non-specific "side-effects" may become noxious and intolerable, resulting in significant patient morbidity. See M Pirisi et al., New Engl. J. Med. 330:1279 (1994); S M Grunberg et al., New Engl. J. Med. 329:1790–1796 (1993); O'Dwyer, supra. In clinical pharmacotherapeutics, it is considered beneficial to increase the selectivity or "therapeutic index" of a cytotoxic agent. Gilman, supra. Thus, important objectives of therapeutic drug development or improvements in therapeutic drug application include efforts to increase the ratio of specific cytotoxic benefits, e.g., the intended killing or damage of a designated cell population, to non-specific side effects which produce host morbidity or environmental disruptions. In addition, there is also a need to develop more potent pharmaceuticals.

A major limitation of cancer chemotherapy has been perceived to be the inability to escalate doses of effective anticancer agents, such as TCIs, into the high end of dose-response curves due to intolerable side effects. DeVita, supra (1994). It is also a current concern that omission of one agent from a designed combination may allow overgrowth by a cell lineage susceptible to that agent, but resistant to other agents. Another concern is that the use of an effective agent in less than maximum strength may vitiate the objectives of a combined agent protocol.

An increase in therapeutic TCI effects would be valuable during both primary induction or adjuvant chemotherapy, R Arriagada et al., New Engl. J. Med. 329:1848–52 (1993); W C Wood et al., New Engl. J. Med. 33:1253–9 (1994); for post-remission chemotherapy, R J Mayer et al., New Engl. J. Med. 331:896–903 (1994); for high dose chemotherapy followed by autologous hematopoietic rescue, W P Peters, et al., J. Clin. Oncol. 11:1132–43 (1993); A M Marmont, Lupus 2:151–6 (1993); for extracorporeal purging of malignant cells from tissues intended for transplantation, F. Sieber and M. Sieber Blum 46:2072–6 (1986); F. Lin et al., Cancer Res. 52:5282–90 (1992); or for debulking of metastatic tumor in body cavities, MEL van der Burg et al, New Engl. J. Med. 332:629–34 (1995); R. Arnold, Eur. J. Clin. Invest. 20 Suppl 1:S82–S90 (1990).

Therefore, there is a need in the art for new combinations of cell killing agents, including new combinations of dosage strategies, whereby the first agent modulates the cell cycle so as to maximize the toxic effect of the second agent on target cells, while minimizing the toxic effect on non-target cells. This need in the art is particularly acute in the area of cancer chemotherapy.

BRIEF DESCRIPTION OF THE DRAWINGS

FIG. 5 depicts the results of a flow cytometric analysis showing how cell cycle dynamics of human promonocytic lymphoma cells changes upon treatment with various concentrations of dThd. Specifically FIG. 5 A shows increasing concentrations up to 3 mM dThd and FIG. 5 B shows concentrations well below the $IC_{40}$

FIG. 26 is a schematic depicting the effects of dynamic retardation on the cell cycle.

SUMMARY OF THE INVENTION

Figure 1:
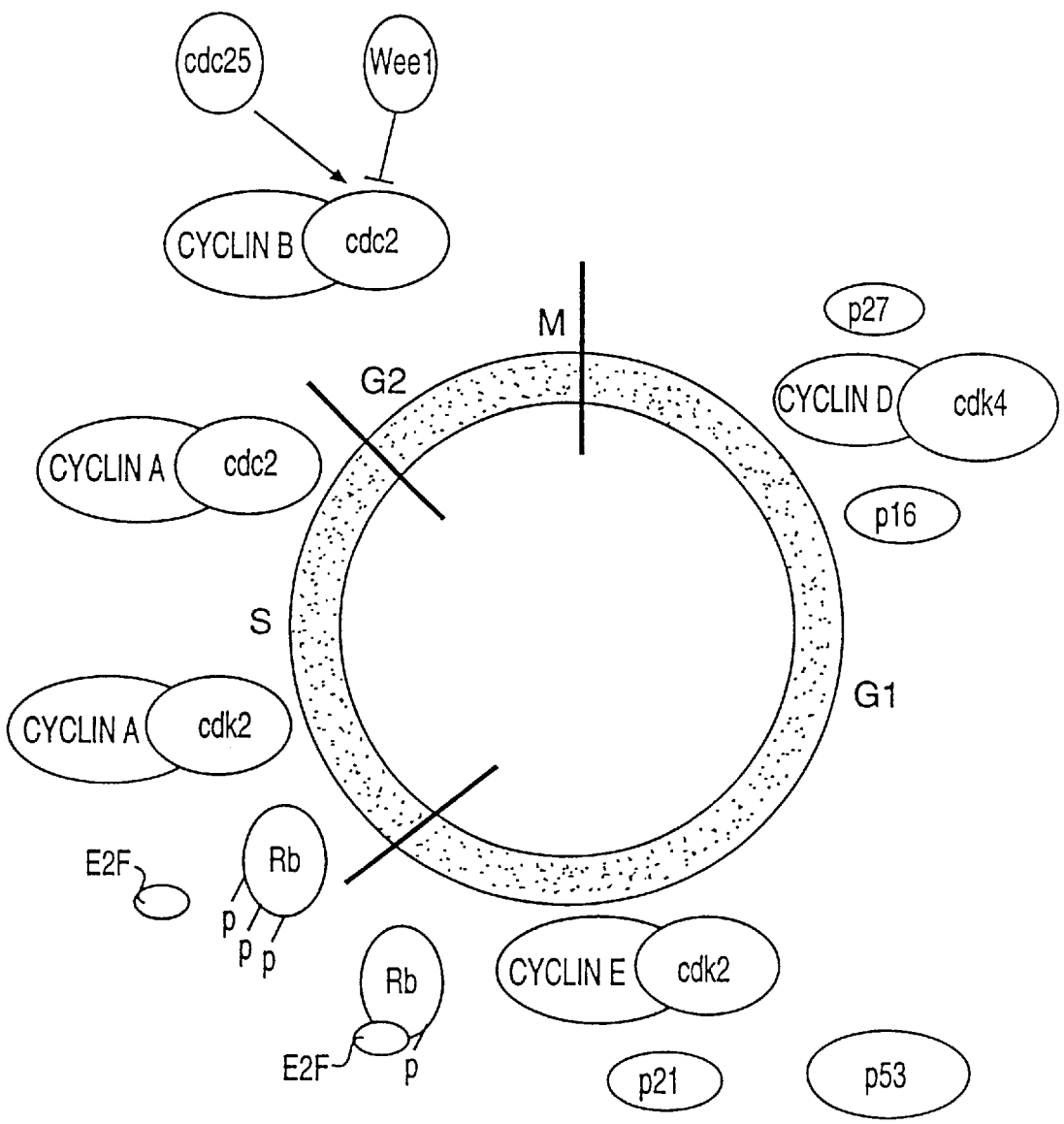
FIG. 1 is a diagram of the cell-division cycle and associated major cyclins, cyclin kinases and other and regulatory proteins.

The present invention fulfills a need in the art for new and improved combinations of cell-killing agents and new methods of identifying, evaluating, and administering synergistic combinations of agents for inflicting cell damage on target populations. The invention provides an improved method for inducing cell damage by administering a restraining agent (RA) to a target cell population at a concentration and under conditions sufficient to retard but not arrest the progress of the target cells through the cell cycle, and administering a targeted cytotoxic insult (TCI) concomitant with or subsequent to the application of the RA. The invention also relates to a microculture indicator system and auxiliary data analysis procedures for identifying, designing and using new agents as restraining agents or targeted cytotoxic insults, and for improving synergistic combinations of existing agents.

In embodiments of the invention, the RA can be a ribonucleotide reductase inhibitor, a dihydrofolate reductase inhibitor, a thymidylate synthase inhibitor, a DNA polymerase inhibitor, a protein kinase inhibitor or a topoisomerase inhibitor. In addition, embodiments of the invention include, as TCI, indole carbazoles, such as staurosporine, K252a, KT5926, and KT5720. In a specific embodiment, the RA is thymidine and the TCI is staurosporine. In another specific embodiment, the RA is bromodeoxyuridine and the TCI is staurosporinc. Other specific embodiments are disclosed in the working examples.

In specific applications, the method of inducing cell damage of the invention is a method of treating patients suffering from cancer. The method of the invention can also be applied to the treatment of malaria. The invention can improve conventional chemotherapy or radiotherapy of neoplasms or diseases of the immune system, provide a basis for methods of selective delivery of an RA or TCI, and afford new applications of specific antisense molecules as an RA or TCI, uses of RAs or TCIs in conjunction with gene transfection therapies, and utilization of RAs or TCIs in conjunction with radiotherapies or other physical modalities of cell killing. The invention may also be used for early destruction of cells infected by viruses or infectious nucleic acids, in anti-fungal or other anti-microbial therapies, and to aid in eradication of certain parasitic infestations.

Other objects and advantages of the present invention are set forth in the following description. The accompanying drawings and tables, which constitute a part of the disclosure, illustrate and, together with the description, explain the principle of the invention.

DETAILED DESCRIPTION OF THE INVENTION

This invention relates to a method for potentiating cell damage by identifying and/or administering a restraining agent (RA) and a targeted cytotoxic insult (TCI). A restraining agent refers to an agent administered under conditions that retard but do not arrest downstream progress of a target cell population through the cell cycle. Thus, the role of an RA is to impose a dynamic retardation in cells designated for damage.

The concept of dynamic retardation rests on key axioms regarding the cell cycle. First, the processes of the cell cycle are segregated into linked subsets of processes ("phrased processes"). Segregation of processes into phrases results from braking points in the forward momentum of the cell cycle due to a succession of regulatory checks. The latter include START and checkpoint controls discussed by Hartwell and Weinert, supra (1989) and by Nurse, supra. The beginning point of phrased processes may only be detected during perturbations of the cell cycle or in cells with specific mutations altering cell cycle regulatory controls. For example, see Beach et al., Current Communications in Molecular Biology, pp. 1–211, Cold Spring Laboratory (1988). Second, the "phrased processes" behave physicochemically as an "order dependent continuum," i.e., once a regulatory checkpoint is cleared, (beginning of the phrase) successive processes are activated in order, like falling dominoes, until the next regulatory checkpoint is reached (end of the phrase). Finally, for each set of phrased processes, momentum changes can be transmitted through linked complexes such as biochemical reactions, biomolecular cascades, or macromolecular configurational changes.

The initiation of dynamic retardation by an RA is a negative change in the momentum (a slowing) of a subset of the cell cycle hierarchy. The point within the cell cycle hierarchy at which an RA first acts to curb momentum through the cell cycle is its reference point. An RA generates a physicochemical equilibrium shift in the biochemical reactions downstream from its reference point. Thus, an RA initiates a slowing of the processes in a subset of the cell cycle hierarchy. Dynamic retardation represents the downstream propagation of this slowing through one or more phrased processes. The portion of the cell cycle slowed by En RA is a retardation field.

RAs can act at various points during the cell cycle. In those portions of the cell cycle where phrased processes are redundant, such as S phase, an RA may impose its effect at different times or at multiple reference points.

An agent acting as a TCI initiates cell damage after a reference point and during a, specific portion of the cell cycle, known as its target interval. A target interval is a subset of a retardation field consisting of phrased processes that are vulnerable to interaction with a TCI that results in initiation of cell damage.

Figure 2A:
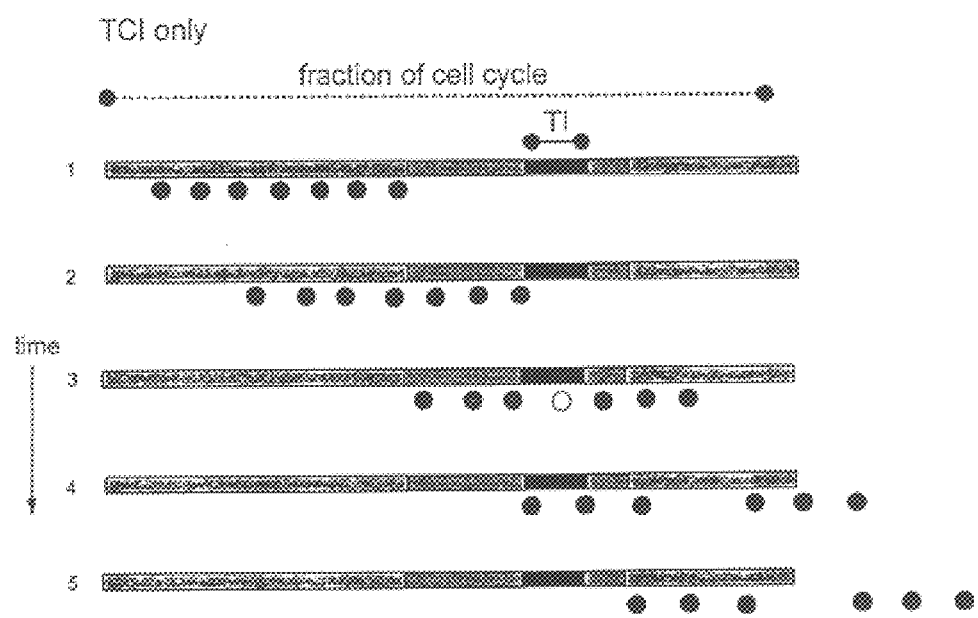
FIG. 2 depicts bar diagrams representing transit of cells through a target interval of a TCI (A) and the slowed transit of cells through such a target interval in the presence of an RA, resulting in "cell stacking" (B).
Figure 2B:
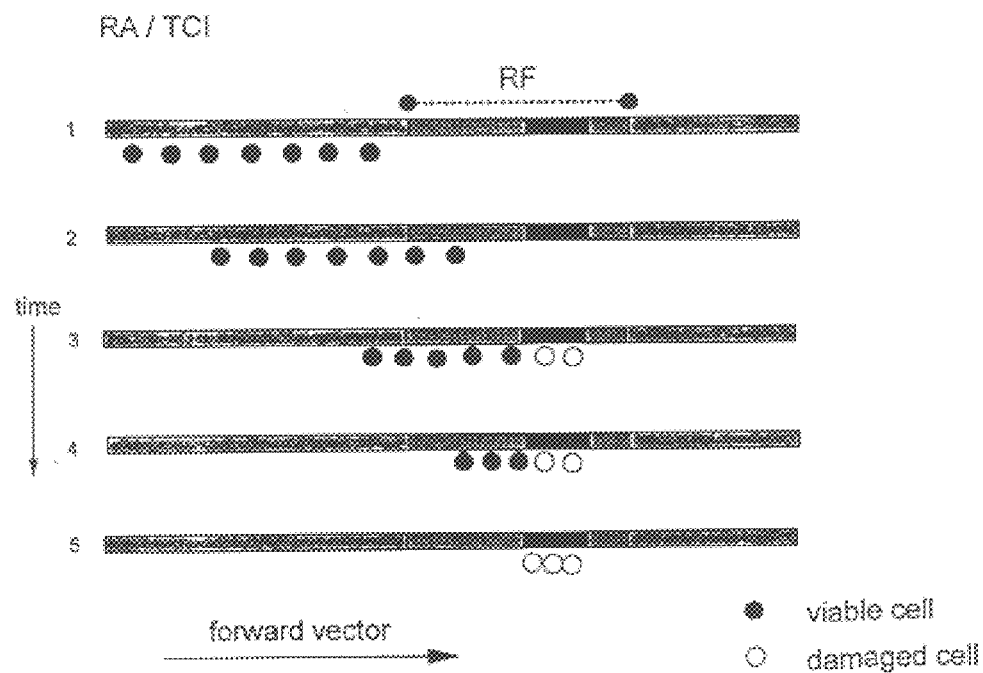

Since an RA acts to retard movement through the cell cycle, it increases the time that cells of a target cell population are located within a target interval, thus increasing the extent to which the target population is vulnerable to the action of a given TCI. The probability that the cell cycle of cells in a targeted population will be traversing a retardation field and a target interval within the retardation field increases as a result of dynamic retardation. This probability is depicted schematically in FIG. 2, and can be interpreted as a cell-cycle stacking. Cell cycle stacking indicates a relative "compression" of the intervals separating cells in different positions of the cell cycle hierarchy. A useful analogy is the stacking of jets entering the air space of a crowded airport.

Dynamic retardation potentates the biologic damage inflicted by a TCI increasing the probability that target cells will traverse the target interval. A synergistic match refers to a set of two or more agents acting as RAs and TCIs that function synergistically to inflict cell damage or retard cell growth as a result of dynamic retardation. A target interval of the TCI must reside downstream of a reference point in order for the synergistic match to succeed. A synergistic match of an RA and a TCI increases the effective damaging exposure (EDE), or the detrimental effect of a TCI, proportional to the effective strength or intensity of the TCI and to the operative duration of the TCI's relevant process interactions during the target interval.

After an RA has been applied, cells remain free to move through the cell cycle during dynamic retardation. In a cycling population, this helps ensure that all of the cells intended for damage by a selected TCI, are likely to cycle into the relevant target interval. In terms discussed above, these are the circumstances that create the potential for a synergistic match of RA and TCI.

The strength or intensity of an RA used in practicing the invention will be sufficient to retard, but not arrest, movement of target cells through the cell cycle at the point where the RA acts. In this context, any agent or factor already known to cause cell-division cycle arrest or "static synchronization" has a potential to function in the role of RA at an appropriately reduced strength or for an appropriately limited duration. The optimal strengths or intensities of an RA can be determined experimentally for a specific treatment, as discussed in more detail below.

Restraining agents can include natural products of microbial or other cellular origins, a range of synthetic or semi-synthetic compounds or antisense oligonucleotides designed to perturb the cell cycle. Transfected genes could serve as direct modulators of genes controlling cell cycle kinetics. In principle, multiple agents that can constrain momentum of the cell cycle could be used in a combination as the operative RA. The multiple agents may act either simultaneously or in a cascade of effects.

Environmental deprivation or physical changes can act as restraining agents. Deprivations can include insufficiency of a nutritional factor essential to cell growth or sustenance. Physical changes can include external temperature modulation or cell exposure to radiant or particulate energies, vibrational waves or other mechanical forces.

It should be clear, however, that not every agent that detains population transit through the cell cycle has potential to operate in the capacity of an RA. Deregulation of a checkpoint control, for example, could abort the cell cycle or short circuit a portion of the cell cycle, e.g., Powell S N et al., Cancer Res 55:1643–48 (1995); Fan S et al., Cancer Res 55:1649–54 (1995), yet this type of event would not necessarily change the physicochemical kinetics of engaged biochemical processes in the manner of an RA.

Identifying Operative Characteristics of an RA

Figure 3:
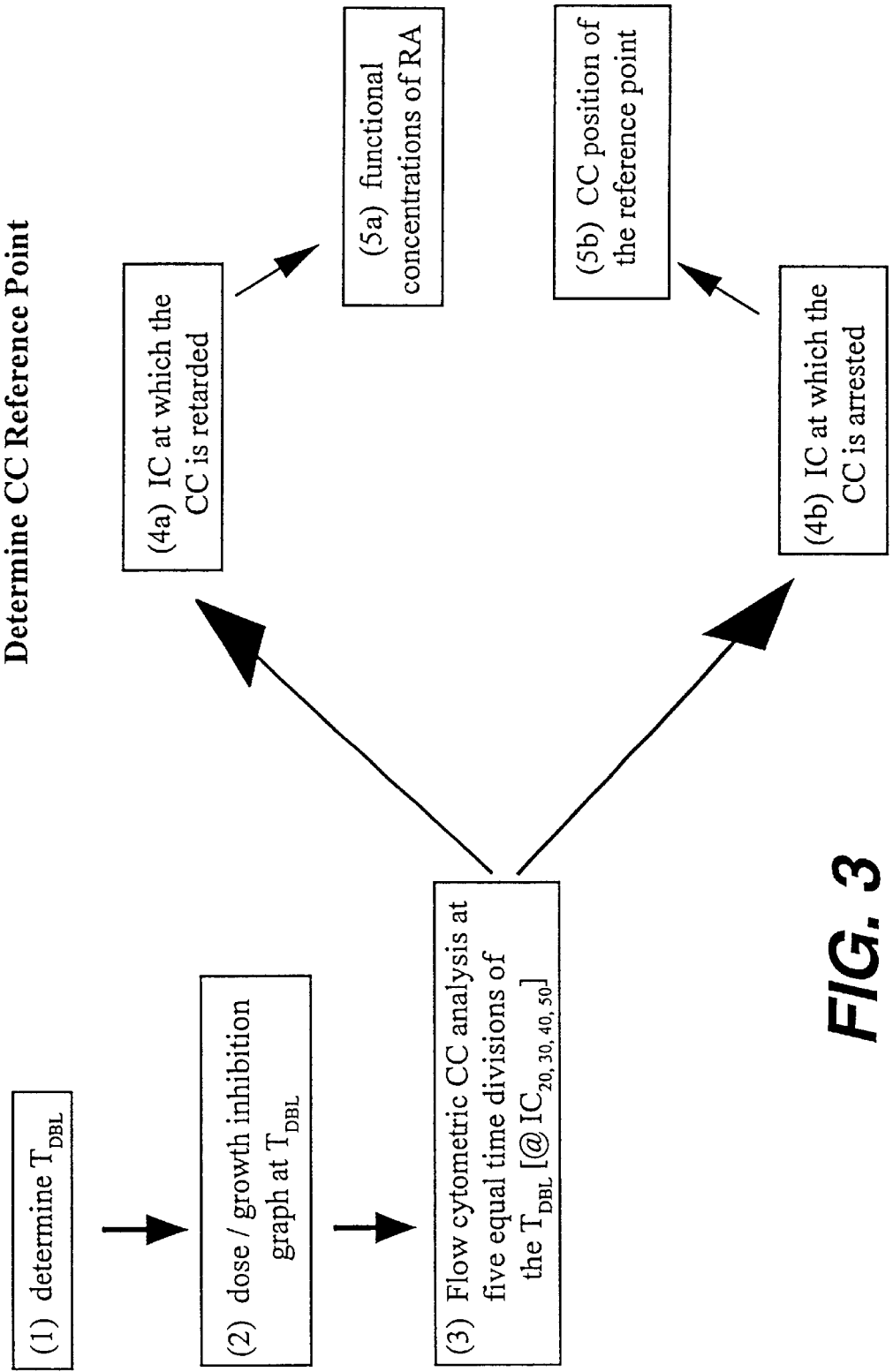
FIG. 3 depicts an algorithm to identify agent concentrations with operative characteristics of RA to determine their reference point cell cycle position.

FIG. 3 shows a general algorithm for identifying concentrations at which a given agent can act as an RA and for determining a reference point of the agent. The first step is to determine the population doubling time ($T_{DBL}$) of specified cells (i.e. a targetpopulation). The target population includes proliferating cells or cells undergoing DNA repair in a population to be damaged. They can include, for example, neoplastic cells, hyperplastic cells, virus infected cells, parasite infected cells, free living parasites or fungi. This step 1 is accomplished by a series of manual or automated cell counts or by flow cytometry. Alternatively, it can be accomplished by other methods known to those ordinarily skilled in the art of tissue culture (e.g. total DNA, new DNA synthesis, total protein or cell mass measured by radioisotope uptake, dye chromogenic metabolism, or dye staining). The $T_{DBL}$ provides the time frame for determining the growth inhibitory effect of an RA.

Figure 4:
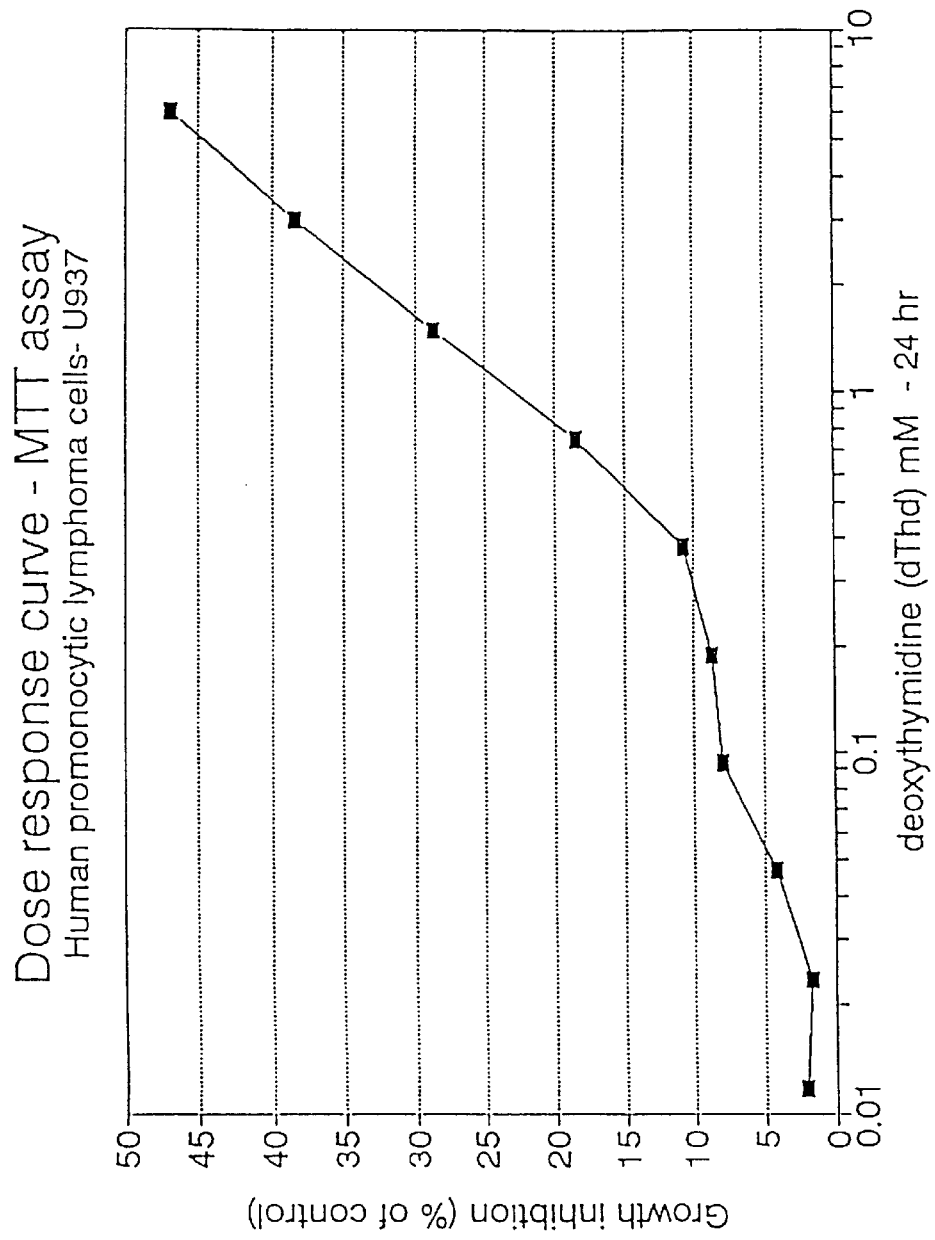
FIG. 4 depicts the results of an MTT assay showing that during approximately one doubling time of 24 hours of human promonocytic lymphoma cells, the 40% inibitory concentration of dThd exceeded 2 mM.

The second step is to graph the dose response of the target population, showing growth inhibition in relation to the $T_{DBL}$. Generally, an RA will maximize synergy at a strength or intensity less than 40% of its inhibitory concentration ($IC_{40}$) at the $T_{DBL}$. An inhibitory concentration relates to growth inhibition as compared to the growth of untreated controls. Thus, an $IC_{40}$ for a given RA is the concentration at which treated cells show 40% less growth than untreated controls at the $T_{DBL}$. Although the $T_{DBL}$ will likely be easiest to use as a consistent standard, a convenient time interval less than $T_{DBL}$ may also be used, provided it is consistently applied. Generally, the interval should be at least greater than 50% $T_{DBL}$ to provide useful data. Step 2 is performed as shown in Example 1. FIG. 4 shows the relationship of progressively increased concentrations of an agent preferred for use as an RA, deoxythymidine (dThd), on growth inhibition of a population of human malignant cells during the mean time of a single cycle of cell-division. As shown with one cell line in FIG. 4, during the time for approximately one population doubling, the 40% inhibitory concentration of dThd occurred at a concentration range of approximately 2 mM.

Example 2 shows the third step: performing flow cytometric analyses during the $T_{DBL}$ at, for instance five equal divisions, using different concentrations of the agent being tested at, for example, $IC_{20, 30, 40, 50}$. In practice, fewer analyses or concentrations may be used, for instance when pilot data, previous experience, or scientific literature provide good indication of expected results.

The results of the flow cytometry, shown in FIG. 5, allow one to determine the IC at which the cell cycle is retarded (Step 4a in the algorithm). Step 4a is particularly well demonstrated with dThd. As shown in FIG. 5, concentrations of dThd less than $IC_{40}$ were sufficient to retard the cell cycle kinetics. In addition, FIG. 5 shows that the proportion of the cell population present within S phase ($F_S$) could become enormously increased with concentrations of less than 1 mM dThd. In principle, these dramatic effects on the cell cycle S phase or $G_2$ & M phase ($F_{G2\&M}$) could be explained either by a static expansion of S phase or $G_2$ & M phase due to the arrest or stationary trapping of cells, or by a real increase in the time required for each viable cell to transit each phase (i.e. a real increase of the $T_S$ or $T_{G2\&M}$). As set forth in FIG. 5, these cells continued in flux through S phase, so that transit into $G_2$ and M phases was persistent at times up to 40 hours. These effects were interpreted as a dynamic retardation of the cell cycling, in contrast to the cell cycle arrest or static synchronization, which occurred at higher concentrations of dThd, (Example 7 provides additional support for such dynamic retardation. See also FIG. 9) Thus, these steps indicated that dThd in an appropriate concentration range is a restraining agent in the terms of the invention (Step 5a).

Any agent known to cause cell cycle arrest or static synchronization has the potential to operate in the role of RA when used at a concentration or intensity less than that-necessary to arrest the cell cycle. When a concentration of any agent serving as an RA does produce cell cycle arrest, then the locus of the arrest can be assumed to represent a reference point of the RA. In this perspective, cell cycle arrest represents the limiting effective strength of any agent as an RA.

Example 3 demonstrates step 4b, determining the inhibitory concentration at which the cell cycle is arrested. Excess dThd has been used as a reversible means of cell cycle arrest in late $G_1$ or early S phase. Zielke, supra; Kufe, supra, Krek W, DeCaprio J A, Methods Enzymol. 254:114–124 1995. Based upon earlier experience with cell cycle arrest in established lines of human lymphoma cells, Grimley P M et al., Cancer Res 144:3480–88 (1984); Hulanicka B et al., Cancer Res. 37:2105–2113 (1977), the inventors exposed human promonocytic lymphoma cells (U937) to up to 3 mM dThd at intervals of up to 24 h and analyzed changes in the dynamics of the cell cycle. FIG. 5 shows that the cells treated with 3 mM dThd were detained in transition from $G_1$ phase to S phase at 8 and 16 h so that the proportion of cells in S phase and $G_2$ & M ($F_S$ & $F_{G2\ \&\ M}$) was stabilized or reduced. This finding was consistent with previous reports that dThd arrested cells in close proximity to the transition from $G_1$ to S phase in the cell cycle. W Vogel et al., Hum. Genet. 45:193–8 (1978). Thus, the reference point for dThd is estimated to be the $G_1$/S boundary of the cell cycle (Step 5b).

Figure 6:
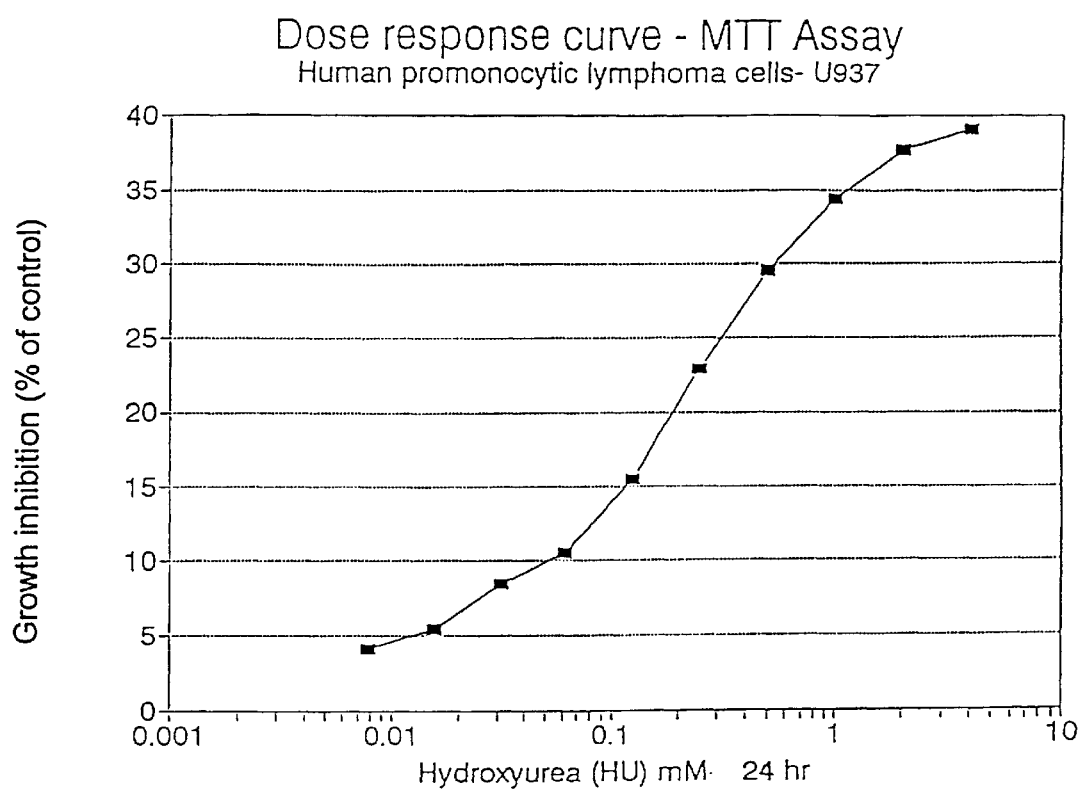
FIG. 6 depicts a dose response curve of increasing concentrations of HU on human promonocytic lymphoma cells. This figure indicates that the $IC_{40}$ for HU exceeds 3 mM.
Figure 7:
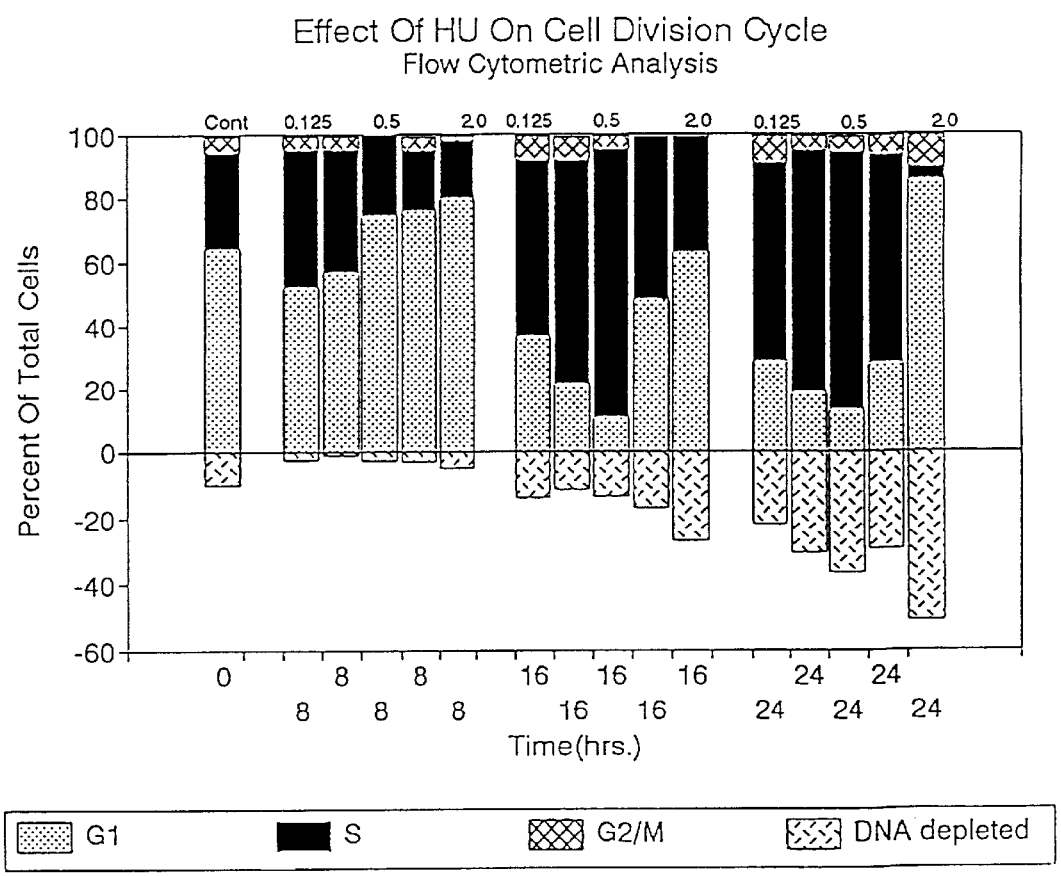
FIG. 7 depicts a flow cytometric analysis of human promonocytic lymphoma cells treated with varying concentration of HU.

The same methods were used to evaluate HU for use as an RA and are described in Example 4. As shown in FIG. 6, during approximately one population doubling, the $IC_{40}$ of HU exceeded 2 mM. As with dThd, concentrations of HU<$IC_{40}$ were sufficient to retard cell cycle kinetics. As shown in FIG. 7 and described in Example 5, HU treatment of a population of human malignant cells increased cell cycle transit times. Thus HU, an inhibitor of ribonucleotide reductase, applied in a range of concentrations less than its $IC_{40}$, increased the $T_S$ of the proliferating malignant cells and is an RA in the claimed invention.

As noted, any agent already known to cause cell cycle arrest or static synchronization has a potential to function in the role of RA at an appropriately reduced strength or for an appropriately limited duration. By the same token, at excessive concentrations, an agent that could function as an RA may cause apoptosis or other DNA-related damage and thereby behave as a TCI rather than as an RA.

For example, the $IC_{\%}$ at which the cell cycle was arrested by HU was determined with progressively increased concentrations. FIG. 7 shows that the long term effects of high concentrations of HU and exposure over 16 hr were not clearly related to dynamic retardation. These concentrations of HU not only detained (i.e. arrested) cells in S phase, but also killed them. Thus, high concentrations of HU operated as a TCI.

Figure 8:
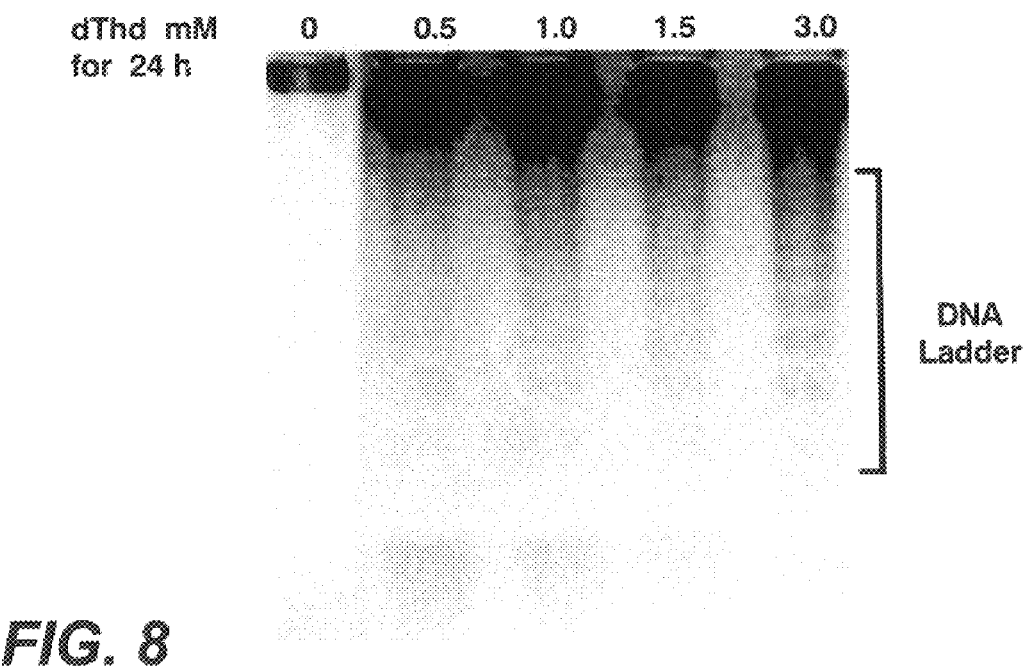
FIG. 8 depicts the results of DNA gel electrophoresis experiments showing fragmentation of DNA extracted from human promonocytic lymphoma cells treated with >0.5 mM dThd.

Excess dTbd, beyond levels associated with dynamic retardation, also produced apoptosis in malignant human cells. Example 6 demonstrates that induction of apoptosis resulted from excess dThd for 24 hours. FIG. 8 shows a DNA gel displaying an electrophoretic ladder pattern typical of DNA fragmentation in apoptosis. Thus, differences in the actions of low and high concentrations of these inhibitors of ribonucleotide reductase, and the flow cytometric evidence of increased $T_S$ in cells treated with relatively low concentrations indicated that a slowing of forward momentum through the S phase was involved in the process by which each agent, acting as an RA, was potentiating cell damage by a TCI.

Since cells can be effectively killed by growth arrest, it is not surprising that several of the agents that operate as RA in the present invention previously have been used as single agents for chemotherapeutic purposes, e.g., dThd and HU. This reiterates the point that discrimination of RAs from TCIs in the context of this invention is functional and not based merely upon the chemical structure or physical nature of a specific agent or factor. The range of operative agent strength and duration appropriate to an RA for dynamic retardation in a given treatment regime is determined for each particular target cell type and TCI.

In a specific embodiment of the invention, dThd acting as an RA retarded progression of a targeted cell population through the cell-division cycle at a reference point near the $G_1$/S transition. For example, as discussed in more detail in the working examples, concentrations of dThd of about $IC_4$ to about $IC_{40}$ with respect to a population generation time can be used as an RA. In preferred embodiments of this invention, concentrations from about $IC_6$ to about $IC_{30}$ can be used as the RA. Especially preferred embodiments of this invention use concentrations of dThd from about $IC_{10}$ to about $IC_{25}$, as the RA. In other embodiments of this invention the RA retards progression of a targeted cell population through the cell-division cycle at a reference point during S phase, or near the $S/G_2$ transition.

Table 1 shows a number of agents that can act as RAs, categorized according to the portion of the cell cycle in which they are known or suspected to act. Not shown are possible secondary reference points that may be determined by practice of this invention.

Most of the RAs shown in Table 1 are commercially available, for example from Sigma Chemical Co., St. Louis, Mo. or Calbiochem, San Diego, Calif. Trimidox was recently synthesized, T. Szekeres et al., Cancer Chemother Pharmacol 34:63–66 (1994). HAG-IQ is synthesized as described by G. Weckbecker et al., J. Natl. Cancer Inst. 80:491–96 (1988).

An RA can be applied to the target cells, or administered, in various ways well-known to one of ordinary skill in the art. For example, in various embodiments of this invention, an RA can be administered in an in vitro setting. In vitro testing may, for instance, be undertaken to rapidly establish synergy between an RA and TCI agents at various strengths or duration for a particular cell line. In an in vitro setting, the RA can be added to the target cells, appropriately diluted in standard biological buffer, such as RPMI 1640. In an in vivo setting, an RA can be delivered in solid, semisolid, liquid, or gaseous form and by various routes. An RA can be introduced by oral, mucosal, topical, intravenous, intrathecal, intramuscular, subcutaneous, intravesicular, intrapleural, intrapelvic, intrauterine, intranasal, intraperitoneal, intraural, or intraocular routes, or by depot injections, or by aerosol, and by itself, or together with a suitable biological carrier. An RA can be delivered as a component of, or in conjunction with another substance or molecule such as a ligand or an antibody or by a carrier such as a liposome or a microcapsule. An RA can be delivered to effect a rapid or sustained release or as multiple intermittent doses. In addition, the delivery of an RA may be aided by gene or nucleic acid transfection, enzyme insertion into a cell membrane, or a virus infection, or any other agent that contributes toward transport or metabolism of an agent acting as an RA, or regulates an agent to act as an RA, including dominant negative regulation. Given the disclosed invention, persons of ordinary skill in the art can determine the most effective administration route of the RA dependent on the needs and reaction of the patient as well as other factors known in the art.

Targeted Cytoxic Insult

As noted above, a cytotoxic agent is any category of agent or circumstance that inflicts damage upon or inhibits growth of living cells, whether for medical, therapeutic or for any other purpose. As defined herein, a TCI is a cytotoxic agent that initiates apoptosis or biologically significant damage during a target interval in the cell cycle hierarchy. Various TCIs can be used in the context of this invention, however a target interval of the TCI should correspond to the portion of the cell cycle slowed by the RA.

Damage inflicted by a TCI may be reversible, permanent, sublethal or lethal. In most practical applications, lethal damage with "total killing" of abnormal cells is preferred. However, practical problems of application, including agent delivery, pharmacokinetic factors, and biologic limits of tolerable side-effects may dictate effective dosages that are sublethal. Nevertheless, limited or reversible biologic damages by a TCI can be advantageous, particularly when the host immune system can target, preferentially kill, and remove damaged or abnormal cells.

TCIs can damage or retard the growth of target cells in various ways. Table 2 shows a number of TCIs, categorized by the estimated position of at least one of their target intervals. Estimation of the target intervals is based in part upon testing performed by the inventors (see for instance Example 12) and upon the known or suspected mechanisms of action as can be found in the scientific literature available to those ordinarily skilled in the art.

When appropriately delivered, a TCI can result in discrete damage to specific biochemical processes. However, when applied in excess strength or intensity, almost any TCI may inflict unexpected cell damage that is unrelated to the primary biochemical or molecular processes and thereby increase side effects. Therefore, a major objective in applying a TCI is to direct its effect to the appropriate subpopulation of cells, i.e., target population, in an optimal strength or intensity. Accordingly, discriminate targeting of specific cell populations for damage(s) inflicted by a TCI can be highly advantageous. Discriminate targeting can be achieved by an appropriate strategy of agent selection or design, first of the RA required to impose the limited restraint condition and second of the TCI. Discriminate targeting can also be achieved by an optimal strategy of agent deliveries to a target population.

TCIs can be applied to a target cell in an in vitro setting, for pre-clinical testing among other reasons, setting at an effective concentration after dilution in a suitable biological buffer. In an in vivo setting, a TCI can be delivered in solid, semisolid, liquid, or gaseous form and by various routes. A TCI can be introduced by oral, mucosal, topical, intravenous, intrathecal, intramuscular, subcutaneous, intravesicular, intrapleural, intrapelvic, intrauterine, intranasal, intraperitoneal, intraural, or intraocular routes, or by depot injections, or by aerosol, and by itself, or together with a suitable biological carrier. A TCI can be delivered as a component of, or in conjunction with another substance or molecule such as a ligand or an antibody or by a carrier such as a liposome or a microcapsule. A TCI can be delivered to effect a rapid or sustained release or as multiple intermittent doses. In addition, the delivery of a TCI may be aided by gene or nucleic acid transfection, enzyme insertion into a cell membrane, or a virus infection, or any other action or agent that contributes toward transport or metabolism of an agent acting as a TCI, or regulates an agent to act as a TCI, including dominant negative regulation. As with RAs, persons in the art would be able to determine the appropriate administrative route using routine skills.

Special means of agent (RA or TCI) deliveries, including receptor or ligand targeting or techniques using liposome or antibody carriers, may facilitate critical targeting to the appropriate cell subpopulation in human or other multicellular hosts (R C Juliano, Ann N.Y. Acad. Sci. 507:89–103 (1987)) and are, therefore, within the invention. In addition, the practice of the invention may also include specific antagonists to protect susceptible normal cells, tissues or organs from undesirable effects of an RA and/or a TCI that is targeted to malignant cells or infected cells. For example, aclarubicin, cardioprotective agent CRF-187, or chloroquine could antagonize the cytotoxicity of etoposide. P B Jensen, Cancer Res. 54:2959–2963 (1994).

A TCI can be added to the target cells concomitant with or following the addition of an RA. In a preferred embodiment of this invention, the TCI is added 0–8 hours after addition of the RA. In particularly preferred embodiments of this invention, the TCI is added 4–6 hours after the addition of an RA. However, the exact time at which the TCI is added will depend upon the exact conditions of treatment including the nature of the RA and TCI employed and the characteristics of the target cell population. An effective cytotoxic concentration (EC) of a TCI is an amount of TCI that, when matched with an RA, is sufficient to damage, inhibit the growth, or kill target cells, depending on the context.

In embodiments of this invention, before, after, or with the administration of an RA, a TCI is administered to the target cells in an amount sufficient to damage or inhibit the growth of target cells. In other embodiments of this invention, before, after, or with the administration of an RA, the TCI is added in amount sufficient to kill the target cell. For example, STSP can be added in an amount from $IC_{10}$ to $IC_{60}$. In preferred embodiments of this invention, STSP can be added in an amount from $IC_{15}$ to $IC_{50}$. In especially preferred embodiments of this invention, STSP can be added in an amount from $IC_{20}$ to $IC_{35}$. The amounts of other agents can be determined experimentally as described below.

Synergistic Matching of an RA and a TCI

The rational selection of synergistic matches of RA and TCI is guided by the principles of dynamic retardation described herein. The assay system and auxiliary data analysis provided herein can also be used to guide selection of synergistic matches. Implementation of a synergistic match between an RA and a TCI uses a set of trial procedures: (1) pilot tests of th, effects of a potential RA, in calibrated serial strengths, on the growth of proliferating cells; (2) pilot tests of the effects of a presumptive RA on the cell cycle perturbation and the re-equilibration of a proliferating cell population at serial points in time; (3) pilot tests of the effects of a potential TCI, in calibrated serial strengths, on the growth of proliferating cells; (4) pilot tests of the effects of a presumptive TCI in a specific portion of the cell cycle of a proliferating cell population; and (5) systematic tests of the synergy of an established RA and a proven TCI, at different intervals between applications, and at different levels of absolute and relative strengths, in inflicting damage upon cells of the proliferating cell population intended for damage.

Figure 10:
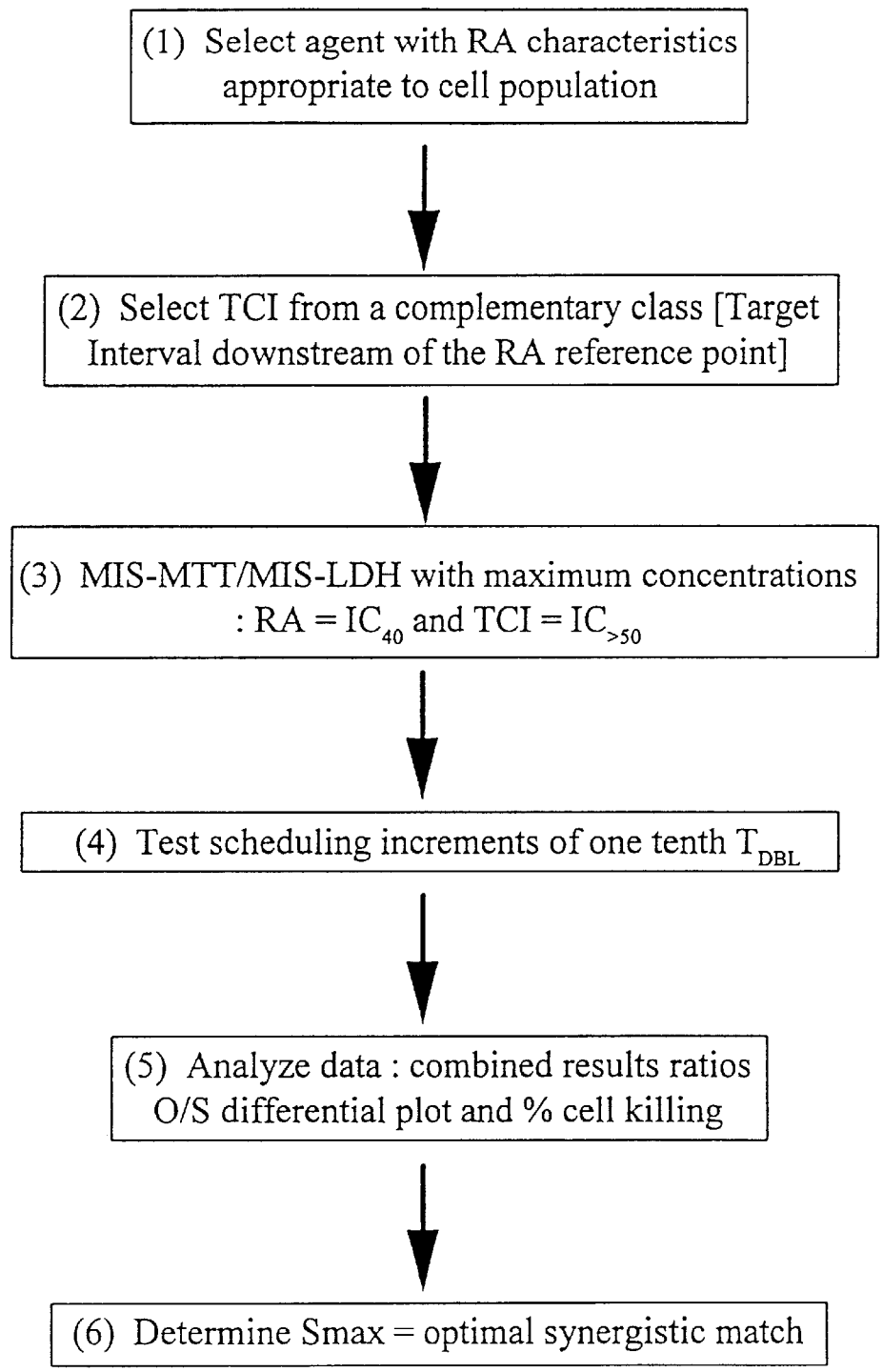
FIG. 10 is an algorithm for synergistically matching an RA and a TCI.

FIG. 10 is a flow diagram showing the selection of a synergistic match of RA and TCI. As shown, the first step is selection of an agent with RA characteristics appropriate to the target population. The second step is selection of a prospective TCI with a target interval downstream of the RA reference point. The TCI may be selected from a complementary class according to the categories in Table 2. Selection can also be based upon a large body of extant pharmacologic, biochemical or molecular biologic data, such as that partially delineated in FIG. 11. The methods of the invention provide an additional basis for which an agent may be selected for testing as a TCI.

An in vitro Microculture Indicator System Discerns and Quantitates Biological Synergy The third step in FIG. 10 involves testing of potential RAs and TCIs for synergistic matching with an in vitro microculture indicator system (MIS) employing cultured eukaryolic cells. The MIS is a series of assays in which two parameters are varied by fixed multiples, i.e., bivariate serial dilutions (BVSD) of RA and TCI, in multiple well plates. For each bivariztte combination, effects related to cell damage are quantitated by calorimetric or other measurable indicators.

Example 8 demonstrates a systematic series of tests of dThd, acting as an RA, and STSP, acting as a TCI. The tests quantitate biologic damage to malignant cells using calorimetric assays, however, many other assays known to those skilled in the art could also be used to provide a measure of growth inhibition or cell killing. Maximum concentrations oF RA=$IC_{40}$ and TCI=$IC_{>50}$ are recommended for use in the assays.

Analysis of the MIS Data Using new Algorithms

Figure 14:
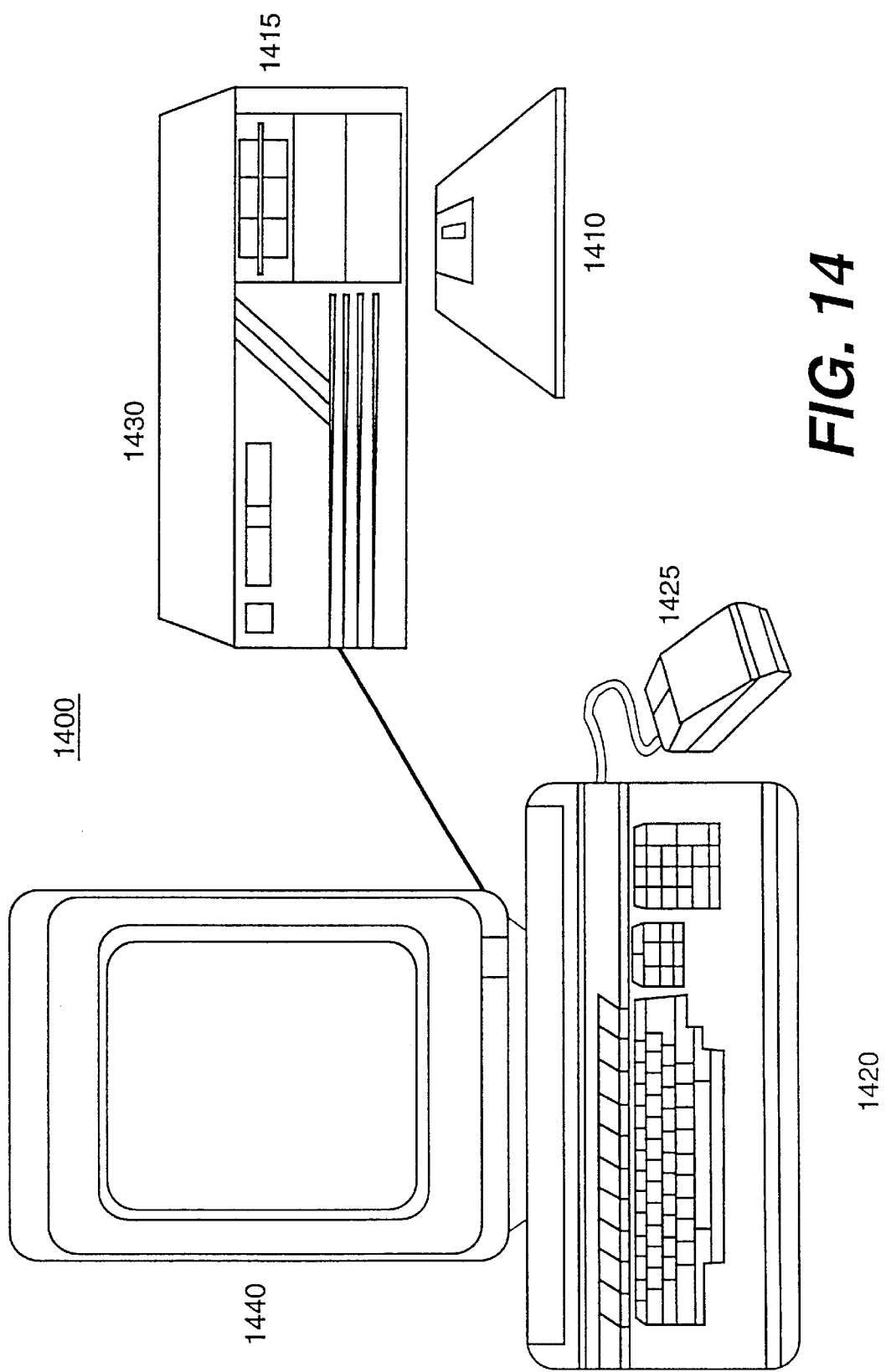
FIG. 14 shows a data processing system capable of carrying out the present invention.

Another aspect of the invention involves a method of analyzing the MIS data for the determination of agent synergy using comparisons of observed results to hypothetical sums. See Berenbaum M C, Pharm Rev 41:93–141 (1989). Briefly, the hypothetical sum for each data point is the expected value for the combination of each agent at a respective concentration if the results for each alone were simply added together. Colorimetric readings or comparable data are imported into any relational spreadsheet, such as Borland Quattro Pro 4, that has been populated as shown in Table 3. The data processor analyzes the data according to the predetermined relationships represented in the populated cells, comparing the results for wells containing both RA and TCI, with hypothetical results derived from the results for wells containing no agents and the results for wells containing each agent alone. FIG. 14 shows a typical computer system 1400 for executing the procedure just described. Data can be entered either through disk 1410 via disk drive 1415, or through keyboard 1420 with or without mouse 1425. Processor 1430 would execute the spreadsheet program and the results can be displayed on monitor 1440.

The data processor may display, in a tabular form, combined results ratios (CRR), which reflect the ratios of the growth inhibition or cytotoxic effect observed in each well to that which would be expected in a hypothetical summation of the effects of the TCI and RA. For example, Table 4 shows a printout of percent growth inhibition (columns with %) and combined results ratios (interspersed columns) for bivariate strength combinations of dThd and STSP. Table 4 was generated through application of the formulas shown in Table 3A–E, to the data generated in Example 8. When the CRR equals 1 a summation effect is observed (i.e. hypothetical zero interaction); when the CRR is >1, a synergistic effect is observed; and when <1 an antagonistic effect is observed. Therefore, in Table 4 a synergistic effect is observed, for example, for the concentration of 25 nM STSP and 0.19 mM dThd (CRR 1.7, at $IC_{74}$). Both the degree of synergy and the amount of cell depletion or damage are considered in devising a therapeutic regimen for an RA and a TCI.

Figure 15:
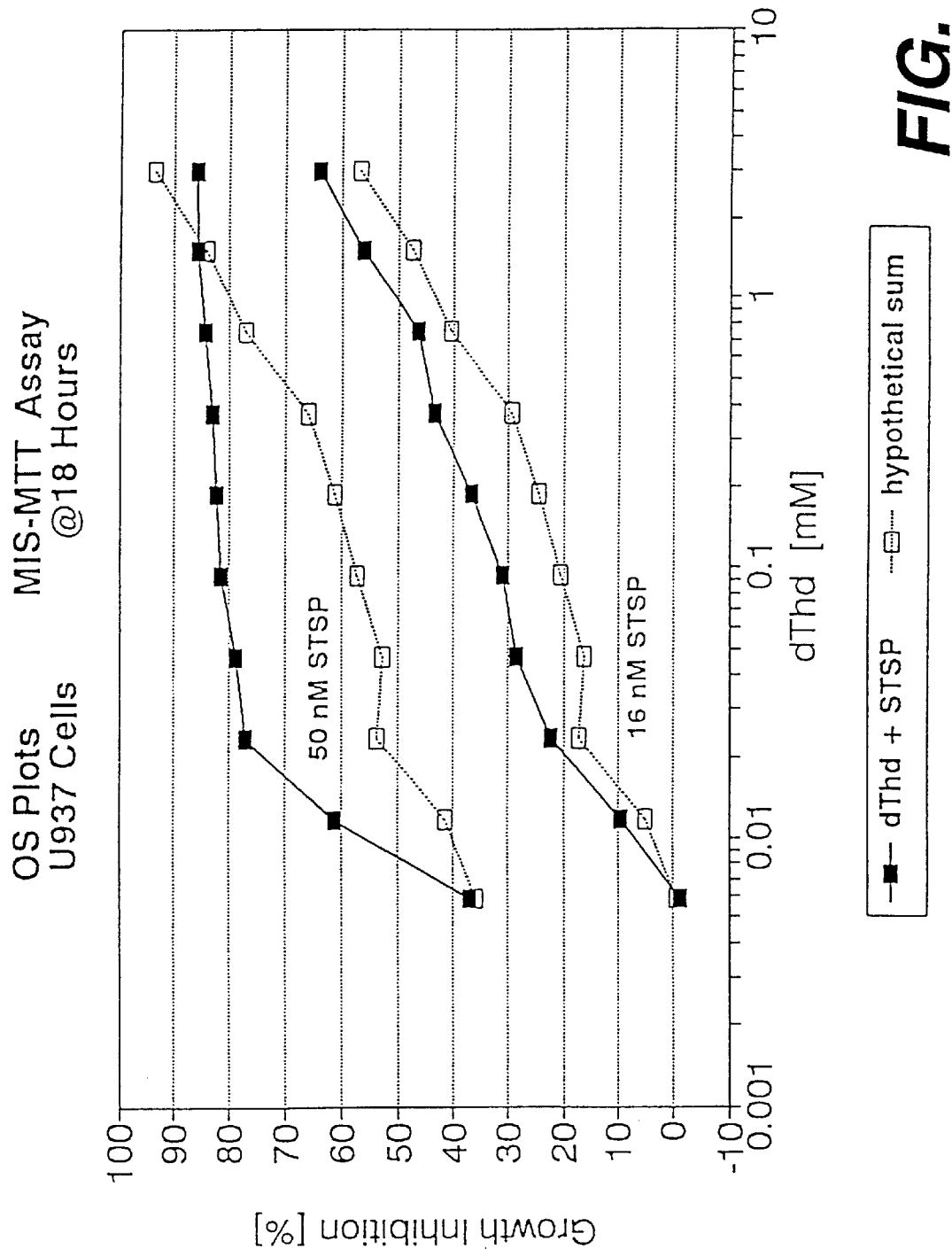
FIG. 15 depicts the results of MTT tests with dThd and STSP plotted as line graphs of observed results and summation results against two-fold serial dilutions of dThd.

In addition, using the formulas shown in Table 3A–G, the data processor may display the results in graphical form as two superimposed plots showing, for each concentration of a TCI, the observed results ("O") as a function of an RA concentration in one graph and the hypothetical summation ("S") results as a function of an RA concentration in the other graph ("O/S" plots). For example, FIG. 15 shows O/S plots for two of the strength combinations of dThd and STSP. In each of the graphs shown in FIG. 15, the maximum difference between the plots for O and S occurs at approximately 0.1 mM dThd.

Figure 16:
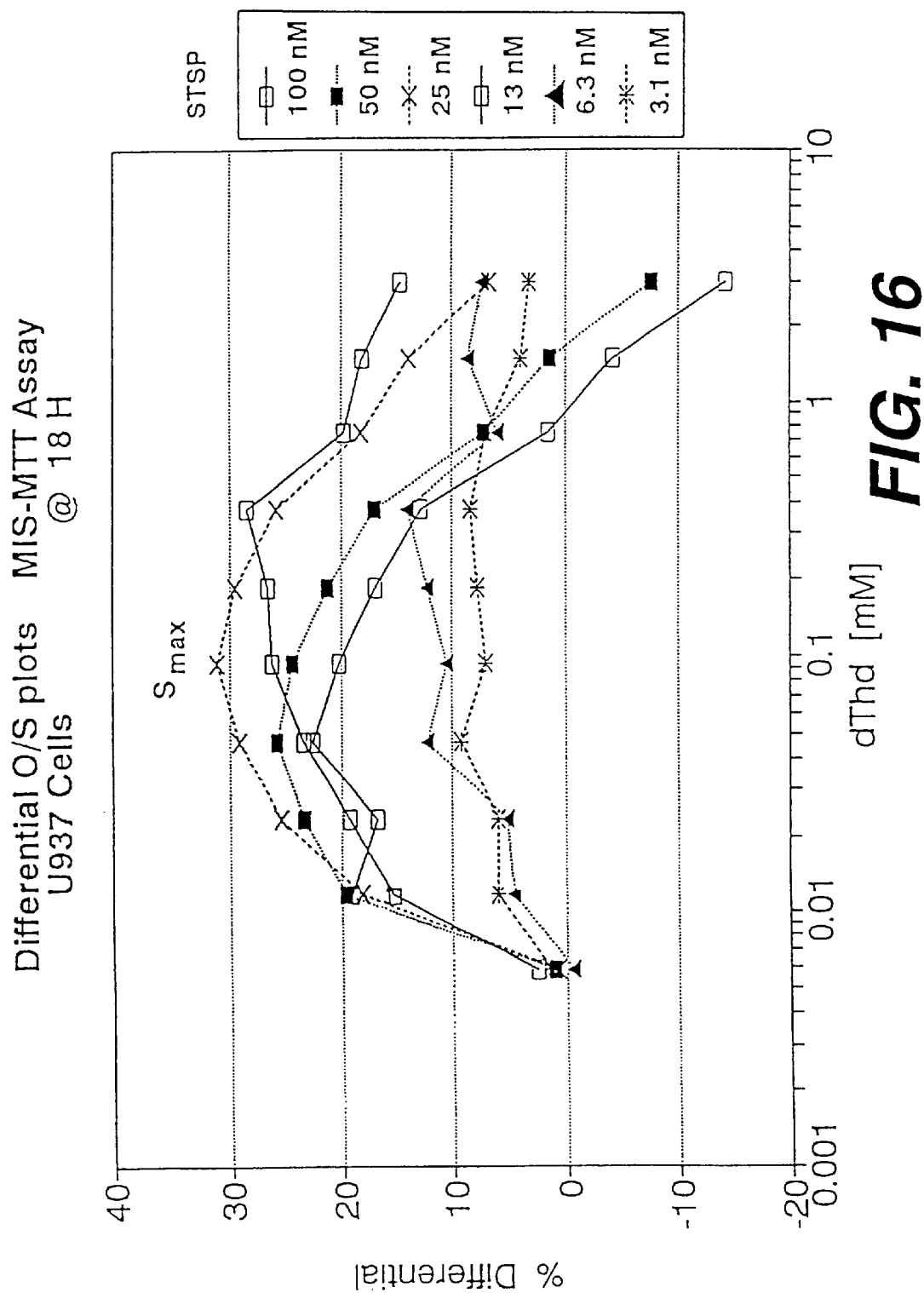
FIG. 16 depicts the results of MTT tests with dThd and STSP in a multiwell microculture plate graphed as the differences between the observed results and the summation results against two-fold serial dilutions of the dThd.

Applying the formulas shown in Table 3A–H, the data processor may also display in superimposed plots for each concentration of a TCI, the differences between the O and S as a function of RA concentration (differential O/S plot). FIG. 16 shows differential O/S plots for various strength combinations of dThd and STSP. The most synergistic concentrations of an RA for a given concentration of TCI are found along the parabolic maximum. Conversely, the most antagonistic concentrations of an RA for a given concentration of TCI are found along the parabolic maximum of a downwardly displaced parabola. While antagonistic interactions are not of direct interest in potentiating cell damage, they may be useful in other contexts, for example, protecting cells from damage.

It is preferred to repeat these experiments with progressively shorter exposure periods suggested because, at a hypothetical summation cytotoxicity of 100%, the analysis may become inaccurate for those concentration combinations. In addition, although the CRR table contains all the information of differential O/S plots and O/S plots, it does not provide exact representation of the data trends. Consequently, obtaining a concrete synergistic interaction range and optimal synergistic match with the CRR alone might involve extrapolations of data beyond reasonable ranges or many additional plates testing each agent in different ranges of concentrations.

In sum, the MIS and auxiliary data analysis procedures may provide: (i) an estimation of the potential operative range for specific RA and TCI interactions from a tabular presentation of the CRR in each well; (ii) a graphic comparison of potentially useful concentrations of the TCI by plotting line graphs of both the observed and summation results against serial concentrations of the RA; and (iii) a graphic display of bivariate synergy maxima or ranges ($S_{MAX}$) by plotting line graphs of the differences between the observed results and summation results.

Interpretation and Verification of MIS and Data Analysis Results

In examples of this invention showing synergistic matches of dThd and STSP, for instance Example 8, an assay for growth inhibition was used. For those combinations, the combined cell damaging effect was sufficiently rapid that a depletion (killing) of treated cells rather than just a growth inhibition could be presumed. Nevertheless, in general, growth inhibition cannot be completely assessed from cell depletion in a single assay for growth inhibition; and growth inhibition is not necessarily synonymous with structural damage to cells by a DNA damaging agent.

The results from these assays can therefore be supplemented by measuring another indicator of cell damage such as, for instance, a calorimetric assay for release of lactate dehydrogenase (LDH) into the tissue culture supernatant. Release of LDH is considered a useful indicator of cell membrane damage. See Li L and Lau BHS, In Vitro Cell Devel Biol 29A:531–536 (1993); Mitchell D B et al., J. Tissue Cult. Meth. 6:113 (1980). (See Example 9). In performing the auxiliary data analysis step for this type of assay, instead of percent growth inhibition, absolute amount of cell damage is shown in the CRR.

More assurance that a synergistic match produces cell killing may be obtained from the ratio of cell mass at completion of the test (N) to cell mass at the outset ($N_0$). This ratio can be obtained by serial assays. This ratio ($N/N_0$)

also may be presented graphically as a function of RA concentration by populating the spreadsheet as shown in Table 3A–C, J–M. When less than 1, this ratio reflects a net loss of cells in a target population. Another presentation shows a ratio less than 1 as a percentage of population loss $(1-N/N_0)$. This percentage also may be presented graphically as a function of RA concentration by populating the spreadsheet as shown in Table 3A–C, J–N.

The MTT and LDH procedures demonstrated in Examples 8 and 9 detected effects on growth or damage of the U937 cells during an interval of 18 h, representing less than one mean generation time. Although the damage inflicted by STSP was potentiated by dThd during that time interval, delayed effects upon succeeding generations of progeny cells would also be significant in clinical chemotherapy. An aspect of the invention is a "delayed proliferation assay" based upon the MIS shown in Example 8 to show that the rapid effect of STSP on DNA damage in cells treated with dThd affected cell growth inhibition for at least 48 hr.

Figure 20:
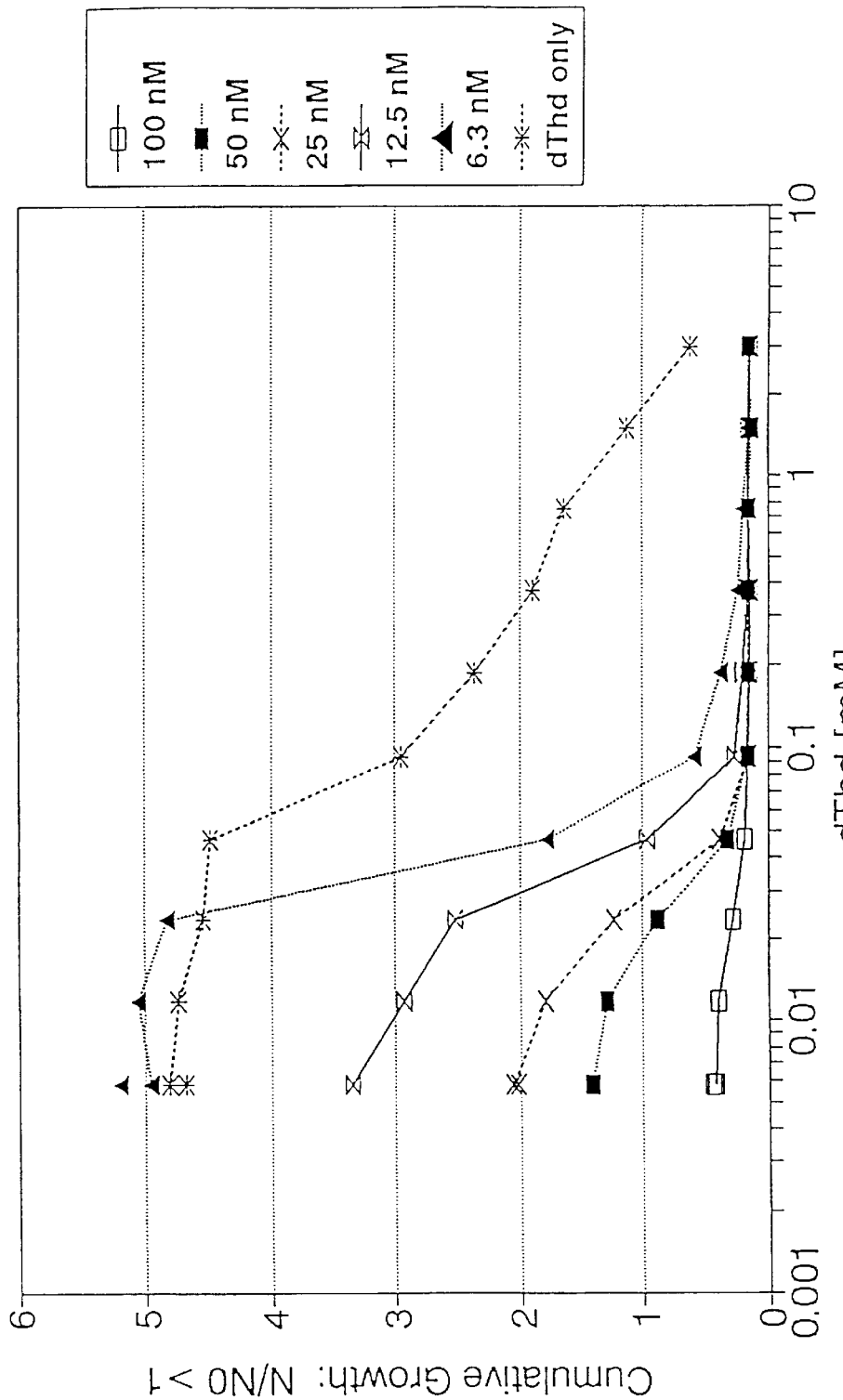
FIG. 20 depicts cumulative growth curves for human promonocytic lymphoma cells treated with varying concentrations of dThd and staurosporine showing effects in a delayed proliferation assay.
Figure 21:
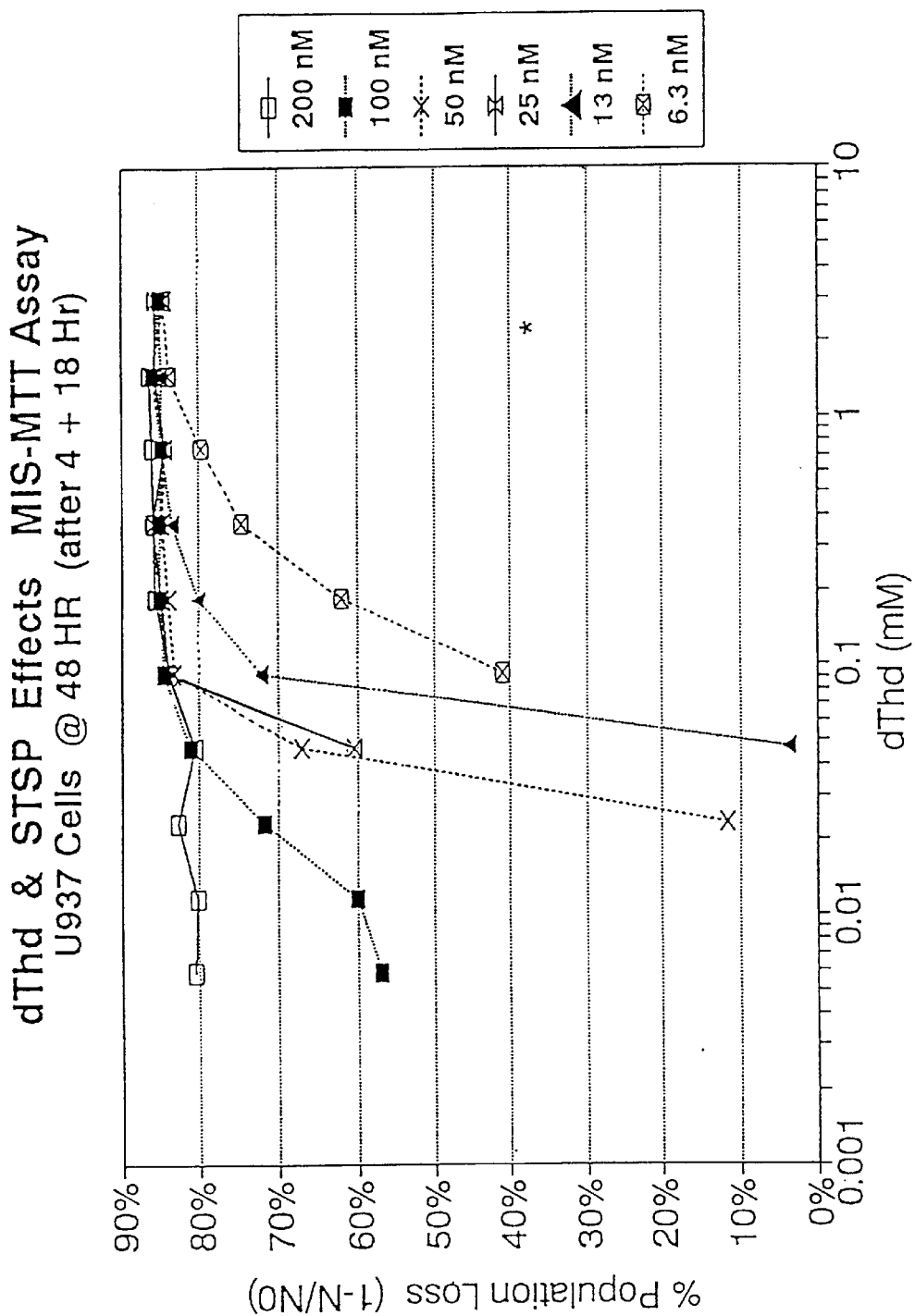
FIG. 21 is a graph depicting percent population loss for HPLC treated with varying concentrations of dThd and STSP in a delayed proliferation assay.

Example 10 demonstrates such a delayed proliferation assay. The results obtained proved that the dThd treatment potentiation of STSP shown in Example 8 by MTT assays for growth inhibition and in Example 9 by LDH release, caused a persistent growth suppression of the targeted population. In addition, as shown in FIGS. 20 and 21 the effects of low concentrations of STSP and dThd, which by themselves were reversible by washing, became irreversible once the agents were combined in synergistic matches. In comparison to CRR data, cumulative growth graphs are more revealing.

Spread sheet formulations and graphic analyses are quick, facile, and efficient as compared to isobologram analysis in interpreting experimental results during the practice of this invention. The results are highly reproducible and provide the optimal synergistic range for combinations of RA and TCI. In addition, this analysis is minimally time consuming, no special experimental design is required, and analysis can be made even if one of the drugs is less toxic than the other agent.

Step 4 of FIG. 10 recommends test scheduling increments within the $T_{DBL}$ to optimize any synergistic match. In this step, MIS and data analysis are performed for simultaneous administration of the RA and TCI and for gradually staggered application where the second agent is given after a fixed increment of delay for each test schedule. The order of application may also be varied. For instance, the TCI could be given first, followed by the RA and vice versa. Example 11 demonstrates that the effect of dThd in potentiating cell damage by STSP was schedule-dependent, see Table 7. Thus, the MIS and auxiliary data analysis can be used to estimate optimal times for RA and TCI deliveries.

Use of MIS to Identify Agent or Agent Concentration as TCI

Figure 22:
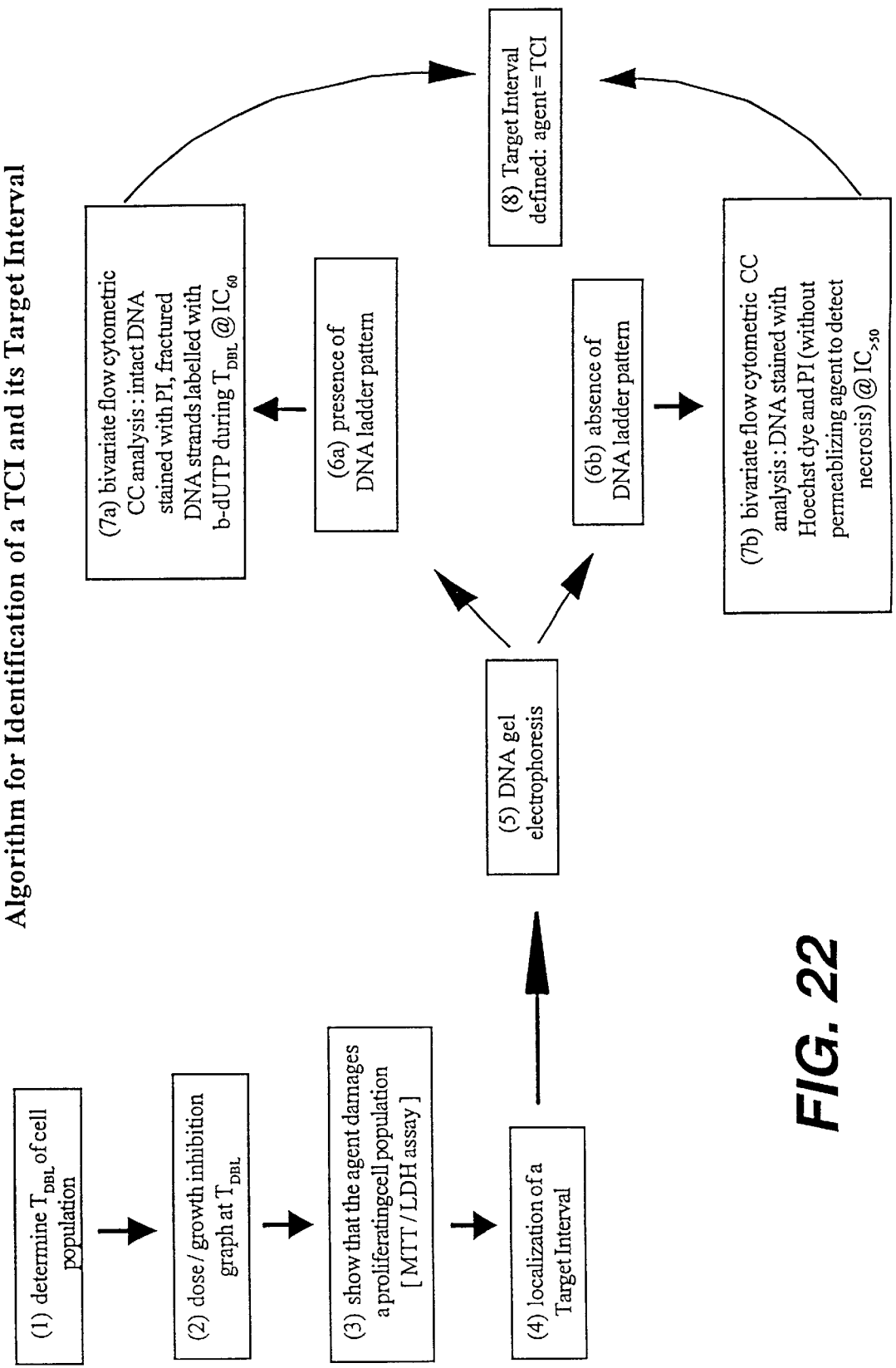
FIG. 22 depicts an algorithm for identifying a TCI in its target interval

The identification of an unknown agent or prospective TCI in appropriate strength and duration both for function in synergistic match with an RA and for the determination of the target interval in S or $G_2$ phases is charted in FIG. 22. Examples with STSP provide a prototype for identification and successful application of a TCI complementary to an RA. In reference to FIG. 22, the first step of determining $T_{DBL}$ and the second step of determining the dose/growth inhibition graph at $T_{DBL}$ parallel the first steps for identifying an RA. (See Example 1.)

The next steps assess whether the prospective agent alone can damage a proliferating cell population and localize the position of a target interval in the cell cycle. Many TCIs, such as high concentrations of dThd or STSP, cause DNA fragmentation when used a single agents. Assessment of the relationship of DNA damage to a target interval ideally involves a combination of techniques which may include conventional flow cytometry for cell cycle analysis shown in Example 2 and DNA gel electrophoresis shown in Example 6. Example 12 demonstrates methods for evaluating the DNA damage initiated by a prospective TCI using the measurement of fractional population loss shown in Example 10. In addition, Example 12 shows the localization of a target interval for a TCI, confirmed by both DNA gel electrophoresis and flow cytometry.

Interaction of an RA and a TCI

In S phase, the strand replication of eukaryotic DNA originates at multiple and different time points. However, the replication hierarchies share important enzymes or metabolic intermediates. Murray A W and Kirschner M W, Science 246:614–621 (1989); Laskey et al., Science 246:609–613 (1989). Therefore, an RA acting by initiating dynamic retardation during S phase likely imposes effects at multiple reference points.

As an illustration, FIG. 26 shows the basic principles of dynamic retardation and the importance of the relative hierarchical positions of the reference point of the RA and the target interval of the TCI. In FIG. 26(b and c), the RA are shown acting during S phase, with the arrows indicating possible different reference points of an RA in relation to the cell cycle. The resultant retardation fields ("RF1" and "RF2", respectively) are represented as distortions in different portions of the S phase, and are intended to reflect a local increase in the S phase transit time. The reference point for RA I (FIG. 26(b)) is shown close to the $G_1/S$ boundary, while the reference point for RA II is shown closer to the $S/G_2$ boundary. Thus, a target interval in early S phase ("A") would be included in the retardation field of RA I, whereas a target interval further downstream in late S phase ("B") might not. In contrast, the reference point of RA II (FIG. 26(c)) is shown to be located downstream of an early S phase target interval ("A"). Therefore, only a later target interval ("B") might be included in the retardation field.

FIG. 26 is a simplification of the real events. In certain portions of the eukaryotic cell cycle, particularly S phase, macromolecular replication or other critical biochemical or biomolecular processes simultaneously occur at different positions. Thus, dynamic retardation in S phase presumes the possibility that certain RA will impose effects at multiple reference points. In consequence, retardation fields also may occur simultaneously at different positions and may encompass portions of multiple target intervals with differing vulnerabilities to various TCI. The possibility of retardation fields being generated upstream of an RA is not theoretically excluded.

As noted, dynamic retardation also requires movements through some portion of the cell cycle and will not occur in non-cycling cells. In experiments with TPA, cells forced into $G_1/(G_0)$ phase or in a state of terminal differentiation escaped the damaging effects associated with dynamic retardation in the presence of a TCI. This was evident in DNA gel analyses. (See Example 13 and FIG. 27.) This protective effect also was observed in the MIS assay. Addition of TPA together with STSP rather than prior to the dThd was significantly less effective than the TPA pre-treatment. This excluded a direct biochemical inhibition of STS)L by TPA. Results thus were consistent with a physicochemical effect of dThd related to kinetic changes during S phase.

Potentiation by dThd of STSP Cell is due to dThd Inhibition of RNR

As shown in Example 12, STSP was shown to induce apoptosis during S phase, yet dThd, which acts in $G_1/S$ was able to act as a potent RA. Concentrations of dThd$\geq$3 mM, which almost totally arrested U937 cells in progression from $G_1$ phase to S phase of the cell cycle (FIG. 5), proved to be less synergistic with STSP than log lower dThd concentrations which permitted continuous cell cycle progression. Although dThd uptake and metabolic pool sizes could be time related factors, potentiation of STSP by dThd clearly is not based upon the stoichiometry expected in a simple metabolic competition.

Enzymes involved in pyrimidine biosynthesis, particularly RNR and deoxycytidylic deaminase, are associated with the initiation of DNA synthesis in all forms of living cells. Elledge, supra. The biologically active R2 submit of RNR contains a coupled iron center and tyrosyl free radical. Transcription of the messenger RNA for RNR, or an active submit of RNR, increases during S phase in mammalian cells. Id.; Bjorklund S et al., Biochem 29:5452–58 (1990). Excess dThd inhibits RNR and deoxycytidylic deaminase by a metabolic feedback inhibition. Xu YZ et al., Biochem Pharmacol 44:1819–27 (1992) and Ellims P H, Cancer Chemother Pharmacol 10:1–6 (1982). The particular effect of dThd was ascribed to intracellular accumulation of deoxythymidine 5'-triphosphate (dTTP), feedback inhibition of ribonucleotide reductase (RNR) and deoxycytidylic deaminase, and a resultant depletion of the intracellular pool of deoxycytidine 5'-triphosphate (dCTP). Elledge, supra.; Xu, supra; and Ellims, supra. This effect of excess dThd or BrdU can be mitigated by equimolar deoxycytidine (dCyt). Kim et al., Biochem Pharnacol 14:1821–9 (1965); Hulanicka, supra.

In the present work, the role of RNR inhibition in the potentiation of STSP by dThd was shown by adding dCyt prior to or concomitantly with dThd. This significantly decreased the effect of dThd in its potentiation of DNA fragmentation by STSP (Example 14, FIG. 28).

Inhibition of RNR by Other Agents also Potentiates STSP

Additional known RNR inhibitors were compared for their ability to act as RAs and potentiate STSP. These included dAde and dGuo which also inhibit reduction of nucleoside diphosphate substrates, and HU, which is a direct inactivator of RNR by scavenging the tyrosyl free radical. J W Yarbo, Semin Oncol 19:1–10 (1992). The halogenated pyrimidine analog bromodeoxyuridine (BrdU) acted almost identically to dThd both in its effects on S phase prolongation as well as on STSP potentiation. In additional experiments, BrdU produced a slowing of S phase similar to that caused by dThd. This was shown by bivariate flow cytometry using PI staining of total DNA and a fluorescein-labelled antibody to BrdU.

Each agent that was effective as an RA worked in a range of concentrations less than the $IC_{40}$ (similar to results with dThd). In a fashion similar to excess dThd, each of the other RNR inhibitors caused cell cycle arrest and induced apoptosis when used alone at sufficiently high concentrations. The concentrations of RNR effective in potentiating STSP consistently were up to several-fold lower than concentrations most active in direct growth inhibition. Each RNR inhibitor used at reduced concentrations proved similar to dThd in potentiating cell damages by STSP. Table 8 lists the results of tests of these agents as RA. CRR data for such. testing appears as Tables 9–12. In the specific examples of dThd, BrdU and HU, the RA concentration for STSP potentiation was at least one log lower than the concentration that caused cell cycle arrest.

The potentiation of cell damage by STSP in the presence of RNR inhibitors could not be explained by stoichiometry and is not explained by any known pathway of metabolic or molecular interactions. Indeed, STSP and related compounds and the inhibitors of RNA evidently act upon enzymes with different substrates and temporal functions in the cell cycle hierarchy. The targeted enzymes are not known to be cooperatively involved in the biosynthesis of common metabolic intermediates, in the biosynthesis of nucleotides, or in the replication or repair of DNA. Flow cytometric analyses demonstrated that a prolongation of S phase occurred during the action of each of the additional RNR inhibitors tested, and in the range of concentrations useful for potentiating STSP.

The specific mechanism(s) by which an RA induces retardation of cell cycle momentum and potentiates the TCI activity is not fully understood for all combinations. However, for HU action, it has been shown, based on a combination of isotopic labelling and two dimensional gel mapping of DNA during replication, that even when HU maximally inhibited incorporation of radiolabelled dThd into DNA, by inhibition of RNR, it did not completely prevent DNA chain initiation or elongation and allowed continued molecular action at replication forks. V Levenson et al., Nucleic Acids Res. 21:3997–4004 (1993).

These data are consistent with dynamic retardation during S phase prolonging a vulnerable physicochemical or configurational state that otherwise would occur only transiently during the processes of replication or repair of DNA macromolecules. A closely related explanation, from a kinetic perspective, would be that dynamic retardation shifts the biochemical equilibrium, leading to accelerated interaction between a transient intermediate product and a TCI.

These theoretical explanations are not essential to the use or operation of this invention but they are internally consistent with the idea that the cell cycle hierarchy is comprised of "phrased processes." They serve as a utilitarian first order approximation of events that can aid in prediction of synergistic matches or exclude useless matches.

Choices of RA in groups other than RNR inhibitors stemmed from initial observations with dThd and a general knowledge of other chemotherapeutic agents known to be capable of arresting the cell cycle when used in high concentrations. (See FIG. 11.) G P V Reddy and A Pardee, Proc. Natl Acad. Sci. 77:3312–16 (1980), postulated a close functional interrelationship between the enzymes involved in nucleic acid metabolism and the polymerases required for DNA strand replication, and the presence of a deoxynucleotide synthesis and polymerization complex called "replitase" has been substantiated. Plucinski T M et al., Mol. Pharmacol. 38:114–20 (1990). For instance, cross inhibition of thymidylate synthase activity was reported during the use of RNR inhibitors, such as, in particular, aphidicolin (Aph) and 1-β-D-arabinofuranosylcytosine, (commonly designated cytarabine, cytosine arabinoside or ara-C) are well known to inhibit polymerases involved in DNA synthesis, C. Sessa et al., J. Natl. Cancer Inst. 83:1160–4 (1991). The action of ara-C is complex, since it may substitute for dCyt in replicating DNA and have other effects. M. Tanaka et al., Jpn. J. Cancer Res. 76:729–735 (1985). Based on these considerations, a dihydrofolate reductase inhibitor (MTX); a thymidylate synthase inhibitor (floxuridine); and two inhibitors of DNA polymerase α (Aph and ara-C) were selected for testing as RA with STSP as the TCI, generally following the algorithm set forth in FIG. 10 and Example 8. Each agent tested at concentrations less than $IC_{40}$ proved successful in potentiating DNA damage by STSP in the U937 cell. The CRR for each of these agents are shown as Tables 13–16.

Figure 29:
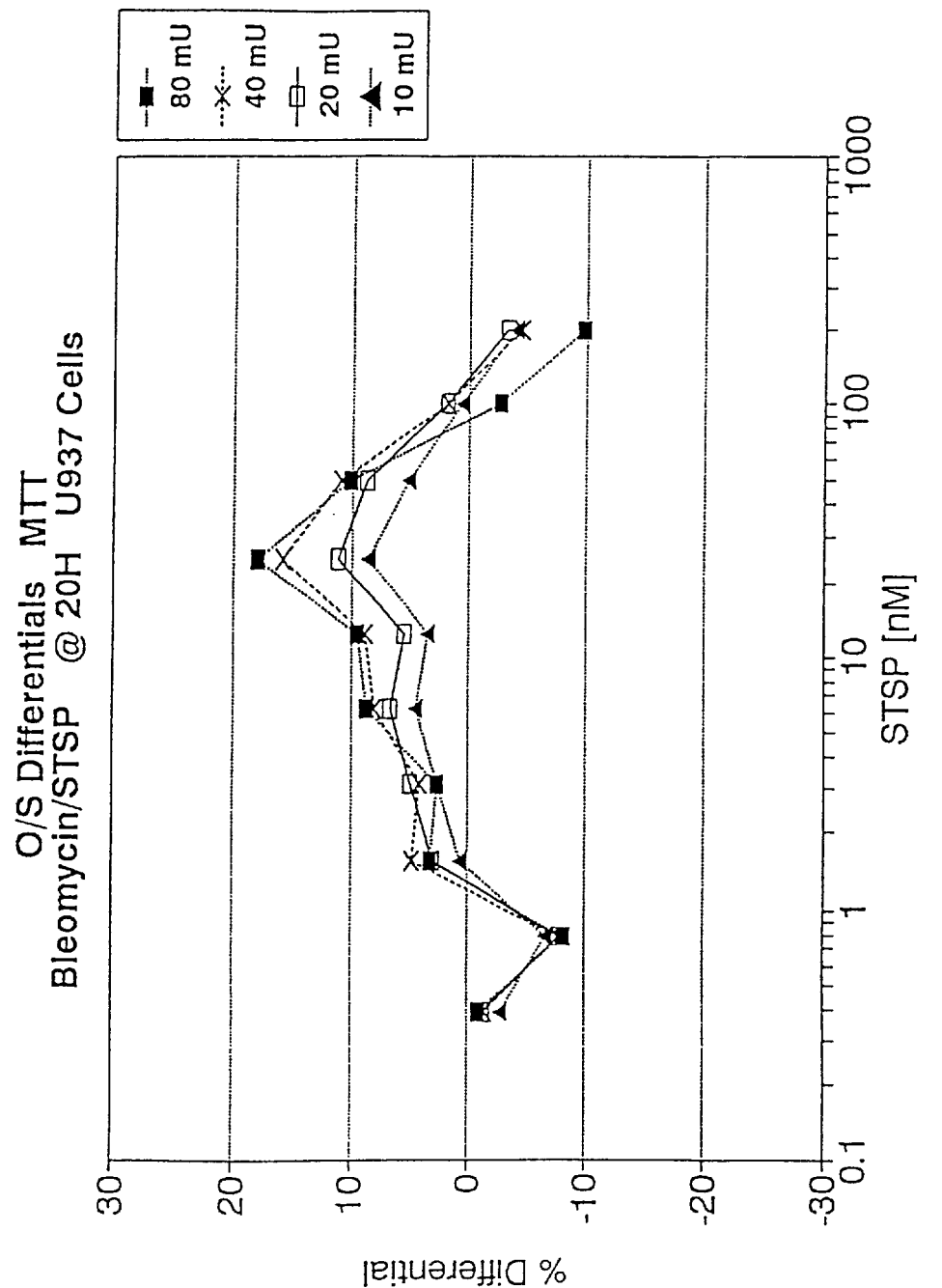
FIG. 29 depicts a differential O/S plot of human promonocytic lymphoma cells treated with varying concentrations of STSP and bleomycin.

In addition, low concentrations of STSP were tested as RA with the following agents acting as TCI: Bleomycin; mitomycin C; Cisplatin (CDDP); etoposide; and daunorubicin. CRP for these tests appear as Tables 17–21. In addition, FIG. 29 depicts O/S differential plots for combinations of STSP and bleomycin.

Figure 30:
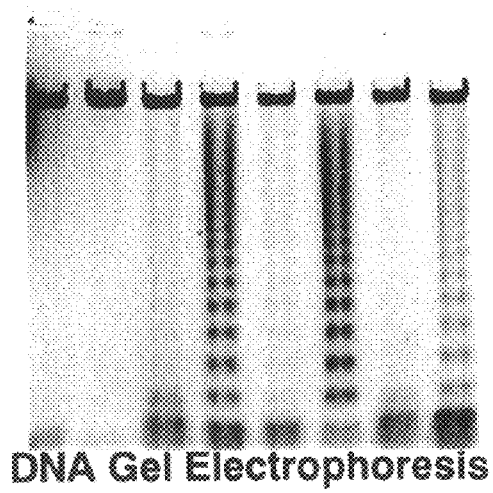
FIG. 30 depicts the results of a DNA gel electrophoresis of DNA extracted from human promonocytic lymphoma cells after treatments with dThd alons and as an RA and various indole carbazoles and as TCI in combinations with dThd.

Using the RA previously identified described herein, other chemotherapeutic agents were tested in the combinations shown in Table 33. CRR for these combinations appear in Table 9–32. In addition, FIG. 30 is a DNA gel showing the synergistic interaction of dThd with indole carbazoles other than STSP, as evidenced by DNA ladder formation. With different TCI, including STSP, KT5926, and Cisplatin, the $S_{MAX}$ for dThd was very similar.

Role of Target Cell Type

When the method of the invention is used in the context of treating a patienft, for example one suffering from cancer or infection, the choice of potential RAs and TCIs should be made so as to maximize the damage to cancer cells or infected cells, while minimizing the damage to normal cells. The combination of the MIS and auxiliary data analysis procedures affords flexibility for the individualization of clinical chemotherapy or radiotherapy. In addition, in vitro testing using either established tumor cell lines or direct cultures of patient tumor cells as the indicator cells can provide a relatively rapid and clinically focused testing, tool to individualize treatment parameters for specific neoplasms in particular patients.

The invention may be most promising in treating malignant cells that seem resistant to chemotherapy. Such resistance of malignant cells to chemotherapy is often associated with deletions or mutations in the p53 gene. Rouach E. et al., Mol Cell Biol 13:1415–23 (1993); Fisher, supra; Lowe, supra; Lotem, supra; Fan, suplra. Large cell lymphomas have been occurring with increasing frequency in patients with immunodeficiency conditions in the United States, and mutation or absence of p53 has been associated with resistance to chemotherapy or radiotherapy. The U937 cells tested in many embodiments of this invention lacked p53, as reported by Calabresse C. et al., Biophys Biochem Res Commun 201:266–83 (1994). This was confirmed by the inventors using a comparable immunoblot methodology and a pantropic antibody to p53 that was obtained from Oncogene Sciences. The U937 cells, therefore, were useful to test agents as RA and TCI because the cells are of histiocytic (large cell) malignant lymphoma origin, Sundstrom, supra, and negative for p53. See Calabresse, supra.

In synergistic matches of dThd and STSP, effective killing of U937 cells occurred. Delayed proliferation assay results supporting such effective killing (Example 10) were confirmed in clonogenic (Example 15, FIG. 31) and tumorigenic (Example 16, Table 34) assays.

In addition, synergistic matches were effective in another cell line (HL60), also reported to have homozygous abnormalities in expression of the p53 gene. See, Calabresse C et al., Biophys Biochem. Res. Comm. 201:266–8 (1994). Protein kinase inhibitors are of interest for human chemotherapy, since some are capable of damaging neoplastic cells that have evolved mechanisms for drug resistance, Sampson, supra; Versantvoort, supra; Hiyamoto, supra; Utz, supra, and mutagenic damage to DNA is minimized in comparison to alkylating agents.

The present invention can help to circumvent the dilemma posed by malignant cells that have evolved drug resistance mechanisms both by intensifying the damaging effects of a TCI and by identifying strategic RA and TCI combinations specifically effective in resistant cell lines, delivered by techniques directed to achieving optimal results. Intensification of TCI effects can also be valuable in treatments of malignancy involving bone marrow transplantation, where either the patient or the extracorporeal tissue can be subjected to a more rigorous regimen of malignant cell eradication.

Figure 32:
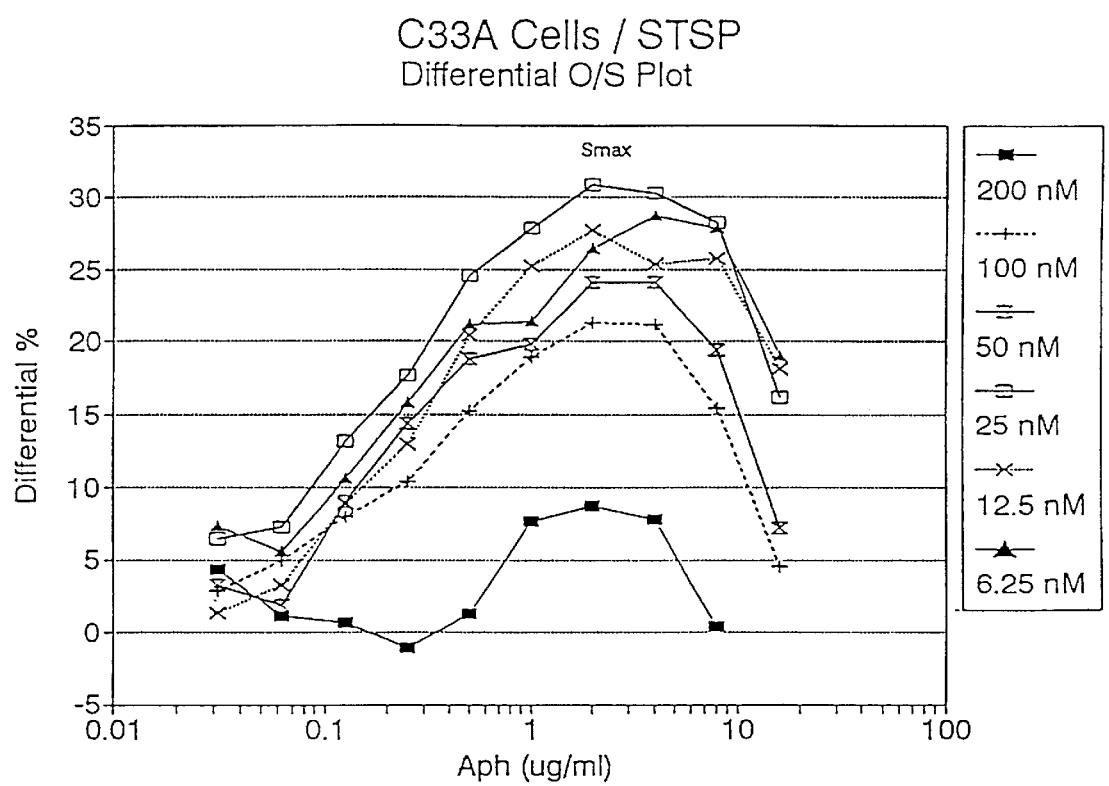
FIG. 32 depicts differential O/S plots of C33A cells treated with various concentrations of Aph and STSP.

Effects of dynamic retardation were observed in a number of other tissue culture lines developed from human malignancies shown in Table 36. The effects of Aph as RA and STSP as TCI on a line of malignant cells of epithelial origin is illustrated in FIG. 32. This cell line (C33A) originated from a human cervical carcinoma, Auersperg N et al., J Natl. Cancer Inst 32:135–148 (1964) and is negative for p53. Shivastrava, supra.

A useful result shown by the testing in various cell lines was that once the $S_{MAX}$ of an RA for a particular synergistic match and cell population was established, the same range of RA concentrations operated successfully with other TCI in classes complementary to that particular RA. Thus, the conditions for $S_{MAX}$ must be established for each specified population of cells, since differences in both the $IC_{40}$ and the $S_{MAX}$ were observed with different populations of malignant cells.

Figure 33:
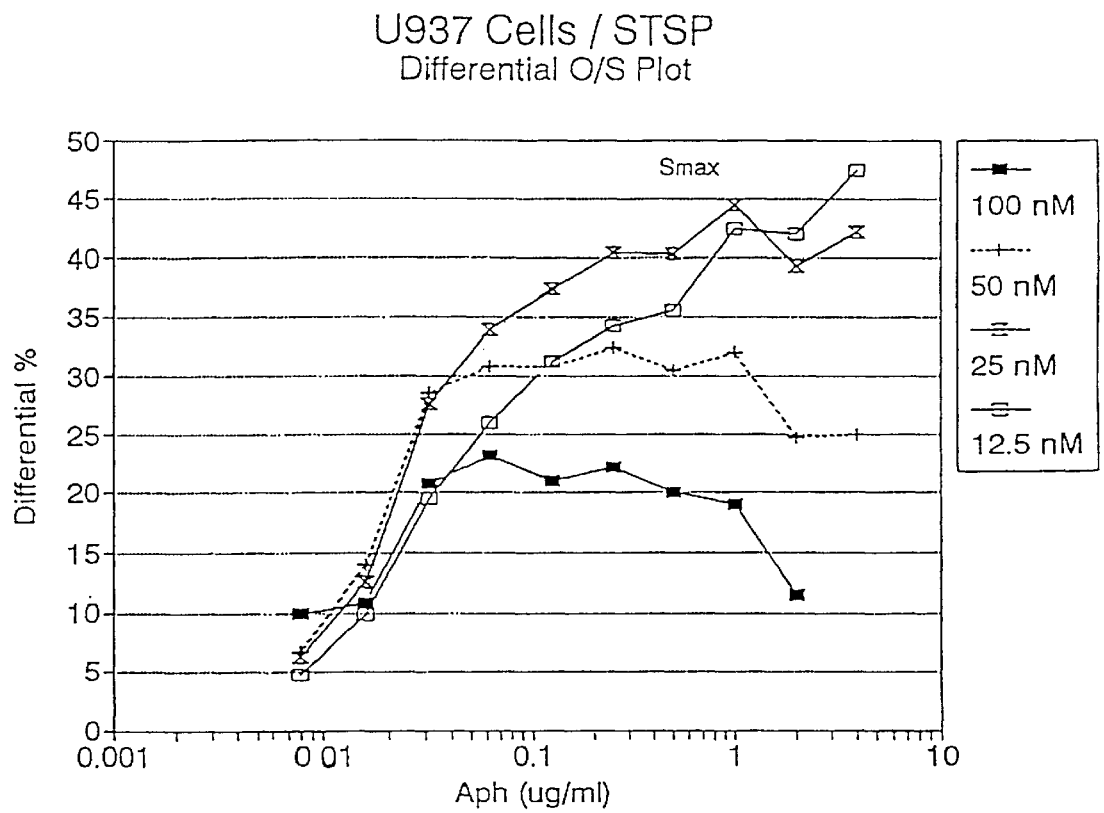
FIG. 33 depicts differential O/S plots of C33A cells treated with various concentrations of U937 cells.
Figure 34:
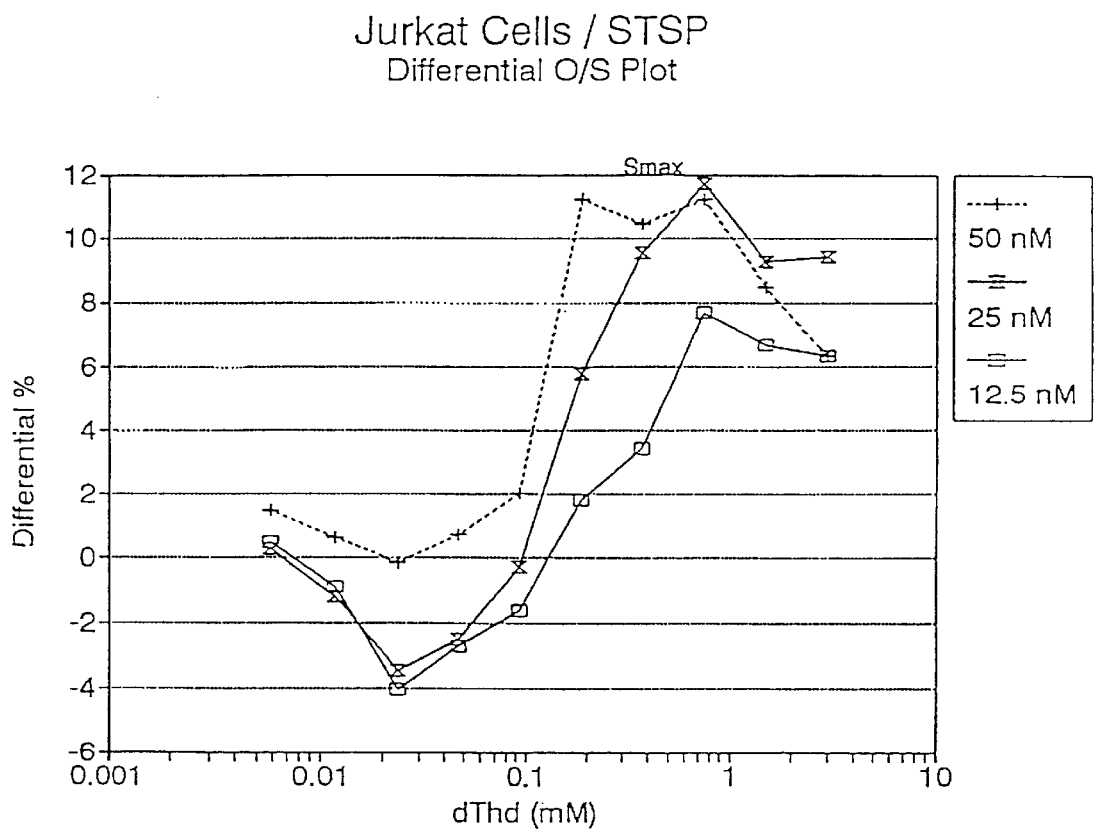
FIG. 34 depicts differential O/S plots of Jurkat cells treated with various concentrations of dThd and STSP.
Figure 35:
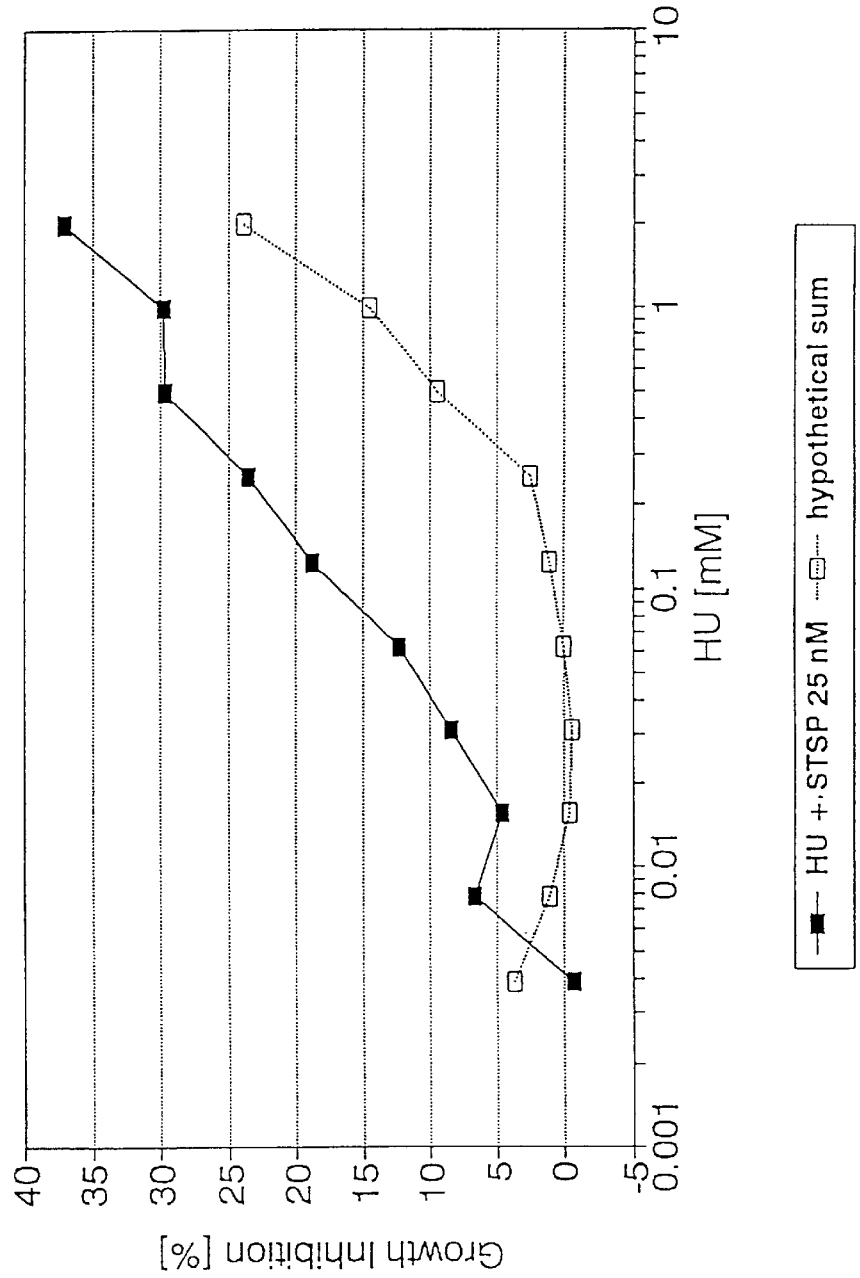
FIG. 35 depicts O/S plots of Raji cells treated with various concentrations of HU and STSP.

The O/S differential plots in FIG. 32 represent effects of Aph on STSP-treated human cervical carcinoma cells (C33A), which can be compared to effects on STSP-treated human promonocytic lymphoma cells (U937) shown in FIG. 33. The O/S differential plots in FIG. 34 represent effects of dThd on STSP-treated Jurkat leukemic T cells which can be compared to effects on STSP-treated human promonocytic lymphoma cells (p937) shown in FIG. 15. The O/S differential plots in FIG. 35 represent effects of HU on STSP-treated Raji cells. These examples and others are listed in Table 33 and the pertinent combined results ratios obtained from MTT assays are provided in Tables 38–42.

The tests of RNR inhibitors shown in Table 8 provided the initial evidence that an agent operated as an RA when used in a range less than the $IC_{40}$ with respect to the growth of human promonocytic lymphoma cells (U937). Table 37 shows a similar relationship between the $IC_{40}$ and the $S_{MAX}$ for several different cell lines with synergistic matches involving either dThd or Aph and STSP. These results also provided evidence that differences in the selectivity, of agents acting at operative concentrations of RA can be exploited to direct damages to a particular malignant cell population by an appropriate selection of RA and complementary TCI for synergistic matches. This applied approach must be based upon a practical knowledge of differences in the chemosusceptibility of particular normal or malignant cell populations in the treated host.

Cellular incorporation and metabolism to deoxythymidine triphosphate (dTTP) is mediated by thymidine kinase (Th). Thus, the RA effect of dThd in a given cell population depends upon a Tk$^+$ phenotype. Certain neoplastic cell lines are deficient in Tk and, therefore, relatively resistant to excess dThd. This was exemplified in tests of the Burkitt's lymphoma cell line Raji: the $IC_{40}$ for dThd was >4 mM, compared to an $IC_{40}$ of >1 mM in U937 cells. The clinical treatment of a human malignant lymphoma with characteristics of Raji cells using dThd as the RA would be problematical because the relatively higher concentrations necessary for dThd to operate as an RA might produce intolerable side effects. A solution to this type of transport enzyme deficiency is substitution of an alternative RNR inhibitor, such as HU, which enters cells by diffusion. See Yarbo, supra. FIG. 35 shows that HU produced a synergistic match with STSP in the Raji cells.

Dynamic retardation also proved successful in potentiating STSP damage to cells of malignant epithelial origin. Examples included the cell line C33A, which originated from a human cervical carcinoma and is negative for p53, Shivastrava, supra, and the cell line ZR-75-1 which originated from a human breast carcinoma. Engel, Cancer Res. 38:3352–3364, 4327–4339 (1978). The C33A cells and ZR-75-1 cells grow on the surfaces of microwells rather than in suspension, and cell damage results in detachment of cells from the substrate. Thus, an MIS assay using crystal violet as a stain for attached cells proved informative and in some cases preferable to the MTT. (See Grando S A et al. Skin Pharmacol 6:135–147 (1993)).

In principle, cells susceptible to the effects of dynamic retardation may be of any type, including eukaryotic, prokaryotic and archaebacterial; organized, free-living, and parasitic, or growing in living hosts of the animal or plant or growing in manufactured environments. This invention can be expected to increase the damaging effects of TCI which are calibrated for delivery to various sizes of populations of normal, abnormal, atypical, neoplastic or infected cells in living hosts or in manufactured environments. Thus, the invention may potentiate damage inflicted upon an entire population of living cells or upon an entire plant, animal, or other living organism, or upon a discrete population or clone of living cells within any organism of the animal or plant kingdoms, or upon any population or clone of free-living cells or upon any population or clone of infected cells within a delineated environment.

Clinical Strategy for Delivery of an RA and TCI

Application of a TCI for medical therapeutic purposes requires that its damaging effect be inflicted upon the appropriate cell population in a patient. Discriminate targeting of specific cell populations is highly advantageous, since side-effects may threaten survival of the host or cause severe morbidity.

The in vitro MIS system in conjunction with data analyses provides a useful surrogate to living hosts for the identification of synergistic matches.

A relatively simple strategy for delivery of an RA in an intact host involves using a relatively high dose of the chosen agent. Blood levels are monitored at intervals to determine the appropriate point for introduction of the TCI. See O'Dwyer, supra; Schilsky R L et al., Cancer Res 46:4184–88 (1986); Donehower R C, Hydroxyurea, In Chabner B A (ed.) Pharmacologic Principles of Cancer Treatment, pp. 269–75, Philadelphia, Pa., Saunders (1982); Sessa, supra. In this approach, the initial level of RA can exceed the optimal range of synergy. This system offers maximum clinical advantages if the RA is minimally cytotoxic and long acting while the TCI is highly cytotoxic and short acting. In one such scenario, the RA is delivered orally, or by depot injection, while the TCI is injected or infused intravascularly for a period of several hours defined by MIS. Blood levels of the RA can be manipulated by auxiliary strategies affecting the pharmacokinetics, including an appropriately scheduled multiple dose regimen.

Confirmation of in vitro data by clinical trials, nevertheless, may require other types of pre-clinical testing including animal studies to calibrate agent dosages more precisely and to divulge unanticipated toxicities. See A F Gazdar et al., J. Natl. Cancer Inst. 82:117–24 (1990); B A Chabner, J. Natl. Cancer Inst. 82:1083–85 (1990); M R Boyd, In Cancer, Principles and Practice of Oncology Update, pp. 1–12, ed. DeVita et al., vol. 3: Lipincott, Philadelphia (1989). Dosages are calibrated in relation to a cell mass or number, the weight, surface area or blood volume of a host.

A "pharmacokinetic elimination strategy" would work very effectively with either dThd, Schilsky, supra, HU, Donehower, supra, or Aph, Sessa, supra, as the RA. Significant blood and cerebrospinal fluid levels of dThd or HU have been achieved with continuous intravenous infusions and levels can be maintained for several days. Blumenreich M S et al., Cancer Res 44:2203–07 (1984); Schilsky, supr=. A major advantage of HU is that it is readily absorbed after oral ingestion and blood levels peak in 2–4 hours. Donehower, supra. It also distributes into the cerebrospinal fluid. When Aph is administered by continuous infusion, peak plasma levels of 3 $\mu$g/ml can be achieved with minimal toxicity. Sessa, supra.

The ultimate choice of timing and routes of administration of an RA and TCI depends upon specific pharmacodynamic characteristics of absorption or metabolism of each agent in a particular biologic system.

Direct methods for evaluating change in kinetics of the cell cycle in tissues removed from a human host use DNA-specific labels and flow cytometry. Riccardi A. et al., Europ. J. Cancer 27: 882–7 (1991); Mitsuhashi et. al. Cancer 70:2540–6, 1992; Raza A. et al., Arch Pathol. Lab. Med 115:873–9 (1991); Spyratos F et al., Cancer 69: 470–5 (1992); Kuo S-H and Luh K-T, Acta Cytol. 37:355–7 (1993); Am J Surg Pathol 17:1003–10 (1993).

A major advantage of the present invention, however, is that such knowledge is not essential for some degree of synergy to be achieved, even with simultaneous application of the RA and TCI. In the body of a living host, catabolism or elimination of any agent must be gradual. Thus, the optimal blood concentration level of an agent might be reached at some point during the pharmacokinetics of elimination.

Major advantages of the invented method are that the range of concentrations of agents for effective synergistic actions can be relatively broad as indicated by $S_{MAX}$ data shown herein, and that the target interval during which the effect of a TCI will be maximum need not be rigorously restricted.

A number of the agent concentrations found to be operative as RA in synergistic matches, as demonstrated by MTT previously had been utilized as single chemotherapeutic agents in humans or in animal trials. Several of these agents have been tested in dose ranges that produced, or could be estimated to produce, plasma levels well above the in vitro ranges sufficient to achieve $S_{MAX}$ shown by the MTT. Moreover, many of these agents would like be safe for therapeutic use, particulary at the lowered dosages made possible through practice of this invention. Table 35 lists examples of relevant data previously reported in the scientific, or medical literature. References are Blumenreich, supra; Belt R J et al., Cancer 46:455 (1980); Allegra C J et al., In Cancer Chemotherapy Principles and Practice, pp. 110–153, ed. Chabner B A and Collins J M, JB Lippincott Co. Philadelphia (1990); Sessa, supra; Calabressi, supra;

Buchholz, supra. The plasma levels shown in Table 35 represent values directly measured in humans and published, or values estimated from reported dosages and blood volume of dogs.

With this invention, the observed interaction of RNR inhibitors with STSP or K252A and the interaction of STSP with cisplatin or alkylating agents may provide significant new chemotherapeutic utilization or development of STSP and homologues. Although STSP and homologues or analogues have been considered as anti-neoplastic agents, Schwartz, supra, clinical use has thus far been circumscribed. The invention should permit their use and development.

This invention can also be used to control microbial or parasitic infections where the cell cycle of each infectious organism is much shorter than the cell cycle in human cells. Thus, even the brief application of a limited restraint condition and TCI might prove clinically significant. See Examples 17 and 22.

This invention is also useful in the application of herbicides, insecticides or other pesticides designed for the killing of a complex organism, extermination of agricultural or domestic pests, selective poisoning of any number of living unicellular or multicellular organisms including any member of the animal and plant kingdoms, or cells infected by mycoplasma, viruses, prions or other infectious agents may be possible.

In other specific embodiments of the invention, when the RA is ara-C, the TCI is not dGuo. In other embodiments, when the RA is dThd or BrdU, the TCI is not ara-C. In still other embodiments, when the RA is dGuo, the TCI is not camptothecin; when the RA is ara-C, the TCI is not cisplatin; and when the RA is dipyridamole, the TCI is not cisplatin. In further embodiments of the invention, when the RA is bryostatin, the TCI is not cisplatin; when the RA is quercetin, the TCI is not cisplatin; when the RA is STSP, the TCI is not cisplatin; and when the RA is tamoxifen, the TCI is not cisplatin.

The following other uses are also contemplated:

(1) uses in chemotherapy or radiant energy therapies to exterminate neoplastic cells in the human body or in tissues removed for autotransplantation or heterotransplantation;

(2) uses in immunotherapy or transplantation medicine to control the excessive proliferation of abnormally destructive immunocytic clones, such as in graft vs. host reactions;

(3) uses in fertility control including destruction of germ line or conceptus tissues;

(4) medical anti-microbial therapies, systemic use with anti-viral, anti-bacterial or anti-fungal agents;

(5) medical anti-malarial or other anti-parasitic chemotherapies;

(6) procedures for preventing in vitro contamination of cell or organ cultures by microbial infections;

(7) killing of neoplastic cells in vitro prior to autotransplantation of bone marrow;

(8) destruction of non-neoplastic but functionally abnormal cell clones, e.g., excessively proliferating immune cells (autoimmune disease) and psoriatic epidermal cells;

(9) to guide the synthesis or identification of new classes of agents which can be applied as RA or TCI, and to lead to new utilizations of presently available; and

(10) to effect a biochemical organ ablation, e.g., thymectomy or prostatectomy.

The strategy designed to potentiate TCI actions during the somatic cell cycle may prove to exert similar effects in germ line cells undergoing complete or reduction divisions, so that the methods employed can in principle be applied to fertility control or sterilization.

The following examples set forth various aspects of the invention.

EXAMPLE 1

This example shows the relationship of progressively increased concentrations of dThd to growth inhibition of a population of human malignant cells during the mean time of a single cycle of cell-division.

Microcultures of human promonocytic lymphoma cells (U937) ("the U937 cells") originally obtained from the American Type Culture Collection (CRL 1593) and later grown by Dr. K. Zoon at the FDA in Bethesda, Md. were set up in a multiwell plate with serial two-fold dilutions of dThd in tissue culture growth medium (RPMI 1640 plus 10% Nurserum and antibiotics). The volume of medium per well was 100 $\mu$l and the cell number per well was about $1 \times 10^5$. The plate was incubated at 37° C. for 24 hr.

A dye, 3-[4,5-dimethylthiazol-2-yl]-2,5-diphenyl-tetrazolium bromide (MTT), was used as a chromogenic indicator of the metabolically active cell mass. Viable cells metabolize the dye and accumulate a reduced formazan product (blue color) which is solubilized for colorimetry. Mossman T, J. Immunol. Methods 5:55–63 (1983); Li L and Lau BHS, In Vitro Cell Dev. Biol. 29A:531–536 (1993). The MTT assay has been established as useful for measuring either growth inhibition or population killing. Plowman, supra. The MTT method is ideal for cells tested in suspension growth, and can also be used for some cells growing in monolayers. It correlates well with in vivo biologic activities of agents used in clinical chemotherapies and has been shown to be an appropriate indicator of cell sensitivity for clinical applications of agents intended for use in chemotherapy. Alley, supra; Hofs, supra; Wilson J K et al., Br. J. Cancer 62:189–94 (1990); Plowman, supra.

Thirty $\mu$l of 0.5% MTT in phosphate buffered saline was added to each microcultute well at the appropriate time. After incubation at 37° C. for 3 hr, 120 $\mu$l of an aqueous solution of 10% SDS with 0.01 N HCl was added to release and dissolve formazan product. This was accomplished by overnight incubation of the plate at 37° C. After careful mixing of the microwell contents by placing the plates on an orbital shaker for 5 minutes the absorbencies were quantitated by spectrophotometry at 570 nr with a Ceres UV 900 HDI microwell plate reader (from Biotek Instruments Inc, Winooski, Vt. 05404-0998). Absorbance data was normalized to a blank well containing all reagents without cells and was collected semi-automatically.

An alternative method for cells growing in monolayers utilizes a crystal violet (CV) stain for cell proteins. Damaged cells detach from the substrate so that wells in which cells have been depleted or where cell growth is inhibited stain relatively weakly in comparison to controls. In this method cells adherent to microwells are fixed by addition of 25 $\mu$l of 4% formaldehyde to the well medium. After 30 min. at room temperature, adherent cells are washed and stained for 15 min. with a solution of 0.5% crystal violet. Excess stain is washed off by repeated and gentle aqueous rinses and the plates are dried overnight in the dark. After adding 100 $\mu$l of 50% ethanol to each well, the plates are agitated at slow speed on a Mini-Orbital shaker for 20 minutes. After an additional 40–60 minutes adsorbance in each well is measured on an ELISA reader at 570 nm. Example 11. This procedure is valid when viable cells adhere to plastic (see Grando S A et. al. Skin Pharmacol 6:137–47 (1993)).

FIG. 4 shows a plot of percent of growth inhibition for U937 cells as a function of treatment with increasing concentrations of dThd.

EXAMPLE 2

This Example shows flow cytometric analysis of the U937 cells exposed to a range of concentrations of dThd below the $IC_{40}$. Flow cytometric analyses were performed with a Coulter Epics System (purchased from Coulter Corp, Hialeah, Fla.). Cells were disrupted in buffer with 0.1% Triton-X 100 (or 0.6% NP40), so that the nuclei could be stained with 0.05% propidium iodide (PI). See Shapiro N M, Practical Flow Cytometry, Man R Liss, N.Y. (1988); Nicoletti I et al., J Immunol Methods 139:271–9 (1991). Analyses of 10,000 nuclei were performed with graduated concentrations of dThd at serial time points. Histograms of PI fluorescent emissions at 675±10 nm were used to discriminate cell cycle fractions of the target population. The results are shown in FIG. 5. The proportion of cells in each phase of the cell cycle is represented by stack bars above the X-axis as a fraction of those cells with intact DNA structure. The fraction of cells with depleted DNA in each sample is represented below the X-axis as a percentage of the total cell number. Cells with depleted DNA are presumed apoptotic. Crompton S T et. al. Biophys. Biochem. Res. Comm. 183:532–537 (1992). Each stack bar in FIG. 5 represents the cell cycle distribution of a population sample of >10,000 cells, analyzed for each indicated dThd concentration at indicated treatment times.

EXAMPLE 3

This Example shows flow cytometric analysis of the U937 cells exposed to up to 3 mM dThd at intervals of up to 24 hr, in order to demonstrate the relationship of progressively increased concentrations of dThd to detention or static synchronization of human lymphoma cells in the cell cycle hierarchy. Flow cytometric analyses were performed as in Example 2. The results are shown in plot A of FIG. 5 from Example 2.

EXAMPLE 4

This Example shows the relationship of progressively increased concentrations of HU to growth inhibition of a population of the U937 cells during the mean time of a single cycle of cell-division. An MTT assay was performed as in Example 1 except that the agent tested was HU. The results, shown in FIG. 6, demonstrated that the $IC_{40}$ for HU exceeded 2 mM.

EXAMPLE 5

This Example shows that HU treatment increased cell cycle transit times, according to flow cytometric analysis. The U937 cells were exposed to a range of concentrations below the $IC_{40}$ and sampled for flow cytometry at intervals of 8, 16, and 24 hours. Flow cytometric analysis was performed as described in Example 2.

As shown in FIG. 7, in a range of 0.125–1 mM HU treated cells continued to enter S phase for up to 16 hr and no more than 20% of cells became DNA depleted. At the lowest concentration of 0.13 mM HU there was evidence of a minimal population movement into $G_2$ and M phases from the expanded S phase. This was consistent with a dynamic retardation of S phase, as is also shown in FIG. 4 in cells treated with dThd.

At concentrations of HU>1 mM, shown in FIG. 7 (see the 2 mM stack bar at 24 hr), a major increase in cells with depleted DNA became evident. This reflected significant cell damage by high concentrations of HU as the malignant cells transited S phase.

Similar cell cycle changes to those obtained with low concentration of HU were obtained with the RNR inhibitors dAde and dGuo when used in ranges below the $IC_{40}$. At appropriate concentrations, each of these RNR inhibitory agents functioned as RA.

EXAMPLE 6

This Example demonstrates that excess dThd produced apoptosis in malignant human cells.

Some damaging effect of >1 mM dThd in human lymphoma cell cultures was indicated from earlier studies, e.g., Lockshin A et al., Cancer Res 44:2534–2349 (1984); Peterson A P et al., Basic Life Sci 31:313–34 (1985). Nevertheless, 3 mM dThd was used as a "mock control" to emulate effects of the cytokine interferon on growth inhibition and static synchronization of human malignant lymphoma cells in the $G_1$ to S phase transition, since it is known to cause cell cycle arrest and is currently used for this purpose. See Grimley, supra. Krek W and DeCaprio J A, Methods Enzymol 1995;254:114–24 (1995). During those tests, unexpectedly, the cell cycle arrest caused by 3 mM dThd itself was accompanied by a pronounced DNA fragmentation.

Samples of the U937 cells were exposed to a series of concentrations of dThd for 24 hr. Their DNA was isolated by lysis of cell samples in TE buffer containing TRIS 10 mM, EDTA 10 mM, SDS 0.5% and proteinase K 200 μg/ml at 50° C. for 2 h. The proteins were precipitated in a 1M solution of NaCl and centrifuged at 2,500×g for 30 min at 40° C. DNAse free RNase (25 μg/ml) was added to the supernatant and incubated for 30 min at 37° C. Spectrophotometric quantitation of the DNA in the supernatant was quantitated by absorbance spectrophotometry at 260 nm. Volumes adjusted to contain equal amounts of DNA were mixed with a loading buffer of 40% (w/v) sucrose, 0.1M EDTA pH 8.0, 0.5% (w/v) sodium lauryl sulphate and 0.05% (w/v) bromophenol blue. Samples were applied to separate lanes of a 1.2% agarose gel and electrophoresed in a horizontal apparatus (BRL, Bethesda, Md.) with TE buffer for 3 h at 5 volts/cm. Separated bands of DNA were stained with ethidium bromide ann. photographed in UV light (Fotodyne Inc.). FIG. 8 shows a negative image of photographed results, showing multiple bands of low molecular weight oligonucleotides in cells treated with dThd (bracketed portion of the image). The lowest molecular weight (about 180 bp) was determined with a standard 123 bp ladder from Sigma Chemical Co. (Cat. #D5042). The result shown is a classical "DNA ladder," characteristic of the fragmentation of DNA macromolecule in apoptosis. See Tomei, supra; Obeid, supr; Gold, supra.

EXAMPLE 7

This Example shows that low concentrations of dThd act as an RA to retard S phase.

Whole cell extracts (U937 cells) were prepared in an SDS 2× sample buffer (100 mM Tris.HCl (pH 6.8), 200 mM DTT and 4% sodium dodecyl sulfate) and boiled for 5 minutes. Protein concentrations were assayed, and samples of 100 μg of protein per lane were applied to 7.5% SDS-polyacrylamide gels (PAGE). Resolved proteins were transferred to Immobilon P (Millipore), and pRb was localized with monoclonal anti-pRb (Santa Cruz, IF8) and a chemiluminescence procedure (Amersham ECL). Samples for flow cytometry were prepared and flow cytometry was performed as described in Example 2.

Figure 9D:
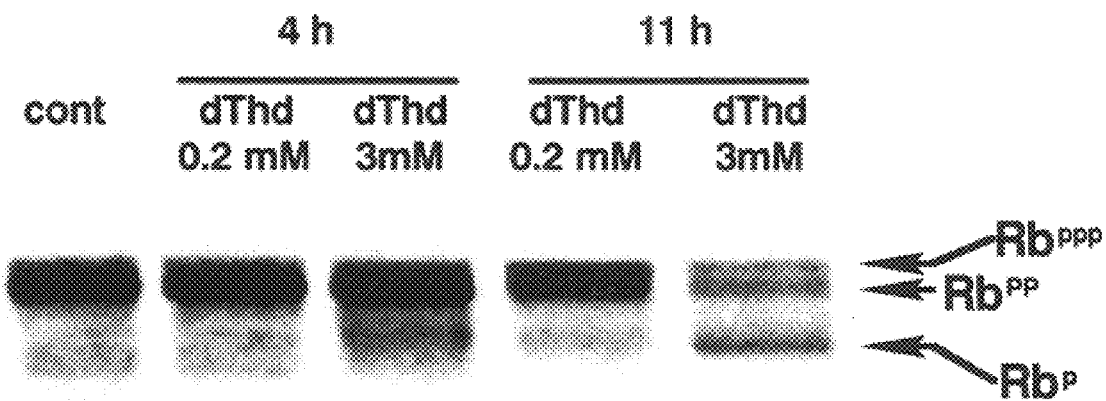
FIG. 9 is a series of flow cytometric DNA histograms showing the effect of dThd on cellcycle progression (a–c) and an inmmunoblot for pRb mobility reflecting phosphorylation status (d).

FIG. 9 contrasts the effects of low and high concentrations of dThd. Whereas 0.2 mM dThd permitted continuous cell transit, 3 mM dThd arrested cell cycle progression at G1/S. For flow cytometry FIGS. 8 a–c, samples were: (a) untreated controls; cells treated with (b) 0.2 mM dThd for 4 hrs showing that $F_S$ was decreased, but that the cell distribution remained unform, or with (c) 3 mM dThd, showing progressive depletion of the $F_S$ with a trough in early S phase (position of arrow), both indicative of $G_1/S$ phase arrest. These findings were consistent with dynamic retardation of S phase transit by low dThd concentrations. The immunoblot (d), shows protein mobility differences of pRb, specifically an accumulation of $pRb^P$ (the hypophosphorylated form) in the sample treated with 3 mM dThd for 4 or 11 hours, in comparison with either the control sample or the 0.2 mM dThd sample treated for 4 hours or 11 hours.

Phosphorylation of pRb is essential to progression of the cell cycle from $G_1$ into S phase. Wiman K G FASEB J 7:841–5 (1993). In a hypophosphorylated state, pRb fails to release the transcriptional activation factor $E_2F$ required for initiation of S phase (see FIG. 1). Therefore, hypophosphorylated $pRb^P$ is associated with $G_1$ phase, while phosphorylated $pRb^{PPP}$ is associated with S phase transition. At the relatively low concentration of 0.2 mM dThd, shown by flow cytometry to be associated with S phase retardation, the phosphorylation of pRb, did not appear to be grossly inhibited compared to control cells. In contrast, the more concentrated 3 mM dThd, shown by flow cytometry to be associated with $G_1/S$ phase arrest, pRb phosphorylation was inhibited.

EXAMPLE 8

This Example shows how the biological interactions of dThd and STSP were quantitated by an in vitro microculture indicator system.

Figure 12:
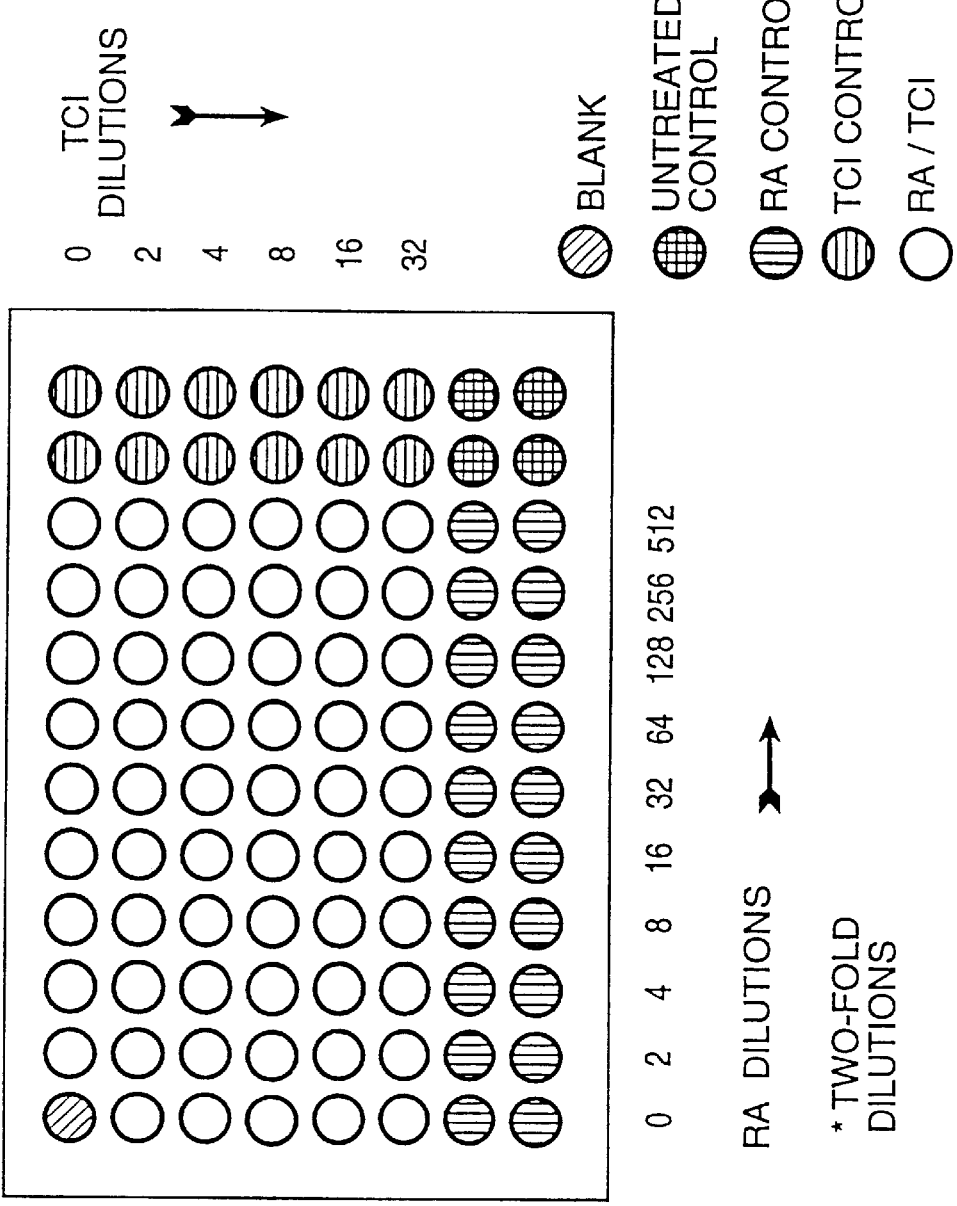
FIG. 12 is a diagrammatic representation of the set-up of a multiwell microculture plate with bivariate two-fold serial dilutions of agents for the microculture indicator system.

Flat-bottom 96-well plates of tissue culture quality (Coming or Costar) were set up with two-fold serial dilutions of each agent to be tested, e.g., the RA and TCI, using a multichannel pipettor with adjustable volume, e.g., Costar or Rainin, to perform serial mixing. This set-up is diagrammed in FIG. 12. Two rows and two columns in each plate were reserved as single agent controls (RA or TCI), four wells were reserved in the lower right comer as untreated cell controls and one well was reserved in the upper left comer as a blank with reagents only. In each plate, a total of 59 wells then contained bivariate agent combinations, the bivariate serial dilutions.

Agents were serially diluted by serial mixing in two separate plates or series of wells, and then were combined prior to addition of a fixed volume and density of the U937 cells in a suspension calculated to deliver about $1 \times 10^5$ cells per well. In this Example, the dThd concentrations and ratios to STSP were varied in two-fold steps along horizontal and vertical rows. Thus, the diagonal axis from top left to bottom right showed constant ratios, while the diagonal axis from bottom left to top right shows four fold increasing ratios of TCI/RA. When present, a maximum of synergistic effects of RA and TCI usually have been found along this diagonal.

The range of serial concentrations of dThd was 3 mM through 0.01 mM and the range of serial concentrations of STSP was 100 nM through 3 nM. Cells were added after serial dilutions of the dThd had been dispensed. Cells were dispensed at about $10 \times 10^4$ cells per microwell to provide optimal sensitivity of detection of cell damage in subsequent colorimetric assays. The plate was incubated at 37° C. for 4 h before the addition of serial dilutions of the STSP. The final volume of medium was 100 µl/well. The plates were further incubated at 37° C. for a total duration of 18–24 h. The dye MTT was used as a chromogenic indicator of the residual and metabolically active cell mass. (Described in Example 1.)

Figure 13:
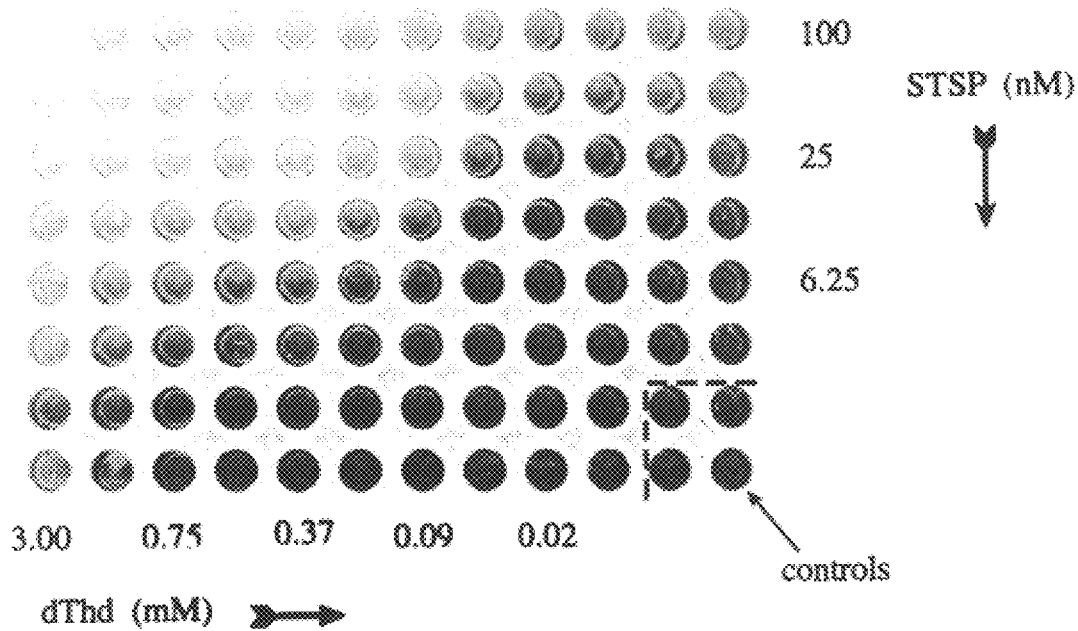
FIG. 13 depicts the digitized reflectance image of an MIS assay, testing the interactive effects of dThd and STSP on human promonocytic lymphoma cells.

FIG. 13 shows a digitized reflectance image of the actual plate used for this Example of BVSD as captured by a Scanmaker 2 (Microtek) with Adobe photoshop software in a Mackintosh Quadra 800 and transferred to Aldus Persuasion 3.0 for labelling and printing at 300 dpi. In this MTT assay, normalized absorbance data was collected semiautomatically from each microculture well with a Ceres UV 900 HD1 plate reader, from Biotek Instruments Inc., Winooski, Vt. 05404-0998, stored in an EIA file under the Ceres 900 program, transferred in comma delimited format to a floppy diskette, and imported into a spread sheet program (Borland Quattro Pro) for data manipulations. Table 4 shows the imported MTT data as manipulated into a tabular format using an algorithm presented in Tables 3A–E. Table 4 shows data for dThd and STSP mathematically translated into a percent inhibition of cell growth (columns with %) by comparison to the averaged absorbance in microcultures of untreated control cells (mean values from four wells in lower right comer of microplate, see FIG. 12).

EXAMPLE 9

This Example demonstrates a correspondence of cell depletion, or growth inhibition, as quantitated by MTT assays with cell damage quantitated by an assay for lactic dehydrogenase (LDH) enzyme release. As a means to assure the significance of the MTT assay in Example 8, results were compared in duplicate assays for MTT and release of LDH.

The MIS set up was identical to that described in Example 8. The relative activity of LDH released into supernatant from each microculture well was detected by a coupled enzymatic assay, Decker et al., J. Immunol. Methods 15:61 (1988), in which the chromogen 2-(p-iodophenyl)-3-(p-nitrophenyl)-5-phenyl tetrazolium chloride (INT) is converted to a red INT-formazan product by NADH in the presence of diaphorase.

Figure 17:
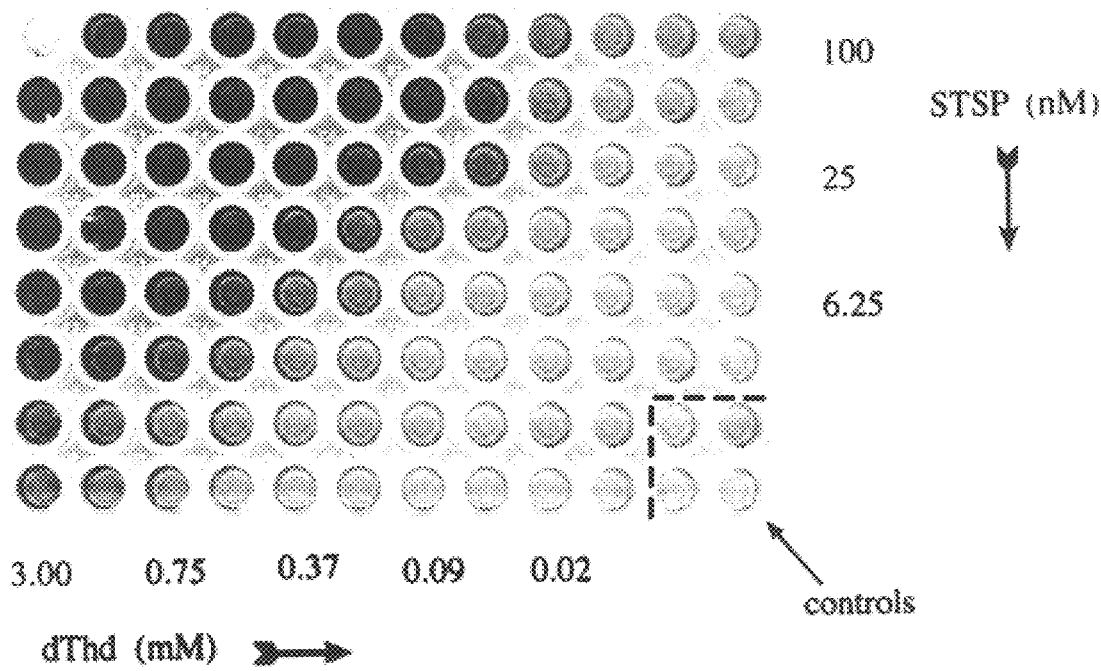
FIG. 17 depicts a digitized reflectance image of the LDH assay testing the interactive effects of dThd and STSP on human promonocytic lymphoma cells.

In this procedure, after incubation and at the time for assay, 50 µl of fresh medium was added to each microculture well prior to assay and microcultures in the entire 96 well plate were simultaneously sedimented at 400×G for 10 min in a Becton Dickinson refrigerated table top centrifuge using a plate carrier. A 50 µl sample from each microwell then was removed carefully and transferred to a corresponding well in a clean 96 well plate. LDH activity was quantitated by means of the CytoTox96 assay, Promega Corp., Madison, Wis. 53711, according to the manufacturers instructions. In tests to determine the total LDH in each microwell, 10 µl of lysing reagent (from the CytoTox96 assay kit) was added to the fixed 100 µl volume with cells and medium prior to the above step. UV 900 HD1 plate reader. The LDH activity proved stable in refrigerated samples for at least 5 days. FIG. 17, shows a digitized reflectance image of the LDH plate (captured as in Example 8, FIG. 12).

Figure 18:
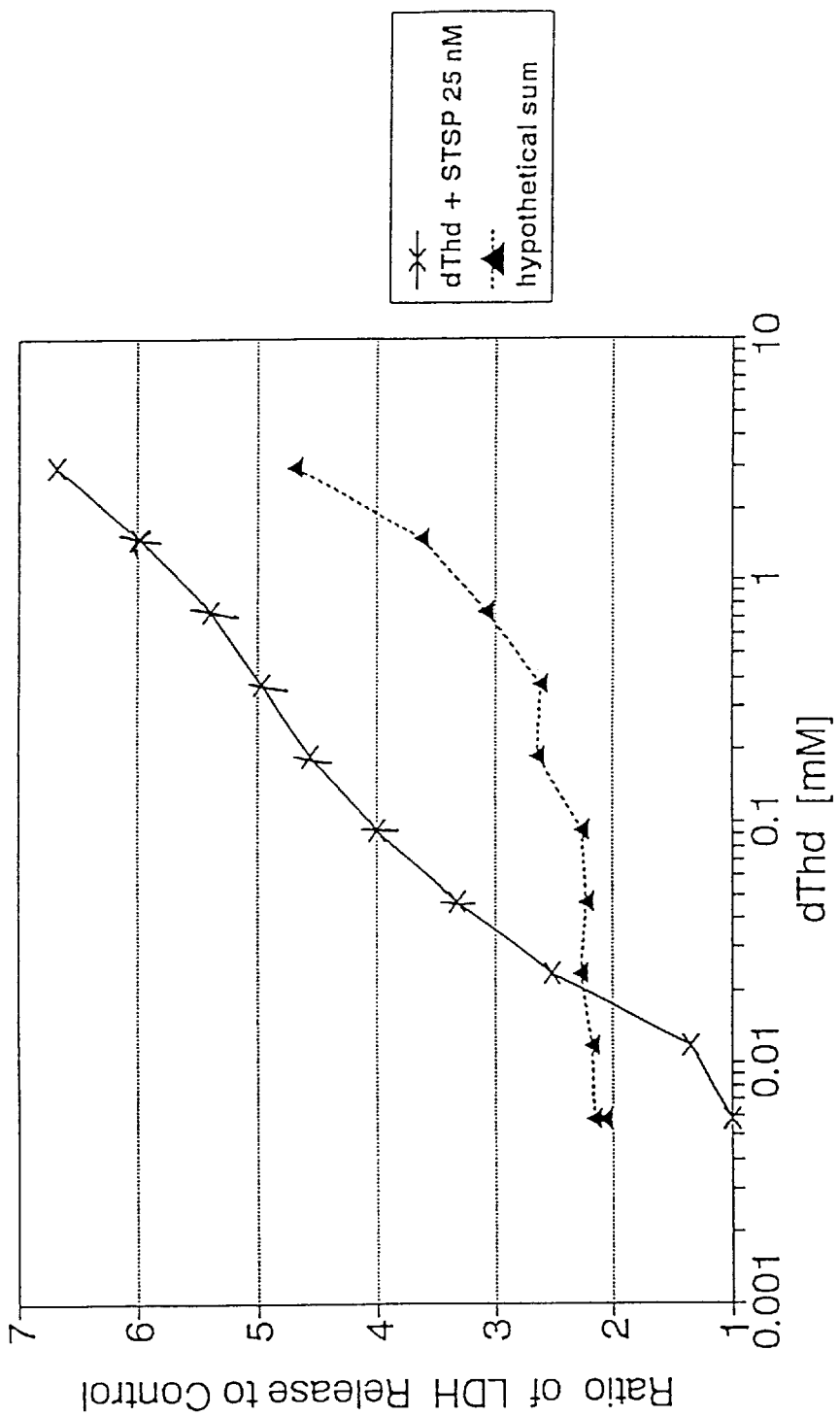
FIG. 18 depicts O/S plots of human promonocytic lymphoma cells treated with varying concentrations of dThd and STSP as measured in an LDH assay.
Figure 19:
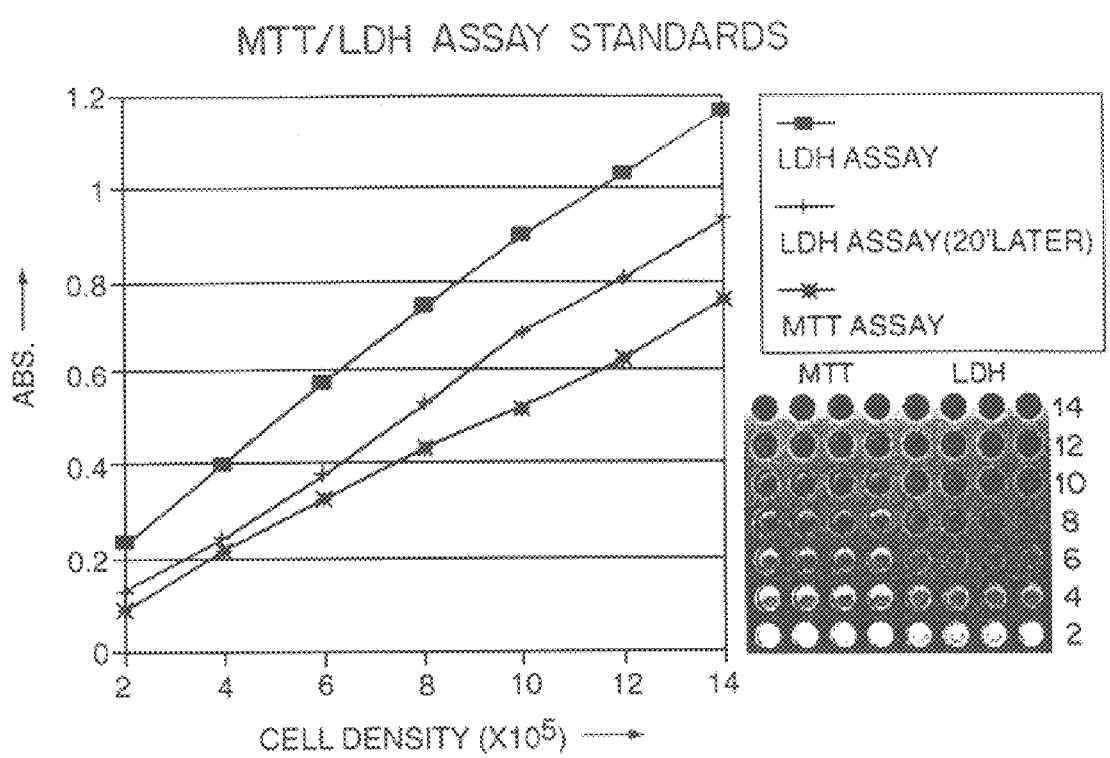
FIG. 19 depicts a graph and digitized reflectance image demonstrating the comparable linearity of the MTT and LDH assays.

Table 5 shows the CRR for an LDH assay performed as described herein. This CRF was generated using the formulas shown in Table 3A–C, O and P. FIG. 18 is an O/S plot for the data shown in Table 5, for one concentration of STSP. These formulas use useful forum assay in which positive numbers are obtained as compared to % inhibition used above. FIG. 19 demonstrates the comparable linearity and accuracy of MTT and LDH assays, as a function of U937 cell numbers from $2-14 \times 10^4$/cell in a test plate. Particularly for the latter purpose, all of the cells in each microculture well were totally lysed with Promega lysing reagent prior to the calorimetric measurement.

EXAMPLE 10

This Example shows a delayed proliferation assay to verify that the effect of a synergistic match between dThd and STSP on cell killing extended beyond a single mean doubling time of the targeted population.

Microcultures treated with an agent or agents for a defined period (exactly as in Example 8) were washed. Seventy-five percent of the well volume was removed without disturbing the sedimented cells, and medium was added to yield a 1/5 dilution. In three additional washes and cell sedimentations, 50% of the medium was replaced such that the original concentration of agents was reduced to <5%. The metabolic mass of cells surviving or proliferating at 48 hr after the washings, including the untreated control cells, was then assayed by the MTT method (total elapsed time of 70 hours). CRR are shown in Table 6.

As an adjunct to the delayed proliferative assay, we utilized an "immediate plate" to quantitate the cell mass at the beginning of the experiment ($N_0$=original cell mass). The "immediate plate" was prepared in parallel to the usual "test plate" shown in FIG. 12. It required no more than a single column of microwells filled with 50 μl of growth medium each, and aliquots of cells in 50 μl identical to those transferred to the usual "test plate". The immediate plate was incubated at 37° C. to complete the MTT assay for the same time as used for the test plate (i.e. 3 hr).

FIG. 20 is a plot of the U937 cell population growth in various concentrations of STSP as a function of dThd concentration. Taking the mean final cell mass at 70 hours as N, each data point represents a ratio of the mean cell mass of dThd-treated cells as fraction of $N/N_0$. A ratio of $N/N_0=1$ indicates no change in original cell mass (i.e. no growth of the targeted population). A ratio of $N/N_0>1$ indicates overall growth of the targeted population. A ratio of $N/N_0<1$ indicates overall population loss (cell killing).

FIG. 21 is a plot of the cell population loss in various concentrations of STSP as a function of dThd concentration in relation to the mean original cell mass ($N_0$) as determined in an "immediate plate". Taking the mean final cell mass at 70 hours as N, positive percentages represent the % effective cytotoxicity ($EC_\%$) expressed as $1-N/N_0$ and converted to a percentage, in relation to concentration. Thus, EC obtained only for ratios of $N/N_0<1$ (i.e. positive percentages). FIG. 21 shows that at 70 hours after treatment the maximum effective cytotoxicity for cells treated with 175 nM STSP was about 85%. The same result could be achieved with 25 nM STSP in the presence of 0.1 mM dThd or 13 nM STSP in the presence of 0.5 mM dThd. Comparison to FIG. 20, shows that 0.1 mM dThd itself had minimal effect on cell growth as compared to controls.

More than 3 mM dThd was required to achieve effective cytotoxicity of just 40% ($EC_{40}$).

EXAMPLE 11

This Example shows scheduled testing of STSP as a TCI with dThd as the RA.

An MIS was performed as described in Example 8, except that results were compared when STSP was added to each microculture well at 0 or 4 h after the beginning of treatment with dThd. The total duration of STSP treatment in each plate was identical. Consistent with, a dynamic retardation of S phase by dThd, potentiation of STSP by dThd was greater when cells were treated with dThd for 4 hr prior to STSP (top) rather than coincidentally at zero time (bottom). Time for dThd uptake and equilibration with metabolic pools could explain an action lag. However, the consistent absence of a linear dose effect relationship and the greater activity in the range of 0.05 mM–0.5 mM dThd as compared to effects of concentrations >0.5 mM supported the concept of a potentiating effect by dynamic retardation rather than by a stoichiometric metabolic competition. Table 7 shows the results of schedule dependent testing.

EXAMPLE 12

This Example confirms that STSP induces apoptosis during S phase of the cell cycle and that DNA fragmentation was enhanced by dThd.

Figure 23:
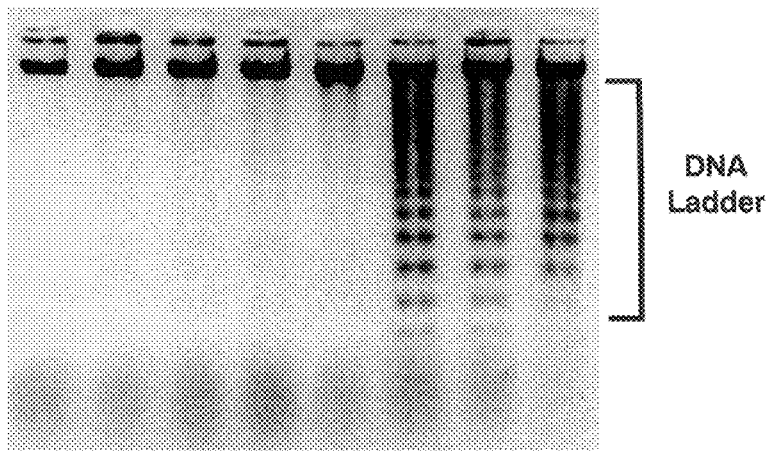
FIG. 23 depicts the results of DNA gel electrophoresis showing a ladder pattern of DNA fragmentation in extracts from human promonocytic lymphoma cells exposed to dThd and/or STSP.

The U937 cells treated with 50 nM STSP for 0–12 hours were analyzed by DNA gel electrophoresis as described in Example 6. FIG. 23 is a DNA gel demonstrating that 50 nM STSP could induce some "ladder pattern" DNA fragmentation in U937 cells in 8 hours. The effect became more conspicuous in cells treated for longer times (not shown) or with higher concentrations of STSP, and was accentuated by dThd.

Figure 24:
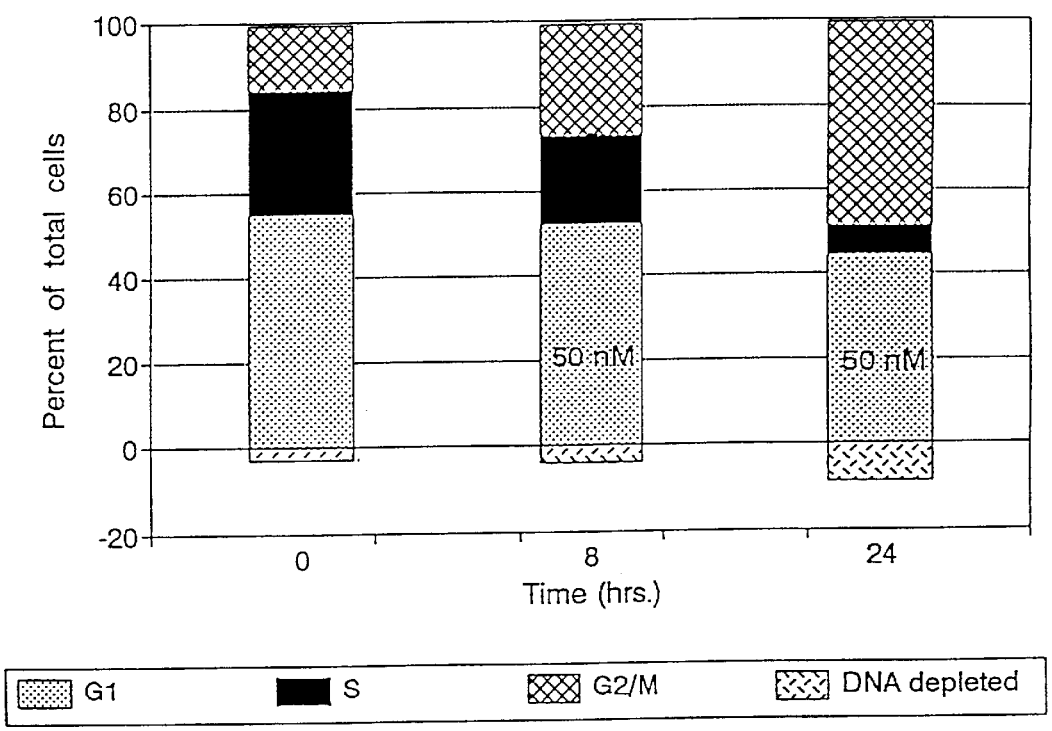
FIG. 24 depicts the results of flow cytometric analyses of human promonocytic lymphoma cells treated with STSP, showing accumulation in the $G_2$ and M phases of the cell cycle.

Using standard flow cytometry as described in Example 2, it was observed that U937 cells treated with 50 nM STSP gradually accumulated in the $G_2$ and M phases (FIG. 24). This effect was evident beginning at 4 hours after treatment and is shown at 8 hr and 24 hours after treatment. In FIG. 24, the proportion of cells in each phase of the cell cycle is represented by stack bars above the X-axis as a fraction of those cells with intact DNA structure, while the fraction of cells with depleted DNA in each sample is represented below the X-axis as a percentage of the total cell number. This fraction of presumed apoptotic cells was quantitated by the relatively decreased PI fluorescence of cells during flow cytometry (see Cromptons, supra). An accompanying reduction of cells in S phase indicated that the accumulation of cells observed in $G_2$ and M phases might represent survivors of a more numerous population that became depleted during S phase. Thus, 50 nM STSP behaved as a TCI with a target interval in S phase.

In a more sophisticated use of flow cytometry, DNA strand breaks were detected in nuclei by means of terminal transferase and homopolymer tailing as described by Gorczyca W. et al., Cancer Res 53:1945–1951 (1993). Samples of $1 \times 10^6$ cells were fixed in 1% buffered formaldehyde at 0° C. for 5 minutes, washed with PBS, resuspended in 70% ethanol and stored at −20° C. for 48 hours. Cells were rehydrated in PBS, then suspended in 100 μl of cacodylate buffer and 2.5 mM $CoCl_2$ to prepare them for the terminal transferase reaction. Biotin-labelled 16-dUTP and terminal transferase (Boehringer Mannheim, GmbH) were added to provide the final concentration of 0.5 nM and 500 units/ml, respectively, and reacted with the cells at 37° C. for 30 minutes. Cells were rinsed in PBS, resuspended in a 4× saline-citrate buffer with 0.1% triton X100, 5% (w/v) non-fat powdered milk and 2.5 μg/ml FITC-labelled avidin, Boehringer Mannheim, supra and incubated at room temperature for 30 minutes. Excess avidin-FITC was removed by washing the cells with PBS containing 0.1% triton X-100. In the cells with DNA damage, biotin-labelled dUTP was localized by the avidin-FITC: avidin and biotin form a strong linkage and reveal the extent of dUTP homopolymer tailing.

FIG. 25 shows flow cytometric cell cycle bivariate analyses concurrent with a test for, DNA fragmentation to establish that S phase is a target interval of STSP. Each histogram shows a 3-dimensional view of cell DNA content and quantity. The x axis, moving in the direction of the arrow, shows increasing amounts of DNA content per cell as measured by propidium iodide staining. The z axis, moving in the direction of the arrow, shows increasing number of cells. The y axis, moving in the direction of the arrow, shows increasing amounts of dUTP incorporation at sites of DNA fragmentation (evidence of apoptosis). The amount of DNA per cell reflects the cell cycle position of each cell.

Figure 25I:
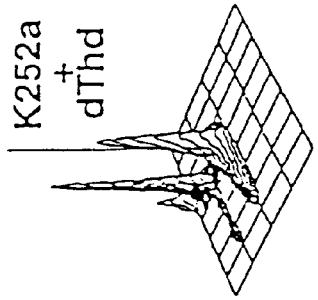
FIG. 25 is a series of bivariate flow cytometric DNA histograms (A–I) showing the results of analyses of human promonocytic lymphoma cells labelled with dUTP. Panel A is untreated control cells; panel B and C are cells treated with dThd; panels D is cells treated with STSP only; and panel E is cells treated with dThd prior to STSP, panel F is cells treated with KT5926, alone, panel G is cells treated with KT5926 and dThd; panel H is cells treated with KT252a alone; and panel I depicts cells treated with K252a and dThd.
Figure 25H:
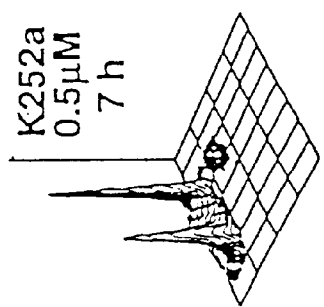
Figure 25G:
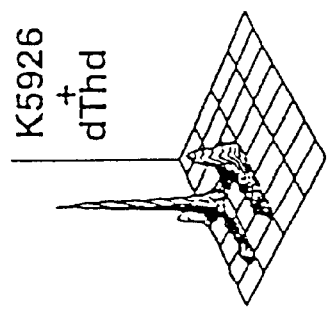
Figure 25F:
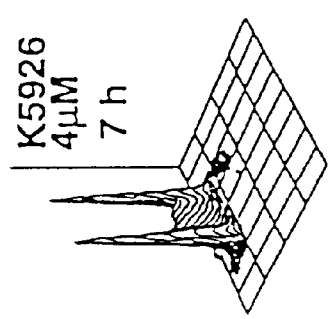

FIG. 25(a) shows an untreated U937 cell population in a normal distribution of cell cycle positions. FIG. 25(b) shows the appearance of cells with dUTP labelling, indicating DNA fragmentation, after 11 hours of treatment with 3 mM dThd. The position of these cells and the reduction of PI stained cells in S phase, suggests that the DNA damage occurred during S phase. FIG. 25(c and d) show very few cells labelled with dUTP, indicating minimal apoptosis. The large increase in cells positioned in $G_2$/M phase shown in FIG. 25(d) is characteristic of STSP and other indole carbazoles. FIG. 25(e) shows a marked increase in the number of dUTP labelled cells after 4 hours of treatment of 0.2 M dThd followed by addition of 25 nM STSP lasting an additional 7 hours.

Similar results are shown for cells treated similarly with two other indole carbazoles (KT5926, FIGS. 25(f and g) and K252a, FIGS. 25(h and i). Thus, the presence of dThd was associated with a dramatic concomitant reduction in the accumulation of cells in $G_2$ and M phases compared with that produced by STSP or related indole carbazole compounds alone.

Flow cytometry, with or without a DNA probe is almost essential for defining the target interval even when a DNA ladder pattern is shown, since DNA damage might be initiated in one phase and expressed in another. Zakeri Z F et al., FASEB J 7:470–478 (1993); Fisher, supra; Cotter T G et al., Anticancer Res 12:773–9 (1992); Lindenboi M L et al., Cancer Res 55:1242–7 (1995). If DNA fragmentation is not identified by DNA gel electrophoresis, other techniques such as employing Hoechst dye may be employed to analyze the cell cycle position of DNA damage. Sun X M et al., Analytic Biochem. 204:351–356 (1992); Chen U, Immunology 85:366–379 (1992).

EXAMPLE 13

This Example shows that detention of cells in $G_1$ or $G_0$ phase of the cell cycle reduced potentiation by dThd of STSP-induced apoptosis.

Treatment of human promonocytic lymphoma cells (U937) with 12-0-tetradecanoyl-phorbol-13-acetate (TPA) causes them to undergo macrophage-like differentiation and adhere to the surface of the plastic. Kurcz, supra. In this example, U937 cells were differentiated by treatment in suspension with 10 nM TPA (Sigma Chemicals) for 48 hours. After 48 hours in floatation, followed by 24 h of substrate attachment, the fraction of cells in S phase (Fs) was analyzed by flow cytometry as in Example 2, and results showed that TPA forced these cells into $G_1$ or $G_0$ phases of the cell cycle.

Figure 27:
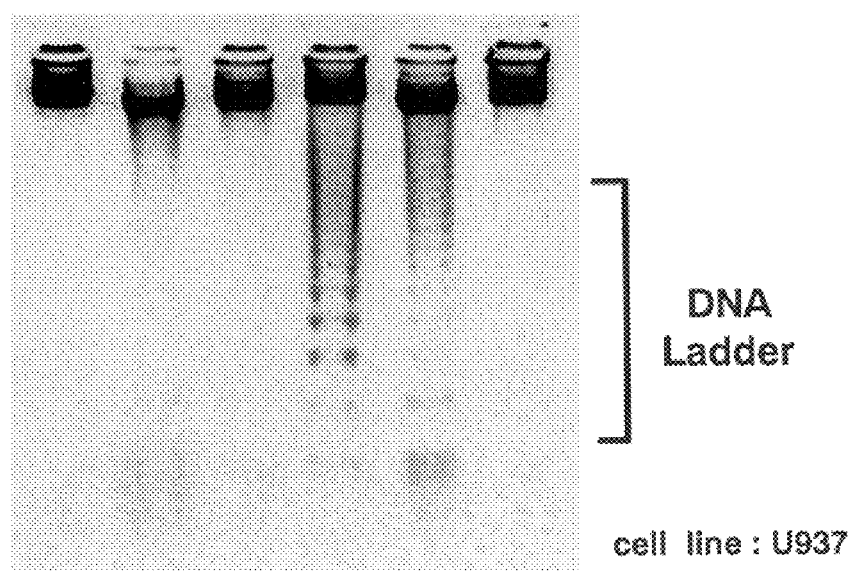
FIG. 27 depicts the results of a DNA gel electrophoresis experiment of DNA extracted from human promonocytic lymphoma cells incubated with TPA prior to addition of dThd and STSP.

After washing, the cells were placed in fresh growth medium, and treated ±dThd (0.19 mM) or ±STSP (25 nM) for 7 more hours. DNA extraction and gel electrophoresis was performed as in Example 6. FIG. 27 shows that TPA differentiation significantly reduced dThd potentiation of DNA fragmentation during STSP treatment.

EXAMPLE 14

This example shows that potentiation by dThd of STSP damage was due to dThd inhibition of ribonucleotide reductase (RNR)

In this Example, dCyt was added into cultures of U937 cells treated with dThd and ±STSP. MTT assays were performed as described in Example 8 and DNA extraction and gel electrophoresis were performed as described in Example 6.

Figure 28:
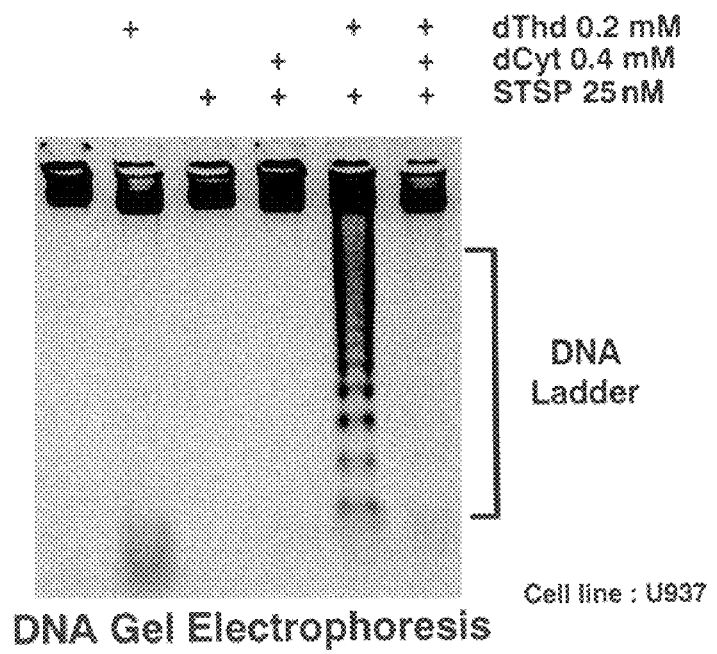
FIG. 28 depicts the results of DNA gel electrophoresis experiments showing decreased fragmentation of DNA extracted from human promonocytic lymphoma cells exposed to dThd and STSP in the presence of dCyt.

FIG. 28 shows decreased DNA fragmentation in samples subjected to both dThd and STSP when they also were treated with dCyt.

EXAMPLE 15

This Example shows, by means of a clonogenic assay, that exposure of cells to a synergistic match of an RA (dThd) and a TCI (STSP) for less than a mean generation time produced long term biologic damage to a targeted population of human malignant lymphoma cells (U937).

Figure 31:
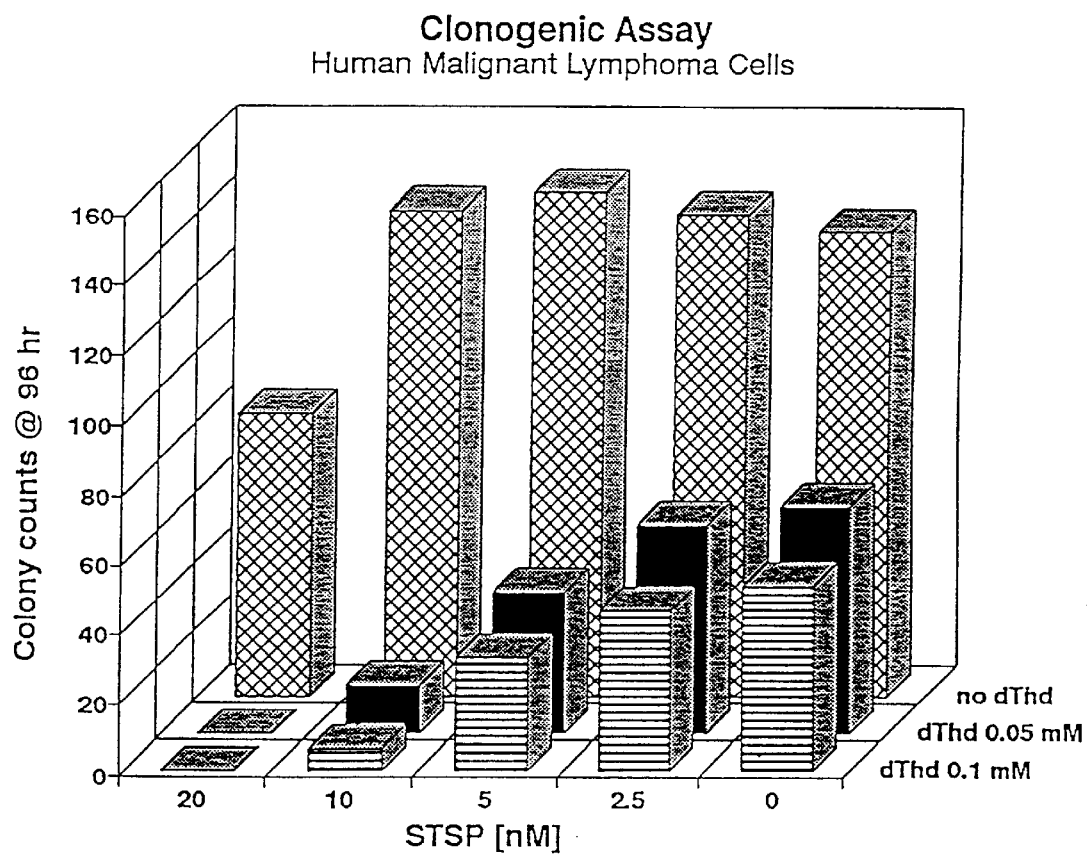
FIG. 31 is a bar graph depicting the numbers of colony counts of HPLC treated with indicated concentrations of dThd and/or STSP based upon combinations which were found to be synergistic matches.

Elimination of a targeted cell population by a cytotoxic agent or agent combinations can not be assured if cells with generative capacity survive. The clonogenic assay in soft agar or methylcellulose is a practical and useful means of determining long-term effects of cytotoxic agents on a malignant cell population, since malignant cells are often capable of growing and forming colonies in these media. The colony forming efficiency of any line or population of malignant cells must be established from the colony count in relationship to the inoculum number and varies over a wide range. With U937 cells, control studies showed an efficiency of at least 50% after 3–5 days of culture in methylcellulose. In this method, stock cell suspension was prepared in fresh growth medium ($8 \times 10^5$ cells/ml), and two-fold serial dilutions of dThd and STSP were made up to 40× final concentration in bivariate serial dilutions as described in Example 8. U937 cell suspensions in fresh growth medium were dispensed to a 24-well plate at 1 ml per well, and 50 μl of selected concentrations of dThd and/or STSP were transferred to designated wells and incubated at 37° C. (same protocol as Example 2A, Table 7). Methylcellulose (MC) solution 2.1–2.3% was obtained from Stem Cell Technologies in Vancouver, B.C. and made up in a series of sterile tubes: (a) 0.4 ml MC stock solution, (b) 50 μl of NuSerum, (c) $2 \times 10^4$ cells from the treated cell suspension from the 24-well plate (about 250 μl) and (d) complete growth medium to make a final volume of 1 ml (final cell density= about $2 \times 10^4$ cells). A syringe with 18 g. needle was used to transfer load 100 μl of each sample the final cell preparation to each of triplicate wells in a 96-well plate. Thus the final cell number was about 2,000 cells/well. Plates were examined daily for colony formation. At days 3–5, colonies were counted. and colonies were overlaid with MTT: 25 μl, incubated overnight at 37° C. and 100 μl of 4% formalin was added to aid visualization and photography. FIG. 31 shows results of a clonogenic assay at 96 hours. The effective. cytotoxicity was calculated as $1-C/C_0$ where C=the number of colonies formed by a sample of treated cells and $C_0$=the number of colonies formed by an equal sample of untreated cells. Whereas the maximum effective cytotoxicity of either 0.1 mM dThd or 20 nM STSP alone was 40–60% at 96 hours, almost total cytotoxicity was observed when cells were treated with an optimal synergistic match of both agents.

EXAMPLE 16

This Example shows, by means of a tumorigenic assay, that exposure of cells to a synergistic match of an RA (dThd) and a TCI (STSP) for less than a mean generation time produced long term biologic damage to a targeted population of human malignant lymphoma cells (U937).

The biologic behavior of xenografts of human malignant cells in immunosuppressed mice can approximate natural growth conditions in a patient, since the cells receive a local supply of plasma nutrients and can survive for several weeks. Thus, inoculated cells may survive in a latent state prior to growth, a condition not readily duplicated in vitro. Inoculura size is critical for observation of tumor growth within a practical time frame. Although immunocompromised mice do not mount an effective cell-mediated immune response to xenografted tissue, small inocula may be damaged by macrophages or natural killer cells before developing an effective vascular support. Preliminary experiments showed that subcutaneous inoculation of $1 \times 10^7$ human malignant lymphoma cells (U937) was tumorigenic in athymic nude mice. For test of tumorigenicity, U937 cells cultivated in plastic flasks with growth medium as described in Example 1 and growing logarithmically according to repeated cell counts at intervals of 24 hours, were treated: (a) dThd 0.2 mM for 12 hr; (b) STSP 25 nM for 8 hours; (c) a combination of dThd 0.2 mM for 4 hr followed by STSP 25 nM for 7 hr; or ((I) no treatment (controls). After treatment, cells were sedimented and resuspended in serum-free RPMI 1640. In each group four athymic Nu/Nu weanling mice of mean weight 17 gm were inoculated subcutaneously into both subscapular regions with 0.1 ml of RPMI 1640 containing $10^7$ cells (viability >90%). Formation of tumors in these subcutaneous sites was observed during the next 14 days. One control mouse died prematurely. At 14 days, all animals were sacrificed, tumors were photographed, tumors were carefully dissected, and tumor weights were recorded. Tumors were verified histologically. The animals receiving both dThd and STSP developed no tumors.

Table 34 shows the mean weights of tumors for animals receiving dThd only, STSP only, and no agent statistical evaluation. Differences in the fate of the dThd/STSP treated cells and single agent treated or control cells all were statistically significant.

Comparison of the results of Examples 10, 15 and 16 to the results of Examples 7 and 8 shows that an MIS for synergistic matching of RA and TCI may underestimate the effective cytotoxicity as reflected in delayed cell killing, clonogenic assay or tumorigenic assay.

The feasibility of therapeutic applications in man or in animals within the latter respective ranges of agent combinations is obvious from published data showing toleration of plasma levels of up to 6 mM dThd in human subjects, Blumenreich, supra, and animal tests of STSP as an antihypertensive with up to 700 $\mu$g/kg IV in rats and 130 $\mu$g/kg in dogs. See Buchholz R A et al. In Cellular and Molecular Mechanisms in Hypertension, p. 199–204, Plenum Press, N.Y. (1991) and Hypertension 17:91–100 (1991). And see Table 35.

EXAMPLE 17

This Example demonstrates a use of this invention in treatment of a yeast or fungal infections:

In this example, the $IC_{40}$ for an HU or other RA and the $IC_{50}$ for STSP or other TCI are determined with respect to growth inhibition of a yeast or fungal population during a predetermined generation time. A series of 96-well plates is filled with appropriate liquid or semi-solid agar-based growth medium, see McGinnis M R and Rinaldi M G in Lorian, supra, containing bivariate concentrations of the RA (maximum concentration=$IC_{40}$) and the TCI (maximum concentration=$IC_{50}$) as described in Example 8. Each microwell is inoculated with an equal number of the yeast or fungal organisms (100–2000 colony forming units/well). At 16–96 h after inoculation, and incubation at 30–35° C., parallel tests are performed to measure effects of the bivariate RI and TCI combinations on fungal growth using: (1) visible turbidity is noted in liquid medium and a digitized transmission or reflectance image is obtained for computer analysis, or (2) the MTT assay or other calorimetric assay is performed; and collected data are analyzed by combined results ratios and O/S differential plots; or (3) colony formation.

Colony formation is described as follows. Plates with liquid media are agitated on an orbital shaker and 5–10 $\mu$l of medium is aspirated from each well and diluted up to 1:100. Samples from plates with semi-solid medium are obtained by mixing each well contents in 100 $\mu$l of saline and macerating the agar with thorough mixing. From either plate, an aliquot of 0.5 ml then is plated on semi-solid growth medium in a petri dish; the petri dishes are incubated at 37° C. overnight and the yeast or fungal colonies are counted on each plate according to standard microbiologic procedures. Lorian, supra, pp. 53–197. The percentage inhibition of proliferation is calculated by taking the ratio of number of colonies formed by treated organisms to the number of colonies formed by untreated control organisms. Results, of the data analysis by data algorithms show a potentiating action of the RA on colony growth, inhibition by a TCI in a range of concentrations below the RA $IC_{40}$.

EXAMPLE 18

This Example demonstrates a use of the invention in potentiating damage to cells infected by a virus and selectivity due to changes in thymidine kinase (Tk) or pRb In cells infected by DNA viruses, the DNA biosynthesis is susceptible to dynamic retardation. Such viruses include members of the herpesvirus family. Many human malignant cells of Burkitt's lymphoma origin carry incomplete genomes of the Epstein-Barr herpesvirus, group virus and may express a thymidine kinase (Tk) of viral origin in addition to any endogenous Tk activity. Infection of cells with herpesvirus thus provides potential avenues for selective potentiation of TCI damage to the virus-infected cells using dThd acting as the RA.

In this example, cells are infected with a strain of cytomegalovirus according to procedure described by Berezesky I K et al., Exp and Mol Pathol. 14:337–49 (1971) and seeded into 96-well plates. The $IC_{40}$ of dThd is determined for uninfected cells. The virus infection proceeds over a period of several days with visible changes in infected foci: cells become enlarged and rounded with increases in both nuclear and cytoplasmic volume. Beginning at times from 0–24 h after infection, the cells in multiwell plates are. exposed to a series of scheduled and bivariate combinations with RA including dThd, HU, or Aph (maximum concentrations=

IC$_{40}$) for 24 hrs followed by STSP (maximum concentration=50 nM) for up to 24 h total duration. Cell damage is assessed using either the the LDH, MTT, or crystal violet assays. Results are compared to uninfected control cells treated identically with the bivariate combinations of dThd and STSP and data are analyzed using the appropriate set of formulas for CRR or O/S plots as described in Example 8.

As compared to the uninfected controls, cells in the infected culture show increased rates of cell damage as determined by increased LDH release at serial time points for each combination of RA and STSP.

In a related procedure, human malignant lymphoma cells are infected by herpes simple virus as described by Bedoya V et al., J. Natl. Cancer Inst. 41:635–52 (1968). The IC$_{40}$ of dThd is determined for uninfected cells. Beginning at times from 0 to 2 h after infection the potentiation of cell damage by bivariate combinations of RA (IC$_{40}$ maximum) and STSP (50 nM maximum) are applied in 96-well plates as described above, and data are analyzed after MTT, LDH or crystal violet methods. Cells in the infected culture show increased rates of cell damage at serial time points during the combined agent treatments. Analysis of the data and calculations of S$_{max}$ show action of dThd as an RA and potentiation of STSP in a range of dThd concentrations below the IC$_{40}$.

Cells infected by oncogenic DNA viruses, such as human papillomaviruses implicated in human carcinogenesis are dynamically retarded by the action of a virus that synthesizes a protein able to inhibit the function of pRb. Wimnan K G, FASEB J. 7:841–5, 1993. Virus transformed cells, such as cells that antecede development of human cervical carcinoma are particularly vulnerable to induction of apoptosis by STSP since they are not impeded from, moving through G$_1$/S into the target interval for STSP. Thus, they are selectively vulnerable to dynamic retardation by an RA and killing with STSP. Moreover, transfection of cells with oncogenic virus proteins serves as an RA to synergize with effects of STSP or other TCI.

EXAMPLE 19

This Example shows that the MIS and auxiliary data algorithms may be used to test for antagonistic interactions of drugs, or other agents used in medical therapeutics.

Drug interactions are an issue of major medical and pharmacologic concern. In chemotherapy, agent antagonisms can diminish specificity of agent actions and increase side effects. In tests with STSP as a TCI, which was shown in Example to exert biochemical effects during G$_2$ phase of the cell cycle, the inventors attempted to learn whether other agents acting in late S phase or early G$_2$ phase might enhance its effect by acting as RA. In fact, the inventors discovered that caffeine which is reported to influence the cell cycle at G$_2$ phase (Schlegel R; Harris M O; Belinsky G S J Cell Biochem 57:351–61(1995) strongly antagonized the action of STSP. This is shown in a differential O/S plot where the concentrations of caffeine tested were in a range of 0.1–2 mM and the concentrations of caffeine were in a range of 3.1–50 nM.

EXAMPLE 20

This Example shows that the MIS and auxiliary data algorithms may be used to test for synergistic interactions of drugs, toxic substances or other environmental hazards for genotoxicty.

Figure 11:
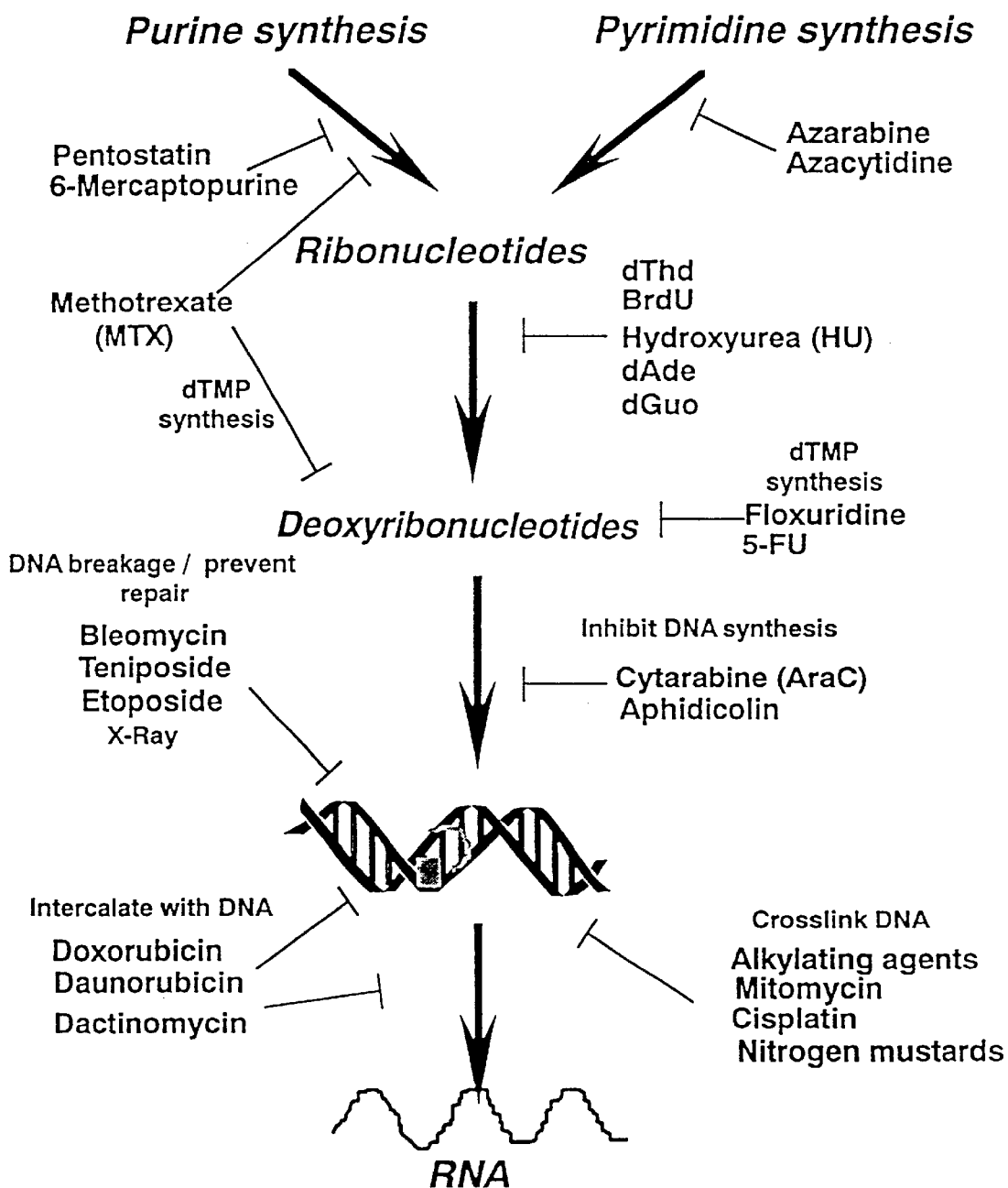
FIG. 11 is a schematic showing the actions of chemotherapeutic agents related to events in S phase.

Environmental of medical exposure of humans, animals or plant life to potentially hazardous agents which are genotoxic such as some of the compounds producing DNA lesions shown in Table 2 or FIG. 11 is a matter of considerable societal concern. By means of the MIS, cell cultures can be employed as a surrogate target population to analyze potential genotoxic effects to the extent that such effects may be cell cycle related. In this approach effects of a compound with unknown properties is tested according to the algorithms discussed herein. Agents which have effects related to the cell cycle are potentially genotoxic, but may be reversible. On the other hand, an agent which is not primarily genotoxic may become genotoxic when synergistically matched with a low and overtly non-hazardous concentration of another agent. This type of occurrence has been a major concern in the aftermath of episodes of major environmental stress such as oil or forest fires, or in military operations where toxic substances may be released with malicious intent.

In this example, the agent tested was DEET (N,N-Diethyl-m-toluamide) which is commonly applied in minimal dilutions as a topical insect repellant and has been a subject of safety investigations Osimitz T G and Grothaus R H J Am Mosq Control Assoc; 11:274–3 (1995). At concentrations above 0.5 mM, applicants identified induction of apoptosis in the U937 cells as well as in Jurkat T cells and Daudi B cells. In MTT tests, preliminary results with dThd or HU as prospective RA in ranges of about 0.05 to 3 mM showed no significant enhancement of the DEET-induced apoptosis. Additional tests of this and other agents using the MIS and auxiliary data analysis are thus possible.

EXAMPLE 21

This Example shows that the MIS and auxiliary data algorithms can be used to measure effects of a radiation source as a TCI or an RA for use in synergistic matches.

The role of p53 expression, and the cell cycle in determining cell sensitivity to radiation exposure has been a subject of many investigations (See, Kuerbitz S J et al. Proc. Natl. Acad. Sci. USA 89:7491–5 1992)

Using tritiated water as a low energy (beta ray) radiation source, tests are conducted for radiation effects on growth inhibition and % population loss at times up to 24 hours using the MTT assay. Serial two-fold changes in calibrated radioactive dosages are combined with two-fold serial dilutions of an agent being tested as an RA or a TCI. Data are analyzed by the auxiliary analytic methods shown in Examples 8 and 10. The tritiated water is obtained at specific activity of 100 mCi/gm or 5 Ci/gm (DuPont) is dispensed by serial dilution from a working stock solution (no less than 1:25) into usual cell culture growth medium. The IC$_{40}$ and EC$_{50}$ are determined by MTT assay as shown in Example 1 and in Example 10 at approximately 24 hr. The specific range of activity required is based upon dosimetry calculations. Using pilot data, the U937 cells are exposed to gamma radiation in an irradiator and cumulative exposures in the range of 2.5–20 Grey produce apoptosis. The equivalent tritium required is estimated to be in the range of 1 to 4 mCi/ml of medium. The pilot data also suggest that the beta radiation should have a target interval during S or G$_2$ phases. This is anticipated from extensive published literature (See for example Kuerbitz, supra, Giocanti N et al. Cancer Res 53:2105–11(1993)

The effect of dThd, HU, aphidicolin or other RA becomes evident if it is administered to the cell cultures at 2–6 hr prior to the radiation source; and the radiation exposure is continued for up to 24 hours. It is possible; however, that administration of the RA at some time after the radiation may be advantageous if secondary effects of the radiation within the cell are the indirect cause of the radiation effect and require a time interval for manifestation. Therefore various doseages of the radiation and of a prospective agent as RA or TCI must be tested pragmatically. In pilot data with STSP as an RA in a range of approximately 25 nM, we discerned an enhancing effect upon damage produced by a single exposure of the U937 cells to 2.5 to 10 Gy of gamma radiation. Thus, STSP is a candidate for testing either as RA or TCI.

The use of tritiated water in these experiments is a matter of convenience and safety. The radioactive water will equilibrate uniformly through cells without respect to DNA synthesis in contrast to other isotopes which might be selectively incorporated into replicating DNA and bias results. The tritiated water is a relatively low energy beta emitter which produces damage in short ranges. Nevertheless it can produce DNA breaks analogous to those produced by higher energy gamma rays used in medical therapeutics. A closer approximation of medical conditions can be achieved with a gamma radiator or other physical device, such as a series of radiolabelled beads or platens, in which rows of wells are exposed to progressively incremental doseages of radiation for defined periods using the general approach of the MIS with BVSD so that formulas described in Example 8 can be applied.

EXAMPLE 22

This Example demonstrates a use of the invention in the treatment of a falciparum malaria infection.

The malaria plasmodium falciparum (p. falciparum) is a eukaryotic organism that grows by division within human erythrocytes of mammalian hosts in cycles of 44 hours from ring to trophozoite to schizont stage. There is also a tissue phase during which parasites replicate in the human liver. In humans, p. falcipanum is particularly dangerous because of its rapid and uncontrolled proliferation and clogging of cerebral microvasculature.

The malarial parasite is susceptible to certain agents which we have shown camract as class I of RA. Genes for ribonucleotide reductase have been characterized for the malarial parasite. Chakarabarti et al., Proc. Natl. Acad. Sci. 90:12020–4 (1993). Susceptibility to iron chelators which inhibit RNR has been shown, Lytton S D et al., Blood 84:910–15 (1994), and the parasites can take up dThd or fluorodeoxyuridine. Rathod P K and Reshmi S, Antimicro Agents and Chemother. 38:476–80 (1994); Wright M and Tollon Y, J. Cell Physiol. 139:346–53 (1989). Parasites are also susceptible to effects of STSP as a single agent. Ward G E et al., Exp. Parasitol. 79:480–7 (1994).

In a series of experiments, human A positive erythrocytes (RBCs) infected with p. falciparum W2 or D6 strains (Oduola A M J et al. Exper. Parasitol. 66: 86–95 (1988)) by an in vitro method (Milhous W K et al. Antimicrob. Agents Chemother. 27:525–530 (1985) were exposed to serial concentrations of staurosporine, hydroxyurea or aphidicolin during the stage of rapid multiplication at 24 hr after the RBC infection. Parasite growth was monitored by uptake of $^3$H-hypoxanthine which becomes incorporated into the parasitic DNA. Based upor radioactivity measurements in 96-well plates with serial agent dilutions, the inhibitory concentrations ($IC_{50}$) in strain W2/D6 were staurosporine, 0.15 $\mu$M/0.19 $\mu$M, hydroxyurea, 219 $\mu$M/175.2 $\mu$M and aphidicolin 0.123 $\mu$M/0.40 $\mu$M respectively.

These results show that use of HU or APH as RA with STSP as a TCI is practicable. In further work, the MIS method of agent combinations in serial dilutions is applied, using the parasite infected RBC system. Absolute radioactivity counts in each well are used as an indication of the extent of parasitic infection (i.e. higher counts indicate greater infection) Thus in synergistic action of an RA and TCI, the number of counts is lower than expected by summation of the results using either agent alone. The algorithm applied for data analysis therefore is the same as that used analysis of LDH release in Example 9. Using Table 3A–C, both CRR and O/S plots may be obtained.

For tests in vivo, inbred Swiss Albino mice of either sex weighing 25–30 g in groups of 6–8 are infected with *Plasmodium yoelii* or *Plasmodium berghii*. The infection is transmitted by sacrificing an infected animal when the percentage parasitemia is approximately 40%: 0.5; ml of blood is aspirated from the heart of an anesthetized mouse, diluted into 5 ml with phosphate-buffered sodium citrate anticoagulant and injected intraperitoneally into a fresh animal (0.5 ml of the diluted sample).

In one type of treatment of the animals, HU is administered orally, beginning on day zero or at 24 hours after an infection, to achieve a plasma concentration in a range up to 150 $\mu$M. After 2–24 hr, in different experiments, STSP at 700 $\mu$g/kg (Buchholz, supra), is administered IV in a single dose. Parasitemia is monitored in groups of 6 mice at subsequent intervals of 12 hr: untreated mice; mice treated with HU only; mice treated with STSP only; and mice treated with both agents. Survival of the mice is recorded, and treatments may be repeated as indicated by initial results. Thin blood smears are prepared with drops of blood from tail veins. Smears are fixed in methanol, stained with Giemsa and numbers of infected red blood cells per 50 oil immersion fields (100x) are counted. Reduction of parasitemia is maximum in the HU/STSP treated mice and the mean survival time of these mice is increased relative to the other groups of mice.

EXAMPLE 23

This Example demonstrates that the success of STSP as a TCI in inducing apoptosis with multiple RA in cells lacking functional p53 may be explained by some key molecular and cell biologic changes associated with the actions of STSP.

In the present Example human malignant lymphoma cells (U937) were treated with STSP or a synergistic match of dThd and STSP. For immunoblot analyses of CDC2 and MAP kinases samples of 5×10$^6$ cells were extracted in SDS sample buffer and subjected to 12% SDS-PAGE and immunoblotting as described in Example 4. The cyclin-dependent kinase p34$^{cdc2}$ was detected with antibody clone #1 from Signal Transduction Laboratories. For detection of histone phosphorylation activity p34$^{cdc2}$ was immunoprecipitated with monoclonal antibody (Santa Cruz, #17) using protein A sepharose and reacted with H1 substrate (Boehringer Mannheim) in the presence of $\gamma^{32}$P-ATP (Amersham). Phosphorylated product was separated and resolved by 12%

SDS-PAGE and visualized by autoradiography with X-Omat film (Kodak). MAP kinases were detected by immunoblotting with monoclonal antibodies from Pharmingen (San Diego, Calif.). For assay of enzymatic activities, MAP kinases were immunoprecipitated as above with polyclonal antibody to erk2 or with a GST-JNK substrate for JNK. The substrate for erk2 was myelin basic protein substrate and for JNK was GST-JNK (Pharmingen). The protooncogene product c-myc was detected by immunoblotting with an antibody from Oncogene Sciences.

Figure 36:
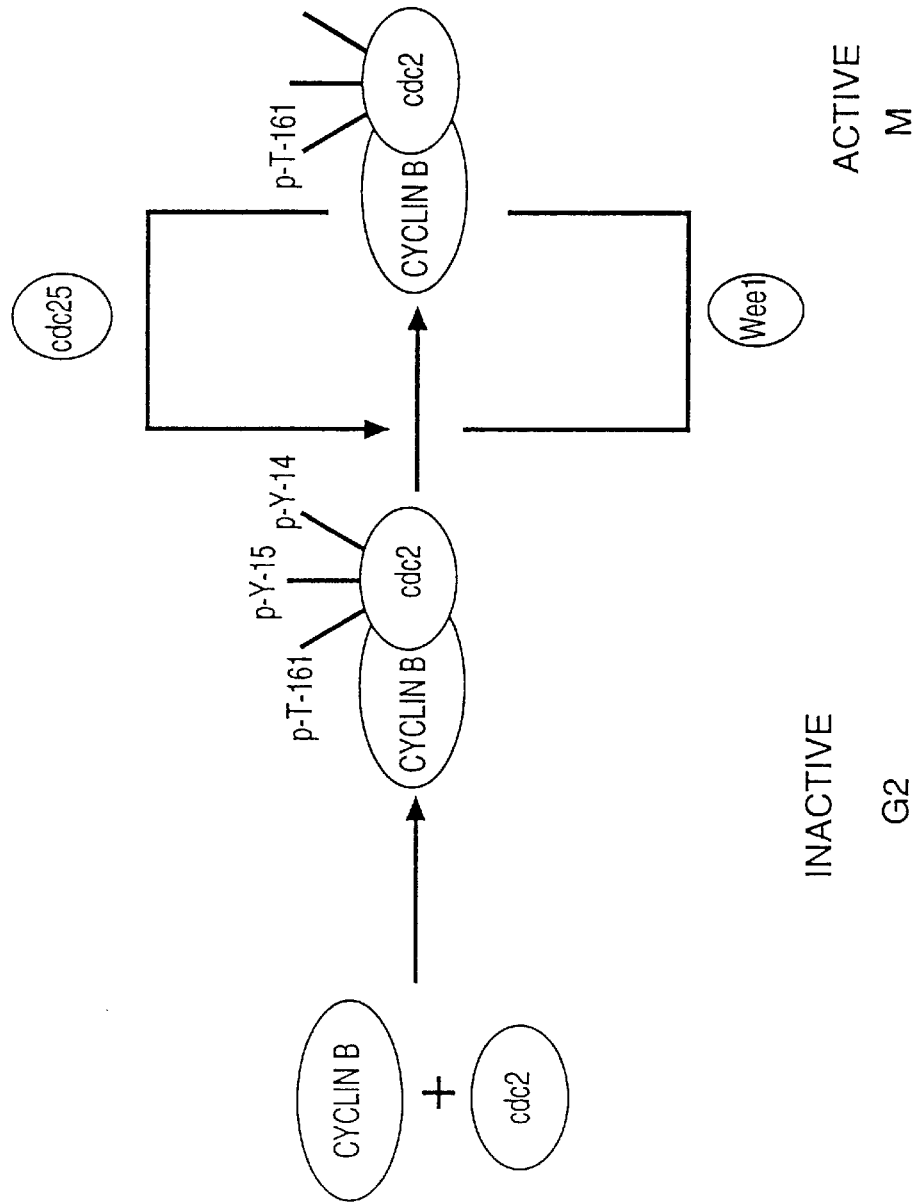
FIG. 36 is a diagram depicting dephosphorylation of $p34^{CDC2}$ as a critical factor in regulating cell movement through $G_2$ phase into M phase.

All of the above proteins were of interest in relation to the action of STSP in causing apoptosis and acting in synergistic match with dThd. FIG. 36 shows that dephosphorylation of $p34^{cdc2}$ on p-Y-15 and p-T-14 is a critical factor in regulating cell movement through $G_2$ phase into M phase. The ratio of MAP kinases JunK (JNK) and Erk-2 were of interest in relation to the molecular mechanism of apoptosis due to evidence that STSP altered the balance of activity of the MAP kinases JNK and ERK2 (Xia Z. et al. Science 270:1326–1331. (Xia et al, supra) and increased expression of the protein c-myc is a critical factor in the initiation and maintenance of S phase (Eisenman R N and Cooper J A, Nature 378:438–439, 1995). The agent aurintricarboxylic acid (ATA) has been of interest as an inhibitor of endonucleases and apoptosis.

Figure 37A:
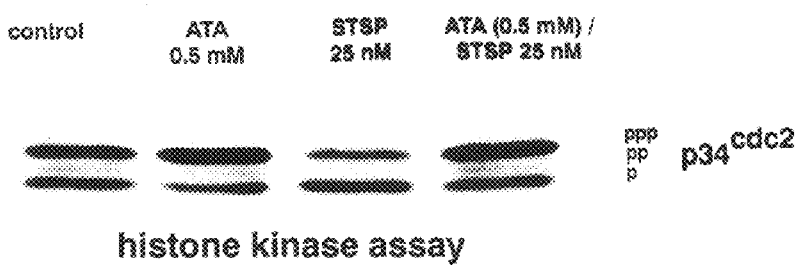
FIG. 37A is an inmmunoblot showing the effect of STSP and ±ATA on the phosphorylation of $p34^{CDC2}$.

FIG. 37A is an immunoblot showing the effect of STSP and ±ATA on the phosphorylation of $p34^{CDC2}$.

Figure 37B:
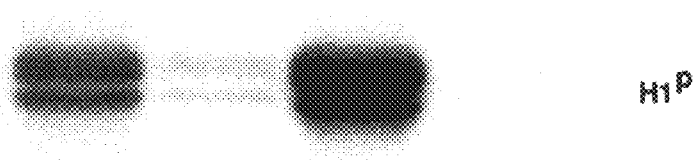
FIG. 37B is an immunoblot demonstrating that STSP induced a functional activation of cdc2 as shown both by the ability to phosphorylate histone protein (H1).

FIG. 37B is an immunoblot demonstrating that STSP induced a functional activation of cdc2 as shown both by the ability to phosphorylate histone protein (H1).

Figure 37C:
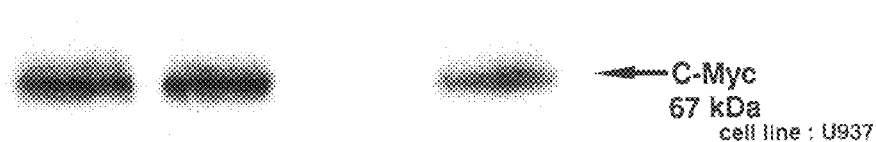
FIG. 37C is an immunoblot showing the effect of STSP and ±ATA on c-myc expression.

FIG. 37C is an immunoblot showing the effect of STSP and ±ATA on c-myc expression.

Figure 38A:
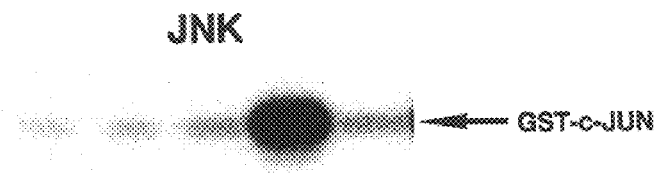
FIG. 38 is an immunoblot showing the effect of STSP and ±dThd on MAP kinases, JNK (A) and ERK(B).
Figure 38B:
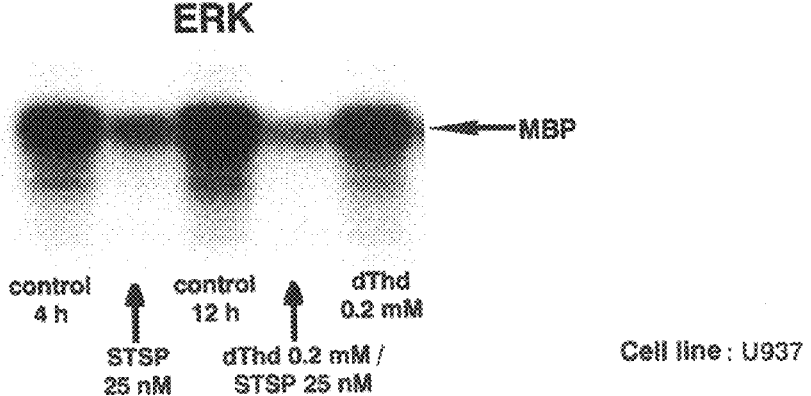

FIG. 38 is an immunoblot showing the effect of STSP and ±dThd on MAP kinases.

Results demonstrated that phosphorylation of $CDC_2$ was inhibited by STSP ±dThd, but not by dThd alone, and that levels of c-myc normally elevated in S phase were reduced. In addition, the synergistic combination of dThd and STSP was associated with strikingly increased JunK and decreased Erk-2 MAP kinase activities. This may be significant in relationship to cell cycle control mechanisms.

DESCRIPTION OF TABLES

Table 1A&B: Functional categories and examples of proven or potential RA*.

Table 2: Functional categories and examples of proven or potential TCI*.

Table 3A–P: Example 8 Relational formulas used by us for calculation of MIS-MTT combined results ratios from tabular format.

Table 4: Example 8 Combined results ratios from MTT data for example of dThd and STSP (% cytotoxicity of three plates was averaged for this example.

Table 5: Example 9 Combined results ratios from LDH data for example of dThd and STSP (% cytotoxicity of three plates was averaged for this example.

Table 6: Example 10 Combined results ratios from MTT data showing dThd potentiation of STSP cell damage at 48 hr after washing.

Table 7: Example 11 Combined results ratios from MTT data showing schedule testing of dThd potentiation of STSP cell damage.

Table 9: Combined results ratios from MTT data for BrdU and STSP

Table 10: Combined results ratios from MTT data for dAde and STSP

Table 11: Combined results ratios from MTT data for dGuo and STSP

Table 12: Combined results ratios from MTT data for HU and STSP

Table 13: Combined results ratios from MTT data for MTX and STSP

Table 14: Combined results ratios from MTT data for floxuridine (flox) and STSP

Table 15: Combined results ratios from MIT data for Aph and STSP

Table 16: Combined results ratios from MTT data for ara-C and STSP

Table 17: Combined results ratios from MTT data for STSP and bleomycin

Table 18: Combined results ratios from MTT data for STSP and mitomycin C

Table 19: Combined results ratios from MTT data for STSP and cisplatin

Table 20: Combined results ratios from MTT data for STSP and daunorubicin

Table 21: Combined results ratios from MIT data for STSP and etoposide

Table 22: Combined results ratios from MTT data for dThd and K252a

Table 23: Combined results ratios from MTT data for dThd and KT5926

Table 24: Combined results ratios from MTT data for dThd and KT5720

Table 25: Combined results ratios from MTT data for Thd and Aph

Table 26: Combined results ratios from MTT data for dThd and ara-C

Table 27: Combined results ratios from MTT data for HU and K252A

Table 28: Combined results ratios from MTT data for HU and Aph

Table 29: Combined results ratios from MTT data for dThd and cisplatin

Table 30: Combined results ratios from MTT data for HU and cisplatin

Table 31: Combined results ratios from MTT data for Aph and K252a

Table 32: Combined results ratios from MTT data for etoposide and daunorubicin.

Table 33: Summary of data for synergistic matches in U937 cells.

Table 34: Tumor formation in athymic nude mice innoculated with U937 cells.

Table 35: Examples relating $S_{MAX}$ for specified RA to blood levels previously reported in chemotherapy.

Table 36: Characteristics of human malignant cells lines successfully treated by dThd or other RA to potentiate the action of STSP or other TCI.

Table 37: Evidence for Cell dependence of $IC_{40}$ and $S_{MAX}$ in synergistic matches with STSP.

Table 38: Combined results ratios from MTT data for dThd and STSP in HL-60 cells.

Table 39: Combined results ratios from MTT data for dThd and STSP in Jurkat cells.

Table 40: Combined results ratios from MTT data for Aph and STSP in Daudi cells.

Table 41: Combined results ratios from MTT data for Aph and STSP in C33A cells.

Table 42: Combined results ratios from MTT data for HU and STSP in Raji cells.

TABLE 1

Functional categories and examples of potential restraining agents (RA)*

| Estimated position of Reference Point | Potential Restraining Agent (RA) | |
|---|---|---|
| | Specific target of action | Representative examples |
| | class I | |
| G1 / S transition | nucleoside transport | dipyridamole, Tk antagonist@ |
| | purine or pyrimidine metabolism | 6-thioguanine, pentostatin, 5'-azacytidine, |
| | ribonucleotide reductase (RNR) | dThd, BrdU, dAde, dGuo, HU, trimidox, desferoxamine N-hydroxy-N'-aminoguanidine (HAG) Schiff bases |
| expression of early S phase genes | dihydrofolate reductase thymidylate synthase pRb phosphorylation, gene expression | MTX, aminopterin fluorinated uracils E6 oncoprotein@ transferred dominant negative gene@, antisense molecules@ growth factor inhibitor receptor antibody |
| | class IIA | |
| S phase nascent DNA synthesis | DNA polymrases | aphidicolin, ara-C |
| | class IIB | |
| S phase DNA lesions | DNA intercalation DNA breakage/repair DNA alkylation DNA cross-linkage | daunorubicin, isoquinolines bleomycins, gammarays etoposide, camptothecin nitrogen mustards mitomycin C, cisplatin |
| | class III | |
| S to G2 phase | protein kinases, (including cyclin-dependent kinases) | STSP@, K252A@, KT5926@, quercetin |
| DNA supramolecular organization, chromosome condensation | histone phophorylation, nucleoprotein associations | STSP@, growth factor inhibitor: competitive ligand or antibody |

* Actions of agents underlined are demonstrated in working examples, potential actions of other agents are inferred from previously published data. Some RA such as STSP and K252a may function in more than one category of action depending upon the cell type or strength and duration of application. Agents marked with @ have not been clinically tested in humans.

TABLE 2

Functional classes of targeted cytotoxic insults (TCI) *

| Estimated position of Target Interval | Targeted Cytotoxic Insults (TCI) | |
|---|---|---|
| | Targets of damaging action | Representative examples |
| | class A | |
| G1 to S phase | initiation of S phase | oncoproteins@ |
| | nucleotide metabolism | metabolic enzyme inhibitors |
| early S phase gene expression | gene expression | growth factor antagonists, antisense molecules@ |

TABLE 2-continued

Functional classes of targeted cytotoxic insults (TCI) *

| Estimated position of Target Interval | Targeted Cytotoxic Insults (TCI) | |
|---|---|---|
| | Targets of damaging action | Representative examples |
| | class B1 | |
| S phase | DNA polymerases | aphidicolin, Ara-C |
| | class B2 | |
| S to G$_2$ phase DNA lesions | DNA intercalation | dactinomycin, daunorubicin, isoquinolines |
| | DNA cross-linkage | cisplatin carboplatin, multiple alkylating agents, nitrosourea, mitomycin C |
| | DNA methylation | 5'-azacytidine |
| | DNA strand integrity | bleomycin, gamma rays, etoposide |
| | class C | |
| G$_2$ phase | nucleoproteins, protein kinases, cyclin-dependant kinases | STSP, K252A@, KT5926@, other protein kinase inhibitors, olomoucine@, caffeine, ilmofosine@ |
| | DNA supramolecular organization | etoposide |

* Actions of agents underlined are demonstrated in present examples. Actions of other agents have been inferred from previously published data. Some TCI such as STSP may function in more than one category of action depending upon the cell type or strength and duration of application. Agents marked with @ have not yet been tested clinically.

TABLE 3

ALGORITHM WITH SPREADSHEET FORMULAS FOR ANALYSIS OF MIS DATA
(formula locations indicated by cell letter and number, e.g. C19)

General Headings and spreadsheet cells
in which experiment variables are entered
A1: (T) [W8] ^DATE
C1: (T) [W31] ^EXP #
E1: (T) [W32] ^CELL TYPE
G1: (T) [W32] ^ASSAY A2: (T) [W8] ^enter date
C2: (T) [W31] ^enter experiment #
E2: (T) [W32] ^enter cell type
G2: (T) [W32] ^enter assay D4: (T) [W31] ^MAXIMUM CONCENTRATION
E4: (T) [W32] Moles or micrograms/ml
F4: (T) [W32] HOURS OF TREATMENT
A5: (T) [W8] ^TCl (vertical)
C5: (T) [W31] ^enter name of TCl
D5: (T) [W31] ^enter value
E5: (T) [W32] ^enter units
F5: (T) [W32] ^enter hours A7: (T) [W8] ^RA (horizontal)
C7: (T) [W31] ^enter name of TCl
D7: (T) [W31] ^enter value
E7: (T) [W31] ^enter units
F7: (T) [W31] ^enter hours F9: (T) [W32] ^enter hours
G9: (T) [W32] ^HOURS TOTAL A11: (T) [W8] ^PURPOSE:
B11: (T) [W10] "Detect agent interactions
D11: (T) [W31] 'and synergistic
E11: (T) [W32] 'match for growth
F11: (T) [W32] ^inhibition A13: (T) [W8] ^ABSORBANCE DATA
C13: (T) [W31] ^enter absorbance nm
G13: (T) [W32] ^immdedate assay value
I13: (T) [W32] +G2

Numbers in C18 to O18 indicate positions
of columns in the 96-well plate
C18: (T) [W31] 1
D18: (T) [W31] 2
E18: (T) [W32] 3
F18: (T) [W32] 4
G18: (T) [W32] 5
H18: (T) [W31] 6
I18: (T) [W32] 7
J18: (T) [W32] 8
K18: (T) [W32] 9
L:18: (T) [W32] 10
M18: (T) [W29] 11
N18: (T) [W16] ^12
O18: (T) [W28] ^MEANS
Beginning of Table with transferred absorbance date
B19: (T) [W10] ^A
C19: (T) [W31] +A15 = Blank background well
D19: (T) [W31] +A16
E19: (T) [W32] +A17
F19: (T) [W32] +A18
G19: (T) [W32] +A19
H19: (T) [W31] +A20
I19: (T) [W32] +A21
J19: (T) [W32] +A22
K19: (T) [W32] +A23
L19: (T) [W32] +A24
M19: (T) [W29] +A25
N19: (T) [W16] +A26
O19: (T) [W28] @AVG(M19..N19)

B20: (T) [W10] ^B
C20: (T) [W31] +A27
D20: (T) [W31] +A28
E20: (T) [W31] +A29
F20: (T) [W31] +A30
G20: (T) [W31] +A31
H20: (T) [W31] +A32
I20: (T) [W31] +A33
J20: (T) [W31] +A34

TABLE 3-continued

ALGORITHM WITH SPREADSHEET FORMULAS FOR ANALYSIS OF MIS DATA
(formula locations indicated by cell letter and number, e.g. C19)

A14: (T) [W8] '{/File, Import/Comma}}Clear}a:†eia†*,(-
G14: (T) [W32] ^enter plate number A15: (T) [W 8] 'ABSORBANCE OF BACKGROUNDN
BLANK
Absorbance data from a diskette is entered inot
cells A15 trought A110 by the macro in spreadsheet cell A14
This data (not shown) is transferred to a tabular formatin cells
B19 through N26 as indicated below (in B19 through N26)

B16: (T) [W10] ^CONTROLS
C16: (T) [W31] ^ REM: CHECK POSITION OF
BACKGROUND BLANK!
G16: (T) [W32] ^REM: CHECK LOCATION FOR N0

B17: (T) [W10] 'MEAN
C17: (T) [W31] @AVG(M25..n26)
D17: (T) [W31] 'COEFFECIENT OF VARIATION =
E17: (T) [W32] +5NS29/SNS28 continuation of Table with transferred absorbance data
B22: (T) [W10] ^D
C22: (T) [W31] +A51
D22: (T) [W31] +A52
E22: (T) [W32] +A53
F22: (T) [W32] +A54
G22: (T) [W32] +A55
H22: (T) [W31] +A56
I22: (T) [W32] +A57
J22: (T) [W32] +A58
K22: (T) [W32] +A59
L22: (T) [W32] +A60
M22: (T) [W29] +A61
N22: (T) [W16] +A62
O22: (T) [W28] +@AVG(M22..N22)
B23: (T) [W10] ^E
C23: (T) [W31] +A63
D23: (T) [W31] +A64
E23: (T) [W32] +A65
F23: (T) [W32] +A66
G23: (T) [W32] +A67
H23: (T) [W31] +A68
I23: (T) [W32] +A69
J23: (T) [W32] +A70
K23: (T) [W32] +A71
L23: (T) [W32] +A72
M23: (T) [W29] +A73
N23: (T) [W16] +A74
O23: (T) [W28] +A75

B24: (T) [W10] ^F
C24: (T) [W31] +A75
D24: (T) [W31] +A76
E24: (T) [W32] +A77
F24: (T) [W32] +A78
G24: (T) [W32] +A79
H24: (T) [W31] +A80
I24: (T) [W32] +A81
J24: (T) [W32] +A82
K24: (T) [W32] +A83
L24: (T) [W32] +A84
M24: (T) [W29] +A85
N24: (T) [W16] +A86
O24: (T) [W28] +@AVG(M24..N24)
Beginning of analyses of absorbance data
Delta = absolute differences from means of absorbances for
control RA and TCl dilutions intended to reveal any outlier
values
B27: (T) [W10] ^DELTA
C27: (T) [W31] @ABS(+C29–C25)
D27: (T) [W31] @ABS(+D29–D25)
E27: (T) [W32] @ABS(+E29–E25)
F27: (T) [W32] @ABS(+F29–F25)
G27: (T) [W32] @ABS(+G29–G25)
H27: (T) [W31] @ABS(+H29–H25)
I27: (T) [W32] @ABS(+I29–I25)

K20: (T) [W31] +A35
L20: (T) [W31] +A36
M20: (T) [W31] +A37
20: (T) [W31] +A38
O20: (T) [W28] @AVG(M20..N20)

B21L (T) [W10] ^C
C21: (T) [W31] +A39
D21: (T) [W31] +40
E21: (T) [W32] +41
F21: (T) [W32] +A42
G21: (T) [W32] +A43
H21: (T) [W31] +A44
I21: (T) [W32] +A45
J21: (T) [W32] +A46
K21: (T) [W32] +A47
L21: (T) [W32] +48
M21: (T) [W 29] +A49
N21: (T) [W16] +A50
O21: (T) [W28] @AVG(M21..N21)

B25: (T) [W10] ^G
C25: (T) [W31] +A87
D25: (T) [W31] +A88
E25: (T) [W32] +A89
F25: (T) [W32] +A90
G25: (T) [W32] +A91
H25: (T) [W31] +A92
I25: (T) [W31] +A93
J25: (T) [W32] +A94
K25: (T) [W32] +A95
L25: (T) [W32] +A96
M25: (T) [W29] +A97
N25: (T) [W16] +A98
O25: (T) [W32] +@AVG(M25..N25)
B26: (T) [W10] ^H
C26: (T) [W31] +A99
D26: (T) [W31] +A100
E26: (T) [W32] +A101
F26: (T) [W32] +A102
G26: (T) [W32] +A103
H26: (T) [W31] +A104
I26: (T) [W32] +A105
J26: (T) [W32] +A106
K26: (T) [W32] +A107
L26: (T) [W32] +A108
M26: (T) [W29] +A109
N26: (T) [W16] +A110

End of Table with transferred absorbance data

B30: (T) [W10] 'INHIBITION
C30: (T) [W31] (1-C29/SNS28)
D30: (T) [W31] (1-D29/SNS28)
E30: (T) [W32] (1-E29/SNS28)
F30: (T) [W32] (1-F29/SNS28)
G30: (T) [W32] (1-G29/SNS28)
H30: (T) [W31] (1-H29/SNS28)
I30: (T) [W32] (1-I29/SNS28)

TABLE 3-continued

ALGORITHM WITH SPREADSHEET FORMULAS FOR ANALYSIS OF MIS DATA
(formula locations indicated by cell letter and number, e.g. C19)

J27: (T) [W32] @ABS(+J29–J25)
K27: (T) [W32] @ABS(+K29–K25)
L27: (T) [W32] @ABS(+L29–L25)
N27: (T) [W16] ˆCONTROL

B28: (T) [W10] ˆVALUES
C28: (T) [W31] @ABS(+C29–C26)
D28: (T) [W31] @ABS(+D29–D26)
E28: (T) [W32] @ABS(+E29–E26)
F28: (T) [W32] @ABS(+F29–F26)
G28: (T) [W32] @ABS(+G29–G26)
H28: (T) [W31] @ABS(+H29–H26)
I28: (T) [W32] @ABS(+I29–I26)
J28: (T) [W32] @ABS(+J29–J26)
K28: (T) [W32] @ABS(+K29–K26)
L28: (T) [W32] @ABS(+L29–L26)
M28: (T) [W29] *MEAN
N28: (T) [W16] @ABS(M25..N26)

Mean values of RA absorbances used to calculate % growth
inhibition in the spreadsheet cells B30..J30
B29: (T) [W10] ˆMEAN
C29: (T) [W31] @AVG(C25..C26)
D29: (T) [W31] AVG(D25..D26)
E29: (T) [W32] @AVG(E25..E26)
F29: (T) [W32] @AVG(E25..E26)
G29: (T) [W32] @AVG(E25..E26)
H29: (T) [W31] @AVG(E25..E26)
I29: (T) [W32] @AVG(E25..E26)
J29: (T) [W32] @AVG(E25..E26)
K29: (T) [W32] @AVG(E25..E26)
L29: (T) [W32] @AVG(E25..E26)
M29: (T) [W29] *STANDARD DEVIATION
N29: (T) [W16] @STD(M25..N26)
Beginning of formulas for the CRR
B42: (T) [W10] +D5
C42: (T) [W31] (1-@AVG(M19..N19)/SCS17)
D42: (T) [W31] +C42/(SC42+DS50)
E42: (T) [W32] ˆBACKGROUND BLANK
G42: (T) [W32] 1-(D19/SCS17)
H42: (T) [W31] +G42/(SC42+GS50)
I42: (T) [W32] 1-(E19/SCS17)
J42: (T) [W32] +I42/(SC42+IS50)
K42: (T) [W32] 1-(F19/SCS17)
L42: (T) [W32] +K42/(SC42+KS50)
M42: (T) [W29] 1-(G19/SCS17)
N42: (T) [W16] +M42/(SC42+MS50)
O42: (T) [W28] 1-(H19/SCS17)
P42: (T) [W17] +O42/(SC42+OS50)
Q42: (T) [W27] 1-(I19/SCS17)
R42: (T) [W18] +Q42/(SC42+QS50)
S42: (T) [W25] 1-(J19/SCS17)
T42: (T) [W19] +S42/(SC42+SS50)
U42: (T) [W28] 1-(K19/SCS17)
V42: (T) [W19] +U42/(SC42+US50)
W42: (T) [W25] 1-(L19/SCS17)
X42: (T) [W18] +W42/(SC42+WS50)

B43: (T) [W10] +B42/2
C43: (T) [W31] (1-@AVG(M20..N20)/SCS17)
D43: (T) [W31] +C43/(SC43+DS50)
E43: (T) [W32] 1-(C20/SCS17)
F43: (T) [W32] +E43/(SC43+ES50)
G43: (T) [W32] 1-(D20/SCS17)
H43: (T) [W31] +G43/(SC43+GS50)
I43: (T) [W32] 1-(E20/SCS17)
J43: (T) [W32] +I43/(SC43+IS50)
K43: (T) [W32] 1-(F20/SCS17)
L43: (T) [W32] +K43/(SC43+KS50)
M43: (T) [W29] 1-(G20/SCS17)
N43: (T) [W16] +M43/(SC43+MS50)
O43: (T) [W28] 1-(H20/SCS17)
P43: (T) [W17] +O43/(SC43+OS50)
Q43: (T) [W27] 1-(I20/SCS17)
R43: (T) [W18] +Q43/(SC43+QS50)
S43: (T) [W25] 1-(J20/SCS17)

J30: (T) [W32] (1-J29/SNS28)
K30: (T) [W32] (1-K29/SNS28)
L30: (T) [W32] (1-L29/SNS28)
M30: (T) [W29] "COEFFICIENT OF VARIATION
N30: (T) [W16] SNS29/SNS28

Headers for the table to analyze BVSD
B31: (T) [W10] +C7
C31: (T) [W31] +F7
D31: (T) [W31] ˆHrs
D33: (T) [W31] ˆBIVARIATE SERIAL
E33: (T) [W32] 'DILUTION ANALYSIS (BVSD)

D35: (T) [W31] ˆTABULATION OF
E35: (T) [W32] ˆCOMBINED RESULTS RATIOS (CRR)

B36: (T) [W10] +G2
C36: (T) [W31] +A2
D38: (T) [W31] +F9
E38: (T) [W32] ˆH
G38: (T) [W32] +C5
I38l (T) [W32] ˆfor
J38: (T) [W32] +F5
K38: (T) [W32] ˆH B39: (T) [W10] +SCS5
G39: (T) [W32] +C7
I39: (T) [W32] ˆfor
J39: (T) [W32] +F7
K39: (T) [W32] ˆH

B40: (T) [W10] +SES5

B41: (T) [W10] ˆGrowth Ihibition [%]

B44: (T) [W10] +B43/2
C44: (T) [W31] (1-@AVG(M21..N21)/SCS17)
D44: (T) [W31] +C44/(SC44+DS50)
E44: (T) [W32] 1-(C21/(SCS17)
F44: (T) [W32] +E44/SC44+ES50)
G44: (T) [W32] 1-(D21/SCS17)
H44: (T) [W31] +G44/(SC44+GS50)
I44: (T) [W32] 1-(E21/SCS17)
J44: (T) [W32] +I44/(SC44+IS50)
K44: (T) [W32] 1-(F21/SCS17)
L44: (T) [W32] +K44/(SC44+KS50)
M44: (T) [W29] 1-(G21/SCS17)
N44: (T) [W16] +M44/(SC44+MS50)
O44: (T) [W28] 1-(H21/SCS17)
P44: (T) [W17] +O44/(SC44+OS50)
Q44: (T) [W27] 1-(I21/SCS17)
R44: (T) [W18] +Q44/(SC44+QS50)
S44: (T) [W25] 1-(J21/SCS17)
T44: (T) [W19] +S44/(SC44+SS50)
U44: (T) [W28] 1-(K21/SCS17)
V44: (T) [W19] +U44/(SC44+US50)
W44: (T) [W25] 1-(L21/SCS17)
X44: (T) [W18] +W44/(SC44+WS50)

B45: (T) [W10] +B43/2
C45: (T) [W31] (1-@AVG(M21..N21)/SCS17)
D45: (T) [W31] +C45/(SC45+DS50)
E45: (T) [W32] 1-(C22/SCS17)
F45: (T) [W32] +E45/SC45+ES50)
G45: (T) [W32] 1-(D22/SCS17)
H45: (T) [W31] +G45/(SC45+GS50)
I45: (T) [W32] 1-(E22/SCS17)
J45: (T) [W32] +I45/(SC45+IS50)
K45: (T) [W32] 1-(F22/SCS17)
L45: (T) [W32] +K45/(SC45+KS50)
M45: (T) [W29] 1-(G22/SCS17)
N45: (T) [W16] +M45/(SC45+MS50)
O45: (T) [W28] 1-(H22/SCS17)
P45: (T) [W17] +O45/(SC45+OS50)
Q45: (T) [W27] 1-(I22/SCS17)
R45: (T) [W18] +Q45/(SC45+QS50)

TABLE 3-continued

ALGORITHM WITH SPREADSHEET FORMULAS FOR ANALYSIS OF MIS DATA
(formula locations indicated by cell letter and number, e.g. C19)

T43: (T) [W19] +S43/(SC43+SS50)
U43: (T) [W28] 1-(K20/SCS17)
V43: (T) [W19] +U43/(SC43+US50)
W43: (T) [W25] 1-(L20/SCS17)
X43: (T) [W18] +W43/(SC43+WS50)

B46: (T) [W10] +B45/2
C46: (T) [W31] (1-@AVG(M23..N23)/SCS17)
D46: (T) [W31] +C46/(SC46+DS50)
E46: (T) [W32] 1-(C23/SCS17)
F46: (T) [W32] +E46/(SC46+ES50)
G46: (T) [W32] 1-(D23/SCS17)
H46: (T) [W31] +G46/(SC46+GS50)
I46: (T) [W32] 1-(E23/SCS17)
J46: (T) [W32] +I46/(SC46+IS50)
K46: (T) [W32] 1-(F23/SCS17)
L46: (T) [W32] +K46/(SC46+KS50)
M46: (T) [W29] 1-(G23/SCS17)
N46: (T) [W16] +M46/(SC46+MS50)
O46: (T) [W28] 1-(H23/SCS17)
P46: (T) [W17] +O46/(SC46+OS50)
Q46: (T) [W27] 1-(I23/SCS17)
R46: (T) [W18] +Q46/(SC46+QS50)
S46: (T) [W25] 1-(J23/SCS17)
T46: (T) [W19] +S46/(SC46+SS50)
U46: (T) [W28] 1-(K23/SCS17)
V46: (T) [W19] +U46/(SC46+US50)
W46: (T) [W25] 1-(L23/SCS17)
X46: (T) [W18] +W46/(SC46+WS50)
B47: (T) [W10] +B46/2
C47: (T) [W31] (1-@AVG(M24..N24)/SCS17)
D47: (T) [W31] +C47/(SC47+DS50)
E47: (T) [W32] 1-(C24/SCS17)
F47: (T) [W32] +E47/(SC47+ES50)
G47: (T) [W32] 1-(D24/SCS17)
H47: (T) [W31] +G47/(SC47+GS50)
I47: (T) [W32] 1-(E24/SCS17)
J47: (T) [W32] +I47/(SC47+IS50)
K47: (T) [W32] 1-(F24/SCS17)
L47: (T) [W32] +K47/(SC47+KS50)
M47: (T) [W29] 1-(G24/SCS17)
N47: (T) [W16] +M47/(SC47+MS50)
O47: (T) [W28] 1-(H24/SCS17)
P47: (T) [W17] +O47/(SC47+OS50)
Q47: (T) [W27] 1-(I24/SCS17)
R47: (T) [W18] +Q47/(SC47+QS50)
S47: (T) [W25] 1-(J24/SCS17)
T47: (T) [W19] +S47/(SC47+SS50)
U47: (T) [W28] 1-(K24/SCS17)
V47: (T) [W19] +U47/(SC47+US50)
W47: (T) [W25] 1-(L24/SCS17)
X47: (T) [W18] +W47/(SC47+WS50)
Beginning of formulas for graphic presentations Headers for O/S plots E54: (T) [W32] ^TABULATION OF OBSERVED RESULTS ("O")
E55: (T) [W32] ^AND HYPOTHETICAL SUMMATION ("S")

B57: (T) [W10] +SCS5
E57: (T) [W32] 'REM: CORRECT ANY SUM > 100
                TO BE = 100
Formulas for O/S plots
B58: (T) [W10] +SES5

B59: (T) [W10] D5
D59: (T) [W31] 100-(D19/SCS17)*100
E59: (T) [W32] 100-(E19/SCS17)*100
F59: (T) [W32] 100-(F19/SCS17)*100
G59: (T) [W32] 100-(G19/SCS17)*100
H59: (T) [W31] 100-(H19/SCS17)*100
I59: (T) [W32] 100-(I19/SCS17)*100
J59: (T) [W32] 100-(J19/SCS17)*100
K59: (T) [W32] 100-(K19/SCS17)*100

S45: (T) [W25] 1-(J22/SCS17)
T45: (T) [W19] +S45/(SC45+SS50)
U45: (T) [W28] 1-(K22/SCS17)
V45: (T) [W19] +U45/(SC45+US50)
W45: (T) [W25] 1-(L22/SCS17)
X45: (T) [W18] +W45/(SC45+WS50)
F48: (T) [W32] +E50/(SD50+ES50)
H48: (T) [W31] +G50/(SD50+GS50)
J48: (T) [W32] +I50/(SD50+IS50)
L48: (T) [W32] +K50/(SD50+KS50)
N48: (T) [W16] +M50/(SD48+MS50)
P48: (T) [W17] +O50/(SD48+OS50)
R48: (T) [W18] +Q50/(SD48+QS50)
T48: (T) [W19] +S50/(SD48+SS50)
V48: (T) [W19] +U50/(SD48+US50)
X48: (T) [W18] +W50/(SD48+WS50)

B50: (T) [W10] ^Growth Inhibition
D50: (T) [W31] 1-@AVG(B25..B26)/SCS17
E50: (T) [W32] 1-@AVG(C25..C26)/SCS17
G50: (T) [W32] 1-@AVG(D25..D26)/SCS17
I50: (T) [W32] 1-@AVG(E25..E26)/SCS17
K50: (T) [W32] 1-@AVG(F25..F26)/SCS17
M50: (T) [W29] 1-@AVG(G25..G26)/SCS17
O50: (T) [W28] 1-@AVG(H25..H26)/SCS17
Q50: (T) [W27] 1-@AVG(I25..I26)/SCS17
S50: (T) [W25] 1-@AVG(J25..J26)/SCS17
U50: (T) [W28] 1-@AVG(K25..K26)/SCS17
W50: (T) [W25] 1-@AVG(L25..K26)/SCS17
B51: (T) [W10] +E7
C51: (T) [W31] +C7
E51: (T) [W32] +D7
G51: (T) [W32] +E51/2
I51: (T) [W32] +G51/2
K51: (T) [W32] +I51/2
M51: (T) [W29] +K51/2
O51: (T) [W28] +M51/2
Q51: (T) [W27] +O51/2
S51: (T) [W25] +Q51/2
U51: (T) [W28] +S51/2
W51: (T) [W25] +U51/2

End of formulas for the CRR

B63: (T) [W10] +B61/2
C63: (T) [W31] 100-(C21/SCS17)*100
D63: (T) [W31] 100-(D21/SCS17)*100
E63: (T) [W32] 100-(E21/SCS17)*100
F63: (T) [W32] 100-(F21/SCS17)*100
G63: (T) [W32] 100-(G21/SCS17)*100
H63: (T) [W31] 100-(H21/SCS17)*100
I63: (T) [W32] 100-(I21/SCS17)*100
J63: (T) [W32] 100-(J21/SCS17)*100
K63: (T) [W32] 100-(K21/SCS17)*100
L63: (T) [W32] 100-(L21/SCS17)*100

M63: (T) [W29] 100-@AVG(M21..N21)/SCS17*100

B64: (T) [W10] ^SUM
C64: (T) [W31] +CS71+SM63
D64: (T) [W31] +DS71+SM63
E64: (T) [W32] +ES71+SM63
F64: (T) [W32] +FS71+SM63
G64: (T) [W32] +GS71+SM63
H64: (T) [W31] +CH71+SM63
I64: (T) [W32] +CI71+SM63
J64: (T) [W32] +CJ71+SM63
K64: (T) [W32] +CK71+SM63

TABLE 3-continued

ALGORITHM WITH SPREADSHEET FORMULAS FOR ANALYSIS OF MIS DATA
(formula locations indicated by cell letter and number, e.g. C19)

L59: (T) [W32] 100-(L19/SCS17)*100
M59: (T) [W29] 100-(1-@AVG(M19..N19)/SCS17)*100
B60: (T) [W10] ^SUM
C60: (T) [W31] +CS71+SM59
D60: (T) [W31] +DS71+SM59
E60: (T) [W32] +ES71+SM59
F60: (T) [W32] +FS71+SM59
G60: (T) [W32] +GS71+SM59
H60: (T) [W31] +CH71+SM59
I60: (T) [W32] +CI71+SM59
J60: (T) [W32] +CJ71+SM59
K60: (T) [W32] +CK71+SM59
L60: (T) [W32] +CL71+SM59
M60: (T) [W29] +CM71+SM59
B61: (T) [W10] +B59/2
C61: (T) [W31] 100-(C20/SC597)*100
D61: (T) [W31] 100-(D20/SCS17)*100
E61: (T) [W32] 100-(E20/SCS17)*100
F61: (T) [W32] 100-(F20/SCS17)*100
G61: (T) [W32] 100-(G20/SCS17)*100
H61: (T) [W31] 100-(H20/SCS17)*100
I61: (T) [W32] 100-(I20/SCS17)*100
J61: (T) [W32] 100-(J20/SCS17)*100
K61: (T) [W32] 100-(K20/SCS17)*100
L61: (T) [W32] 100-(L20/SCS17)*100
M61: (T) [W29] 100-@AVG(M20..N20)/SCS17*100

B62: (T) [W10] ^SUM
C62: (T) [W31] +CS71+SM61
D62: (T) [W31] +DS71+SM61
E62: (T) [W32] +ES71+SM61
F62: (T) [W32] +FS71+SM61
G62: (T) [W32] +GS71+SM61
H62: (T) [W31] +CH71+SM61
I62: (T) [W32] +CI71+SM61
J62: (T) [W32] +CJ71+SM61
K62: (T) [W32] +CK71+SM61
L62: (T) [W32] +CL71+SM61
M62: (T) [W29] +CM71+SM61

B68: (T) [W10] ^SUM
C68: (T) [W31] +CS71+SM67
D68: (T) [W31] +DS71+SM67
E68: (T) [W32] +ES71+SM67
F68: (T) [W32] +FS71+SM67
G68: (T) [W32] +GS71+SM67
H68: (T) [W31] +CH71+SM67
I68: (T) [W32] +CI71+SM67
J68: (T) [W32] +CJ71+SM67
K68: (T) [W32] +CK71+SM67
L68: (T) [W32] +CL71+SM67
M68: (T) [W29] +CM71+SM67

B69: (T) [W10] +B67/2
C69: (T) [W31] 100-(C24/SC597)*100
D69: (T) [W31] 100-(D24/SCS17)*100
E69: (T) [W32] 100-(E24/SCS17)*100
F69: (T) [W32] 100-(F24/SCS17)*100
G69: (T) [W32] 100-(G24/SCS17)*100
H69: (T) [W31] 100-(H24/SCS17)*100
I69: (T) [W32] 100-(I24/SCS17)*100
J69: (T) [W32] 100-(J24/SCS17)*100
K69: (T) [W32] 100-(K24/SCS17)*100
L69: (T) [W32] 100-(L24/SCS17)*100
M69: (T) [W29] 100-@AVG(M24..N24)/SCS17*100

B70: (T) [W10] ^SUM
C70: (T) [W31] +CS71+SM69
D70: (T) [W31] +DS71+SM69
E70: (T) [W32] +ES71+SM69
F70: (T) [W32] +FS71+SM69
G70: (T) [W32] +GS71+SM69
H70: (T) [W31] +CH71+SM69
I70: (T) [W32] +CI71+SM69
J70: (T) [W32] +CJ71+SM69
K70: (T) [W32] +CK71+SM69

L64: (T) [W32] +CL71+SM63
M64: (T) [W29] +CM71+SM63
B65: (T) [W10] +B63/2
C65: (T) [W31] 100-(C22/SC597)*100
D65: (T) [W31] 100-(D22/SCS17)*100
E65: (T) [W32] 100-(E22/SCS17)*100
F65: (T) [W32] 100-(F22/SCS17)*100
G65: (T) [W32] 100-(G22/SCS17)*100
H65: (T) [W31] 100-(H22/SCS17)*100
I65: (T) [W32] 100-(I22/SCS17)*100
J65: (T) [W32] 100-(J22/SCS17)*100
K65: (T) [W32] 100-(K22/SCS17)*100
L65: (T) [W32] 100-(L22/SCS17)*100
M65: (T) [W29] 100-@AVG(M22..N22)/SCS17*100

B66: (T) [W10] ^SUM
C66: (T) [W31] +CS71+SM65
D66: (T) [W31] +DS71+SM65
E66: (T) [W32] +ES71+SM65
F66: (T) [W32] +FS71+SM65
G66: (T) [W32] +GS71+SM65
H66: (T) [W31] +CH71+SM65
I66: (T) [W32] +CI71+SM65
J66: (T) [W32] +CJ71+SM65
K66: (T) [W32] +CK71+SM65
L66: (T) [W32] +CL71+SM65
M66: (T) [W29] +CM71+SM65

B67: (T) [W10] +B65/2
C67: (T) [W31] 100-(C23/SC597)*100
D67: (T) [W31] 100-(D23/SCS17)*100
E67: (T) [W32] 100-(E23/SCS17)*100
F67: (T) [W32] 100-(F23/SCS17)*100
G67: (T) [W32] 100-(G23/SCS17)*100
H67: (T) [W31] 100-(H23/SCS17)*100
I67: (T) [W32] 100-(I23/SCS17)*100
J67: (T) [W32] 100-(J23/SCS17)*100
K67: (T) [W32] 100-(K23/SCS17)*100
L67: (T) [W32] 100-(L23/SCS17)*100
M67: (T) [W29] 100-@AVG(M23..N23)/SCS17*100
C72: (T) [W31] +CS71+SM71
D72: (T) [W31] +DS71+SM71
E72: (T) [W32] +ES71+SM71
F72: (T) [W32] +FS71+SM71
G72: (T) [W32] +GS71+SM71
H72: (T) [W31] +CH71+SM71
I72: (T) [W32] +CI71+SM71
J72: (T) [W32] +CJ71+SM71
K72: (T) [W32] +CK71+SM71
L72: (T) [W32] +CL71+SM71
M72: (T) [W29] +CM71+SM71

B73: (T) [W10] +SES7
C73: (T) [W31] +D7
D73: (T) [W31] +C73/2
E73: (T) [W32] +C73/2
F73: (T) [W32] +C73/2
G73: (T) [W32] +C73/2
H73: (T) [W31] +C73/2
I73: (T) [W32] +C73/2
J73: (T) [W32] +C73/2
K73: (T) [W32] +C73/2
L73: (T) [W32] +C73/2
M73: (T) [W29] +C73/2

B74: (T) [W10] +C7

B75: (T) [W10] ^to graph
C75: (T) [W31] 1-(@AVG(C25..C26)/SCS17)
D75: (T) [W31] 1-(@AVG(D25..D26)/SCS17)
E75: (T) [W32] 1-(@AVG(E25..E26)/SCS17)
F75: (T) [W32] 1-(@AVG(F25..F26)/SCS17)
G75: (T) [W32] 1-(@AVG(G25..G26)/SCS17)
H75: (T) [W31] 1-(@AVG(H25..H26)/SCS17)
I75: (T) [W32] 1-(@AVG(I25..I26)/SCS17)
J75: (T) [W32] 1-(@AVG(J25..J26)/SCS17)

TABLE 3-continued

ALGORITHM WITH SPREADSHEET FORMULAS FOR ANALYSIS OF MIS DATA
(formula locations indicated by cell letter and number, e.g. C19)

L70: (T) [W32] +CL71+SM69
M70: (T) [W29] +CM71+SM69

B71: (T) [W10] 0
C71: (T) [W31] 1-(@AVG(C25..C26)/SCS17)*100
D71: (T) [W31] 1-(@AVG(D25..D26)/SCS17)*100
E71: (T) [W32] 1-(@AVG(E25..E26)/SCS17)*100
F71: (T) [W32] 1-(@AVG(F25..F26)/SCS17)*100
G71: (T) [W32] 1-(@AVG(G25..G26)/SCS17)*100
H71: (T) [W31] 1-(@AVG(H25..H26)/SCS17)*100
I71: (T) [W32] 1-(@AVG(I25..I26)/SCS17)*100
J71: (T) [W32] 1-(@AVG(J25..J26)/SCS17)*100
K71: (T) [W32] 1-(@AVG(K25..K26)/SCS17)*100
L71: (T) [W32] 1-(@AVG(L25..L26)/SCS17)*100
M71: (T) [W29] 1-(@AVG(M25..M26)/SCS17)*100
Formulas for differential O/S plots
D78: (T) [W31] ^TABULATIONS OF
H78: (T) [W31] ^TABULATIONS OF
D79: (T) [W31] ^O/S DIFFERENTIALS
H79: (T) [W31] ^O/S DIFFERENTIALS
B80: (T) [W10] +SCS5
B81: (T) [W10] +SES5
Numbers in C81 to L11 indicate positions
of columns in the 96-well plate
C81: (T) [W31] 1
D81: (T) [W31] 2
E81: (T) [W32] 3
F81: (T) [W32] 4
G81: (T) [W32] 5
H81: (T) [W31] 6
I81: (T) [W32] 7
J81: (T) [W32] 8
K81: (T) [W32] 9
L81: (T) [W32] 10

B82: (T) [W10] +D5
C82: (T) [W31] +C59-C60
D82: (T) [W31] +D59-D60
E82: (T) [W32] +E59-E60
F82: (T) [W32] +F59-F60
G82: (T) [W32] +G59-G60
H82: (T) [W31] +H59-H60
I82: (T) [W32] +I59-I60
J82: (T) [W32] +J59-J60
K82: (T) [W32] +K59-K60
L82: (T) [W32] +L59-L60

B83: (T) [W10] +B82/2
C83: (T) [W31] +C61-C62
D83: (T) [W31] +D61-D62
E83: (T) [W32] +E61-E62
F83: (T) [W32] +F61-F62
G83: (T) [W32] +G61-G62
H83: (T) [W31] +H61-H62
I83: (T) [W32] +I61-I62
J83: (T) [W32] +J61-J62
K83: (T) [W32] +K61-K62
L83: (T) [W32] +L61-L62

K75: (T) [W32] 1-(@AVG(K25..K26)/SCS17)
L75: (T) [W32] 1-(@AVG(L25..L26)/SCS17)
M75: (T) [W29] 1-(@AVG(M25..M26)/SCS17)

B84: (T) [W10] +B83/2
C84: (T) [W31] +C63-C64
D84: (T) [W31] +D63-D64
E84: (T) [W32] +E63-E64
F84: (T) [W32] +F63-F64
G84: (T) [W32] +G63-G64
H84: (T) [W31] +H63-H64
I84: (T) [W32] +I63-I64
J84: (T) [W32] +J63-J64
K84: (T) [W32] +K63-K64
L84: (T) [W32] +L63-L64

B85: (T) [W10] +B84/2
C85: (T) [W31] +C65-C66
D85: (T) [W31] +D65-D66
E85: (T) [W32] +E65-E66
F85: (T) [W32] +F65-F66
G85: (T) [W32] +G65-G66
H85: (T) [W31] +H65-H66
I85: (T) [W32] +I65-I66
J85: (T) [W32] +J65-J66
K85: (T) [W32] +K65-K66
L85: (T) [W32] +L65-L66

B86: (T) [W10] +B85/2
C86: (T) [W31] +C67-C68
D86: (T) [W31] +D67-D68
E86: (T) [W32] +E67-E68
F86: (T) [W32] +F67-F68
G86: (T) [W32] +G67-G68
H86: (T) [W31] +H67-H68
I86: (T) [W32] +I67-I68
J86: (T) [W32] +J67-J68
K86: (T) [W32] +K67-K68
L86: (T) [W32] +L67-L68
B87: (T) [W10] +B86/2
C87: (T) [W31] +C69-C70
D87: (T) [W31] +D69-D70
E87: (T) [W32] +E69-E70
F87: (T) [W32] +F69-F70
G87: (T) [W32] +G69-G70
H87: (T) [W31] +H69-H70
I87: (T) [W32] +I69-I70
J87: (T) [W32] +J69-J70
K87: (T) [W32] +K69-K70
L87: (T) [W32] +L69-L70

An X-asis series used for graph of % growth inhibition
(with RA and TC1 data)
C91: (T) [W31] 1
D91: (T) [W31] +C91/2
E91: (T) [W32] +D91/2
F91: (T) [W32] +C91/2

TABLE 3-continued

ALGORITHM WITH SPREADSHEET FORMULAS FOR ANALYSIS OF MIS DATA
(formula locations indicated by cell letter and number, e.g. C19)

G91: (T) [W32] +C91/2
H91: (T) [W31] +C91/2
I91: (T) [W32] +C91/2
K91: (T) [W32] +C91/2
L91: (T) [W32] +C91/2
M91: (T) [W32] +C91/2
Formulas for analysis of cell growth
based upon ratios of absorbances at the end of a test
to absorbances at telronset of a test (as applied for MTT assay)

Headers for section of formulas
D94: (T) [W31] ^TABULATIONS FO GROWTH = N/N0
F94: (T) [W32] 'FROM IMMEDIATE PLATE:
J94: (T) [W32] ^Ratio
K94: (T) [W32] ^Fraction E95: (T) [W32] ^N0 = immediate assay =
F95: (T) [W32] 'enter mean absorbance value
J95: (T) [W32] +C17/+H95
K95: (T) [W32] +H95/C17

B98: (T) [W10] +SES5
B98: (T) [W10] +SES5
N98: (T) [W16] 11

B99: (T) [W10] +SES5

Numbers in C99 to N99 indicate positions
of columns in the 96-well plate
C99: (T) [W31] 1
D99: (T) [W31] 2
E99: (T) [W32] 3
F99: (T) [W32] 4
G99: (T) [W32] 5
H99: (T) [W31] 6
I99: (T) [W32] 7
H99: (T) [W32] 8
J99: (T) [W32] 9
K99: (T) [W32] 10
M99: (T) [W16] 11
N99: (T) [W16] 12

Formulas
B100: (T) [W10] +SDS5
D100: (T) [W31] +D19/SHS95
E100: (T) [W31] +E19/SHS95
F100: (T) [W32] +F19/SHS95
G100: (T) [W32] +G19/SHS95
H100: (T) [W31] +H19/SHS95
I100: (T) [W32] +I19/SHS95
J100: (T) [W32] +J19/SHS95
K100: (T) [W32] +K19/SHS95
L100: (T) [W32] +L19/SHS95
N100: (T) [W16] +O19/SHS95

B101: (T) [W10] +B100/2
C101: (T) [W31] +C20/SHS95
D101: (T) [W31] +D20/SHS95
E101: (T) [W32] +E20/SHS95
F101: (T) [W32] +F20/SHS95
G101: (T) [W32] +G20/SHS95
H101: (T) [W31] +H20/SHS95
I101: (T) [W32] +I20/SHS95
J101: (T) [W32] +J20/SHS95
K101: (T) [W32] +K20/SHS95
L101: (T) [W32] +L20/SHS95
N101: (T) [W16] +O20/SHS95

B102: (T) [W10] +B101/2
C102: (T) [W31] +C21/SHS95
D102: (T) [W31] +D21/SHS95
E102: (T) [W32] +E21/SHS95
F102: (T) [W32] +F21/SHS95
G102: (T) [W32] +G21/SHS95
H102: (T) [W31] +H21/SHS95
I102: (T) [W32] +I21/SHS95
J102: (T) [W32] +J21/SHS95
K102: (T) [W32] +K21/SHS95
L102: (T) [W32] +L21/SHS95
N102: (T) [W16] +O21/SHS95

B103: (T) [W10] +B102/2
C103: (T) [W31] +C22/SHS95
D103: (T) [W31] +D22/SHS95
E103: (T) [W32] +E22/SHS95
F103: (T) [W32] +F22/SHS95
G103: (T) [W32] +G22/SHS95
H103: (T) [W31] +H22/SHS95
I103: (T) [W32] +I22/SHS95
J103: (T) [W32] +J22/SHS95
K103: (T) [W32] +K22/SHS95
L103: (T) [W32] +L22/SHS95
N103: (T) [W16] +O22/SHS95

B104: (T) [W10] +B103/2
C104: (T) [W31] +C23/SHS95
D104: (T) [W31] +D23/SHS95
E104: (T) [W32] +E23/SHS95
F104: (T) [W32] +F23/SHS95
G104: (T) [W32] +G23/SHS95
H104: (T) [W31] +H23/SHS95
I104: (T) [W32] +I23/SHS95
J104: (T) [W32] +J23/SHS95
K104: (T) [W32] +K23/SHS95
L104: (T) [W32] +L23/SHS95
N104: (T) [W16] +O23/SHS95

B105: (T) [W10] +B104/2
C105: (T) [W31] +C24/SHS95
D105: (T) [W31] +D24/SHS95
E105: (T) [W32] +E24/SHS95
F105: (T) [W32] +F24/SHS95
G105: (T) [W32] +G24/SHS95
H105: (T) [W31] +H24/SHS95
I105: (T) [W32] +I24/SHS95
J105: (T) [W32] +J24/SHS95
K105: (T) [W32] +K24/SHS95
L105: (T) [W32] +L24/SHS95
N105: (T) [W16] +O24/SHS95

B107: (T) [W10] +B104/2
C107: (T) [W31] +C29/SHS95
D107: (T) [W31] +D29/SHS95
E107: (T) [W32] +E29/SHS95
F107: (T) [W32] +F29/SHS95
G107: (T) [W32] +G29/SHS95
H107: (T) [W31] +H29/SHS95
I107: (T) [W32] +I29/SHS95
J107: (T) [W32] +J29/SHS95
K107: (T) [W32] +K29/SHS95
L107: (T) [W32] +L29/SHS95
N107: (T) [W16] +C17/SHS95

Formulas continued
B109: (T) [W10] +SES7
C109: (T) [W31] +D7
D109: (T) [W31] +C109/2

TABLE 3-continued

ALGORITHM WITH SPREADSHEET FORMULAS FOR ANALYSIS OF MIS DATA
(formula locations indicated by cell letter and number, e.g. C19)

E109: (T) [W32] +D109/2
F109: (T) [W32] +E109/2
G109: (T) [W32] +F109/2
H109: (T) [W31] +G109/2
I109: (T) [W32] +H109/2
J109: (T) [W32] +I109/2
K109: (T) [W32] +J109/2
L109: (T) [W32] +K109/2
N109: (T) [W16] 0
Section of spreadsheet for acquisition of immediate data Headers for section
B110: (T) [W10] +D7

D113: (T) [W31] "IMMEDIATE DATA
E113: (T) [W32] 'EXP #
F113: (T) [W32] +G14

A114 (T) [W8] '{/File, Import/Comma}{Clear}a:\eia\*.*-
Absorbance data from a sidette is entered into
cells A115 throught a210 by the macro in spreadsheet cell A114
This data (not shown) is transferred to a tabular format in cells
C118 through N125 as indicated below (in C118 through N125)

Headers for section
C116: (T) [W31] ^IMMEDIATE MTT DATA
D116: (T) [W31] 'PLATE #
E116: (T) [W32] 'enter plate #

Numbers iin C117 to N117 iindicate postions
of columns in the 96-well plate
C117: (T) [W31] 1
D117: (T) [W31] 2
E117: (T) [W32] 3
F117: (T) [W32] 4
G117: (T) [W32] 5
H117: (T) [W31] 6
I117: (T) [W32] 7
J117: (T) [W32] 8
K117: (T) [W32] 9
L117: (T) [W32] 10
M117: (T) [W29] 12
N117: (T) [W16] 13

Beginning of Table (spreadsheet cells)
with transferred "immediate" absorbance data
C118: (T) [W31] +A115
D118: (T) [W31] +A116
E118: (T) [W32] +A117
F118: (T) [W32] +A118
G118: (T) [W32] +A119
H118: (T) [W31] +A120
I118: (T) [W32] +A121
J118: (T) [W32] +A122
K118: (T) [W32] +A123
L118: (T) [W32] +A124
M118: (T) [W29] +A125
N118: (T) [W16] +A126

C118: (T) [W31] +A127
D118: (T) [W31] +A128
E118: (T) [W32] +A129
F118: (T) [W32] +A130
G118: (T) [W32] +A131
H118: (T) [W31] +A132
I118: (T) [W32] +A133
J118: (T) [W32] +A134
K118: (T) [W32] +A135
L118: (T) [W32] +A136
M118: (T) [W29] +A137
N118: (T) [W16] +A138

C120: (T) [W31] +A139
D120: (T) [W31] +A140
E120: (T) [W32] +A141
F120: (T) [W32] +A142
G120: (T) [W32] +A143
H120: (T) [W31] +A144
I120: (T) [W32] +A145
J120: (T) [W32] +A146
K120: (T) [W32] +A147
L120: (T) [W32] +A148
M120: (T) [W29] +A149
N120: (T) [W16] +A150

C121: (T) [W31] +A151
D121: (T) [W31] +A152
E121: (T) [W32] +A153
F121: (T) [W32] +A154
G121: (T) [W32] +A155
H121: (T) [W31] +A156
I121: (T) [W32] +A157
J121: (T) [W32] +A158
K121: (T) [W32] +A159
L121: (T) [W32] +A160
M121: (T) [W29] +A161
N121: (T) [W16] +A162

C122: (T) [W31] +A163
D122: (T) [W31] +A164
E122: (T) [W32] +A165
F122: (T) [W32] +A166
G122: (T) [W32] +A167
H122: (T) [W31] +A168
I122: (T) [W32] +A169
J122: (T) [W32] +A170
K122: (T) [W32] +A171
L122: (T) [W32] +A172
M122: (T) [W29] +A173
N122: (T) [W16] +A174

C123: (T) [W31] +A175
D123: (T) [W31] +A176
E123: (T) [W32] +A177
F123: (T) [W32] +A178
G123: (T) [W32] +A179
H123: (T) [W31] +A180
I123: (T) [W32] +A181
J123: (T) [W32] +A182
K123: (T) [W32] +A183
L123: (T) [W32] +A184
M123: (T) [W29] +A185
N123: (T) [W16] +A186

C124: (T) [W31] +A187
D124: (T) [W31] +A188
E124: (T) [W32] +A189
F124: (T) [W32] +A190
G124: (T) [W32] +A191
H124: (T) [W31] +A192
I124: (T) [W32] +A193
J124: (T) [W32] +A194
K124: (T) [W32] +A195
L124: (T) [W32] +A196
M124: (T) [W29] +A197
N124: (T) [W16] +A198
Mean data from columns of wells in immediate assay plate
for use as $N_0$ (MTT assay in Examples)

TABLE 3-continued

ALGORITHM WITH SPREADSHEET FORMULAS FOR ANALYSIS OF MIS DATA
(formula locations indicated by cell letter and number, e.g. C19)

C125: (T) [W31] +A199
D125: (T) [W31] +A200
E125: (T) [W32] +A201
F125: (T) [W32] +A202
G125: (T) [W32] +A203
H125: (T) [W31] +A204
I125: (T) [W32] +A205
J125: (T) [W32] +A206
K125: (T) [W32] +A207
L125: (T) [W32] +A208
M125: (T) [W29] +A209
N125: (T) [W16] +A210

Headers for Tabulation of Cells Loss in %
C136: (F2) [W31] 1-C103
D136: (F2) [W31] 1-C103
E136: (F2) [W32] 1-C103
F136: (F2) [W32] 1-C103
G136: (F2) [W32] 1-C103
H136: (F2) [W31] 1-C103
I136: (F2) [W32] 1-C103
J136: (F2) [W32] 1-C103
K136: (F2) [W32] 1-C103
L136: (F2) [W32] 1-C103
B137: (F2) [W10] +B136/2
C137: (F2) [W31] 1-C104
D137: (F2) [W31] 1-C104
E137: (F2) [W32] 1-C104
F137: (F2) [W32] 1-C104
G137: (F2) [W32] 1-C104
H137: (F2) [W31] 1-C104
I137: (F2) [W32] 1-C104
J137: (F2) [W32] 1-C104
K137: (F2) [W32] 1-C104
B133: (F2) [W10] +SDS5
C133: (F2) [W31] 1-C100
D133: (F2) [W31] 1-D100
E133: (F2) [W32] 1-E100
F133: (F2) [W32] 1-F100
G133: (F2) [W32] 1-G100
H133: (F2) [W31] 1-H100
I133: (F2) [W32] 1-I100
J133: (F2) [W32] 1-J100
K133: (F2) [W32] 1-K100
L133: (F2) [W32] 1-L100

B134: (F2) [W10] +B133/2
C134: (F2) [W31] 1-C101
D134: (F2) [W31] 1-C101
E134: (F2) [W32] 1-C101
F134: (F2) [W32] 1-C101
G134: (F2) [W32] 1-C101
H134: (F2) [W31] 1-C101
I134: (F2) [W32] 1-C101
J134: (F2) [W32] 1-C101
K134: (F2) [W32] 1-C101
L134: (F2) [W32] 1-C101

B134: (F2) [W10] +B134/2
C135: (F2) [W31] 1-C102
D135: (F2) [W31] 1-C102
E135: (F2) [W32] 1-C102
F135: (F2) [W32] 1-C102
G135: (F2) [W32] 1-C102
H135: (F2) [W31] 1-C102
I135: (F2) [W32] 1-C102
J135: (F2) [W32] 1-C102
K135: (F2) [W32] 1-C102
L135: (F2) [W32] 1-C102
Formulas for the CRR to be used in an LDH
or comparable assay-
B42: (F0) [W9] +E5

D126: (T) [W31] 1
E126: #32] 2
F126: (T) [W32] 3

B127: (T) [W10] 'MEAN
C127: (T) [W31]@AVG(C118..C125)
D127: (T) [W31]@AVG(D118..D125)
E127: (T) [W32]@AVG(E118..E125)
F127: (T) [W32]@AVG(F118..F125)
G127: (T) [W32]@AVG(G118..G125)
H127: (T) [W31]@AVG(H118..H125)
I127: (T) [W32]@AVG(I118..I125)
J127: (T) [W32]@AVG(J118..J125)
K127: (T) [W32]@AVG(K118..K125)
L127: (T) [W32]@AVG(L118..L125)
M127: (T) [W29]@AVG(M118..M125)
N127: (T) [W16]@AVG(N118..N125)
B136: (F2) [W10] +B135/2

L137: (F2) [W32] 1-C104

B138: (F2) [W10] +B137/2
C138: (F2) [W31] 1-C105
D138: (F2) [W31] 1-C105
E138: (F2) [W32] 1-C105
F138: (F2) [W32] 1-C105
G138: (F2) [W32] 1-C105
H138: (F2) [W31] 1-C105
I138: (F2) [W32] 1-C105
J138: (F2) [W32] 1-C105
K138: (F2) [W32] 1-C105
L138: (F2) [W32] 1-C105

B140: (F2) [W10] "Means
C140: (F2) [W31] 1-C107
D140: (F2) [W31] 1-C107
E140: (F2) [W32] 1-C107
F140: (F2) [W32] 1-C107
G140: (F2) [W32] 1-C107
H140: (F2) [W31] 1-C107
I140: (F2) [W32] 1-C107
J140: (F2) [W32] 1-C107
K140: (F2) [W32] 1-C107
L140: (F2) [W32] 1-C107

D142: (F2) [W31] +C142/2
E142: (F2) [W32] +D142/2
F142: (F2) [W32] +E142/2
G142: (F2) [W32] +F142/2
H142: (F2) [W31] +G142/2
I142: (F2) [W32] +H142/2
J142: (F2) [W32] +I142/2
K142: (F2) [W32] +J142/2
L142: (F2) [W32] +K142/2

B44: (F0) [W9] +B43/2

TABLE 3-continued

ALGORITHM WITH SPREADSHEET FORMULAS FOR ANALYSIS OF MIS DATA
(formula locations indicated by cell letter and number, e.g. C19)

C42: (F2) [W7] @AVG(M19..N19)/SCS17
D42: (F1) [W7] +C42/(SC42+DS50)
E42: (F0) [W6] 'blank well
G42: (F2) [W6] +D19/SCS17
H42: (F1) [W6] +G42/(SC42+GS50)
I42: (F2) [W6] (E19/SCS17)
J42: (F1) [W6] +I42/(SC42+IS50)
K42: (F2) [W6] (F19/SCS17)
L42: (F1) [W6] +K42/(SC42+KS50)
M42: (F2) [W7] (G19/SCS17)
N42: (F1) [W7] +M42/(SC42+MS50)
O42: (F2) [W7] (H19/SCS17)
P42: (F1) [W6] +O42/(SC42+OS50)
Q42: (F2) [W6] (I19/SCS17)
R42: (F1) [W6] +Q42/(SC42+QS50)
S42: (F2) [W6] (J19/SCS17)
T42: (F1) [W5] +S42/(SC42+SS50)
U42: (F2) [W6] (K19/SCS17)
V42: (F1) [W5] +U42/(SC42+US50)
W42: (F2) [W6] (L19/SCS17)
X42: (F1) [W5] +W42/(SC42+WS50)

B43: (F0) [W9] +B42/2
C43: (F2) [W7] @AVG(M20..N20)/SCS17
D43: (F1) [W7] +C43/(SC43+DS50)
E43: (F2) [W6] +C20/SCS17
F43: (F1) [W6] E43/(SC43+ES50)
G43: (F2) [W6] +D20/SCS17
H43: (F1) [W6] +G43/(SC43+GS50)
I43: (F2) [W6] (E20/SCS17)
J43: (F1) [W6] +I43/(SC43+IS50)
K43: (F2) [W6] (F20/SCS17)
L43: (F1) [W6] +K43/(SC43+KS50)
M43: (F2) [W7] (G20/SCS17)
N43: (F1) [W7] +M43/(SC43+MS50)
O43: (F2) [W7] (H20/SCS17)
P43: (F1) [W6] +O43/(SC43+OS50)
Q43: (F2) [W6] (I20/SCS17)
R43: (F1) [W6] +Q43/(SC43+QS50)
S43: (F2) [W6] (J20/SCS17)
T43: (F1) [W5] +S43/(SC43+SS50)
U43: (F2) [W6] (K20/SCS17)
V43: (F1) [W5] +U43/(SC43+US50)
W43: (F2) [W6] (L20/SCS17)
X43: (F1) [W5] +W43/(SC43+WS50)

B46: (F0) [W9] +B45/2
C46: (F2) [W7] @AVG(M23..N23)/SCS17
D46: (F1) [W7] +C46/(SC42+DS50)
E46: (F2) [W6] +C23/SCS17
F46: (F1) [W6] E45/(SC46+ES50)
G46: (F2) [W6] +D23/SCS17
H46: (F1) [W6] +G46/(SC45+GS50)
I46: (F2) [W6] (E23/SCS17)
J46: (F1) [W6] +I46/(SC45+IS50)
K46: (F2) [W6] (F23/SCS17)
L46: (F1) [W6] +K46/(SC45+KS50)
M46: (F2) [W7] (G23/SCS17)
N46: (F1) [W7] +M46/(SC45+MS50)
O46: (F2) [W7] (H23/SCS17)
P46: (F1) [W6] +O46/(SC45+OS50)
Q46: (F2) [W6] (I23/SCS17)
R46: (F1) [W6] +Q46/(SC45+QS50)
S46: (F2) [W6] (J23/SCS17)
T46: (F1) [W5] +S46/(SC45+SS50)
U46: (F2) [W6] (K23/SCS17)
V46: (F1) [W5] +U46/(SC45+US50)
W46: (F2) [W6] (L23/SCS17)
X46: (F1) [W5] +W46/(SC45+WS50)

B47: (F0) [W9] +B44/2
C47: (F2) [W7] @AVG(M24..N24)/SCS17
D47: (F1) [W7] +C45/(SC47+DS50)
E47: (F2) [W6] +C22/SCS17
F47: (F1) [W6] E45/(SC47+ES50)
G47: (F2) [W6] +D22/SCS17

C44: (F2) [W7] @AVG(M21..N21)/SCS17
D44: (F1) [W7] +C44/(SC42+DS50)
E44: (F2) [W6] +C21/SCS17
F44: (F1) [W6] E44/(SC44+ES50)
G44: (F2) [W6] +D21/SCS17
H44: (F1) [W6] +G44/(SC44+GS50)
I44: (F2) [W6] (E21/SCS17)
J44: (F1) [W6] +I44/(SC44+IS50)
K44: (F2) [W6] (F21/SCS17)
L44: (F1) [W6] +K44/(SC44+KS50)
M44: (F2) [W7] (G21/SCS17)
N44: (F1) [W7] +M44/(SC44+MS50)
O44: (F2) [W7] (H21/SCS17)
P44: (F1) [W6] +O44/(SC44+OS50)
Q44: (F2) [W6] (I21/SCS17)
R44: (F1) [W6] +Q44/(SC44+QS50)
S44: (F2) [W6] (J21/SCS17)
T44: (F1) [W5] +S44/(SC44+SS50)
U44: (F2) [W6] (K21/SCS17)
V44: (F1) [W5] +U44/(SC44+US50)
W44: (F2) [W6] (L21/SCS17)
X44: (F1) [W5] +W44/(SC44+WS50)

B45: (F0) [W9] +B44/2
C45: (F2) [W7] @AVG(M22..N22)/SCS17
D45: (F1) [W7] +C45/(SC42+DS50)
E45: (F2) [W6] +C22/SCS17
F45: (F1) [W6] E45/(SC45+ES50)
G45: (F2) [W6] +D22/SCS17
H45: (F1) [W6] +G45/(SC45+GS50)
I45: (F2) [W6] (E22/SCS17)
J45: (F1) [W6] +I45/(SC45+IS50)
K45: (F2) [W6] (F22/SCS17)
L45: (F1) [W6] +K45/(SC45+KS50)
M45: (F2) [W7] (G22/SCS17)
N45: (F1) [W7] +M45/(SC45+MS50)
O45: (F2) [W7] (H22/SCS17)
P45: (F1) [W6] +O45/(SC45+OS50)
Q45: (F2) [W6] (I22/SCS17)
R45: (F1) [W6] +Q45/(SC45+QS50)
S45: (F2) [W6] (J22/SCS17)
T45: (F1) [W5] +S45/(SC45+SS50)
U45: (F2) [W6] (K22/SCS17)
V45: (F1) [W5] +U45/(SC45+US50)
W45: (F2) [W6] (L22/SCS17)
X45: (F1) [W5] +W45/(SC45+WS50)
B50: [W9] 'Release Multiple
E50: (F2) [W6] @ AVG(C25..C26)/SCS17
G50: (F2) [W6] @ AVG(D25..E26)/SCS17
I50: (F2) [W6] @ AVG(E25..D26)/SCS17
K50: (F2) [W6] @ AVG(F25..F26)/SCS17
M50: (F2) [W7] @ AVG(G25..G26)/SCS17
O50: (F2) [W7] @ AVG(H25..H26)/SCS17
Q50: (F2) [W6] @ AVG(I25..I26)/SCS17
S50: (F2) [W6] @ AVG(J25..J26)/SCS17
U50: (F2) [W6] @ AVG(K25..K26)/SCS17
W50: (F2) [W6] @ AVG(L25..L26)/SCS17

B51: U[W9] F7
C51: U[W7] C7
E51: (F1) [W6] +E7
G51: (F1) [W6] +E1/2
IS1: (F1) [W6] G51/2
K51: (F1) [W6] I51/2
M51: (F1) [W7] K51/2
O51: (F1) [W7] M51/2
Q51: (F1) [W6] O51/2
S51: (F1) [W6] Q51/2
U51: (F1) [W6] S51/2
W51: (F1) [W6] U51/2

TABLE 3-continued

ALGORITHM WITH SPREADSHEET FORMULAS FOR ANALYSIS OF MIS DATA
(formula locations indicated by cell letter and number, e.g. C19)

H47: (F1) [W6] +G47/(SC47+GS50)
I47: (F2) [W6] (E24/SCS17)
J47: (F1) [W6] +I47/(SC47+IS50)
K47: (F2) [W6] (F22/SCS17)
L47: (F1) [W6] +K47/(SC47+KS50)
M47: (F2) [W7] (G22/SCS17)
N47: (F1) [W7] +M47/(SC47+MS50)
O47: (F2) [W7] (H22/SCS17)
P47: (F1) [W6] +O47/(SC47+OS50)
Q47: (F2) [W6] (I22/SCS17)
R47: (F1) [W6] +Q47/(SC47+QS50)
S47: (F2) [W6] (J22/SCS17)
T47: (F1) [W5] +S47/(SC47+SS50)
U47: (F2) [W6] (K22/SCS17)
V47: (F1) [W5] +U47/(SC47+US50)
W47: (F2) [W6] (L22/SCS17)
X47: (F1) [W5] +W47/(SC47+WS50)

TABLE 4

TABULATIONS OF COMBINED RESULTS RATIOS

U937  062994

Total Time 18 H   STSP for 14 H
                  dThd for 4 H

STSP mM STSP only

| mM | % | ratio | | | | | | | | | | | | | | | | | | | |
|---|---|---|---|---|---|---|---|---|---|---|---|---|---|---|---|---|---|---|---|---|---|
| 100 | 46% | 1.0 | 83% | 0.9 | 83% | 1.0 | 82% | 1.0 | 82% | 1.2 | 82% | 1.3 | 81% | 1.3 | 79% | 1.4 | 74% | 1.3 | 64% | 1.4 | Blank |
| 50 | 43% | 1.0 | 86% | 0.9 | 85% | 1.0 | 84% | 1.1 | 83% | 1.3 | 82% | 1.4 | 82% | 1.4 | 79% | 1.5 | 77% | 1.4 | 61% | 1.5 | 37% 1.0 |
| 25 | 26% | 1.0 | 84% | 1.1 | 81% | 1.2 | 79% | 1.3 | 75% | 1.5 | 74% | 1.7 | 72% | 1.8 | 65% | 1.8 | 63% | 1.7 | 43% | 1.8 | 20% 1.0 |
| 12.5 | 9% | 1.0 | 74% | 1.3 | 68% | 1.4 | 63% | 1.5 | 61% | 1.9 | 54% | 2.0 | 50% | 2.1 | 43% | 2.3 | 39% | 2.0 | 23% | 3.2 | 4% 2.3 |
| 6.25 | 6% | 1.0 | 64% | 1.1 | 56% | 1.2 | 46% | 1.2 | 43% | 1.5 | 37% | 1.5 | 31% | 1.5 | 28% | 1.8 | 22% | 1.3 | 9% | 2.1 | -2% 1.6 |
| 3.125 | 1% | 1.0 | 55% | 1.1 | 47% | 1.1 | 43% | 1.2 | 33% | 1.4 | 28% | 1.4 | 23% | 1.5 | 21% | 1.8 | 18% | 1.5 | 6%-22.6 | | -4% 0.8 |
| 0 | 0% | | 50% 1.0 | | 41% 1.0 | | 34% 1.0 | | 23% 1.0 | | 18% 1.0 | | 14% 1.0 | | 10% 1.0 | | 11% 1.0 | | -2% 1.0 | | -7% 1.0 |
| dThd mM | | | 3.00 | | 1.50 | | 0.75 | | 0.38 | | 0.19 | | 0.09 | | 0.05 | | 0.02 | | 0.01 | | 0.01 | |

TABLE 5

BIVARIATE SERIAL DILUTION ANALYSIS (BVSD)

TABULATIONS OF
LDH Method     COMBINED RESULTS RATIOS     U937 Cells

Total Time 18 H   STSP for 14 H
STSP              dThd for 4 H
nM

LDH release multiple

| nM | | | | | | | | | | | | | | | | | | | | | |
|---|---|---|---|---|---|---|---|---|---|---|---|---|---|---|---|---|---|---|---|---|---|
| 100 | 1.66 | 10 | Blank well | | 4.92 | 1.2 | 4.43 | 1.2 | 4.00 | 1.2 | 3.61 | 1.1 | 4.07 | 1.4 | 4.23 | 1.5 | 3.11 | 1.1 | 1.96 | 0.7 | 1.61 0.6 |
| 50 | 1.30 | 1.0 | | | 6.36 | 1.3 | 5.75 | 1.5 | 5.29 | 1.6 | 4.93 | 1.7 | 4.90 | 1.7 | 4.75 | 1.9 | 4.75 | 1.9 | 3.38 | 1.4 | 1.79 0.7 | 1.31 0.6 |
| 25 | 1.08 | 1.0 | | | 6.67 | 1.4 | 5.98 | 1.6 | 5.40 | 1.8 | 4.96 | 1.9 | 4.55 | 1.7 | 4.00 | 1.8 | 3.31 | 1.5 | 2.52 | 1.1 | 1.33 0.6 | 1.00 0.5 |
| 13 | 0.96 | 1.0 | | | 5.91 | 1.3 | 5.41 | 1.5 | 4.77 | 1.6 | 4.14 | 1.7 | 3.42 | 1.4 | 2.60 | 1.2 | 1.82 | 0.9 | 1.36 | 0.6 | 0.96 0.5 | 0.88 0.4 |
| 6 | 0.91 | 1.0 | | | 4.80 | 1.1 | 4.24 | 1.2 | 3.69 | 1.3 | 2.74 | 1.1 | 2.29 | 0.9 | 1.69 | 0.8 | 1.09 | 0.5 | 0.97 | 0.5 | 0.86 0.4 | 0.83 0.4 |
| 3 | 0.89 | | | | 4.40 | 1.0 | 3.69 | 1.1 | 2.86 | 1.0 | 2.15 | 0.9 | 1.58 | 0.6 | 1.21 | 0.6 | 0.95 | 0.5 | 0.89 | 0.4 | 0.88 0.4 | 0.86 0.4 |

Release Multiple 0%   3.61   2.55   2.00   1.54   1.56   1.19   1.14   1.20   1.10   1.09
mM    dThd          3.00   1.50   0.75   0.38   0.19   0.09   0.05   0.02   0.01   0.01

TABLE 6

BIVARIATE SERIAL DILUTION ANALYSIS (BVSD)

TABULATIONS OF
MTT Assay #515   COMBINED   RESULTS   RATIOS   DELAYED PROLIFERATION ASSAY U937 Cells Total Time   70 H       STSP   for   18 + 48 Hours
STSP                    dThd   for   22 + 48 Hours
nM Growth Inhibition (%)

| STSP nM | STSP only | blank well | | | | | | | | | | | | | | | | |
|---|---|---|---|---|---|---|---|---|---|---|---|---|---|---|---|---|---|---|
| 200.0 | 96% | 1.0 | 97% | 0.6 | 97% | 0.6 | 97% | 0.6 | 97% | 0.7 | 97% | 0.7 | 96% | 1.0 | 96% | 1.0 | 96% | 1.0 | 96% | 1.0 |
| 100.0 | 90% | 1.0 | 97% | 0.5 | 97% | 0.6 | 97% | 0.6 | 97% | 0.6 | 97% | 0.7 | 96% | 1.0 | 94% | 1.0 | 91% | 1.0 | 91% | 1.0 |
| 50.0 | 70% | 1.0 | 97% | 0.6 | 97% | 0.7 | 97% | 0.7 | 97% | 0.7 | 97% | 0.8 | 96% | 0.9 | 93% | 1.2 | 81% | 1.1 | 73% | 1.1 | 70% | 1.0 |
| 25.0 | 57% | 1.0 | 97% | 0.7 | 97% | 0.7 | 97% | 0.8 | 97% | 0.8 | 97% | 0.9 | 97% | 1.0 | 92% | 1.5 | 74% | 1.2 | 62% | 1.1 | 56% | 1.0 |
| 12.5 | 29% | 1.0 | 97% | 0.8 | 97% | 0.9 | 97% | 1.0 | 96% | 1.1 | 96% | 1.2 | 94% | 1.4 | 79% | 2.4 | 46% | 1.5 | 37% | 1.3 | 29% | 1.1 |
| 6.3 | -11% | 1.0 | 97% | 1.3 | 97% | 1.5 | 96% | 1.8 | 95% | 1.9 | 92% | 2.4 | 87% | 3.3 | 62% | 9.7 | -3% | 0.4 | -8% | 0.8 | -6% | 0.4 |

Growth Inhibition 0%   87% 1.0  76% 1.0  65% 1.0  60% 1.0  50% 1.0  37% 1.0  4% 1.0  3% 1.0  -1% 1.0  -3% 1.0
mM    dThd   3.00   1.50   0.75   0.38   0.19   0.09   0.05   0.02   0.01   0.01

TABLE 7

TABULATIONS OF
U937       COMBINED   RESULTS   RATIOS

Total Time   18 H       STSP   for   14 H
                        dThd   for   4 H

| STSP nM | STSP only | | | | | | | | | | | | | | | | | | | | |
|---|---|---|---|---|---|---|---|---|---|---|---|---|---|---|---|---|---|---|---|---|---|
| 100 | 46% | 1.0 | 83% | 0.9 | 83% | 1.0 | 82% | 1.0 | 82% | 1.2 | 82% | 1.3 | 81% | 1.3 | 79% | 1.4 | 74% | 1.3 | 64% | 1.4 | Blank |
| 50 | 43% | 1.0 | 86% | 0.9 | 85% | 1.0 | 84% | 1.1 | 83% | 1.3 | 82% | 1.4 | 82% | 1.4 | 79% | 1.5 | 77% | 1.4 | 61% | 1.5 | 37% | 1.0 |
| 25 | 26% | 1.0 | 84% | 1.1 | 81% | 1.2 | 79% | 1.3 | 75% | 1.5 | 74% | 1.7 | 72% | 1.8 | 65% | 1.8 | 63% | 1.7 | 43% | 1.8 | 20% | 1.0 |
| 12.5 | 9% | 1.0 | 74% | 1.3 | 68% | 1.4 | 63% | 1.5 | 61% | 1.9 | 54% | 2.0 | 50% | 2.1 | 43% | 2.3 | 39% | 2.0 | 23% | 3.2 | 4% | 2.3 |
| 6.25 | 6% | 1.0 | 64% | 1.1 | 56% | 1.2 | 46% | 1.2 | 43% | 1.5 | 37% | 1.5 | 31% | 1.5 | 28% | 1.8 | 22% | 1.3 | 9% | 2.1 | -2% | 1.6 |
| 3.125 | 1% | 1.0 | 55% | 1.1 | 47% | 1.1 | 43% | 1.2 | 33% | 1.4 | 28% | 1.4 | 23% | 1.5 | 21% | 1.8 | 18% | 1.5 | 6%-22.6 | -4% | 0.8 |

0   0%   50% 1.0   41% 1.0   34% 1.0   23% 1.0   18% 1.0   14% 1.0   10% 1.0   11% 1.0   -2% 1.0   -7% 1.0
dThd   mM   3.00   1.50   0.75   0.38   0.19   0.09   0.05   0.02   0.01   0.01

TABULATIONS OF
U937   09 02 8452   COMBINED   RESULTS   RATIOS

Total Time   18 H       STSP   for   18 H
                        dThd   for   0 H

| STSP nM | STSP only | MTT blank well | | | | | | | | | | | | | | | | | | |
|---|---|---|---|---|---|---|---|---|---|---|---|---|---|---|---|---|---|---|---|---|
| 100 | 47% | 1.0 | | 62% | 0.8 | 63% | 0.9 | 63% | 0.9 | 63% | 1.0 | 63% | 1.1 | 60% | 1.1 | 56% | 1.1 | 53% | 1.0 | 51% | 1.0 |
| 50 | 39% | 1.0 | | 62% | 0.8 | 61% | 0.9 | 62% | 0.9 | 61% | 1.0 | 62% | 1.1 | 61% | 1.2 | 58% | 1.3 | 55% | 1.3 | 48% | 1.1 | 43% | 1.0 |
| 25 | 26% | 1.0 | | 56% | 0.9 | 56% | 1.0 | 55% | 1.0 | 54% | 1.2 | 52% | 1.2 | 51% | 1.3 | 47% | 1.5 | 37% | 1.3 | 31% | 1.0 | 30% | 1.0 |
| 12.5 | 14% | 1.0 | | 47% | 0.9 | 48% | 1.0 | 46% | 1.1 | 43% | 1.2 | 38% | 1.3 | 34% | 1.3 | 32% | 1.6 | 23% | 1.4 | 18% | 1.0 | 14% | 0.9 |
| 6.25 | 5% | 1.0 | | 42% | 1.0 | 38% | 1.0 | 35% | 1.1 | 32% | 1.3 | 26% | 1.3 | 23% | 1.3 | 19% | 1.8 | 11% | 1.4 | 10% | 1.0 | 8% | 1.0 |
| 3.13 | 2% | 1.0 | | 38% | 1.0 | 37% | 1.1 | 29% | 1.0 | 26% | 1.2 | 19% | 1.1 | 18% | 1.3 | 15% | 2.0 | 8% | 1.7 | 6% | 1.1 | 3% | 0.6 |

0   0%   38% 1.0   33% 1.0   27% 1.0   20% 1.0   15% 1.0   12% 1.0   10% 1.0   6% 1.0   4% 1.0   3% 1.0
dThd   mM   3.00   1.50   0.75   0.38   0.19   0.09   0.05   0.02   0.01   0.01

TABLE 8

Results of test of RNR inhibitors as RA with STSP in U937 cells

| RNR inhibitor | concentrations resulting in >IC$_{40}$ | range of S$_{MAX}$ for 12.5–50 nM STSP |
|---|---|---|
| dThd | >1 mM | 0.02–0.4 mM |
| BrdU | >0.2 mM | .05–.019 mM |
| dAde | >0.4 mM | .08–.3 mM |
| dGuo | >0.06 mM | 0.01–0.06 mM |
| HU | >2 mM | 0.06–0.5 mM |

TABLE 9

TABULATIONS OF COMBINED RESULTS RATIOS — U937

Total Time 22 H; STSP for 18 H; BrdU for 4 H

| STSP nM | STSP only | MTT blank well | | | | | | | | | | | | | | | | | |
|---|---|---|---|---|---|---|---|---|---|---|---|---|---|---|---|---|---|---|---|
| 200 | 49% | 1.0 | 81% | 0.7 | 81% | 0.8 | 82% | 0.9 | 83% | 1.0 | 81% | 1.2 | 69% | 1.3 | 55% | 1.1 | 52% | 1.0 | 49% | 0.9 |
| 100 | 42% | 1.0 | 80% | 0.8 | 84% | 0.8 | 85% | 0.9 | 86% | 1.0 | 86% | 1.1 | 84% | 1.3 | 76% | 1.6 | 52% | 1.1 | 44% | 1.0 | 42% | 0.9 |
| 50 | 19% | 1.0 | 79% | 1.0 | 84% | 1.0 | 84% | 1.1 | 83% | 1.3 | 80% | 1.5 | 76% | 1.9 | 63% | 2.7 | 32% | 1.4 | 23% | 1.0 | 21% | 0.8 |
| 25 | 11% | 1.0 | 74% | 1.0 | 78% | 1.1 | 78% | 1.1 | 77% | 1.4 | 71% | 1.6 | 61% | 1.9 | 44% | 2.8 | 20% | 1.4 | 14% | 0.9 | 13% | 0.8 |
| 12.5 | 3% | 1.0 | 69% | 1.1 | 72% | 1.1 | 73% | 1.2 | 68% | 1.4 | 60% | 1.6 | 46% | 2.0 | 28% | 3.6 | 11% | 1.7 | 8% | 1.2 | 5% | 0.8 |
| 6.25 | 0% | 1.0 | 67% | 1.1 | 70% | 1.0 | 69% | 1.2 | 63% | 1.4 | 52% | 1.5 | 36% | 1.7 | 20% | 4.0 | 4% | 1.0 | 7% | 1.6 | 6% | 1.6 |
| 0 | 0% | | 61% 1.0 | 61% 1.0 | 58% 1.0 | 46% 1.0 | 35% 1.0 | 21% 1.0 | 10% 1.0 | 5% 1.0 | 4% 1.0 | 4% 1.0 |
| BrdU mM | | 3.00 | 1.50 | 0.75 | 0.38 | 0.19 | 0.09 | 0.05 | 0.02 | 0.01 | 0.01 |

TABLE 10

TABULATIONS OF COMBINED RESULTS RATIOS — U937

Total Time 17 H; STSP for 17 H; dAde for 0 H

| STSP nM | STSP only | MTT blank well | | | | | | | | | | | | | | | | | |
|---|---|---|---|---|---|---|---|---|---|---|---|---|---|---|---|---|---|---|---|
| 100 | 33% | 1.0 | 92% | 0.8 | 86% | 0.9 | 75% | 1.3 | 68% | 1.6 | 60% | 1.6 | 51% | 2.0 | 41% | 1.3 | 40% | 1.3 | 39% | 1.3 |
| 50 | 27% | 1.0 | 96% | 0.8 | 93% | 0.9 | 87% | 1.0 | 75% | 1.5 | 67% | 1.8 | 58% | 1.9 | 47% | 2.3 | 35% | 1.4 | 35% | 1.3 | 32% | 1.3 |
| 25 | 18% | 1.0 | 97% | 0.9 | 93% | 0.9 | 81% | 1.0 | 68% | 1.6 | 56% | 2.0 | 41% | 1.9 | 27% | 2.4 | 17% | 1.1 | 16% | 1.0 | 13% | 0.2 |
| 12.5 | 7% | 1.0 | 97% | 1.0 | 92% | 1.0 | 76% | 1.1 | 47% | 1.5 | 40% | 2.2 | 19% | 1.7 | 12% | 19.7 | 5% | 0.9 | 6% | 1.1 | 5% | 0.9 |
| 6.25 | 2% | 1.0 | 93% | 1.0 | 87% | 1.1 | 65% | 1.0 | 32% | 1.2 | 19% | 1.5 | 2% | 0.4 | 4% | -0.9 | -3% | -26.0 | 3% | 5.2 | 4% | 36.0 |
| 3.13 | -3% | 1.0 | 96% | 1.1 | 84% | 1.1 | 61% | 1.0 | 28% | 1.4 | 12% | 1.6 | 3% | 3.0 | 5% | -0.5 | -2% | 0.3 | 1% | -0.2 | 2% | -0.5 |
| 0 | 0% | | 93% 1.0 | 81% 1.0 | 61% 1.0 | 24% 1.0 | 10% 1.0 | 4% 1.0 | 1% 1.0 | -7% 1.0 | -1% 1.0 | -2% 1.0 |
| dAde mM | | 3.00 | 1.50 | 0.75 | 0.38 | 0.19 | 0.09 | 0.05 | 0.02 | 0.01 | 0.01 |

TABLE 11

TABULATIONS OF COMBINED RESULTS RATIOS — U937

Total Time 17 H; STSP for 17 H; dGuo for 0 H

| STSP nM | STSP only | MTT blank well | | | | | | | | | | | | | | | | | |
|---|---|---|---|---|---|---|---|---|---|---|---|---|---|---|---|---|---|---|---|
| 100 | 37% | 1.0 | 89% | 0.7 | 87% | 0.7 | 87% | 0.7 | 85% | 0.8 | 81% | 0.9 | 77% | 1.7 | 67% | 1.7 | 51% | 1.3 | 43% | 1.1 |
| 50 | 29% | 1.0 | 93% | 0.8 | 91% | 0.8 | 88% | 0.8 | 88% | 0.8 | 86% | 0.8 | 81% | 1.0 | 74% | 1.9 | 68% | 2.2 | 52% | 1.7 | 39% | 1.2 |
| 25 | 17% | 1.0 | 93% | 0.8 | 91% | 0.9 | 87% | 0.8 | 86% | 0.9 | 86% | 0.9 | 77% | 1.1 | 62% | 2.3 | 58% | 3.1 | 35% | 1.9 | 23% | 1.2 |
| 12.5 | 8% | 1.0 | 91% | 0.9 | 89% | 0.9 | 86% | 0.9 | 84% | 1.0 | 84% | 1.0 | 69% | 1.1 | 51% | 2.9 | 42% | 4.2 | 27% | 2.7 | 16% | 1.6 |
| 6.25 | 5% | 1.0 | 93% | 0.9 | 91% | 1.0 | 86% | 1.0 | 82% | 1.0 | 79% | 1.0 | 65% | 1.1 | 45% | 3.1 | 32% | 4.6 | 19% | 2.7 | 8% | 1.2 |
| 3.13 | 1% | 1.0 | 94% | 1.0 | 90% | 1.0 | 86% | 1.0 | 84% | 1.0 | 79% | 1.0 | 63% | 1.1 | 39% | 3.6 | 22% | 7.1 | 12% | 3.6 | 5% | 1.5 |
| 0 | 0% | | 93% 1.0 | 90% 1.0 | 85% 1.0 | 81% 1.0 | 75% 1.0 | 57% 1.0 | 25% 1.0 | 10% 1.0 | 2% 1.0 | 2% 1.0 |
| dGuo mM | | 3.00 | 1.50 | 0.75 | 0.38 | 0.19 | 0.09 | 0.05 | 0.02 | 0.01 | 0.01 |

TABLE 12

TABULATIONS OF COMBINED RESULTS RATIOS

U937

Total Time 18 H    STSP for 18 H
                   HU   for  0 H

| STSP nM | STSP only | MTT blank well | | | | | | | | | | | | | | | | | | |
|---|---|---|---|---|---|---|---|---|---|---|---|---|---|---|---|---|---|---|---|---|
| 100 | 49% | 1.0 | 73% | 0.9 | 71% | 1.2 | 70% | 1.4 | 68% | 1.3 | 76% | 1.3 | 70% | 1.5 | 61% | 1.3 | 55% | 1.1 | 51% | 1.0 |
| 50 | 37% | 1.0 | 81% | 1.2 | 77% | 1.1 | 72% | 1.5 | 70% | 1.8 | 68% | 1.6 | 72% | 1.5 | 61% | 1.7 | 45% | 1.2 | 37% | 0.9 | 41% | 1.0 |
| 25 | 21% | 1.0 | 77% | 1.5 | 70% | 1.4 | 60% | 1.9 | 57% | 2.4 | 53% | 2.0 | 54% | 1.7 | 38% | 1.9 | 27% | 1.4 | 19% | 0.8 | 23% | 0.9 |
| 12.5 | 11% | 1.0 | 67% | 1.5 | 58% | 1.4 | 46% | 2.0 | 38% | 2.9 | 33% | 2.0 | 31% | 1.4 | 19% | 1.8 | 13% | 1.3 | 11% | 0.8 | 11% | 0.7 |
| 6.25 | -2% | 1.0 | 55% | 1.8 | 40% | 1.4 | 22% | 2.4 | 14% | 25.5 | 9% | 2.5 | 12% | 1.3 | 4% | -1.5 | 0% | -0.1 | -2% | -2.0 | 2% | 0.8 |
| 3.13 | -3% | 1.0 | 39% | 1.4 | 29% | 1.1 | 11% | 1.4 | 6% | -6.9 | 1% | 0.3 | 9% | 1.2 | 3% | -0.8 | 1% | -0.1 | -5% | 23.8 | -3% | -2.8 |
|   |   |   | 1.0 | | 1.0 | | 1.0 | | 1.0 | | 1.0 | | 1.0 | | 1.0 | | 1.0 | | 1.0 | | 1.0 |
| 0 | 0% |   | 32% | | 30% | | 11% | | 2% | | 5% | | 11% | | -1% | | -1% | | 3% | | 4% |
|   | HU | mM | 2.00 | | 1.00 | | 0.50 | | 0.25 | | 0.13 | | 0.06 | | 0.03 | | 0.02 | | 0.01 | | 0.004 |

TABLE 13

TABULATIONS OF COMBINED RESULTS RATIOS

U937

Total Time 20 H    STSP for 16 H
                   MTX  for  4 H

| STSP nM | STSP only | MTT blank well | | | | | | | | | | | | | | | | | | |
|---|---|---|---|---|---|---|---|---|---|---|---|---|---|---|---|---|---|---|---|---|
| 200 | 55% | 1.0 | 82% | 0.7 | 78% | 0.7 | 79% | 0.7 | 79% | 0.8 | 77% | 0.8 | 73% | 0.7 | 69% | 0.7 | 58% | 0.8 | 57% | 1.2 |
| 100 | 44% | 1.0 | 81% | 0.8 | 78% | 0.7 | 77% | 0.8 | 77% | 0.8 | 77% | 0.8 | 74% | 0.9 | 73% | 0.8 | 67% | 0.8 | 52% | 0.8 | 45% | 1.1 |
| 50 | 31% | 1.0 | 84% | 0.9 | 83% | 0.9 | 82% | 0.9 | 81% | 1.0 | 81% | 1.0 | 79% | 1.1 | 75% | 1.0 | 65% | 0.9 | 42% | 0.8 | 35% | 1.4 |
| 25 | 16% | 1.0 | 82% | 1.1 | 82% | 1.0 | 79% | 1.1 | 79% | 1.2 | 78% | 1.2 | 75% | 1.3 | 68% | 1.1 | 63% | 1.0 | 31% | 0.9 | 19% | 1.7 |
| 12.5 | 13% | 1.0 | 77% | 1.0 | 74% | 1.0 | 74% | 1.1 | 72% | 1.1 | 72% | 1.2 | 68% | 1.2 | 61% | 1.0 | 48% | 0.9 | 30% | 0.9 | 15% | 1.4 |
| 6.25 | 5% | 1.0 | 70% | 1.1 | 69% | 1.0 | 67% | 1.1 | 65% | 1.1 | 63% | 1.2 | 60% | 1.2 | 52% | 1.0 | 43% | 1.0 | 26% | 1.0 | 8% | 16.4 |
|   |   |   | 1.0 | | 1.0 | | 1.0 | | 1.0 | | 1.0 | | 1.0 | | 1.0 | | 1.0 | | 1.0 | | 1.0 |
| 0 | 0% |   | 61% | | 62% | | 57% | | 52% | | 47% | | 43% | | 48% | | 38% | | 20% | | -5% |
|   | MTX | mM | 1000 | | 500 | | 250 | | 125 | | 63 | | 31 | | 16 | | 8 | | 4 | | 2 |

TABLE 14

TABULATIONS OF COMBINED RESULTS RATIOS

U937

Total Time 20 H    STSP for 16 H
                   FLOX for  4 H

| STSP nM | STSP only | MTT blank well | | | | | | | | | | | | | | | | | | |
|---|---|---|---|---|---|---|---|---|---|---|---|---|---|---|---|---|---|---|---|---|
| 200 | 43% | 1.0 | 74% | 1.0 | 82% | 1.0 | 84% | 1.1 | 84% | 1.0 | 80% | 1.2 | 75% | 1.2 | 64% | 1.2 | 52% | 1.0 | 46% | 1.1 |
| 100 | 33% | 1.0 | 74% | 1.1 | 74% | 1.1 | 82% | 1.2 | 85% | 1.3 | 87% | 1.2 | 84% | 1.5 | 80% | 1.5 | 71% | 1.5 | 43% | 1.0 | 37% | 1.1 |
| 50 | 27% | 1.0 | 74% | 1.2 | 76% | 1.3 | 84% | 1.3 | 88% | 1.5 | 89% | 1.3 | 86% | 1.8 | 81% | 1.7 | 67% | 1.7 | 41% | 1.1 | 36% | 1.3 |
| 25 | 11% | 1.0 | 66% | 1.4 | 70% | 1.6 | 79% | 1.7 | 82% | 1.9 | 82% | 1.6 | 77% | 2.4 | 67% | 2.1 | 40% | 1.7 | 32% | 1.6 | 22% | 2.0 |
| 13 | 6% | 1.0 | 55% | 1.3 | 61% | 1.6 | 68% | 1.6 | 72% | 1.9 | 70% | 1.5 | 55% | 2.0 | 42% | 1.5 | 28% | 1.5 | 22% | 1.4 | 18% | 3.0 |
| 6 | 12% | 1.0 | 41% | 0.9 | 52% | 1.1 | 51% | 1.0 | 58% | 1.3 | 55% | 1.1 | 42% | 1.3 | 31% | 0.9 | 22% | 0.9 | 19% | 0.9 | 14% | 1.1 |
|   |   |   | 1.0 | | 1.0 | | 1.0 | | 1.0 | | 1.0 | | 1.0 | | 1.0 | | 1.0 | | 1.0 | | 1.0 |
| 0 | 0% |   | 36% | | 33% | | 37% | | 32% | | 40% | | 21% | | 21% | | 12% | | 10% | | -0% |
|   | 6-FU | mM | 100.0 | | 50.0 | | 25.0 | | 12.5 | | 6.3 | | 3.1 | | 1.6 | | 0.8 | | 0.4 | | 0.2 |

TABLE 15

TABULATIONS OF COMBINED RESULTS RATIOS
U937

Total Time 18 H  STSP for 14 H
Aph for 4 H

| STSP nM | STSP only | MTT | | | | | | | | | | | | | | | | | | |
|---|---|---|---|---|---|---|---|---|---|---|---|---|---|---|---|---|---|---|---|---|
| 100 | 38% | 1.0 | blank well | 81% | 1.2 | 80% | 1.3 | 80% | 1.3 | 78% | 1.5 | 74% | 1.7 | 71% | 1.8 | 65% | 1.7 | 56% | 1.5 | 50% | 1.3 |
| 50 | 32% | 1.0 | 87% | 1.4 | 87% | 1.4 | 86% | 1.6 | 84% | 1.6 | 82% | 1.8 | 77% | 2.0 | 72% | 2.2 | 66% | 2.1 | 53% | 1.7 | 40% | 1.5 |
| 25 | 16% | 1.0 | 88% | 1.9 | 86% | 1.8 | 83% | 2.2 | 77% | 2.1 | 73% | 2.4 | 68% | 3.1 | 59% | 3.4 | 49% | 3.1 | 35% | 2.2 | 23% | 1.5 |
| 12.5 | 4% | 1.0 | 81% | 2.4 | 77% | 2.2 | 69% | 2.6 | 61% | 2.4 | 56% | 3.0 | 50% | 4.9 | 39% | 7.1 | 30% | 7.0 | 21% | 5.0 | 10% | 2.4 |
| 6.25 | 5% | 1.0 | 68% | 2.0 | 59% | 1.6 | 49% | 1.8 | 45% | 1.7 | 37% | 2.0 | 31% | 3.0 | 22% | 3.6 | 18% | 3.8 | 10% | 2.1 | 10% | 2.1 |
| 3.13 | 6% | 1.0 | 54% | 1.5 | 46% | 1.2 | 38% | 1.3 | 33% | 1.2 | 28% | 1.3 | 23% | 1.9 | 15% | 1.9 | 12% | 1.8 | 9% | 1.4 | 6% | 0.9 |
| | | | | 1.0 | | 1.0 | | 1.0 | | 1.0 | | 1.0 | | 1.0 | | 1.0 | | 1.0 | | 1.0 | | 1.0 |
| 0 | 0% | | 30% | | 31% | | 22% | | 21% | | 17% | | 14% | | 9% | | 6% | | 7% | | 1% | |
| Aph ug/ml | | | 4.00 | | 2.00 | | 1.00 | | 0.50 | | 0.25 | | 0.13 | | 0.06 | | 0.03 | | 0.02 | | 0.01 | |

TABLE 16

TABULATIONS OF COMBINED RESULTS RATIOS
U937

Total Time 13.5 H  STSP for 13.5 H
Ara-C for 0 H

| STSP nM | STSP only | MTT | | | | | | | | | | | | | | | | | | |
|---|---|---|---|---|---|---|---|---|---|---|---|---|---|---|---|---|---|---|---|---|
| 100 | 47% | 1.0 | blank well | 84% | 0.9 | 83% | 0.9 | 81% | 0.9 | 80% | 0.9 | 77% | 1.0 | 75% | 1.3 | 72% | 1.5 | 69% | 1.3 | 64% | 1.3 |
| 50 | 37% | 1.0 | 88% | 1.0 | 87% | 1.1 | 87% | 1.1 | 85% | 1.1 | 81% | 1.1 | 76% | 1.2 | 73% | 1.6 | 67% | 1.7 | 61% | 1.4 | 56% | 1.4 |
| 25 | 15% | 1.0 | 82% | 1.3 | 82% | 1.4 | 80% | 1.4 | 75% | 1.3 | 66% | 1.3 | 60% | 1.4 | 53% | 2.2 | 46% | 2.6 | 33% | 1.6 | 32% | 1.8 |
| 12.5 | 6% | 1.0 | 73% | 1.4 | 72% | 1.4 | 69% | 1.4 | 61% | 1.3 | 50% | 1.2 | 44% | 1.3 | 34% | 2.2 | 27% | 3.2 | 17% | 1.6 | 14% | 1.7 |
| 6.25 | 2% | 1.0 | 66% | 1.4 | 63% | 1.4 | 59% | 1.3 | 51% | 1.2 | 41% | 1.1 | 34% | 1.1 | 25% | 2.2 | 17% | 4.1 | 11% | 1.6 | 7% | 1.6 |
| 3.13 | 1% | 1.0 | 59% | 1.2 | 55% | 1.2 | 51% | 1.1 | 44% | 1.1 | 38% | 1.0 | 31% | 1.1 | 20% | 1.8 | 14% | 4.1 | 7% | 1.2 | 4% | 1.1 |
| | | | | 1.0 | | 1.0 | | 1.0 | | 1.0 | | 1.0 | | 1.0 | | 1.0 | | 1.0 | | 1.0 | | 1.0 |
| 0 | 0% | | 47% | | 44% | | 43% | | 40% | | 37% | | 28% | | 18% | | 9% | | 5% | | 2% | |
| Ara-C mM | | | 20.00 | | 10.00 | | 5.00 | | 2.50 | | 1.25 | | 0.63 | | 0.31 | | 0.16 | | 0.08 | | 0.04 | |

TABLE 17

BIVARIATE SERIAL DILUTION ANALYSIS (BVSD)

TABULATIONS OF COMBINED RESULTS RATIOS
MTT #523

Total Time 20 H  Bleomycin for 16 H
Bleomycin  STSP for 4 H
mU
Growth Inhibition [%]

| | | | | | | | | | | | | | | | | | | | | |
|---|---|---|---|---|---|---|---|---|---|---|---|---|---|---|---|---|---|---|---|---|
| 160.00 | 39% | 1.0 | blank well | 71% | 0.9 | 74% | 1.1 | 67% | 1.3 | 57% | 1.2 | 54% | 1.2 | 50% | 1.1 | 46% | 1.1 | 42% | 0.9 | 42% | 1.0 |
| 80.00 | 27% | 1.0 | 65% | 0.9 | 63% | 1.0 | 67% | 1.2 | 58% | 1.4 | 47% | 1.3 | 43% | 1.3 | 37% | 1.1 | 34% | 1.1 | 29% | 0.8 | 30% | 1.0 |
| 40.00 | 17% | 1.0 | 60% | 0.9 | 57% | 1.0 | 58% | 1.2 | 46% | 1.5 | 36% | 1.3 | 32% | 1.3 | 28% | 1.2 | 25% | 1.2 | 20% | 0.7 | 19% | 0.9 |
| 20.00 | 10% | 1.0 | 55% | 0.9 | 51% | 1.0 | 49% | 1.2 | 35% | 1.5 | 26% | 1.3 | 25% | 1.4 | 23% | 1.3 | 17% | 1.2 | 13% | 0.6 | 13% | 0.9 |
| 10.00 | 6% | 1.0 | 50% | 0.9 | 45% | 1.0 | 41% | 1.1 | 28% | 1.4 | 20% | 1.2 | 18% | 1.3 | 16% | 1.2 | 10% | 1.1 | 10% | 0.6 | 7% | 0.7 |
| 5.00 | 2% | 1.0 | 50% | 1.0 | 42% | 1.0 | 37% | 1.1 | 22% | 1.4 | 15% | 1.2 | 15% | 1.5 | 10% | 1.0 | 8% | 1.4 | 6% | 0.5 | 5% | 0.8 |
| | | | | 1.0 | | 1.0 | | 1.0 | | 1.0 | | 1.0 | | 1.0 | | 1.0 | | 1.0 | | 1.0 | | 1.0 |
| Growth Inhibition | 0% | | 48% | | 39% | | 30% | | 13% | | 10% | | 8% | | 8% | | 4% | | 11% | | 4% | |
| nM STSP | | | 200 | | 100 | | 50 | | 25 | | 12.5 | | 6.3 | | 3.1 | | 1.6 | | 0.8 | | 0.4 | |

TABLE 18

TABULATIONS OF COMBINED RESULTS RATIOS

U937 — Total Time 19 H — Mitomycin for 16 H — STSP for 4 H

| Mitomycin ug/ml | Mitomycin only | | MTT blank well | STSP 100.0 nM | | STSP 50.0 | | STSP 25.0 | | STSP 12.5 | | STSP 6.3 | | STSP 3.1 | | STSP 1.6 | | STSP 0.8 | | STSP 0.4 | | STSP 0.2 | |
|---|---|---|---|---|---|---|---|---|---|---|---|---|---|---|---|---|---|---|---|---|---|---|
| 5.00 | 61% | 1.0 | 81% | 0.7 | 77% | 0.8 | 75% | 0.8 | 73% | 0.9 | 66% | 0.9 | 61% | 1.0 | 68% | 1.2 | 60% | 1.0 | 61% | 1.0 | | |
| 2.50 | 43% | 1.0 | 79% | 0.8 | 75% | 0.8 | 72% | 0.9 | 69% | 1.0 | 62% | 0.9 | 53% | 1.0 | 46% | 1.0 | 44% | 1.1 | 43% | 1.0 | 41% | 1.0 |
| 1.25 | 28% | 1.0 | 76% | 0.9 | 72% | 0.9 | 67% | 1.0 | 61% | 1.1 | 55% | 1.1 | 42% | 1.1 | 36% | 1.2 | 28% | 1.1 | 30% | 1.1 | 29% | 1.1 |
| 0.63 | 16% | 1.0 | 71% | 1.0 | 66% | 1.0 | 63% | 1.1 | 51% | 1.1 | 44% | 1.1 | 28% | 1.0 | 20% | 1.1 | 15% | 1.1 | 16% | 1.1 | 13% | 0.9 |
| 0.31 | 8% | 1.0 | 69% | 1.0 | 62% | 1.1 | 52% | 1.0 | 42% | 1.1 | 33% | 1.1 | 21% | 1.1 | 16% | 1.5 | 9% | 1.6 | 11% | 1.6 | 9% | 1.4 |
| 0.16 | 1% | 1.0 | 65% | 1.1 | 58% | 1.1 | 50% | 1.2 | 38% | 1.3 | 29% | 1.2 | 15% | 1.3 | 5% | 1.7 | 2% | -1.0 | 1% | -0.7 | -0% | 0.2 |
| 0 | -0% | | 59% | 1.0 | 50% | 1.0 | 42% | 1.0 | 29% | 1.0 | 23% | 1.0 | 11% | 1.0 | 2% | 1.0 | -3% | 1.0 | -1% | 1.0 | -2% | 1.0 |

TABLE 19

TABULATIONS OF COMBINED RESULTS RATIOS

U937 — Total Time 19 H — Cisplatin for 16 H — STSP for 3 H

| Cisplatin uM | Cisplatin only | | MTT blank well | STSP 100.0 nM | | STSP 50.0 | | STSP 25.0 | | STSP 12.5 | | STSP 6.3 | | STSP 3.1 | | STSP 1.6 | | STSP 0.8 | | STSP 0.4 | | STSP 0.2 | |
|---|---|---|---|---|---|---|---|---|---|---|---|---|---|---|---|---|---|---|---|---|---|---|
| 80 | 74% | 1.0 | 93% | 0.7 | 88% | 0.8 | 83% | 0.9 | 79% | 0.9 | 77% | 1.0 | 74% | 0.9 | 72% | 1.0 | 74% | 1.0 | 75% | 1.0 | | |
| 40 | 45% | 1.0 | 84% | 0.8 | 84% | 0.8 | 74% | 1.0 | 69% | 1.1 | 63% | 1.0 | 50% | 1.2 | 51% | 1.0 | 47% | 1.0 | 46% | 1.0 | 47% | 1.0 |
| 20 | 14% | 1.0 | 75% | 1.0 | 71% | 1.0 | 69% | 1.3 | 50% | 1.5 | 43% | 1.4 | 31% | 1.8 | 25% | 1.3 | 22% | 1.5 | 18% | 1.3 | 15% | 1.0 |
| 10 | -1% | 1.0 | 69% | 1.2 | 62% | 1.1 | 44% | 1.4 | 30% | 1.5 | 23% | 1.4 | 14% | 5.7 | 9% | 1.8 | 8% | -10.5 | 6% | -7.2 | 1% | -0.9 |
| 5 | -4% | 1.0 | 66% | 1.2 | 57% | 1.1 | 36% | 1.3 | 38% | 2.4 | 19% | 1.5 | 14% | -17.2 | 7% | 4.3 | 5% | -1.2 | 4% | -1.0 | 2% | -0.8 |
| 2.5 | -2% | 1.0 | 62% | 1.1 | 53% | 1.0 | 33% | 1.1 | 33% | 1.6 | 19% | 1.3 | 11% | 10.8 | 6% | 1.9 | 8% | -3.5 | 6% | -2.5 | 2% | -0.5 |
| 0 | 50% | | 61% | 1.0 | 66% | 1.0 | 31% | 1.0 | 20% | 1.0 | 20% | 1.0 | 17% | 1.0 | 4% | 1.0 | 3% | 1.0 | 7% | 1.0 | 6% | 1.0 |

TABLE 20

TABULATIONS OF COMBINED RESULTS RATIOS

CELLS — Total Time 17 H — Daunomycin for 17 H — STSP for 0 H

| Daun nM | Daunomycin only | | MTT blank well | STSP 100.0 nM | | STSP 50.0 | | STSP 25.0 | | STSP 12.5 | | STSP 6.25 | | STSP 3.13 | | STSP 1.56 | | STSP 0.78 | | STSP 0.39 | | STSP 0.20 | |
|---|---|---|---|---|---|---|---|---|---|---|---|---|---|---|---|---|---|---|---|---|---|---|
| 200 | 61% | 1.0 | 65% | 0.6 | 67% | 0.8 | 64% | 0.8 | 63% | 0.9 | 62% | 0.9 | 61% | 1.0 | 61% | 1.1 | 59% | 1.0 | 61% | 1.1 | | |
| 100 | 55% | 1.0 | 64% | 0.6 | 69% | 0.7 | 69% | 0.9 | 66% | 0.9 | 63% | 1.0 | 61% | 1.0 | 59% | 1.0 | 58% | 1.1 | 58% | 1.1 | 41% | 1.1 |
| 50 | 22% | 1.0 | 61% | 0.9 | 65% | 1.0 | 62% | 1.4 | 54% | 1.4 | 72% | 2.3 | 44% | 1.5 | 42% | 1.7 | 38% | 2.2 | 32% | 1.7 | 29% | 3.6 |
| 25 | 9% | 1.0 | 48% | 0.9 | 48% | 1.0 | 38% | 1.2 | 47% | 1.9 | 48% | 2.6 | 20% | 1.3 | 16% | 1.4 | 10% | 2.3 | 44% | 7.7 | 13% | 4.0 |
| 12.5 | 4% | 1.0 | 45% | 1.0 | 42% | 0.9 | 32% | 1.2 | 23% | 1.1 | 15% | 1.1 | 12% | 1.1 | 9% | 1.5 | 10% | -18.9 | 46% | 69.1 | 9% | -8.6 |
| 6.25 | 2% | 1.0 | 43% | 0.9 | 42% | 1.0 | 28% | 1.1 | 19% | 1.0 | 9% | 0.7 | 11% | 1.2 | 7% | 1.4 | 7% | -4.0 | 4% | -6.9 | -0% | -0.8 |
| 0 | 0% | | 44% | 1.0 | 41% | 1.0 | 23% | 1.0 | 17% | 1.0 | 10% | 1.0 | 7% | 1.0 | 5% | 1.0 | 3% | 1.0 | -3% | 1.0 | -2% | 1.0 |

TABLE 21

TABULATIONS OF COMBINED RESULTS RATIOS — U937

Total Time 20 H; Etoposide for 16 H; STSP for 4 H

| Etoposide uM | Etoposide only | MTT | | | | | | | | | | | | | | | | | | |
|---|---|---|---|---|---|---|---|---|---|---|---|---|---|---|---|---|---|---|---|---|
| 4 | 53% | 1.0 | blank well | | 66% | 0.7 | 61% | 0.8 | 58% | 0.9 | 55% | 0.9 | 54% | 0.9 | 55% | 1.0 | 55% | 0.9 | 53% | 1.0 | 52% | 1.0 |
| 2 | 29% | 1.0 | 62% | 0.8 | 59% | 0.9 | 52% | 1.0 | 47% | 1.1 | 42% | 1.1 | 41% | 1.2 | 39% | 1.3 | 35% | 1.0 | 33% | 1.0 | 31% | 1.1 |
| 1 | 8% | 1.0 | 55% | 1.0 | 51% | 1.1 | 43% | 1.3 | 35% | 1.5 | 28% | 1.7 | 25% | 1.8 | 22% | 2.1 | 17% | 1.2 | 14% | 1.3 | 15% | 1.8 |
| 0.5 | 3% | 1.0 | 48% | 1.0 | 43% | 1.1 | 32% | 1.2 | 23% | 1.4 | 17% | 1.5 | 15% | 1.7 | 11% | 2.1 | 11% | 1.3 | 6% | 1.1 | 8% | 3.3 |
| 0.25 | 1% | 1.0 | 46% | 1.0 | 41% | 1.0 | 29% | 1.1 | 19% | 1.3 | 14% | 1.5 | 11% | 1.6 | 9% | 2.9 | 7% | 1.1 | 2% | 0.7 | 5% | 8.0 |
| 0.13 | 2% | 1.0 | 47% | 1.0 | 40% | 1.0 | 28% | 1.1 | 17% | 1.1 | 13% | 1.2 | 9% | 1.2 | 7% | 1.8 | 8% | 1.0 | 2% | 0.5 | 6% | 4.1 |
| 0 | 0% | | 45% | 1.0 | 38% | 1.0 | 24% | 1.0 | 14% | 1.0 | 8% | 1.0 | 5% | 1.0 | 2% | 1.0 | 6% | 1.0 | 3% | 1.0 | -0% | 1.0 |
| STSP nM | | | 200.0 | | 100.0 | | 50.0 | | 25.0 | | 12.5 | | 6.3 | | 3.1 | | 1.6 | | 0.8 | | 0.4 | |

TABLE 22

TABULATIONS OF COMBINED RESULTS RATIOS — U937

Total Time 20.5 H; K252a for 16 H; dThd for 4.5 H

| K252a nM | K252a only | MTT | | | | | | | | | | | | | | | | | | |
|---|---|---|---|---|---|---|---|---|---|---|---|---|---|---|---|---|---|---|---|---|
| 625 | 41% | 1.0 | blank well | | 77% | 1.0 | 76% | 1.1 | 76% | 1.2 | 76% | 1.6 | 75% | 1.5 | 69% | 1.5 | 60% | 1.6 | 46% | 1.2 | 43% | 1.1 |
| 313 | 36% | 1.0 | 74% | 0.8 | 73% | 1.0 | 73% | 1.1 | 73% | 1.3 | 69% | 1.6 | 67% | 1.5 | 60% | 1.5 | 38% | 1.2 | 35% | 1.0 | 38% | 1.0 |
| 156 | 17% | 1.0 | 68% | 0.9 | 67% | 1.2 | 64% | 1.4 | 62% | 1.7 | 58% | 2.3 | 51% | 1.9 | 37% | 1.7 | 21% | 1.7 | 14% | 0.9 | 17% | 1.1 |
| 78 | 10% | 1.0 | 61% | 0.9 | 60% | 1.2 | 54% | 1.4 | 51% | 1.7 | 39% | 2.2 | 30% | 1.6 | 21% | 1.5 | 8% | 1.6 | 8% | 1.0 | 10% | 1.3 |
| 39 | 6% | 1.0 | 59% | 1.0 | 52% | 1.1 | 41% | 1.1 | 36% | 1.4 | 24% | 1.7 | 19% | 1.3 | 12% | 1.1 | 5% | 3.5 | 4% | 1.0 | 6% | 1.4 |
| 20 | 3% | 1.0 | 56% | 1.0 | 47% | 1.1 | 36% | 1.1 | 27% | 1.2 | 17% | 1.6 | 14% | 1.2 | 8% | 1.1 | 0% | -0.1 | 1% | 0.7 | 2% | 1.9 |
| 0 | 0% | | 55% | 1.0 | 39% | 1.0 | 30% | 1.0 | 20% | 1.0 | 8% | 1.0 | 9% | 1.0 | 4% | 1.0 | -5% | 1.0 | -2% | 1.0 | -2% | 1.0 |
| dThd nM | | | 3.00 | | 1.50 | | 0.75 | | 0.38 | | 0.19 | | 0.09 | | 0.05 | | 0.02 | | 0.01 | | 0.01 | |

TABLE 23

TABULATIONS OF COMBINED RESULTS RATIOS — U937

Total Time 24 H; KT5926 for 20 H; dThd for 4 H

| KT5926 uM | KT5926 only | MTT | | | | | | | | | | | | | | | | | | |
|---|---|---|---|---|---|---|---|---|---|---|---|---|---|---|---|---|---|---|---|---|
| 11.4 | 62% | 1.0 | blank well | | 65% | 0.5 | 65% | 0.5 | 67% | 0.7 | 69% | 0.8 | 71% | 0.9 | 72% | 0.9 | 71% | 1.0 | 68% | 1.0 | 65% | 1.1 |
| 5.7 | 33% | 1.0 | 61% | 0.6 | 59% | 0.7 | 60% | 0.7 | 58% | 0.8 | 59% | 1.0 | 58% | 1.1 | 55% | 1.1 | 50% | 1.3 | 41% | 1.1 | 39% | 1.2 |
| 2.85 | 14% | 1.0 | 61% | 0.8 | 60% | 0.8 | 58% | 1.0 | 56% | 1.1 | 55% | 1.3 | 52% | 1.5 | 40% | 1.3 | 31% | 1.5 | 18% | 1.1 | 14% | 1.0 |
| 1.43 | 2% | 1.0 | 64% | 1.0 | 63% | 1.1 | 61% | 1.3 | 56% | 1.5 | 52% | 1.7 | 46% | 1.9 | 29% | 1.5 | 15% | 1.7 | 6% | 1.2 | 2% | 1.0 |
| 0.71 | 4% | 1.0 | 66% | 1.0 | 65% | 1.1 | 60% | 1.2 | 55% | 1.3 | 49% | 1.5 | 41% | 1.6 | 25% | 1.2 | 16% | 1.4 | 9% | 1.2 | 7% | 1.7 |
| 0.36 | 7% | 1.0 | 65% | 0.9 | 62% | 1.0 | 57% | 1.1 | 50% | 1.1 | 42% | 1.2 | 34% | 1.2 | 21% | 0.9 | 16% | 1.2 | 12% | 1.1 | 10% | 1.4 |
| 0 | 0% | | 84% | 1.0 | 57% | 1.0 | 46% | 1.0 | 36% | 1.0 | 28% | 1.0 | 21% | 1.0 | 17% | 1.0 | 6% | 1.0 | 3% | 1.0 | 0% | 1.0 |
| STSP mM | | | 3.00 | | 1.50 | | 0.75 | | 0.38 | | 0.19 | | 0.09 | | 0.06 | | 0.02 | | 0.01 | | 0.01 | |

TABLE 24

U937 — TABULATIONS OF COMBINED RESULTS RATIOS

Total Time 20.5 H; KT5720 for 16 H; dThd for 4.5 H

| KT5720 uM | KT5720 only | | MTT | | | | | | | | | | | | | | | | | |
|---|---|---|---|---|---|---|---|---|---|---|---|---|---|---|---|---|---|---|---|---|
| 20 | 61% | 1.0 | blank well | 76% | 0.8 | 78% | 0.9 | 77% | 0.9 | 78% | 1.1 | 78% | 1.1 | 74% | 1.0 | 67% | 1.0 | 59% | 0.9 | 56% | 0.9 |
| 10 | 45% | 1.0 | 75% | 0.8 | 75% | 0.9 | 74% | 1.0 | 75% | 1.1 | 74% | 1.3 | 72% | 1.3 | 63% | 1.2 | 50% | 1.0 | 46% | 1.0 | 48% | 1.0 |
| 5 | 21% | 1.0 | 70% | 0.9 | 68% | 1.1 | 66% | 1.4 | 60% | 1.4 | 63% | 2.0 | 48% | 1.5 | 37% | 1.2 | 22% | 0.8 | 22% | 0.9 | 24% | 1.0 |
| 2.5 | 7% | 1.0 | 64% | 1.1 | 58% | 1.3 | 49% | 1.4 | 42% | 1.5 | 31% | 1.7 | 21% | 1.2 | 14% | 0.8 | 11% | 0.8 | 13% | 1.3 | 9% | 0.9 |
| 1.25 | 3% | 1.0 | 58% | 1.0 | 49% | 1.2 | 34% | 1.1 | 28% | 1.1 | 16% | 1.1 | 12% | 0.9 | 8% | 0.6 | 8% | 0.8 | 5% | 0.8 | 8% | 1.2 |
| 0.63 | 1% | 1.0 | 58% | 1.1 | 46% | 1.2 | 33% | 1.2 | 28% | 1.2 | 14% | 1.2 | 10% | 0.8 | 8% | 0.7 | 7% | 0.9 | 2% | 0.4 | 0% | 0.1 |
| 0 | -0% | | 54% | 1.0 | 39% | 1.0 | 27% | 1.0 | 22% | 1.0 | 11% | 1.0 | 11% | 1.0 | 10% | 1.0 | 7% | 1.0 | 3% | 1.0 | 3% | 1.0 |
| dThd mM | | | 3.00 | | 1.50 | | 0.75 | | 0.38 | | 0.19 | | 0.09 | | 0.06 | | 0.02 | | 0.01 | | 0.01 | |

TABLE 25

U937 — TABULATIONS OF COMBINED RESULTS RATIOS

Total Time 20.5 H; APH for 16 H; dThd for 4.5 H

| APH ug/ml | APH only | | MTT | | | | | | | | | | | | | | | | | |
|---|---|---|---|---|---|---|---|---|---|---|---|---|---|---|---|---|---|---|---|---|
| 20 | 32% | 1.0 | blank well | 62% | 0.8 | 58% | 1.0 | 54% | 1.1 | 47% | 1.0 | 41% | 0.9 | 44% | 1.3 | 41% | 1.1 | 42% | 1.0 | 40% | 1.4 |
| 10 | 19% | 1.0 | 62% | 0.8 | 56% | 0.9 | 49% | 1.0 | 43% | 1.2 | 32% | 1.0 | 31% | 1.0 | 31% | 1.5 | 33% | 1.5 | 28% | 1.0 | 26% | 1.6 |
| 5 | 9% | 1.0 | 55% | 0.8 | 47% | 0.9 | 41% | 1.1 | 34% | 1.3 | 30% | 1.3 | 26% | 1.2 | 22% | 2.1 | 30% | 2.4 | 15% | 0.8 | 14% | 2.0 |
| 2.5 | -0% | 1.0 | 50% | 0.9 | 41% | 1.0 | 36% | 1.3 | 28% | 1.7 | 21% | 1.5 | 20% | 1.7 | 10% | 11.5 | 12% | 3.7 | 12% | 1.3 | 2% | -0.0 |
| 1.25 | -1% | 1.0 | 47% | 0.9 | 38% | 0.9 | 29% | 1.1 | 21% | 1.3 | 20% | 1.5 | 13% | 1.2 | 12% | -181.5 | 12% | 5.0 | 8% | 1.1 | 0% | -0.0 |
| 0.63 | -2% | 1.0 | 47% | 0.9 | 38% | 0.9 | 30% | 1.1 | 21% | 1.4 | 14% | 1.1 | 15% | 1.4 | 9% | -34.9 | 11% | 5.2 | 4% | 0.6 | -0% | 0.1 |
| 0 | 0% | | 56% | 1.0 | 42% | 1.0 | 28% | 1.0 | 17% | 1.0 | 15% | 1.0 | 12% | 1.0 | 1% | 1.0 | 4% | 1.0 | 9% | 1.0 | -2% | 1.0 |
| dThd mM | | | 3.00 | | 1.50 | | 0.75 | | 0.38 | | 0.19 | | 0.09 | | 0.06 | | 0.02 | | 0.01 | | 0.01 | |

TABLE 26

U937 — TABULATIONS OF COMBINED RESULTS RATIOS

Total Time 18 H; Ara-C for 12 H; dThd for 6 H

| Ara-C uM | Ara-C only | | MTT | | | | | | | | | | | | | | | | | |
|---|---|---|---|---|---|---|---|---|---|---|---|---|---|---|---|---|---|---|---|---|
| 10 | 28% | 1.0 | blank well | 32% | 0.6 | 37% | 0.7 | 41% | 0.8 | 45% | 1.0 | 33% | 0.8 | 46% | 1.3 | 40% | 1.2 | 35% | 1.1 | 31% | 0.9 |
| 5 | 26% | 1.0 | 29% | 0.6 | 39% | 0.7 | 39% | 0.8 | 43% | 0.9 | 48% | 1.1 | 47% | 1.2 | 41% | 1.3 | 34% | 1.1 | 30% | 1.0 | 29% | 0.9 |
| 2.5 | 18% | 1.0 | 31% | 0.8 | 36% | 0.8 | 39% | 0.9 | 43% | 1.1 | 47% | 1.3 | 45% | 1.4 | 31% | 1.2 | 27% | 1.1 | 21% | 1.0 | 19% | 0.8 |
| 1.25 | 9% | 1.0 | 27% | 0.9 | 37% | 1.0 | 38% | 1.1 | 41% | 1.4 | 43% | 1.6 | 40% | 1.8 | 30% | 2.0 | 21% | 1.4 | 16% | 1.3 | 17% | 1.1 |
| 0.63 | 5% | 1.0 | 27% | 0.9 | 34% | 1.0 | 34% | 1.1 | 35% | 1.4 | 35% | 1.5 | 32% | 1.7 | 21% | 1.8 | 15% | 1.3 | 11% | 1.2 | 11% | 1.0 |
| 0.31 | 3% | 1.0 | 25% | 1.0 | 32% | 1.0 | 29% | 1.1 | 31% | 1.3 | 29% | 1.4 | 25% | 1.5 | 16% | 1.7 | 11% | 1.3 | 11% | 1.6 | 9% | 1.1 |
| 0 | 0% | | 23% | 1.0 | 28% | 1.0 | 25% | 1.0 | 20% | 1.0 | 18% | 1.0 | 13% | 1.0 | 9% | 1.0 | 7% | 1.0 | 4% | 1.0 | 6% | 1.0 |
| dThd mM | | | 3.00 | | 1.50 | | 0.75 | | 0.38 | | 0.19 | | 0.09 | | 0.06 | | 0.02 | | 0.01 | | 0.01 | |

TABLE 27

TABULATIONS OF COMBINED RESULTS RATIOS — U937

Total Time 24 H; K252a for 20 H; dThd for 4 H

| K252a nM | K252a only | MTT blank well | | | | | | | | | | | | | | | | | |
|---|---|---|---|---|---|---|---|---|---|---|---|---|---|---|---|---|---|---|---|
| 625 | 36% | 1.0 | 72% | 0.8 | 69% | 0.8 | 66% | 0.9 | 62% | 1.4 | 59% | 1.7 | 52% | 1.5 | 40% | 1.1 | 39% | 1.1 | 35% | 1.0 |
| 313 | 18% | 1.0 | 75% | 1.0 | 71% | 1.0 | 66% | 1.0 | 61% | 1.1 | 51% | 1.9 | 42% | 2.4 | 26% | 1.6 | 23% | 1.3 | 18% | 1.0 | 19% | 1.1 |
| 156 | 11% | 1.0 | 74% | 1.1 | 70% | 1.1 | 65% | 1.1 | 56% | 1.2 | 43% | 2.2 | 29% | 2.8 | 15% | 1.5 | 17% | 1.5 | 14% | 1.2 | 12% | 1.1 |
| 78.1 | 9% | 1.0 | 71% | 1.0 | 65% | 1.1 | 60% | 1.0 | 50% | 1.1 | 35% | 2.0 | 22% | 2.6 | 12% | 1.5 | 12% | 1.3 | 10% | 1.0 | 8% | 0.9 |
| 39.1 | 5% | 1.0 | 67% | 1.0 | 62% | 1.1 | 55% | 1.0 | 46% | 1.1 | 29% | 2.0 | 15% | 3.3 | 8% | 2.0 | 7% | 1.3 | 5% | 0.9 | 5% | 0.8 |
| 19.5 | 2% | 1.0 | 65% | 1.1 | 59% | 1.1 | 51% | 1.0 | 42% | 1.0 | 26% | 2.4 | 12% | 7.6 | 5% | 7.0 | 4% | 1.7 | 3% | 1.3 | 2% | 0.7 |
| | | | 1.0 | | 1.0 | | 1.0 | | 1.0 | | 1.0 | | 1.0 | | 1.0 | | 1.0 | | 1.0 |
| 0 | 0% | | 59% | | 52% | | 48% | | 36% | | 20% | | 9% | | 1% | | 1% | | -1% | | -2% |
| HU mM | | 2.00 | 1.00 | 0.50 | 0.25 | 0.13 | 0.06 | 0.03 | 0.02 | 0.01 | 0.00 |

TABLE 28

TABULATIONS OF COMBINED RESULTS RATIOS — U937

Total Time 20 H; Aph for 16 H; HU for 4 H

| Aph nM | Aph only | MTT blank well | | | | | | | | | | | | | | | | | |
|---|---|---|---|---|---|---|---|---|---|---|---|---|---|---|---|---|---|---|---|
| 8 | 36% | 1.0 | 71% | 0.9 | 66% | 0.9 | 59% | 0.9 | 51% | 0.8 | 51% | 1.0 | 49% | 1.3 | 43% | 1.2 | 36% | 1.0 | 37% | 0.9 |
| 4 | 28% | 1.0 | 65% | 0.8 | 63% | 0.9 | 55% | 0.9 | 49% | 0.9 | 43% | 0.8 | 38% | 0.9 | 37% | 1.3 | 34% | 1.2 | 27% | 1.0 | 26% | 0.7 |
| 2 | 16% | 1.0 | 56% | 0.8 | 54% | 0.9 | 46% | 0.9 | 38% | 0.9 | 31% | 0.8 | 29% | 0.9 | 27% | 1.7 | 26% | 1.7 | 18% | 1.2 | 19% | 0.8 |
| 1 | 14% | 1.0 | 50% | 0.8 | 47% | 0.8 | 42% | 0.9 | 34% | 0.9 | 28% | 0.7 | 23% | 0.8 | 21% | 1.5 | 19% | 1.4 | 11% | 0.9 | 16% | 0.8 |
| 1 | 11% | 1.0 | 48% | 0.8 | 43% | 0.8 | 37% | 0.8 | 30% | 0.8 | 27% | 0.7 | 20% | 0.8 | 16% | 1.5 | 14% | 1.4 | 11% | 1.1 | 14% | 0.8 |
| 0 | 9% | 1.0 | 46% | 0.8 | 43% | 0.8 | 37% | 0.8 | 30% | 0.8 | 26% | 0.8 | 19% | 0.8 | 19% | 2.1 | 14% | 1.7 | 8% | 1.0 | 8% | 0.5 |
| | | | 1.0 | | 1.0 | | 1.0 | | 1.0 | | 1.0 | | 1.0 | | 1.0 | | 1.0 | | 1.0 |
| 0 | 0% | | 52% | | 45% | | 36% | | 26% | | 25% | | 18% | | -0% | | -0% | | -1% | | 7% |
| HU mM | | 2.00 | 1.00 | 0.50 | 0.25 | 0.13 | 0.06 | 0.03 | 0.02 | 0.01 | 0.00 |

TABLE 29

TABULATIONS OF COMBINED RESULTS RATIOS — U937

Total Time 20 H; Cisplatin for 16 H; dThd for 4 H

| Cisplatin uM | Cisplatin only | MTT blank well | | | | | | | | | | | | | | | | | |
|---|---|---|---|---|---|---|---|---|---|---|---|---|---|---|---|---|---|---|---|
| ***** | 46% | 1.0 | 77% | 0.8 | 75% | 0.8 | 69% | 0.9 | 67% | 0.9 | 68% | 1.0 | 69% | 1.1 | 67% | 1.1 | 65% | 1.2 | 62% | 1.3 |
| ***** | 14% | 1.0 | 68% | 1.0 | 65% | 1.0 | 59% | 1.1 | 56% | 1.2 | 57% | 1.3 | 50% | 1.4 | 51% | 1.5 | 44% | 1.6 | 39% | 1.8 | 30% | 1.6 |
| ***** | -2% | 1.0 | 65% | 1.2 | 55% | 1.2 | 49% | 1.3 | 41% | 1.4 | 40% | 1.5 | 29% | 1.5 | 25% | 1.5 | 16% | 1.6 | 17% | 3.6 | 10% | 6.4 |
| 5.00 | -4% | 1.0 | 63% | 1.2 | 49% | 1.1 | 42% | 1.2 | 29% | 1.0 | 32% | 1.3 | 18% | 1.0 | 16% | 1.0 | 7% | 0.8 | 10% | 2.9 | 1% | 1.4 |
| 2.50 | -6% | 1.0 | 59% | 1.2 | 45% | 1.1 | 39% | 1.1 | 27% | 1.1 | 34% | 1.5 | 20% | 1.2 | 13% | 1.0 | 5% | 0.7 | -1% | -0.5 | -3% | 1.5 |
| 1.25 | -5% | 1.0 | 58% | 1.2 | 46% | 1.1 | 37% | 1.1 | 28% | 1.0 | 28% | 1.2 | 15% | 0.9 | 13% | 1.0 | 6% | 0.9 | 11% | 6.3 | 0% | -0.1 |
| | | | 1.0 | | 1.0 | | 1.0 | | 1.0 | | 1.0 | | 1.0 | | 1.0 | | 1.0 | | 1.0 | | 1.0 |
| 0 | 0% | | 56% | | 48% | | 40% | | 32% | | 29% | | 22% | | 19% | | 12% | | 7% | | 4% |
| dThd mM | | 3.00 | 1.50 | 0.75 | 0.38 | 0.19 | 0.09 | 0.06 | 0.02 | 0.01 | 0.01 |

TABLE 30

TABULATIONS OF COMBINED RESULTS RATIOS

U937

Total Time 24 H    Cisplatin for 20 H
                   HU for 4 H

Cisplatin

| uM | Cisplatin only | MTT blank well | | | | | | | | | | | | | | | | | | |
|---|---|---|---|---|---|---|---|---|---|---|---|---|---|---|---|---|---|---|---|---|
| 40 | 49% | 1.0 | 68% | 0.8 | 66% | 0.8 | 65% | 0.9 | 60% | 1.0 | 58% | 1.0 | 54% | 0.9 | 50% | 1.0 | 49% | 1.0 | 47% | 1.0 |
| 20 | 25% | 1.0 | 61% | 0.9 | 61% | 1.0 | 57% | 1.0 | 52% | 1.2 | 43% | 1.2 | 40% | 1.1 | 35% | 0.9 | 32% | 1.3 | 33% | 1.3 | 31% | 1.3 |
| 10 | 13% | 1.0 | 54% | 1.0 | 55% | 1.1 | 50% | 1.1 | 43% | 1.3 | 33% | 1.4 | 28% | 1.2 | 22% | 0.9 | 21% | 1.7 | 22% | 1.8 | 21% | 1.7 |
| 5 | 10% | 1.0 | 49% | 1.0 | 49% | 1.1 | 44% | 1.1 | 37% | 1.3 | 24% | 1.1 | 22% | 1.0 | 18% | 0.8 | 18% | 1.8 | 21% | 2.0 | 22% | 2.1 |
| 2.5 | 10% | 1.0 | 46% | 0.9 | 46% | 1.0 | 42% | 1.0 | 33% | 1.1 | 21% | 1.0 | 21% | 1.0 | 17% | 0.8 | 21% | 2.0 | 25% | 2.4 | 20% | 2.0 |
| 1.25 | 9% | 1.0 | 44% | 0.9 | 44% | 1.0 | 39% | 1.0 | 30% | 1.1 | 19% | 1.0 | 18% | 0.9 | 15% | 0.7 | 19% | 2.2 | 21% | 2.5 | 20% | 2.3 |
|  |  |  |  | 1.0 |  | 1.0 |  | 1.0 |  | 1.0 |  | 1.0 |  | 1.0 |  | 1.0 |  | 1.0 |  | 1.0 |  | 1.0 |
| 0 | -0% |  | 41% |  | 35% |  | 31% |  | 19% |  | 8% |  | 11% |  | 5% |  | 11% |  | 12% |  | 12% |  |
| HU | mM | 1.33 | 0.67 | 0.33 | 0.17 | 0.08 | 0.04 | 0.02 | 0.01 | 0.01 | 0.00 |

TABLE 31

TABULATIONS OF COMBINED RESULTS RATIOS

U937

Total Time 18 H    K252a for 18 H
                   Aph for 4 H

K252a

| µm | K252a only | MTT blank well | | | | | | | | | | | | | | | | | | |
|---|---|---|---|---|---|---|---|---|---|---|---|---|---|---|---|---|---|---|---|---|
| 2 | 60% | 1.0 | 85% | 1.0 | 82% | 1.1 | 80% | 1.2 | 74% | 1.1 | 69% | 1.1 | 64% | 1.0 | 63% | 1.0 | 61% | 1.0 | 60% | 1.0 |
| 1 | 47% | 1.0 | 87% | 1.0 | 85% | 1.2 | 81% | 1.3 | 76% | 1.4 | 70% | 1.2 | 70% | 1.5 | 62% | 1.2 | 52% | 1.1 | 55% | 1.2 | 49% | 1.5 |
| 0.5 | 35% | 1.0 | 87% | 1.2 | 82% | 1.4 | 79% | 1.6 | 72% | 1.6 | 67% | 1.5 | 59% | 1.7 | 51% | 1.3 | 43% | 1.2 | 44% | 1.3 | 42% | 1.2 |
| 0.25 | 17% | 1.0 | 85% | 1.6 | 78% | 1.9 | 70% | 2.2 | 56% | 2.1 | 50% | 1.8 | 42% | 2.4 | 32% | 1.4 | 30% | 1.7 | 27% | 1.5 | 24% | 1.4 |
| 0.13 | 18% | 1.0 | 82% | 1.5 | 69% | 1.7 | 58% | 1.8 | 49% | 1.8 | 37% | 1.3 | 35% | 1.9 | 27% | 1.2 | 16% | 0.9 | 19% | 1.1 | 17% | 0.9 |
| 0.06 | 13% | 1.0 | 70% | 1.4 | 55% | 1.5 | 46% | 1.7 | 33% | 1.5 | 37% | 1.6 | 30% | 2.2 | 22% | 1.2 | 16% | 1.3 | 18% | 1.4 | 20% | 1.5 |
|  |  |  |  | 1.0 |  | 1.0 |  | 1.0 |  | 1.0 |  | 1.0 |  | 1.0 |  | 1.0 |  | 1.0 |  | 1.0 |  | 1.0 |
| 0 | -0% |  | 38% |  | 24% |  | 14% |  | 8% |  | 10% |  | 10% |  | 14% |  | 1% |  | 0% |  | 5% |  |
| Aph | ug/ml | 4.00 | 2.00 | 1.00 | 0.50 | 0.25 | 0.13 | 0.06 | 0.03 | 0.02 | 0.01 |

TABLE 32

BIVARIATE SERIAL DILUTION ANALYSIS (BVSD)

MTT Assay    TABULATIONS OF COMBINED RESULTS RATIOS    U937 Cells

Total Time 18 H    Daunomycin for 18 H
                   Etoposide for 0 H nM Daunomycin Growth Inhibition [%]

| | | | | | | | | | | | | | | | | | | | | |
|---|---|---|---|---|---|---|---|---|---|---|---|---|---|---|---|---|---|---|---|---|
| 200.0 | 57% | 1.0 | blank well | 81% | 1.2 | 78% | 1.2 | 72% | 1.2 | 69% | 1.1 | 64% | 1.1 | 65% | 1.1 | 67% | 1.2 | 65% | 1.1 | 63% | 1.3 |
| 100.0 | 11% | 1.0 | 76% | 1.3 | 55% | 2.6 | 40% | 2.2 | 28% | 1.8 | 28% | 1.7 | 22% | 1.4 | 24% | 1.6 | 21% | 1.7 | 19% | 1.3 | 18% | 1.3 |
| 50.0 | 4% | 1.0 | 59% | 1.2 | 23% | 1.7 | 11% | 1.0 | 7% | 0.9 | 10% | 1.0 | 10% | 1.2 | 10% | 1.2 | 11% | 2.2 | 11% | 1.6 | 11% | 1.7 |
| 25.0 | 2% | 1.0 | 50% | 1.0 | 8% | 0.7 | 10% | 1.2 | 5% | 0.8 | 6% | 0.9 | 8% | 1.2 | 8% | 1.3 | 10% | 3.4 | 7% | 1.5 | 6% | 1.3 |
| 12.5 | 1% | 1.0 | 47% | 1.0 | 12% | 1.1 | 8% | 1.1 | 7% | 1.6 | 5% | 0.8 | 9% | 1.7 | 7% | 1.3 | 7% | 4.2 | 5% | 1.4 | 7% | 2.2 |
| 6.3 | 2% | 1.0 | 45% | 0.9 | 10% | 0.9 | 7% | 0.9 | 4% | 0.8 | 7% | 1.1 | 5% | 0.8 | 4% | 0.8 | 6% | 2.3 | 6% | 1.3 | 4% | 1.1 |
|  |  |  | 1.0 | 1.0 | 1.0 | 1.0 | 1.0 | 1.0 | 1.0 | 1.0 | 1.0 | 1.0 |

Growth Inhibition 0%   47%   10%   6%   4%   5%   4%   4%   1%   3%   2%
uM Etoposide           2.0   1.0   0.5   0.25   0.13   0.06   0.03   0.02   0.01   0.004

TABLE 33

Summary of Data for Synergistic Matches in U937 cells

| RA | TCI | data for combined results ratio |
|---|---|---|
| BrdU | STSP | Table 9 |
| dAde | STSP | Table 10 |
| dGuo | STSP | Table 11 |
| HU | STSP | Table 12 |
| MTX | STSP | Table 13 |
| Floxuridine | STSP | Table 14 |
| Aph | STSP | Table 15 |
| ara-C | STSP | Table 16 |
| STSP | bleomycin | Table 17 |
| STSP | mitomycin C | Table 18 |
| STSP | cisplatin | Table 19 |
| STSP | daunorubicin | Table 20 |
| STSP | etoposide | Table 21 |
| dThd | K252A | Table 22 |
| dThd | KT5926 | Table 23 |
| dThd | KT5720 | Table 24 |
| dThd | Aph | Table 25 |
| dThd | Ara-C | Table 26 |
| HU | K252A | Table 27 |
| HU | Aph | Table 28 |
| dThd | cisplatin | Table 29 |
| HU | cisplatin | Table 30 |
| Aph | K252a | Table 31 |
| etoposide | daunorubicin | Table 32 |

TABLE 34

Tumor formation in athymic nude mice innoculated with human malignant lymphoma cells (U937)

| Treatment group | # | Mean tumor weight (grams) | Standard Error | p Value compared to control |
|---|---|---|---|---|
| Control | 3 | 2.22 | 0.36 | |
| dThd only | 4 | 1.69 | 0.65 | >0.1 |
| STSP only | 4 | 0.78 | 0.52 | >0.05 |
| dThd/STSP | 4 | 0.0 | | >0.01 |

TABLE 35

Examples relating $S_{MAX}$ for specified RA to blood levels previously reported in chemotherapy

| RA | $S_{MAX}$[@] | Examples | plasma levels[#] | references |
|---|---|---|---|---|
| dThd | 0.05–0.5 mM | Table 4 | up to 6 mM | Blumenreich MS et al. |
| HU | 0.06–0.5 mM | Table 12 | 2.5 mM | Belt RJ et al. |
| MTX | 20–80 nM | Table 13 | up to 1 mM | Allegra CJ et al. |
| Aph | .02–1 ug/ml | Table 15 | up to 3 µg/ml | Sessa C et al. |
| ara-C | 0.05–0.3 µM | Table 16 | up to 50 µM | Calabresi P & Chabner BA |
| STSP | 20–30 nM | Table 17 | [#]up to 500 nM | Buchholz RA |

[@]The range of $S_{MAX}$ was ascertained in relevant examples indicated.
[#]Conservative estimate of maximum plasma level based upon total blood volume in dog and human

TABLE 36

Characteristics of human malignant cell lines which were successfully treated by dThd or other RA to potentiate the action of STSP or other TCI

| Human Cell line | ATCC ID #[@] | Cell Type | p 53 Expression | Clinical Source |
|---|---|---|---|---|
| U937 | CRL 1593 | promonocyte | absent | Malignant lymphoma / large cell histiocytic |
| HL-60 | CCL 240 | promyelocyte | absent | Chronic myelogenous leukemia |
| Daudi | CCL 213 | B-cell | mutant | Malignant lymphoma / Burkitt's type |
| Raji | CCL 86 | B-cell | mutant | Malignant lymphoma/ Burkitt's type |
| Jurkat | TIB 152 | T-cell | mutant | Acute T-cell leukemia |
| C33A | HTB 31 | epithelial | mutant | cervical cancer, negative for human papillomavirus |

[@]Identification number from catalog of American Type Culture Collection, Rockville, MD 20852

TABLE 37

Evidence for cell dependence of $IC_{40}$ and $S_{MAX}$ in synergistic matches with STSP.

| RA | Cell line | $IC_{40}$ | $S_{MAX}$ |
|---|---|---|---|
| dThd | HL-60 promyelocytes | >0.4 mM | 0.04–0.1 mM |
|  | Jurkat T cell leukemia | >3 mM | 0.1–1 mM |
| Aph | Daudi lymphoma cells | >8 µg/ml | 0.5–3 µg/ml |
|  | C33 A cervical carcinoma | >8 µg/ml | 0.8–8 µg/ml |

TABLE 38

TABULATIONS OF COMBINED RESULTS RATIOS

HL-60, Total Time 26 H, STSP for 24 H, dThd for 2 H

| STSP nM | STSP only | MTT blank well | | | | | | | | | | | | | | | | |
|---|---|---|---|---|---|---|---|---|---|---|---|---|---|---|---|---|---|---|
| 100 | 48% | 1.0 | 70% | 0.7 | 66% | 0.7 | 64% | 0.8 | 62% | 1.0 | 60% | 1.1 | 58% | 1.1 | 56% | 1.2 | 55% | 1.1 | 52% | 1.1 |
| 50 | 34% | 1.0 | 59% | 0.7 | 68% | 0.8 | 64% | 0.9 | 59% | 1.0 | 57% | 1.2 | 55% | 1.3 | 51% | 1.3 | 53% | 1.6 | 43% | 1.3 | 39% | 1.2 |
| 25 | 18% | 1.0 | 60% | 0.9 | 64% | 1.0 | 58% | 1.0 | 54% | 1.2 | 48% | 1.6 | 45% | 1.8 | 40% | 1.8 | 40% | 2.3 | 29% | 1.6 | 24% | 1.4 |
| 12.5 | 7% | 1.0 | 56% | 1.0 | 61% | 1.1 | 54% | 1.1 | 49% | 1.4 | 41% | 2.0 | 38% | 2.6 | 36% | 2.9 | 26% | 3.5 | 22% | 2.9 | 15% | 2.0 |
| 6.25 | 5% | 1.0 | 64% | 1.0 | 57% | 1.1 | 51% | 1.1 | 42% | 1.3 | 34% | 1.9 | 32% | 2.5 | 23% | 2.2 | 21% | 4.0 | 12% | 2.3 | 9% | 1.7 |
| 3.13 | 2% | 1.0 | 61% | 1.0 | 54% | 1.1 | 46% | 1.1 | 37% | 1.2 | 28% | 2.0 | 24% | 2.6 | 18% | 2.7 | 19% | 11.8 | 7% | 4.6 | 6% | 4.1 |
|  |  |  | 1.0 |  | 1.0 |  | 1.0 |  | 1.0 |  | 1.0 |  | 1.0 |  | 1.0 |  | 1.0 |  | 1.0 |  | 1.0 |
| 0 | 0% |  | 50% |  | 45% |  | 40% |  | 28% |  | 20% |  | 13% |  | 10% |  | 7% |  | 2% |  | 5% |
| dThd | nM | 3.00 | 1.50 | 0.76 | 0.38 | 0.19 | 0.09 | 0.06 | 0.02 | 0.01 | 0.01 |

TABLE 39

TABULATIONS OF COMBINED RESULTS RATIOS

Jurkat, Total Time 26 H, STSP for 23 H, dThd for 0 H

| STSP nM | STSP only | MTT blank well | | | | | | | | | | | | | | | | |
|---|---|---|---|---|---|---|---|---|---|---|---|---|---|---|---|---|---|---|
| 100 | 38% | 1.0 | 51% | 1.0 | 50% | 1.1 | 49% | 1.2 | 47% | 1.2 | 42% | 1.1 | 40% | 1.0 | 40% | 1.1 | 40% | 1.0 | 40% | 1.1 |
| 50 | 20% | 1.0 | 43% | 1.2 | 42% | 1.3 | 38% | 1.4 | 36% | 1.4 | 31% | 1.6 | 23% | 1.1 | 23% | 1.1 | 21% | 1.1 | 22% | 1.0 | 20% | 1.1 |
| 25 | 9% | 1.0 | 36% | 1.4 | 32% | 1.4 | 29% | 1.7 | 24% | 1.7 | 16% | 1.6 | 10% | 1.0 | 9% | 0.8 | 8% | 0.9 | 9% | 0.9 | 9% | 1.0 |
| 12.5 | 4% | 1.0 | 27% | 1.3 | 24% | 1.4 | 19% | 1.7 | 12% | 1.4 | 6% | 1.4 | 3% | 0.7 | 3% | 0.6 | 1% | 0.5 | 4% | 0.6 | 3% | 1.2 |
| 6.25 | 1% | 1.0 | 20% | 1.1 | 16% | 1.1 | 11% | 1.3 | 6% | 1.1 | 2% | 1.1 | 2% | 1.0 | 2% | 0.8 | -0% | -0.9 | 3% | 1.5 | 0% | 0.1 |
| 3.13 | 3% | 1.0 | 17% | 0.9 | 13% | 0.8 | 6% | 0.6 | 1% | 0.2 | 0% | 0.1 | -1% | -0.2 | -0% | -0.1 | 0% | 0.1 | -0% | -0.0 | -2% | -0.9 |
|  |  |  | 1.0 |  | 1.0 |  | 1.0 |  | 1.0 |  | 1.0 |  | 1.0 |  | 1.0 |  | 1.0 |  | 1.0 |  | 1.0 |
| 0 | 0% |  | 17% |  | 14% |  | 8% |  | 5% |  | 1% |  | 1% |  | 2% |  | 2% |  | 1% |  | -1% |
| dThd | nM | 3.00 | 1.50 | 0.76 | 0.38 | 0.10 | 0.09 | 0.06 | 0.02 | 0.01 | 0.01 |

TABLE 40

TABULATIONS OF COMBINED RESULTS RATIOS — Dauch

Total Time 20 H    STSP for 24 H
               Aph for 4 H

| STSP nM | STSP only | MTT | | | | | | | | | | | | | | | | | | |
|---|---|---|---|---|---|---|---|---|---|---|---|---|---|---|---|---|---|---|---|---|
| 200 | 30% | 1.0 | blank well | 67% | 1.5 | 63% | 1.6 | 60% | 1.5 | 57% | 1.5 | 52% | 1.6 | 53% | 1.6 | 40% | 1.3 | 39% | 1.3 | 33% 1.1 |
| 100 | 26% | 1.0 | 73% | 1.4 | 69% | 1.7 | 64% | 1.8 | 63% | 1.8 | 61% | 1.6 | 58% | 1.8 | 53% | 1.8 | 44% | 1.7 | 34% | 1.3 | 29% 1.1 |
| 50 | 25% | 1.0 | 72% | 1.4 | 67% | 1.6 | 61% | 1.6 | 60% | 1.0 | 58% | 1.7 | 55% | 1.8 | 50% | 1.8 | 38% | 1.5 | 30% | 1.2 | 29% 1.1 |
| 25 | 17% | 1.0 | 54% | 1.5 | 57% | 1.8 | 52% | 2.0 | 50% | 2.0 | 47% | 1.9 | 43% | 1.8 | 37% | 1.8 | 29% | 1.7 | 23% | 1.3 | 20% 1.2 |
| 12.5 | 5% | 1.0 | 53% | 1.7 | 43% | 2.1 | 38% | 2.7 | 34% | 2.6 | 33% | 2.5 | 29% | 2.6 | 22% | 2.6 | 14% | 2.8 | 9% | 1.7 | 8% 1.6 |
| 6.25 | 3% | 1.0 | 44% | 1.5 | 36% | 1.9 | 20% | 2.3 | 27% | 2.3 | 23% | 2.0 | 22% | 2.3 | 16% | 2.3 | 7% | 2.0 | 5% | 1.3 | 2% 0.7 |
|  |  |  |  | 1.0 |  | 1.0 |  | 1.0 |  | 1.0 |  | 1.0 |  | 1.0 |  | 1.0 |  | 1.0 |  | 1.0 | 1.0 |
| 0 | 0% |  | 20% | | 10% | | 8% | | 8% | | 8% | | 8% | | 7% | | 4% | | 1% | | 0% | |
| Aph ug/ml | 8.00 | | 4.00 | | 2.00 | | 1.00 | | 0.50 | | 0.25 | | 0.13 | | 0.06 | | 0.03 | | 0.02 | | | |

TABLE 41

TABULATIONS OF COMBINED RESULTS RATIOS — C33A

Total Time 40 H    STSP for 30 H
               Aphidicolin for 1 H

| STSP nM | STSP only | Method | | | | | | | | | | | | | | | | | | |
|---|---|---|---|---|---|---|---|---|---|---|---|---|---|---|---|---|---|---|---|---|
| 200 | 48% | 1.0 | blank wall | 74% | 1.0 | 74% | 1.1 | 71% | 1.1 | 68% | 1.1 | 63% | 1.0 | 60% | 1.0 | 57% | 1.0 | 52% | 1.0 | 50% 1.1 |
| 100 | 31% | 1.0 | 77% | 1.1 | 75% | 1.3 | 73% | 1.4 | 60% | 1.4 | 66% | 1.4 | 63% | 1.3 | 67% | 1.2 | 50% | 1.2 | 41% | 1.2 | 36% 1.2 |
| 50 | 27% | 1.0 | 75% | 1.1 | 74% | 1.4 | 72% | 1.6 | 67% | 1.6 | 61% | 1.5 | 63% | 1.4 | 67% | 1.3 | 47% | 1.2 | 34% | 1.1 | 30% 1.2 |
| 25 | 16% | 1.0 | 74% | 1.3 | 72% | 1.6 | 67% | 1.8 | 63% | 2.0 | 50% | 1.9 | 57% | 1.6 | 40% | 1.5 | 40% | 1.4 | 28% | 1.4 | 23% 1.6 |
| 12.5 | 11% | 1.0 | 71% | 1.3 | 60% | 1.7 | 57% | 1.8 | 66% | 2.0 | 51% | 1.9 | 48% | 1.8 | 40% | 1.4 | 31% | 1.4 | 20% | 1.2 | 13% 1.3 |
| 0.25 | 2% | 1.0 | 62% | 1.4 | 60% | 1.9 | 51% | 2.3 | 46% | 2.4 | 30% | 2.2 | 39% | 2.2 | 33% | 1.0 | 23% | 1.7 | 13% | 1.0 | 10% 20.2 |
|  |  |  | 1.0 |  | 1.0 |  | 1.0 |  | 1.0 |  | 1.0 |  | 1.0 |  | 1.0 |  | 1.0 |  | 1.0 |  | 1.0 |
|  | -0% |  | 41% | | 21% | | 21% | | 10% | | 15% | | 15% | | 16% | | 12% | | 4% | | -2% | |
| Aphidl ug/ml | 16.00 | | 8.00 | | 4.00 | | 2.00 | | 1.00 | | 0.50 | | 0.25 | | 0.13 | | 0.06 | | 0.03 | | | |

TABLE 42

BIVARIATE SERIAL DILUTION ANALYSIS (BVSD)

TABULATIONS OF COMBINED RESULTS RATIOS — Raji Cells — MTT Assay

Total Time 24 Hours   STSP for 24 Hours
STSP nM               HU for 0 Hours

Growth Inhibition [%]

| | | | | | | | | | | | | | | | | | | | | |
|---|---|---|---|---|---|---|---|---|---|---|---|---|---|---|---|---|---|---|---|---|
| 100.0 | 26% | 1.0 | blank well | 40% | 1.2 | 36% | 1.3 | 35% | 1.0 | 34% | 1.6 | 30% | 1.5 | 27% | 1.4 | 26% | 1.4 | 21% | 1.0 | 24% 1.0 |
| 50.00 | 21% | 1.0 | 41% | 1.1 | 38% | 1.3 | 36% | 1.6 | 35% | 2.1 | 31% | 2.0 | 26% | 1.9 | 20% | 1.5 | 19% | 1.4 | 20% | 1.3 | 15% 0.9 |
| 25.00 | 7% | 1.0 | 37% | 1.6 | 30% | 2.0 | 30% | 3.1 | 24% | 9.4 | 19% | 16.6 | 12% | *** | 6% | 13.9 | 5% | 13.0 | 7% | 6.0 | -1% -0.2 |
| 12.50 | -3% | 1.0 | 30% | 2.2 | 24% | 5.5 | 10% | 20.0 | 13% | 4.5 | 4% | -0.4 | -0% | 0.0 | -5% | 0.4 | -3% | 0.3 | -0% | 0.0 | -7% 1.1 |
| 6.25 | -7% | 1.0 | 19% | 1.9 | 15% | 15.4 | 9% | 2.1 | 4% | 0.3 | -0% | 0.0 | -5% | 0.4 | -6% | 0.6 | -12% | 0.9 | -8% | 0.6 | -10% 1.0 |
| 3.13 | -5% | 1.0 | 22% | 1.6 | 11% | 3.3 | 5% | 2.3 | 2% | 0.3 | -2% | 0.2 | -5% | 0.5 | -10% | 0.0 | -10% | 0.8 | -7% | 0.7 | -12% 1.5 |
|  |  |  | 1.0 |  | 1.0 |  | 1.0 |  | 1.0 |  | 1.0 |  | 1.0 |  | 1.0 |  | 1.0 |  | 1.0 |  | 1.0 |
| Growth Inhibition | 0% | | 17% | | 8% | | 0% | | -4% | | -0% | | -7% | | -7% | | -7% | | -6% | | -3% | |
| mM HU | 2.00 | | 1.00 | | 0.50 | | 0.25 | | 0.13 | | 0.06 | | 0.03 | | 0.02 | | 0.01 | | 0.00 | | | |

What is claimed is:

1. A method of potentiating cell damage, comprising:

a. administering a restraining agent to a target cell population to be damaged at a concentration and under conditions sufficient to dynamically retard but not arrest the progress of the target cell population through a reference point within a phase of the cell cycle, wherein the concentration of the restraining agent is less than 40% of its inhibitory concentration ($IC_{40}$), as measured at a cell population doubling time or at a time interval which is less than the cell population doubling time, and is at least 50% of the cell population doubling time; and b. administering a targeted cytotoxic insult concomitant with or subsequent to the administration of the restraining agent, wherein the targeted cytotoxic insult inflicts biologically significant damage to the target cell population at a point in the cell cycle that is downstream of the reference point of the restraining agent, and wherein the targeted cytotoxic insult is administered at an effective concentration that minimizes the toxic effect on non-target cells; and wherein said restraining agent is a ribonucleotide reductase inhibitor.

2. The method as claimed in claim 1, wherein said restraining agent is BrdU and said targeted cytotoxic insult is selected from the group consisting of staurosporine, K252A, KT5720, and KT5926.

3. The method as claimed in claim 1, wherein said restraining agent is dThd and said targeted cytotoxic insult is selected from the group consisting of staurosporine, K252A, KT5720, and KT5926.

4. The method as claimed in claim 1, wherein said restraining agent is HU and said targeted cytotoxic insult is selected from the group consisting of staurosporine, K252A, KT5720, and KT5926.

5. The method as claimed in claim 1, wherein the restraining agent slows the cell cycle at the $G_1/S$ transition.

6. The method as claimed in claim 1, wherein the restraining agent slows the cell cycle during the S phase.

7. The method as claimed in claim 1, wherein the restraining agent slows the cell cycle during the S to $G_2$ transition.

8. The method as claimed in claim 1, wherein the targeted cytotoxic insult is an indole carbazole.

9. The method according to claim 2, wherein the concentration of BrdU is between 0.05 and 0.019 mM.

10. The method according to claim 3, wherein the concentration of dThd is between 0.05 and 0.5 mM.

11. The method according to claim 4, wherein the concentration of HU is between 0.06 and 0.5 mM.

12. The method according to claim 1, wherein the targeted cytotoxic insult is administered subsequent to the administration of the restraining agent.

13. The method according to claim 1, wherein the concentration of the restraining agent is less than 40% of its inhibitory concentration ($IC_{40}$), as measured at a population doubling time.

14. The method according to claim 1, wherein the concentration of the restraining agent is between about $IC_6$ and $IC_{30}$.

15. The method according to claim 14, wherein the concentration of the restraining agent is between about $IC_{10}$ to $IC_{25}$.

* * * * *